US008216804B2

(12) United States Patent
Schultz et al.

(10) Patent No.: US 8,216,804 B2
(45) Date of Patent: Jul. 10, 2012

(54) ORTHOGONAL TRANSLATION COMPONENTS FOR THE IN VIVO INCORPORATION OF UNNATURAL AMINO ACIDS

(75) Inventors: Peter G. Schultz, La Jolla, CA (US); Jianming Xie, San Diego, CA (US); Huaqiang Zeng, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 1047 days.

(21) Appl. No.: 11/665,083

(22) PCT Filed: Oct. 27, 2005

(86) PCT No.: PCT/US2005/039210

§ 371 (c)(1),
(2), (4) Date: Jun. 18, 2007

(87) PCT Pub. No.: WO2006/110182

PCT Pub. Date: Oct. 19, 2006

(65) Prior Publication Data

US 2008/0233611 A1 Sep. 25, 2008

Related U.S. Application Data

(60) Provisional application No. 60/622,738, filed on Oct. 27, 2004.

(51) Int. Cl.
*C12N 15/09* (2006.01)
*C12N 1/21* (2006.01)
*C12N 1/19* (2006.01)

(52) U.S. Cl. ................. 435/69.1; 435/254.2; 435/252.3; 435/252.33

(58) Field of Classification Search ........................ None
See application file for complete search history.

(56) References Cited

U.S. PATENT DOCUMENTS

| | | | | |
|---|---|---|---|---|
| 5,580,953 | A * | 12/1996 | Albrecht et al. | 530/303 |
| 6,872,574 | B2 * | 3/2005 | Cravatt et al. | 436/119 |
| 6,927,042 | B2 | 8/2005 | Schultz et al. | |
| 7,045,337 | B2 | 5/2006 | Schultz et al. | |
| 7,083,970 | B2 | 8/2006 | Schultz et al. | |
| 7,129,333 | B2 | 10/2006 | Schultz et al. | |
| 7,183,082 | B2 | 2/2007 | Schultz et al. | |
| 7,199,222 | B2 | 4/2007 | Schultz et al. | |
| 7,217,809 | B2 | 5/2007 | Schultz et al. | |
| 7,238,510 | B2 | 7/2007 | Schultz et al. | |
| 7,262,040 | B2 | 8/2007 | Schultz et al. | |
| 2004/0198637 | A1 | 10/2004 | Schultz et al. | |
| 2004/0265952 | A1 | 12/2004 | Deiters et al. | |
| 2005/0009049 | A1 | 1/2005 | Chin et al. | |
| 2005/0136513 | A1 | 6/2005 | Zhang et al. | |
| 2005/0208536 | A1 | 9/2005 | Schultz et al. | |
| 2005/0227318 | A1 | 10/2005 | Alfonta et al. | |
| 2005/0272121 | A1 | 12/2005 | Xie et al. | |
| 2006/0063244 | A1 | 3/2006 | Schultz et al. | |
| 2006/0068478 | A1 | 3/2006 | Schultz et al. | |
| 2006/0073507 | A1 | 4/2006 | Deiters et al. | |
| 2006/0110784 | A1 | 5/2006 | Deiters et al. | |
| 2006/0110796 | A1 | 5/2006 | Schultz et al. | |
| 2006/0134746 | A1 | 6/2006 | Deiters et al. | |
| 2006/0160175 | A1 | 7/2006 | Anderson et al. | |
| 2006/0177900 | A1 | 8/2006 | Anderson et al. | |
| 2006/0234367 | A1 | 10/2006 | Schultz et al. | |
| 2006/0246509 | A1 | 11/2006 | Deiters et al. | |
| 2007/0009990 | A1 | 1/2007 | Alfonta et al. | |
| 2007/0020634 | A1 | 1/2007 | Anderson et al. | |
| 2007/0042461 | A1 | 2/2007 | Anderson et al. | |
| 2007/0111193 | A1 | 5/2007 | Zhang et al. | |
| 2007/0154952 | A1 | 7/2007 | Chin et al. | |
| 2007/0166791 | A1 | 7/2007 | Chin et al. | |
| 2007/0172915 | A1 | 7/2007 | Schultz et al. | |
| 2007/0178448 | A1 | 8/2007 | Tsao et al. | |
| 2007/0184517 | A1 | 8/2007 | Schultz et al. | |
| 2007/0238152 | A1 | 10/2007 | Wang et al. | |

FOREIGN PATENT DOCUMENTS

| | | | |
|---|---|---|---|
| WO | WO 02/085923 | A2 | 10/2002 |
| WO | WO 02/086075 | A2 | 10/2002 |
| WO | WO 2004/035743 | A2 | 4/2004 |
| WO | WO 2007/103490 | | 9/2007 |

OTHER PUBLICATIONS

Deiters et al. (2006) "A Genetically Encoded Photocaged Tyrosine." *Angew. Chem. Intl. Ed.*, 45: 2728-2731.

Summerer et al. (2006) "A Genetically Encoded Fluorescent Amino Acid." *Proceedings of the National Academy of Sciences*, USA, 103(26): 9785-9789.

Tsao et al. (2006) "The Genetic Incorporation of a Distance Probe into Proteins in *Escherichia coli.*" *Journal of the American Chemistry Society*, 128(14): 4572-4573.

Wang and Schultz (2005) "The Expanding Genetic Code." *Angew. Chem. Intl. Ed.*, 44: 34-66.

Xie and Schultz (2005) "Adding amino acids to the genetic repertoire." *Currentl Opinion in Chemical Biology*, 9: 548-554. Zeng et al. (2006) "Genetic introduction of a diketone-containing amino acid into proteins". *Bioorganic & Medicinal Chemistry Letters*, 16: 5356-5359.

Chin et al (2002) "Addition of a photocrosslinking amino acid to the genetic code of *Escherichia coli.*" *Proceedings of the National Academy of Sciences*, 99: 11020-11024.

Wang et al. (2001) "Expanding the Genetic Code of *Escherichia coli.*" 292: 498-500, Science.

Liu et al. (1997) "Engineering a tRNA and aminoacyl-tRNA synthetase for the site-specific incorporation of unnatural amino acids into proteins in vivo." *Proceedings of the National Academy of Sciences*, USA, 94: 10092-10097.

Chin et al. (2003) "An Expanded Eukaryotic Genetic Code." *Science*, 301: 964-967.

Santoro et al. (2003) "An archaebacteria-derived glutamyl-tRNA synthetase and tRNA pair for unnatural amino acid mutagenesis of proteins in *Escherichia coli.*" *Nucleic Acids Research*, 31(23): 6700-6709.

Xie et al. (2004) "The site-specific incorporationof p-iodo-L-phenylalanine into proteins for structure determination." *Nature Biotechnology*, 22(10): 1297-1301.

EP Search Report from EP application No. 11165007.3, dated Sep. 29, 2011.

EP Search Report from EP application No. 11164983.6, dated Sep. 27, 2011.

* cited by examiner

*Primary Examiner* — Nancy Vogel

(74) *Attorney, Agent, or Firm* — Quine Intellectual Property Law Group, P.C.

(57) ABSTRACT

The invention relates to orthogonal pairs of tRNAs and aminoacyl-tRNA synthetases that can incorporate unnatural amino acids into proteins produced in eubacterial host cells such as *E. coli*, or in a eukaryotic host such as a yeast cell. The invention provides, for example but not limited to, novel orthogonal synthetases, methods for identifying and making the novel synthetases, methods for producing proteins containing unnatural amino acids, and translation systems.

27 Claims, 15 Drawing Sheets

| | |
|---|---|
| 3-nitro-L-tyrosine<br><br>aka<br>*m*-nitro-tyrosine |  |
| *p*-nitro-L-phenylalanine<br><br>aka<br>4-nitro-L-phenylalanine |  |
| 3-amino-L-tyrosine |  |
| *p*-carboxymethyl-L-phenylalanine |  |
| biphenyl-alanine |  |
| bipyridyl-alanine |  |
| 1,5-dansyl-alanine |  |
| *o*-nitrobenzyl-serine |  |
| O-(2-nitrobenzyl)-L-tyrosine |  |

| | |
|---|---|
| *p*-cyano-L-phenylalanine<br><br>aka<br>4-cyano-L-phenylalanine |  |
| *m*-cyano-L-phenylalanine<br><br>aka<br>3-cyano-L-phenylalanine |  |
| *p*-(2-amino-1-hydroxyethyl)-L-phenylalanine |  |
| *p*-ethylthiocarbonyl-L-phenylalanine |  |
| *p*-(3-oxobutanoyl)-L-phenylalanine |  |
| *p*-isopropylthiocarbonyl-L-phenylalanine |  |
| 7-amino-coumarin-alanine |  |

| | |
|---|---|
| 7-hydroxy-coumarin alanine |  |

1: X = H
2: X = D

3: X = H
4: X = D

| # | b | $b^{++}$ | $b^{0}$ | $b^{0++}$ | Seq. | y | $y^{++}$ | $y^{*}$ | $y^{*++}$ | $y^{0}$ | $y^{0++}$ | # |
|---|---|---|---|---|---|---|---|---|---|---|---|---|
| 1 | 138.07 | 69.54 | | | H | | | | | | | 14 |
| 2 | 195.09 | 98.05 | | | G | 1347.82 | 674.42 | 1330.80 | 665.90 | 1329.81 | 665.41 | 13 |
| 3 | 294.16 | 147.58 | | | V | 1290.80 | 645.91 | 1273.78 | 637.39 | 1272.79 | 636.90 | 12 |
| 4 | 395.20 | 198.11 | 377.19 | 189.10 | T | 1191.73 | 596.37 | 1174.71 | 587.86 | 1173.72 | 587.37 | 11 |
| 5 | 494.27 | 247.64 | 476.26 | 238.63 | V | 1090.69 | 545.85 | 1073.66 | 537.33 | 1072.68 | 536.84 | 10 |
| 6 | 607.36 | 304.18 | 589.35 | 295.18 | L | 991.62 | 496.31 | 974.59 | 487.80 | 973.61 | 487.31 | 9 |
| 7 | 708.40 | 354.71 | 690.39 | 345.70 | T | 878.53 | 439.77 | 861.51 | 431.26 | 860.52 | 430.77 | 8 |
| 8 | 779.44 | 390.22 | 761.43 | 381.22 | A | 777.49 | 389.25 | 760.46 | 380.73 | | | 7 |
| 9 | 892.53 | 446.77 | 874.51 | 437.76 | L | 706.45 | 353.73 | 689.42 | 345.22 | | | 6 |
| 10 | 949.55 | 475.28 | 931.54 | 466.27 | G | 593.37 | 297.19 | 576.34 | 288.67 | | | 5 |
| 11 | 1112.61 | 556.81 | 1094.60 | 547.80 | Y | 536.34 | 268.68 | 519.32 | 260.16 | | | 4 |
| 12 | 1225.69 | 613.35 | 1207.68 | 604.35 | I | 373.28 | 187.14 | 356.25 | 178.63 | | | 3 |
| 13 | 1338.78 | 669.89 | 1320.77 | 660.89 | L | 260.20 | 130.60 | 243.17 | 122.09 | | | 2 |
| 14 | | | | | K | 147.11 | 74.06 | 130.09 | 65.55 | | | 1 |

| # | b | $b^{++}$ | $b^{0}$ | $b^{0++}$ | Seq. | y | $y^{++}$ | $y^{*}$ | $y^{*++}$ | $y^{0}$ | $y^{0++}$ | # |
|---|---|---|---|---|---|---|---|---|---|---|---|---|
| 1 | 138.07 | 69.54 | | | H | | | | | | | 14 |
| 2 | 195.09 | 98.05 | | | G | 1349.84 | 675.42 | 1332.81 | 666.91 | 1331.83 | 666.42 | 13 |
| 3 | 294.16 | 147.58 | | | V | 1292.82 | 646.91 | 1275.79 | 638.40 | 1274.80 | 637.91 | 12 |
| 4 | 395.20 | 198.11 | 377.19 | 189.10 | T | 1193.75 | 597.38 | 1176.72 | 588.86 | 1175.74 | 588.37 | 11 |
| 5 | 494.27 | 247.64 | 476.26 | 238.63 | V | 1092.70 | 546.85 | 1075.67 | 538.34 | 1074.69 | 537.85 | 10 |
| 6 | 607.36 | 304.18 | 589.35 | 295.18 | L | 993.63 | 497.32 | 976.60 | 488.81 | 975.62 | 488.31 | 9 |
| 7 | 708.40 | 354.71 | 690.39 | 345.70 | T | 880.55 | 440.78 | 863.52 | 432.26 | 862.54 | 431.77 | 8 |
| 8 | 779.44 | 390.22 | 761.43 | 381.22 | A | 779.50 | 390.25 | 762.47 | 381.74 | | | 7 |
| 9 | 892.53 | 446.77 | 874.51 | 437.76 | L | 708.46 | 354.73 | 691.44 | 346.22 | | | 6 |
| 10 | 949.55 | 475.28 | 931.54 | 466.27 | G | 595.38 | 298.19 | 578.35 | 289.68 | | | 5 |
| 11 | 1114.62 | 557.81 | 1096.61 | 548.81 | J | 538.36 | 269.68 | 521.33 | 261.17 | | | 4 |
| 12 | 1227.71 | 614.36 | 1209.70 | 605.35 | I | 373.28 | 187.14 | 356.25 | 178.63 | | | 3 |
| 13 | 1340.79 | 670.90 | 1322.78 | 661.89 | L | 260.20 | 130.60 | 243.17 | 122.09 | | | 2 |
| 14 | | | | | K | 147.11 | 74.06 | 130.09 | 65.55 | | | 1 |

4a 4b 4c 4

| | | | |
|---|---|---|---|
| $mutRNA_{CUA}$ | + | + | + |
| synthetase mutant | wt | mutant | |
| Amino acid **4** | - | + | - |

1a 2a 2b 2c 1b 3a 3b 3c 3d

ORTHOGONAL TRANSLATION COMPONENTS FOR THE IN VIVO INCORPORATION OF UNNATURAL AMINO ACIDS

CROSS-REFERENCE TO RELATED APPLICATIONS

This application is a national phase entry in the United States under 35 U.S.C. §371 from International Application Number PCT/US2005/039210, which has an international filing date of Oct. 27, 2005, and which designated the United States of America, which claims priority to and benefit of U.S. Provisional Patent Application Ser. No. 60/622,738, filed Oct. 27, 2004, the disclosure of which is incorporated herein by reference in its entirety for all purposes.

STATEMENT AS TO RIGHTS TO INVENTIONS MADE UNDER FEDERALLY

A portion of the work described herein was supported by grant numbers GM62159, and AI66507 from the National Institutes of Health, and grant number ER46051 from the Department of Energy. The United States Government has certain rights to this invention.

FIELD OF THE INVENTION

The invention is in the field of translation biochemistry. The invention relates to compositions and methods for making and using orthogonal tRNAs, orthogonal aminoacyl-tRNA synthetases, and pairs thereof, that incorporate unnatural amino acids into proteins. The invention also relates to methods of producing proteins in cells using such pairs and proteins made by the methods.

BACKGROUND OF THE INVENTION

The study of protein structure and function has historically relied upon the properties and reaction chemistries that are available using the reactive groups of the naturally occurring amino acids. Unfortunately, every known organism, from bacteria to humans, encodes the same twenty common amino acids (with the rare exceptions of selenocysteine (see, e.g., A. Bock et al., (1991), *Molecular Microbiology* 5:515-20) and pyrrolysine (see, e.g., G. Srinivasan, et al., (2002), *Science* 296:1459-62). This limited selection of R-groups has restricted the study of protein structure and function, where the studies are confined by the chemical properties of the naturally occurring amino acids, e.g., the natural amino acids limit the ability to make highly targeted protein modifications to the exclusion of all other amino acids in a protein. Additionally, the natural amino acids are limited in their functional activities, e.g., fluorescence, metal chelating, redox-potential, photocaging, etc.

Most modification reactions currently used in the art for the selective modification of proteins involve covalent bond formation between nucleophilic and electrophilic reaction partners that target naturally occurring nucleophilic residues in the protein amino acid side chains, e.g., the reaction of α-halo ketones with histidine or cysteine side chains. Selectivity in these cases is determined by the number and accessibility of the nucleophilic residues in the protein. Unfortunately, naturally occurring proteins frequently contain poorly positioned (e.g., inaccessible) reaction sites or multiple reaction targets (e.g., lysine, histidine and cysteine residues), resulting in poor selectivity in the modification reactions, making highly targeted protein modification by nucleophilic/electrophilic reagents difficult. Furthermore, the sites of modification are typically limited to the naturally occurring nucleophilic side chains of lysine, histidine or cysteine. Modification at other sites is difficult or impossible.

What is needed in the art are new strategies for incorporation of unnatural amino acids into proteins for the purpose of modifying and studying protein structure and function, where the unnatural amino acids have novel properties, e.g., biological properties, not found in the naturally occurring amino acids. There is a considerable need in the art for the creation of new strategies for protein modification reactions that modify proteins in a highly selective fashion, and furthermore, modify proteins under physiological conditions. What is needed in the art are novel methods for producing protein modifications, where the modifications are highly specific, e.g., modifications where none of the naturally occurring amino acids are subject to cross reactions or side reactions. Novel chemistries for highly specific protein modification strategies can find a wide variety of applications in the study of protein structure and function.

One strategy to overcome these limitations is to expand the genetic code and add amino acids that have distinguishing physical, chemical or biological properties to the biological repertoire. This approach has proven feasible using orthogonal tRNA's and corresponding novel orthogonal aminoacyl-tRNA synthetases to add unnatural amino acids to proteins using the in vivo protein biosynthetic machinery of a host cell, e.g., the eubacteria *Escherichia coli* (*E. coli*), yeast or mammalian cells. This approach is described in various sources, for example, Wang et al., (2001), *Science* 292:498-500; Chin et al., (2002) *Journal of the American Chemical Society* 124:9026-9027; Chin and Schultz, (2002), *ChemBioChem* 11:1135-1137; Chin, et al., (2002), *PNAS United States of America* 99:11020-11024; and Wang and Schultz, (2002), *Chem. Comm.,* 1-10. See also, International Publications WO 2002/086075, entitled "METHODS AND COMPOSITIONS FOR THE PRODUCTION OF ORTHOGONAL tRNA AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO 2005/007870, filed Jul. 7, 2004; and WO 2005/007624, filed Jul. 7, 2004.

There is a need in the art for the development of orthogonal translation components that incorporate unnatural amino acids into proteins, where the unnatural amino acids can be incorporated at a defined position, and where the unnatural amino acids impart novel biological properties to the proteins in which they are incorporated. There is also a need to develop orthogonal translation components that incorporate unnatural amino acids with novel chemical properties that allow the amino acid to serve as a target for specific modification to the exclusion of cross reactions or side reactions with other sites in the proteins. There is also a particular need for protein expression systems that have the ability to produce proteins containing unnatural amino acids in significant quantities that permit their use in therapeutic applications and biomedical research. The invention described herein fulfills these and other needs, as will be apparent upon review of the following disclosure.

SUMMARY OF THE INVENTION

The invention provides compositions and methods for incorporating unnatural amino acids into a growing polypeptide chain in response to a selector codon, e.g., an amber stop codon, in vivo (e.g., in a host cell). These compositions include pairs of orthogonal-tRNAs (O-tRNAs) and orthogonal aminoacyl-tRNA synthetases (O—RSs) that do not interact with the host cell translation machinery. That is to say, the O-tRNA is not charged (or not charged to a significant level) with an amino acid (natural or unnatural) by an endogenous host cell aminoacyl-tRNA synthetase. Similarly, the O—RSs provided by the invention do not charge any endogenous tRNA with an amino acid (natural or unnatural) to a significant or in some cases detectable level. These novel compositions permit the production of large quantities of proteins having translationally incorporated unnatural amino acids. Depending on the chemical properties of the unnatural amino acid that is incorporated, these proteins find a wide variety of uses, including, for example, as therapeutics and in biomedical research.

In some aspects, the invention provides translation systems. These systems comprise a first orthogonal aminoacyl-tRNA synthetase (O—RS), a first orthogonal tRNA (O-tRNA), and an unnatural amino acid, where the first O—RS preferentially aminoacylates the first O-tRNA with the first unnatural amino acid. The first unnatural amino acid can be selected from p-ethylthiocarbonyl-L-phenylalanine, p-(3-oxobutanoyl)-L-phenylalanine, 1,5-dansyl-alanine, 7-amino-coumarin-alanine, 7-hydroxy-coumarin-alanine, o-nitrobenzyl-serine, O-(2-nitrobenzyl)-L-tyrosine, p-carboxymethyl-L-phenylalanine, m-cyano-L-phenylalanine, p-cyano-L-phenylalanine, biphenylalanine, 3-amino-L-tyrosine, bipyridylalanine, p-(2-amino-1-hydroxyethyl)-L-phenylalanine and p-isopropylthiocarbonyl-L-phenylalanine.

The translation systems can use components derived from a variety of sources. In one embodiment, the first O—RS is derived from a *Methanococcus jannaschii* aminoacyl-tRNA synthetase, e.g., a wild-type *Methanococcus jannaschii* tyrosyl-tRNA synthetase. In other embodiments, the O—RS is derived from an *E. coli* aminoacyl-tRNA synthetase, e.g., a wild-type *E. coli* leucyl-tRNA synthetase. The O—RS used in the system can comprise an amino acid sequence selected from SEQ ID NOs: 12, 14, 16, 18, 20, 22, 24, 26, 28, 30, 32, 34, 36, 38, 40, 42, 44, 46, 50, 52-55, 57, 59-63, and conservative variants of those sequences. In some embodiments, the O-tRNA is an amber suppressor tRNA. In some embodiments, the O-tRNA comprises or is encoded by SEQ ID NO: 1 or 2.

In some aspects, the translation system further comprises a nucleic acid encoding a protein of interest, where the nucleic acid has at least one selector codon that is recognized by the O-tRNA.

In some aspects, the translation system incorporates a second orthogonal pair (that is, a second O—RS and a second O-tRNA) that utilizes a second unnatural amino acid, so that the system is now able to incorporate at least two different unnatural amino acids at different selected sites in a polypeptide. In this dual system, the second O—RS preferentially aminoacylates the second O-tRNA with a second unnatural amino acid that is different from the first unnatural amino acid, and the second O-tRNA recognizes a selector codon that is different from the selector codon recognized by the first O-tRNA.

In some embodiments, the translation system resides in a host cell (and includes the host cell). The host cell used in not particularly limited, as long as the O—RS and O-tRNA retain their orthogonality in their host cell environment. The host cell can be a eubacterial cell, such as *E. coli*, or a yeast cell, such as *Saccharomyces cerevisiae*. The host cell can comprise one or more polynucleotides that encode components of the translation system, including the O—RS or O-tRNA. In some embodiments, the polynucleotide encoding the O—RS comprises a nucleotide sequence of SEQ ID NO: 13, 15, 17, 19, 21, 23, 25, 27, 29, 31, 33, 35, 37, 39, 41, 43, 45, 47, 51, 56 or 58.

The invention also provides methods for producing proteins having one or more unnatural amino acids at selected positions. These methods utilize the translation systems described above. Generally, these methods start with the step of providing a translation system comprising: (i) a first unnatural amino acid selected from p-ethylthiocarbonyl-L-phenylalanine, p-(3-oxobutanoyl)-L-phenylalanine, 1,5-dansyl-alanine, 7-amino-coumarin-alanine, 7-hydroxy-coumarin-alanine, o-nitrobenzyl-serine, O-(2-nitrobenzyl)-L-tyrosine, p-carboxymethyl-L-phenylalanine, m-cyano-L-phenylalanine, p-cyano-L-phenylalanine, biphenylalanine, 3-amino-L-tyrosine, bipyridyalanine, p-(2-amino-1-hydroxyethyl)-L-phenylalanine and p-isopropylthiocarbonyl-L-phenylalanine; (ii) a first orthogonal aminoacyl-tRNA synthetase (O—RS); (iii) a first orthogonal tRNA (O-tRNA), wherein the O—RS preferentially aminoacylates the O-tRNA with the unnatural amino acid; and, (iv) a nucleic acid encoding the protein, where the nucleic acid comprises at least one selector codon that is recognized by the first O-tRNA. The method then incorporates the unnatural amino acid at the selected position in the protein during translation of the protein in response to the selector codon, thereby producing the protein comprising the unnatural amino acid at the selected position.

This methods can be widely applied using a variety of reagents and steps. In some embodiments, a polynucleotide encoding the O—RS is provided. In some embodiments, an O—RS derived from a *Methanococcus jannaschii* aminoacyl-tRNA synthetase is provided, for example, a wild-type *Methanococcus jannaschii* tyrosyl-tRNA synthetase can be provided. In other embodiments, an O—RS derived from an *E. coli* aminoacyl-tRNA synthetase is provided, e.g., an O—RS derived from a wild-type *E. coli* leucyl-tRNA synthetase can be provided. In some embodiments, the providing step includes providing an O—RS comprising an amino acid sequence selected from SEQ ID NOs: 12, 14, 16, 18, 20, 22, 24, 26, 28, 30, 32, 34, 36, 38, 40, 42, 44, 46, 50, 52-55, 57, 59-63, and conservative variants thereof.

In some embodiments of these methods, the providing a translation system step comprises mutating an amino acid binding pocket of a wild-type aminoacyl-tRNA synthetase by site-directed mutagenesis, and selecting a resulting O—RS that preferentially aminoacylates the O-tRNA with the unnatural amino acid. The selecting step can comprises positively selecting and negatively selecting for the O—RS from a pool of resulting aminoacyl-tRNA synthetase molecules following site-directed mutagenesis. In some embodiments, the providing step furnishes a polynucleotide encoding the O-tRNA, e.g., an O-tRNA that is an amber suppressor tRNA, or an O-tRNA that comprises or is encoded by a polynucleotide of SEQ ID NO: 1 or 2. In these methods, the providing step can also furnish a nucleic acid comprising an amber selector codon that is utilized by the translation system.

These methods can also be modified to incorporate more than one unnatural amino acid into a protein. In those methods, a second orthogonal translation system is employed in conjunction with the first translation system, where the second system has different amino acid and selector codon specificities. For example, the providing step can include providing a second O—RS and a second O-tRNA, where the second O—RS preferentially aminoacylates the second O-tRNA with a second unnatural amino acid that is different from the first unnatural amino acid, and where the second O-tRNA recognizes a selector codon in the nucleic acid that is different from the selector codon recognized by the first O-tRNA.

The methods for producing a protein with an unnatural amino acid can also be conducted in the context of a host cell. In these cases, a host cell is provided, where the host cell comprises the unnatural amino acid, the O—RS, the O-tRNA and the nucleic acid, and where culturing the host cell results in incorporating the unnatural amino acid. In some embodiments, the providing step comprises providing a eubacterial host cell (e.g., *E. coli*) or a yeast host cell. In some embodiments, the providing step includes providing a host cell that contains a polynucleotide encoding the O—RS. Fore example, the polynucleotide encoding the O—RS can comprise a nucleotide sequence of SEQ ID NOs: 13, 15, 17, 19, 21, 23, 25, 27, 29, 31, 33, 35, 37, 39, 41, 43, 45, 47, 51, 56 or 58. In some embodiments, the step of providing a translation system is accomplished by providing a cell extract.

In some aspects, the invention provides translation systems, where the systems are for the incorporation of 3-nitro-L-tyrosine or p-nitro-L-phenylalanine. These systems comprise a first orthogonal aminoacyl-tRNA synthetase (O—RS), a first orthogonal tRNA (O-tRNA), and the unnatural amino acid, where the first O—RS preferentially aminoacylates the first O-tRNA with the first unnatural amino acid with an efficiency that is at least 50% of the efficiency observed for a translation system comprising that same unnatural amino acid, the O-tRNA and an O—RS comprising an amino acid sequence selected from SEQ ID NOs: 7-10.

The translation system can use components derived from a variety of sources. In some embodiments, the first O—RS is derived from a *Methanococcus jannaschii* aminoacyl-tRNA synthetase, e.g., a wild-type *Methanococcus jannaschii* tyrosyl-tRNA synthetase. The O—RS used in the system can comprise an amino acid sequence selected from SEQ ID NOs: 7-10, and conservative variants of those sequences. In some embodiments, the O-tRNA is an amber suppressor tRNA. In some embodiments, the O-tRNA comprises or is encoded by SEQ ID NO: 1.

In some aspects, the translation system further comprises a nucleic acid encoding a protein of interest, where the nucleic acid has at least one selector codon that is recognized by the O-tRNA.

In some aspects, the translation system incorporates a second orthogonal pair (that is, a second O—RS and a second O-tRNA) that utilizes a second unnatural amino acid, so that the system is now able to incorporate at least two different unnatural amino acids at different selected sites in a polypeptide. In this dual system, the second O—RS preferentially aminoacylates the second O-tRNA with a second unnatural amino acid that is different from the first unnatural amino acid, and the second O-tRNA recognizes a selector codon that is different from the selector codon recognized by the first O-tRNA.

In some embodiments, the translation system resides in a host cell (and includes the host cell). The host cell used is not particularly limited, as long as the O—RS and O-tRNA retain their orthogonality in their host cell environment. The host cell can be a eubacterial cell, such as *E. coli*. The host cell can comprise one or more polynucleotides that encode components of the translation system, including the O—RS or O-tRNA. In some embodiments, the polynucleotide encoding the O—RS comprises a nucleotide sequence of SEQ ID NO: 11.

The invention also provides methods for producing proteins having one or more unnatural amino acids at selected positions. These methods utilize the translation systems described above. Generally, these methods start with the step of providing a host cell comprising a translation system comprising: (i) a first unnatural amino acid that is 3-nitro-L-tyrosine or p-nitro-L-phenylalanine; (ii) a first orthogonal aminoacyl-tRNA synthetase (O—RS); (iii) a first orthogonal tRNA (O-tRNA), where the O—RS preferentially aminoacylates the O-tRNA with the unnatural amino acid with an efficiency that is at least 50% of the efficiency observed for the host cell comprising the unnatural amino acid, the O-tRNA and an O—RS comprising an amino acid sequence selected from SEQ ID NOs: 7-10; and, (iv) a nucleic acid encoding the protein, where the nucleic acid comprises at least one selector codon that is recognized by the O-tRNA. The host cell is then grown, and the unnatural amino acid is incorporated at the selected position in the protein during translation of the protein in response to the selector codon, where the selected position in the protein corresponds to the position of the selector codon in the nucleic acid, thereby producing the protein comprising the unnatural amino acid at the selected position.

These methods can be widely applied using a variety of reagents and steps. In some embodiments, a polynucleotide encoding the O—RS is provided. In some embodiments, an O—RS derived from a *Methanococcus jannaschii* aminoacyl-tRNA synthetase is provided, for example, a wild-type *Methanococcus jannaschii* tyrosyl-tRNA synthetase can be provided. In some embodiments, the providing step includes providing an O—RS comprising an amino acid sequence selected from SEQ ID NOs: 7-10, and conservative variants thereof.

In some embodiments of these methods, the providing a translation system step comprises mutating an amino acid binding pocket of a wild-type aminoacyl-tRNA synthetase by site-directed mutagenesis, and selecting a resulting O—RS that preferentially aminoacylates the O-tRNA with the unnatural amino acid. The selecting step can comprises positively selecting and negatively selecting for the O—RS from a pool of resulting aminoacyl-tRNA synthetase molecules following site-directed mutagenesis. In some embodiments, the providing step furnishes a polynucleotide encoding the O-tRNA, e.g., an O-tRNA that is an amber suppressor tRNA, or an O-tRNA that comprises or is encoded by a polynucleotide of SEQ ID NO: 1. In these methods, the providing step can also furnish a nucleic acid comprising an amber selector codon that is utilized by the translation system.

These methods can also be modified to incorporate more than one unnatural amino acid into a protein. In those methods, a second orthogonal translation system is employed in conjunction with the first translation system, where the second system has different amino acid and selector codon specificities. For example, the providing step can include providing a second O—RS and a second O-tRNA, where the second O—RS preferentially aminoacylates the second O-tRNA with a second unnatural amino acid that is different from the first unnatural amino acid, and where the second O-tRNA recognizes a selector codon in the nucleic acid that is different from the selector codon recognized by the first O-tRNA.

The methods for producing a protein with an unnatural amino acid are conducted in the context of a host cell. In these embodiments, the host cell comprises the unnatural amino acid, the O—RS, the O-tRNA and the nucleic acid, and where culturing the host cell results in incorporating the unnatural amino acid. In some embodiments, the providing step comprises providing a eubacterial host cell (e.g., *E. coli*). In some embodiments, the providing step includes providing a host cell that contains a polynucleotide encoding the O—RS. For example, the polynucleotide encoding the O—RS can comprise a nucleotide sequence of SEQ ID NO: 11. In some embodiments, the step of providing a translation system is accomplished by providing a cell extract.

The invention also provides a variety of compositions, including nucleic acids and proteins. The nature of the composition is not particularly limited, other than the composition comprises the specified nucleic acid or protein. The compositions of the invention can comprise any number of additional components of any nature.

For example, the invention provides compositions comprising O—RS polypeptides, where the polypeptides comprise SEQ ID NO: 7-10, 12, 14, 16, 18, 20, 22, 24, 26, 28, 30, 32, 34, 36, 38, 40, 42, 44, 46, 50, 52-55, 57, 59-63, or a conservative variant thereof, where the conservative variant polypeptide aminoacylates a cognate orthogonal tRNA (O-tRNA) with an unnatural amino acid with an efficiency that is at least 50% of the efficiency observed for a translation system comprising the O-tRNA, the unnatural amino acid, and an aminoacyl-tRNA synthetase comprising an amino acid sequence selected from SEQ ID NOs: 7-10, 12, 14, 16, 18, 20, 22, 24, 26, 28, 30, 32, 34, 36, 38, 40, 42, 44, 46, 50, 52-55, 57 and 59-63. The invention also provides polynucleotides that encode any of these polypeptides above. In some embodiments, these polynucleotides can comprise SEQ ID NO: 11, 13, 15, 17, 19, 21, 23, 25, 27, 29, 31, 33, 35, 37, 39, 41, 43, 45, 47, 51, 56 and 58. In some embodiments, the polypeptides are in a cell.

The invention also provides polynucleotide compositions comprising a nucleotide sequence of SEQ ID NO: 11, 13, 15, 17, 19, 21, 23, 25, 27, 29, 31, 33, 35, 37, 39, 41, 43, 45, 47, 51, 56 or 58. In some embodiments, the invention provides vectors comprising the polynucleotides, e.g., expression vectors. In some embodiments, the invention provides cells comprising a vector described above.

DEFINITIONS

Before describing the invention in detail, it is to be understood that this invention is not limited to particular biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes combinations of two or more cells; reference to "a polynucleotide" includes, as a practical matter, many copies of that polynucleotide.

Unless defined herein and below in the reminder of the specification, all technical and scientific terms used herein have the same meaning as commonly understood by one of ordinary skill in the art to which the invention pertains.

Orthogonal: As used herein, the term "orthogonal" refers to a molecule (e.g., an orthogonal tRNA (O-tRNA) and/or an orthogonal aminoacyl-tRNA synthetase (O—RS)) that functions with endogenous components of a cell with reduced efficiency as compared to a corresponding molecule that is endogenous to the cell or translation system, or that fails to function with endogenous components of the cell. In the context of tRNAs and aminoacyl-tRNA synthetases, orthogonal refers to an inability or reduced efficiency, e.g., less than 20% efficiency, less than 10% efficiency, less than 5% efficiency, or less than 1% efficiency, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA. The orthogonal molecule lacks a functionally normal endogenous complementary molecule in the cell. For example, an orthogonal tRNA in a cell is aminoacylated by any endogenous RS of the cell with reduced or even zero efficiency, when compared to aminoacylation of an endogenous tRNA by the endogenous RS. In another example, an orthogonal RS aminoacylates any endogenous tRNA a cell of interest with reduced or even zero efficiency, as compared to aminoacylation of the endogenous tRNA by an endogenous RS. A second orthogonal molecule can be introduced into the cell that functions with the first orthogonal molecule. For example, an orthogonal tRNA/RS pair includes introduced complementary components that function together in the cell with an efficiency (e.g., 45% efficiency, 50% efficiency, 60% efficiency, 70% efficiency, 75% efficiency, 80% efficiency, 90% efficiency, 95% efficiency, or 99% or more efficiency) as compared to that of a control, e.g., a corresponding tRNA/RS endogenous pair, or an active orthogonal pair (e.g., a tyrosyl orthogonal tRNA/RS pair).

Orthogonal tyrosyl-tRNA: As used herein, an orthogonal tyrosyl-tRNA (tyrosyl-O-tRNA) is a tRNA that is orthogonal to a translation system of interest, where the tRNA is: (1) identical or substantially similar to a naturally occurring leucyl or tyrosyl-tRNA, (2) derived from a naturally occurring leucyl or tyrosyl-tRNA by natural or artificial mutagenesis, (3) derived by any process that takes a sequence of a wild-type or mutant leucyl or tyrosyl-tRNA sequence of (1) or (2) into account, (4) homologous to a wild-type or mutant leucyl or tyrosyl-tRNA; (5) homologous to any example tRNA that is designated as a substrate for a leucyl or tyrosyl-tRNA synthetase in Table 5, or (6) a conservative variant of any example tRNA that is designated as a substrate for a leucyl or tyrosyl-tRNA synthetase in Table 5. The leucyl or tyrosyl-tRNA can exist charged with an amino acid, or in an uncharged state. It is also to be understood that a "tyrosyl-O-tRNA" or "leucyl-O-tRNA" optionally is charged (aminoacylated) by a cognate synthetase with an amino acid other than tyrosine or leucine, respectively, e.g., with an unnatural amino acid. Indeed, it will be appreciated that a leucyl or tyrosyl-O-tRNA of the invention is advantageously used to insert essentially any amino acid, whether natural or artificial, into a growing polypeptide, during translation, in response to a selector codon.

Orthogonal tyrosyl amino acid synthetase: As used herein, an orthogonal tyrosyl amino acid synthetase (tyrosyl-O—RS) is an enzyme that preferentially aminoacylates the tyrosyl-O-tRNA with an amino acid in a translation system of interest. The amino acid that the tyrosyl-O—RS loads onto the tyrosyl-O-tRNA can be any amino acid, whether natural, unnatural or artificial, and is not limited herein. The synthetase is optionally the same as or homologous to a naturally occurring tyrosyl amino acid synthetase, or the same as or homologous to a synthetase designated as an O—RS in Table 5. For example, the O—RS can be a conservative variant of a tyrosyl-O—RS of Table 5, and/or can be at least 50%, 60%, 70%, 80%, 90%, 95%, 98%, 99% or more identical in sequence to an O—RS of Table 5.

Similarly, an orthogonal leucyl amino acid synthetase (leucyl-O—RS) is an enzyme that preferentially aminoacylates the leucyl-O-tRNA with an amino acid in a translation system of interest. The amino acid that the leucyl-O—RS loads onto the leucyl-O-tRNA can be any amino acid, whether natural, unnatural or artificial, and is not limited herein. The synthetase is optionally the same as or homologous to a naturally occurring leucyl amino acid synthetase, or the same as or homologous to a synthetase designated as an O—RS in Table 5. For example, the O—RS can be a conservative variant of a leucyl-O—RS of Table 5, and/or can be at least 50%, 60%, 70%, 80%, 90%, 95%, 98%, 99% or more identical in sequence to an O—RS of Table 5.

Cognate: The term "cognate" refers to components that function together, e.g., an orthogonal tRNA and an orthogonal aminoacyl-tRNA synthetase. The components can also be referred to as being complementary.

Preferentially aminoacylates: As used herein in reference to orthogonal translation systems, an O—RS "preferentially aminoacylates" a cognate O-tRNA when the O—RS charges the O-tRNA with an amino acid more efficiently than it charges any endogenous tRNA in an expression system. That is, when the O-tRNA and any given endogenous tRNA are present in a translation system in approximately equal molar ratios, the O—RS will charge the O-tRNA more frequently than it will charge the endogenous tRNA. Preferably, the relative ratio of O-tRNA charged by the O—RS to endogenous tRNA charged by the O—RS is high, preferably resulting in the O—RS charging the O-tRNA exclusively, or nearly exclusively, when the O-tRNA and endogenous tRNA are present in equal molar concentrations in the translation system. The relative ratio between O-tRNA and endogenous tRNA that is charged by the O—RS, when the O-tRNA and O—RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

The O—RS "preferentially aminoacylates an O-tRNA with an unnatural amino acid" when (a) the O—RS preferentially aminoacylates the O-tRNA compared to an endogenous tRNA, and (b) where that aminoacylation is specific for the unnatural amino acid, as compared to aminoacylation of the O-tRNA by the O—RS with any natural amino acid. That is, when the unnatural and natural amino acids are present in equal molar amounts in a translation system comprising the O—RS and O-tRNA, the O—RS will load the O-tRNA with the unnatural amino acid more frequently than with the natural amino acid. Preferably, the relative ratio of O-tRNA charged with the unnatural amino acid to O-tRNA charged with the natural amino acid is high. More preferably, O—RS charges the O-tRNA exclusively, or nearly exclusively, with the unnatural amino acid. The relative ratio between charging of the O-tRNA with the unnatural amino acid and charging of the O-tRNA with the natural amino acid, when both the natural and unnatural amino acids are present in the translation system in equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

Selector codon: The term "selector codon" refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, at this site in the polypeptide. Selector codons can include, e.g., nonsense codons, such as, stop codons, e.g., amber, ochre, and opal codons; four or more base codons; rare codons; codons derived from natural or unnatural base pairs and/or the like.

Suppressor tRNA: A suppressor tRNA is a tRNA that alters the reading of a messenger RNA (mRNA) in a given translation system, e.g., by providing a mechanism for incorporating an amino acid into a polypeptide chain in response to a selector codon. For example, a suppressor tRNA can read through, e.g., a stop codon (e.g., an amber, ocher or opal codon), a four base codon, a rare codon, etc.

Suppression activity: As used herein, the term "suppression activity" refers, in general, to the ability of a tRNA (e.g., a suppressor tRNA) to allow translational read-through of a codon (e.g. a selector codon that is an amber codon or a 4-or-more base codon) that would otherwise result in the termination of translation or mistranslation (e.g., frame-shifting). Suppression activity of a suppressor tRNA can be expressed as a percentage of translational read-through activity observed compared to a second suppressor TRNA, or as compared to a control system, e.g., a control system lacking an O—RS.

The present invention provides various methods by which suppression activity can be quantitated. Percent suppression of a particular O-tRNA and O—RS against a selector codon (e.g., an amber codon) of interest refers to the percentage of activity of a given expressed test marker (e.g., LacZ), that includes a selector codon, in a nucleic acid encoding the expressed test marker, in a translation system of interest, where the translation system of interest includes an O—RS and an O-tRNA, as compared to a positive control construct, where the positive control lacks the O-tRNA, the O—RS and the selector codon. Thus, for example, if an active positive control marker construct that lacks a selector codon has an observed activity of X in a given translation system, in units relevant to the marker assay at issue, then percent suppression of a test construct comprising the selector codon is the percentage of X that the test marker construct displays under essentially the same environmental conditions as the positive control marker was expressed under, except that the test marker construct is expressed in a translation system that also includes the O-tRNA and the O—RS. Typically, the translation system expressing the test marker also includes an amino acid that is recognized by the O—RS and O-tRNA. Optionally, the percent suppression measurement can be refined by comparison of the test marker to a "background" or "negative" control marker construct, which includes the same selector codon as the test marker, but in a system that does not include the O-tRNA, O—RS and/or relevant amino acid recognized by the O-tRNA and/or O—RS. This negative control is useful in normalizing percent suppression measurements to account for background signal effects from the marker in the translation system of interest.

Suppression efficiency can be determined by any of a number of assays known in the art. For example, a β-galactosidase reporter assay can be used, e.g., a derivatived lacZ plasmid (where the construct has a selector codon n the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Qalactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

Translation system: The term "translation system" refers to the components that incorporate an amino acid into a growing polypeptide chain (protein). Components of a translation system can include, e.g., ribosomes, tRNAs, synthetases, mRNA and the like. The O-tRNA and/or the O—RSs of the invention can be added to or be part of an in vitro or in vivo translation system, e.g., in a non-eukaryotic cell, e.g., a bacterium (such as *E. coli*), or in a eukaryotic cell, e.g., a yeast cell, a mammalian cell, a plant cell, an algae cell; a fungus cell, an insect cell, and/or the like.

Unnatural amino acid: As used herein, the term "unnatural amino acid" refers to any amino acid, modified amino acid, and/or amino acid analogue, that is not one of the 20 common naturally occurring amino acids or seleno cysteine or pyrrolysine. For example, FIG. 1 provides 17 unnatural amino acids that find use with the invention.

Derived from: As used herein, the term "derived from" refers to a component that is isolated from or made using a specified molecule or organism, or information from the specified molecule or organism. For example, a polypeptide that is derived from a second polypeptide can include an amino acid sequence that is identical or substantially similar to the amino acid sequence of the second polypeptide. In the case of polypeptides, the derived species can be obtained by, for example, naturally occurring mutagenesis, artificial directed mutagenesis or artificial random mutagenesis. The mutagenesis used to derive polypeptides can be intentionally directed or intentionally random, or a mixture of each. The mutagenesis of a polypeptide to create a different polypeptide derived from the first can be a random event (e.g., caused by polymerase infidelity) and the identification of the derived polypeptide can be made by appropriate screening methods, e.g., as discussed herein. Mutagenesis of a polypeptide typically entails manipulation of the polynucleotide that encodes the polypeptide.

Positive selection or screening marker: As used herein, the term "positive selection or screening marker" refers to a marker that, when present, e.g., expressed, activated or the like, results in identification of a cell, which comprises the trait, e.g., a cell with the positive selection marker, from those without the trait.

Negative selection or screening marker: As used herein, the term "negative selection or screening marker" refers to a marker that, when present, e.g., expressed, activated, or the like, allows identification of a cell that does not comprise a selected property or trait (e.g., as compared to a cell that does possess the property or trait).

Reporter: As used herein, the term "reporter" refers to a component that can be used to identify and/or select target components of a system of interest. For example, a reporter can include a protein, e.g., an enzyme, that confers antibiotic resistance or sensitivity (e.g., β-lactamase, chloramphenicol acetyltransferase (CAT), and the like), a fluorescent screening marker (e.g., green fluorescent protein (e.g., (GFP), YFP, EGFP, RFP, etc.), a luminescent marker (e.g., a firefly luciferase protein), an affinity based screening marker, or positive or negative selectable marker genes such as lacZ, β-gal/lacZ (β-galactosidase), ADH (alcohol dehydrogenase), his3, ura3, leu2, lys2, or the like.

Eukaryote: As used herein, the term "eukaryote" refers to organisms belonging to the Kingdom Eucarya. Eukaryotes are generally distinguishable from prokaryotes by their typically multicellular organization (but not exclusively multicellular, for example, yeast), the presence of a membrane-bound nucleus and other membrane-bound organelles, linear genetic material (i.e., linear chromosomes), the absence of operons, the presence of introns, message capping and poly-A mRNA, and other biochemical characteristics, such as a distinguishing ribosomal structure. Eukaryotic organisms include, for example, animals (e.g., mammals, insects, reptiles, birds, etc.), ciliates, plants (e.g., monocots, dicots, algae, etc.), fungi, yeasts, flagellates, microsporidia, protists, etc.

Prokaryote: As used herein, the term "prokaryote" refers to organisms belonging to the Kingdom Monera (also termed Procarya). Prokaryotic organisms are generally distinguishable from eukaryotes by their unicellular organization, asexual reproduction by budding or fission, the lack of a membrane-bound nucleus or other membrane-bound organelles, a circular chromosome, the presence of operons, the absence of introns, message capping and poly-A mRNA, and other biochemical characteristics, such as a distinguishing ribosomal structure. The Prokarya include subkingdoms Eubacteria and Archaea (sometimes termed "Archaebacteria"). Cyanobacteria (the blue green algae) and mycoplasma are sometimes given separate classifications under the Kingdom Monera.

Bacteria: As used herein, the terms "bacteria" and "eubacteria" refer to prokaryotic organisms that are distinguishable from Archaea. Similarly, Archaea refers to prokaryotes that are distinguishable from eubacteria. Eubacteria and Archaea can be distinguished by a number morphological and biochemical criteria. For example, differences in ribosomal RNA sequences, RNA polymerase structure, the presence or absence of introns, antibiotic sensitivity, the presence or absence of cell wall peptidoglycans and other cell wall components, the branched versus unbranched structures of membrane lipids, and the presence/absence of histones and histone-like proteins are used to assign an organism to Eubacteria or Archaea.

Examples of Eubacteria include *Escherichia coli, Thermus thermophilus* and *Bacillus stearothermophilus*. Example of Archaea include *Methanococcus jannaschii* (Mj), *Methanosarcina mazei* (Mm), *Methanobacterium thermoautotrophicum* (Mt), *Methanococcus maripaludis, Methanopyrus kandleri, Halobacterium* such as *Haloferax volcanii* and *Halobacterium* species NRC-1, *Archaeoglobus fulgidus* (Af), *Pyrococcus furiosus* (Pf), *Pyrococcus horikoshii* (Ph), *Pyrobaculum aerophilum, Pyrococcus abyssi, Sulfolobus solfataricus* (Ss), *Sulfolobus tokodaii, Aeuropyrum pernix* (Ap), *Thernoplasma acidophilum* and *Thermoplasma volcanium.*

Conservative variant: As used herein, the term "conservative variant," in the context of a translation component, refers to a translation component, e.g., a conservative variant O-tRNA or a conservative variant O—RS, that functionally performs similar to a base component that the conservative variant is similar to, e.g., an O-tRNA or O—RS, having variations in the sequence as compared to a reference O-tRNA or O—RS. For example, an O—RS, or a conservative variant of that O—RS, will aminoacylate a cognate O-tRNA with an unnatural amino acid, e.g., an amino acid comprising an N-acetylgalactosamine moiety. In this example, the O—RS and the conservative variant O—RS do not have the same amino acid sequences. The conservative variant can have, e.g., one variation, two variations, three variations, four variations, or five or more variations in sequence, as long as the conservative variant is still complementary to the corresponding O-tRNA or O—RS.

In some embodiments, a conservative variant O—RS comprises one or more conservative amino acid substitutions compared to the O—RS from which it was derived. In some embodiments, a conservative variant O—RS comprises one or more conservative amino acid substitutions compared to the O—RS from which it was derived, and furthermore, retains O—RS biological activity; for example, a conservative variant O—RS that retains at least 10% of the biological activity of the parent O—RS molecule from which it was derived, or alternatively, at least 20%, at least 30%, or at least 40%. In some preferred embodiments, the conservative variant O—RS retains at least 50% of the biological activity of the parent O—RS molecule from which it was derived. The conservative amino acid substitutions of a conservative variant O—RS can occur in any domain of the O—RS, including the amino acid binding pocket.

Selection or screening agent: As used herein, the term "selection or screening agent" refers to an agent that, when present, allows for selection/screening of certain components from a population. For example, a selection or screening agent can be, but is not limited to, e.g., a nutrient, an antibiotic, a wavelength of light, an antibody, an expressed polynucleotide, or the like. The selection agent can be varied, e.g., by concentration, intensity, etc.

In response to: As used herein, the term "in response to" refers to the process in which an O-tRNA of the invention recognizes a selector codon and mediates the incorporation of the unnatural amino acid, which is coupled to the tRNA, into the growing polypeptide chain.

Encode: As used herein, the term "encode" refers to any process whereby the information in a polymeric macromolecule or sequence string is used to direct the production of a second molecule or sequence string that is different from the first molecule or sequence string. As used herein, the term is used broadly, and can have a variety of applications. In some aspects, the term "encode" describes the process of semi-conservative DNA replication, where one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (e.g., by the process of transcription incorporating a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

BRIEF DESCRIPTION OF THE FIGURES

FIG. 6A provides the crystal structure of the editing site of *Thermus thermophilus* leucyl-tRNA synthetase in complex with 2'-(L-norvalyl)-amino-2'-deoxyadenosine mimicking the charged tRNA 3'-terminus. T252 and V340 are shown as sticks. FIG. 6B provides SDS-PAGE analysis of Ni-NTA purified hSOD bearing dansylalanine at position 33 using leucyl-tRNA synthetase clone B8 and the two mutants V338A and T252A. The upper gel is a photograph of a Coomassie stain. The lower gel is a fluorescence image with excitation at 302 nm and emission detection at 520 nm. L=molecular weight ladder; UAA=unnatural amino acid.

FIG. 7A provides the crystal structure of *Thermus thermophilus* leucyl-tRNA synthetase (Cusack et al., *EMBO J.,* 19(10):2351-2361 [2000]). The synthetic domain, editing domain, amino acids randomized in the homologous *E. coli* synthetase, and amino acids changed by error prone PCR present in the G2-6 clone are all indicated. FIG. 7B provides a Coomassie stained SDS-PAGE analysis of expressed hSOD bearing o-nitrobenzylserine at position 33 using *E. coli* leucyl-tRNA mutant synthetase clone 3H11 designed for incorporation of o-nitrobenzylcysteine and mutant *E. coli* leucyl-tRNA synthetase clone G2-6 evolved for efficient suppression with o-nitrobenzylserine. L=molecular weight ladder; UAA=unnatural amino acid (oNBS).

FIG. 18A shows a profile using a 1:1 mixture of 3 and 2 in MeOH. FIG. 18B shows a profile using 3 in PBS (pH=7.4, reaction time: 1 week). FIG. 18C shows a profile using 3 in PBS (pH=3.9, reaction time: 4 days). FIG. 18D shows a profile using 3 in diluted $H_2SO_4$ solution (pH=1.9, reaction time: 12 hrs). All reactions were done at room temperature with constant stirring.

DETAILED DESCRIPTION OF THE INVENTION

Figure 1:
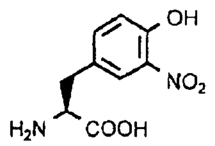
FIG. 1 provides the chemical structures of various unnatural amino acids.
Figure 1:
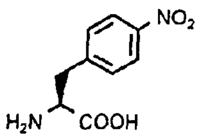
Figure 1:
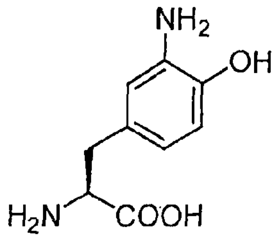
Figure 1:
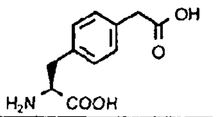
Figure 1:
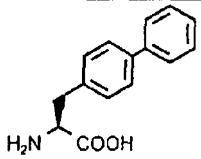
Figure 1:
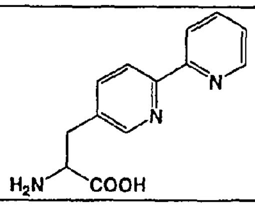
Figure 1:
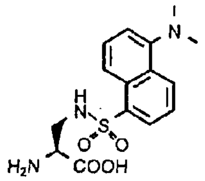
Figure 1:
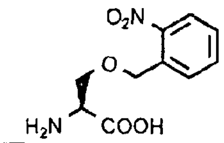
Figure 1:
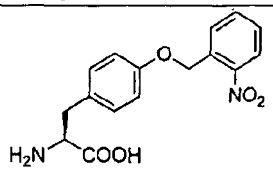
Figure 1:
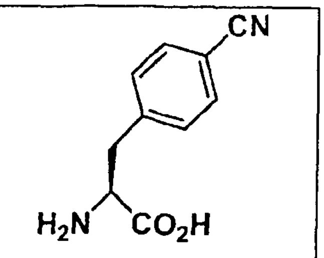
Figure 1:
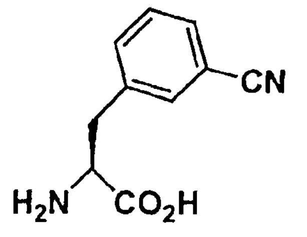
Figure 1:
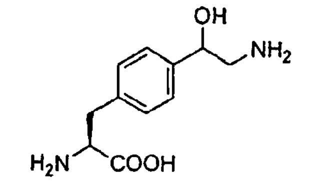
Figure 1:
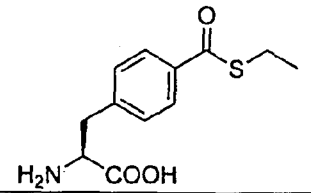
Figure 1:
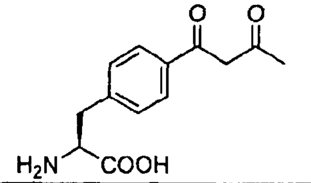
Figure 1:
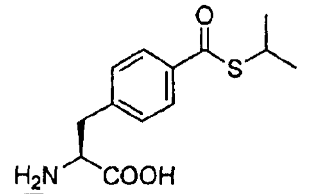
Figure 1:
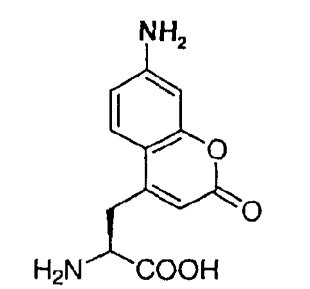
Figure 1:
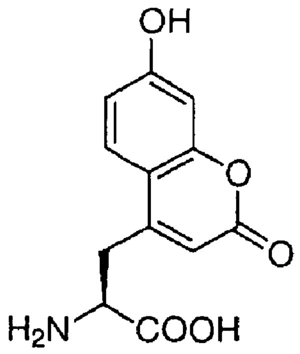

The invention provides solutions to the inherent limitations of using a translation system confined by the 20 naturally occurring amino acids. The solutions include the programmed, site-specific biosynthetic incorporation of unnatural amino acids with novel properties into proteins using orthogonal translation systems. We describe herein novel compositions (e.g., novel aminoacyl-tRNA synthetases) and novel methods for the highly efficient and specific genetic incorporation of a variety of unnatural amino acids into proteins in response to a selector codon (e.g., the amber nonsense codon, TAG).

In some cases, the unnatural amino acid side chains can then be specifically and regioselectively modified. Because of the unique reaction chemistries of these unnatural amino acid substituents, proteins into which they are incorporated can be modified with extremely high selectivity. In some cases, the unnatural amino acid reactive group has the advantage of being completely alien to in vivo systems, thereby improving reaction selectivity. In some aspects, the modification reactions can be conducted using relatively mild reaction conditions that permit both in vitro and in vivo conjugation reactions involving proteins, and preserving protein biological activity. The nature of the material that is conjugated to an unnatural amino acid in a protein is not particularly limited, and can be any desired entity, e.g., dyes, fluorophores, crosslinking agents, saccharide derivatives, polymers (e.g., derivatives of polyethylene glycol), photocrosslinkers, cytotoxic compounds, affinity labels, derivatives of biotin, resins, beads, a second protein or polypeptide (or more), polynucleotide(s) (e.g., DNA, RNA, etc.), metal chelators, cofactors, fatty acids, carbohydrates, and the like.

In other aspects, the incorporated unnatural amino acid imparts novel biological properties to the protein into which it is incorporated. For example, the unnatural amino acid can be a fluorescent amino acid, a photocaged or photoactivatable amino acid, an amino acid that can participate in a FRET pair as a donor or acceptor, a redox-active amino acid, a metal-chelating amino acid, etc.

In some aspects, to demonstrate (but not to limit) the present invention, the disclosure herein demonstrates that the unnatural amino acid moiety can be incorporated into a model protein. It is not intended that the incorporation of the unnatural amino acid be limited to such a model protein. From the present disclosure, it will be clear that the incorporation of an unnatural amino acid into any given protein of interest is advantageous for a wide variety of proteins for use in therapeutic and research purposes.

We have evolved novel orthogonal tRNA/aminoacyl-tRNA synthetase pairs that function in eubacteria and yeast to site specifically incorporate unnatural amino acids (e.g., the unnatural amino acids provided in FIG. 1) in response to selector codons. Briefly, we have identified novel mutants of the *Methanococcus janaschii* tyrosyl-tRNA synthetase and the *Escherichia coli* leucyl-tRNA synthetase that selectively charge a suppressor tRNA with an unnatural amino acid in either *E. coli* host cells or yeast host cells, respectively.

These evolved tRNA-synthetase pairs can be used to site-specifically incorporate the respective unnatural amino acid into a protein. The incorporation of the unnatural amino acid into the protein can be programmed to occur at any desired position by engineering the polynucleotide encoding the protein of interest to contain a selector codon that signals the incorporation of the unnatural amino acid.

Orthogonal tRNA/Aminoacyl-tRNA Synthetase Technology

An understanding of the novel compositions and methods of the present invention is facilitated by an understanding of the activities associated with orthogonal tRNA and orthogonal aminoacyl-tRNA synthetase pairs. Discussions of orthogonal tRNA and aminoacyl-tRNA synthetase technologies can be found, for example, in International Publications WO 2002/085923, WO 2002/086075, WO 204/09459, WO 2005/019415, WO 2005/007870 and WO 2005/007624. See also, Wang and Schultz "Expanding the Genetic Code," *Angewandte Chemie Int. Ed.,* 44(1):34-66 (2005), the content of which is incorporated by reference in its entirety.

In order to add additional reactive unnatural amino acids to the genetic code, new orthogonal pairs comprising an aminoacyl-tRNA synthetase and a suitable tRNA are needed that can function efficiently in the host translational machinery, but that are "orthogonal" to the translation system at issue, meaning that it functions independently of the synthetases and tRNAs endogenous to the translation system. Desired characteristics of the orthologous pair include tRNA that decode or recognize only a specific codon, e.g., a selector codon, that is not decoded by any endogenous tRNA, and aminoacyl-tRNA synthetases that preferentially aminoacylate (or "charge") its cognate tRNA with only one specific unnatural amino acid. The O-tRNA is also not typically aminoacylated by endogenous synthetases. For example, in *E. coli*, an orthogonal pair will include an aminoacyl-tRNA synthetase that does not cross-react with any of the endogenous tRNA, e.g., which there are 40 in *E. coli*, and an orthogonal tRNA that is not aminoacylated by any of the endogenous synthetases, e.g., of which there are 21 in *E. coli.*

The invention described herein provides orthogonal pairs for the genetic encoding and incorporation of unnatural amino acids into proteins in a eubacteria, e.g., an *E. coli*, or in yeast, where the orthogonal components do not cross-react with endogenous *E. coli* or yeast components of the translational machinery of the host cell, but recognize the desired unnatural amino acid and incorporate it into proteins in response to the selector codon (e.g., an amber nonsense codon, TAG). The orthogonal components provided by the invention include orthogonal aminoacyl-tRNA synthetases derived from *Methanococcus jannaschii* tyrosyl tRNA-synthetase, and the mutant tyrosyl $tRNA_{CUA}$ amber suppressor, which function as an orthogonal pair in a eubacterial host cell. The invention also provides orthogonal components derived from *E. coli* leucyl-tRNA-synthetase, and a mutant *E. coli* leucyl $tRNA_{CUA}$ amber suppressor, which function as an orthogonal pair in a yeast host cell. In these systems, the mutant aminoacyl-tRNA synthetases aminoacylate the suppressor tRNA with its respective unnatural amino acid and not with any of the common twenty amino acids.

This invention provides compositions of and methods for identifying and producing additional orthogonal tRNA-aminoacyl-tRNA synthetase pairs, e.g., O-tRNA/O—RS pairs that can be used to incorporate an unnatural amino-acid into a protein. An O-tRNA/O—RS pair of the invention is capable of mediating incorporation of an unnatural amino acid, for example, an unnatural amino acid shown in FIG. 1, into a protein that is encoded by a polynucleotide, where the polynucleotide comprises a selector codon that is recognized by the O-tRNA, e.g., in vivo. The anticodon loop of the O-tRNA recognizes the selector codon on an mRNA and incorporates its amino acid, e.g., an unnatural amino acid shown in FIG. 1, at this site in the polypeptide. Generally, an orthogonal aminoacyl-tRNA synthetase of the invention preferentially aminoacylates (or charges) its O-tRNA with only one specific unnatural amino acid.

The ability to incorporate an unnatural amino acid (e.g., an unnatural amino acid provided in FIG. 1) site-specifically into proteins can facilitate the study of proteins, as well as enable the engineering of proteins with novel properties. For example, expression of proteins containing one or more unnatural amino acids can facilitate the study of proteins by specific labeling, alter catalytic function of enzymes, improve biological activity or reduce cross-reactivity to a substrate, crosslink a protein with other proteins, small molecules or biomolecules, reduce or eliminate protein degradation, improve half-life of proteins in vivo (e.g., by pegylation or other modifications of introduced reactive sites), etc.

Orthogonal tRNA/Orthogonal Aminoacyl-tRNA Synthetases and Pairs Thereof

Translation systems that are suitable for making proteins that include one or more unnatural amino acid are generally described in, for example, International Publication Numbers WO 2002/086075, entitled "METHODS AND COMPOSITION FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" and WO 2004/094593, entitled "EXPANDING THE EUKARYOTIC GENETIC CODE;" WO 2005/019415, filed Jul. 7, 2004; WO 2005/007870, filed Jul. 7, 2004 and WO 2005/007624, filed Jul. 7, 2004. Each of these applications is incorporated herein by reference in its entirety. See also, Wang and Schultz "Expanding the Genetic Code," *Angewandte Chemie Int. Ed.*, 44(1): 34-66 (2005), the content of which is incorporated by reference in its entirety. Such translation systems generally comprise cells (which can be non-eukaryotic cells such as *E. coli*, or eukaryotic cells such as yeast) that include an orthogonal tRNA (O-tRNA), an orthogonal aminoacyl tRNA synthetase (O—RS), and an unnatural amino acid, where the O—RS aminoacylates the O-tRNA with the unnatural amino acid. An orthogonal pair of the invention includes an O-tRNA, e.g., a suppressor tRNA, a frameshift tRNA, or the like, and an O—RS. Individual components are also provided in the invention.

In general, when an orthogonal pair recognizes a selector codon and loads an amino acid in response to the selector codon, the orthogonal pair is said to "suppress" the selector codon. That is, a selector codon that is not recognized by the translation system's (e.g., the cell's) endogenous machinery is not ordinarily translated, which can result in blocking production of a polypeptide that would otherwise be translated from the nucleic acid. An O-tRNA of the invention recognizes a selector codon and includes at least about, e.g., a 45%, a 50%, a 60%, a 75%, a 80%, or a 90% or more suppression efficiency in the presence of a cognate synthetase in response to a selector codon as compared to the suppression efficiency of an O-tRNA comprising or encoded by a polynucleotide sequence as set forth in the sequence listing herein. The O—RS aminoacylates the O-tRNA with an unnatural amino acid of interest. The cell uses the O-tRNA/O—RS pair to incorporate the unnatural amino acid into a growing polypeptide chain, e.g., via a nucleic acid that comprises a polynucleotide that encodes a polypeptide of interest, where the polynucleotide comprises a selector codon that is recognized by the O-tRNA. In certain desirable aspects, the cell can include an additional O-tRNA/O—RS pair, where the additional O-tRNA is loaded by the additional O—RS with a different unnatural amino acid. For example, one of the O-tRNAs can recognize a four base codon and the other can recognize a stop codon. Alternately, multiple different stop codons or multiple different four base codons can specifically recognize different selector codons.

In certain embodiments of the invention, a cell such as an *E. coli* cell or a yeast cell that includes an orthogonal tRNA (O-tRNA), an orthogonal aminoacyl-tRNA synthetase (O—RS), an unnatural amino acid and a nucleic acid that comprises a polynucleotide that encodes a polypeptide of interest, where the polynucleotide comprises the selector codon that is recognized by the O-tRNA. The translation system can also be a cell-free system, e.g., any of a variety of commercially available "in vitro" transcription/translation systems in combination with an O-tRNA/ORS pair and an unnatural amino acid as described herein.

In one embodiment, the suppression efficiency of the O—RS and the O-tRNA together is about, e.g., 5 fold, 10 fold, 15 fold, 20 fold, or 25 fold or more greater than the suppression efficiency of the O-tRNA lacking the O—RS. In some aspect, the suppression efficiency of the O—RS and the O-tRNA together is at least about, e.g., 35%, 40%, 45%, 50%, 60%, 75%, 80%, or 90% or more of the suppression efficiency of an orthogonal synthetase pair as set forth in the sequence listings herein.

As noted, the invention optionally includes multiple O-tRNA/O—RS pairs in a cell or other translation system, which allows incorporation of more than one unnatural amino acid. For example, the cell can further include an additional different O-tRNA/O—RS pair and a second unnatural amino acid, where this additional O-tRNA recognizes a second selector codon and this additional O—RS preferentially aminoacylates the O-tRNA with the second unnatural amino acid. For example, a cell that includes an O-tRNA/O—RS pair (where the O-tRNA recognizes, e.g., an amber selector codon), can further comprise a second orthogonal pair, where the second O-tRNA recognizes a different selector codon, e.g., an opal codon, a four-base codon, or the like. Desirably, the different orthogonal pairs are derived from different sources, which can facilitate recognition of different selector codons.

The O-tRNA and/or the O—RS can be naturally occurring or can be, e.g., derived by mutation of a naturally occurring tRNA and/or RS, e.g., by generating libraries of tRNAs and/or libraries of RSs, from any of a variety of organisms and/or by using any of a variety of available mutation strategies. For example, one strategy for producing an orthogonal tRNA/aminoacyl-tRNA synthetase pair involves importing a heterologous (to the host cell) tRNA/synthetase pair from, e.g., a source other than the host cell, or multiple sources, into the host cell. The properties of the heterologous synthetase candidate include, e.g., that it does not charge any host cell tRNA, and the properties of the heterologous tRNA candidate include, e.g., that it is not aminoacylated by any host cell synthetase. In addition, the heterologous tRNA is orthogonal to all host cell synthetases.

A second strategy for generating an orthogonal pair involves generating mutant libraries from which to screen and/or select an O-tRNA or O—RS. These strategies can also be combined.

Orthogonal tRNA (O-tRNA)

An orthogonal tRNA (O-tRNA) of the invention desirably mediates incorporation of an unnatural amino acid into a protein that is encoded by a polynucleotide that comprises a selector codon that is recognized by the O-tRNA, e.g., in vivo or in vitro. In certain embodiments, an O-tRNA of the invention includes at least about, e.g., a 45%, a 50%, a 60%, a 75%, a 80%, or a 90% or more suppression efficiency in the presence of a cognate synthetase in response to a selector codon as compared to an O-tRNA comprising or encoded by a polynucleotide sequence as set forth in the O-tRNA sequences in the sequence listing herein.

Suppression efficiency can be determined by any of a number of assays known in the art. For example, a β-galactosidase reporter assay can be used, e.g., a derivatized lacZ plasmid (where the construct has a selector codon n the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

Examples of O-tRNAs of the invention are set forth in the sequence listing herein. See also, the tables, examples and figures herein for sequences of exemplary O-tRNA and O—RS molecules. See also, the section entitled "Nucleic Acid and Polypeptide Sequence and Variants" herein. In an RNA molecule, such as an O—RS mRNA, or O-tRNA molecule, Thymine (T) is replace with Uracil (U) relative to a given sequence (or vice versa for a coding DNA), or complement thereof. Additional modifications to the bases can also be present.

The invention also includes conservative variations of O-tRNAs corresponding to particular O-tRNAs herein. For example, conservative variations of O-tRNA include those molecules that function like the particular O-tRNAs, e.g., as in the sequence listing herein and that maintain the tRNA L-shaped structure by virtue of appropriate self-complementarity, but that do not have a sequence identical to those, e.g., in the sequence listing, figures or examples herein (and, desirably, are other than wild type tRNA molecules). See also, the section herein entitled "Nucleic acids and Polypeptides Sequence and Variants."

The composition comprising an O-tRNA can further include an orthogonal aminoacyl-tRNA synthetase (O—RS), where the O—RS preferentially aminoacylates the O-tRNA with an unnatural amino acid. In certain embodiments, a composition including an O-tRNA can further include a translation system (e.g., in vitro or in vivo). A nucleic acid that comprises a polynucleotide that encodes a polypeptide of interest, where the polynucleotide comprises a selector codon that is recognized by the O-tRNA, or a combination of one or more of these can also be present in the cell. See also, the section herein entitled "Orthogonal aminoacyl-tRNA synthetases."

Methods of producing an orthogonal tRNA (O-tRNA) are also a feature of the invention. An O-tRNA produced by the method is also a feature of the invention. In certain embodiments of the invention, the O-tRNAs can be produced by generating a library of mutants. The library of mutant tRNAs can be generated using various mutagenesis techniques known in the art. For example, the mutant tRNAs can be generated by site-specific mutations, random point mutations, homologous recombination, DNA shuffling or other recursive mutagenesis methods, chimeric construction or any combination thereof, e.g., of the example O-tRNA of Table 5.

Additional mutations can be introduced at a specific position(s), e.g., at a nonconservative position(s), or at a conservative position, at a randomized position(s), or a combination of both in a desired loop or region of a tRNA, e.g., an anticodon loop, the acceptor stem, D arm or loop, variable loop, TPC arm or loop, other regions of the tRNA molecule, or a combination thereof. Typically, mutations in a tRNA include mutating the anticodon loop of each member of the library of mutant tRNAs to allow recognition of a selector codon. The method can further include adding additional sequences to the O-tRNA. Typically, an O-tRNA possesses an improvement of orthogonality for a desired organism compared to the starting material, e.g., the plurality of tRNA sequences, while preserving its affinity towards a desired RS.

The methods optionally include analyzing the similarity (and/or inferred homology) of sequences of tRNAs and/or aminoacyl-tRNA synthetases to determine potential candidates for an O-tRNA, O—RS and/or pairs thereof, that appear to be orthogonal for a specific organism. Computer programs known in the art and described herein can be used for the analysis, e.g., BLAST and pileup programs can be used. In one example, to choose potential orthogonal translational components for use in *E. coli*, a synthetase and/or a tRNA is chosen that does not display close sequence similarity to eubacterial organisms.

Typically, an O-tRNA is obtained by subjecting to, e.g., negative selection, a population of cells of a first species, where the cells comprise a member of the plurality of potential O-tRNAs. The negative selection eliminates cells that comprise a member of the library of potential O-tRNAs that is aminoacylated by an aminoacyl-tRNA synthetase (RS) that is endogenous to the cell. This provides a pool of tRNAs that are orthogonal to the cell of the first species.

In certain embodiments, in the negative selection, a selector codon(s) is introduced into a polynucleotide that encodes a negative selection marker, e.g., an enzyme that confers antibiotic resistance, e.g., β-lactamase, an enzyme that confers a detectable product, e.g., β-galactosidase, chloramphenicol acetyltransferase (CAT), e.g., a toxic product, such as barnase, at a nonessential position (e.g., still producing a functional barnase), etc. Screening/selection is optionally done by growing the population of cells in the presence of a selective agent (e.g., an antibiotic, such as ampicillin). In one embodiment, the concentration of the selection agent is varied.

For example, to measure the activity of suppressor tRNAs, a selection system is used that is based on the in vivo suppression of selector codon, e.g., nonsense (e.g., stop) or frameshift mutations introduced into a polynucleotide that encodes a negative selection marker, e.g., a gene for β-lactamase (bla). For example, polynucleotide variants, e.g., bla variants, with a selector codon at a certain position (e.g., A184), are constructed. Cells, e.g., bacteria, are transformed with these polynucleotides. In the case of an orthogonal tRNA, which cannot be efficiently charged by endogenous *E. coli* synthetases, antibiotic resistance, e.g., ampicillin resistance, should be about or less than that for a bacteria transformed with no plasmid. If the tRNA is not orthogonal, or if a heterologous synthetase capable of charging the tRNA is co-expressed in the system, a higher level of antibiotic, e.g., ampicillin, resistance is be observed. Cells, e.g., bacteria, are chosen that are unable to grow on LB agar plates with antibiotic concentrations about equal to cells transformed with no plasmids.

In the case of a toxic product (e.g., ribonuclease or barnase), when a member of the plurality of potential tRNAs is aminoacylated by endogenous host, e.g., *Escherichia coli* synthetases (i.e., it is not orthogonal to the host, e.g., *Escherichia coli* synthetases), the selector codon is suppressed and the toxic polynucleotide product produced leads to cell death. Cells harboring orthogonal tRNAs or non-functional tRNAs survive.

In one embodiment, the pool of tRNAs that are orthogonal to a desired organism are then subjected to a positive selection in which a selector codon is placed in a positive selection marker, e.g., encoded by a drug resistance gene, such a β-lactamase gene. The positive selection is performed on a cell comprising a polynucleotide encoding or comprising a member of the pool of tRNAs that are orthogonal to the cell, a polynucleotide encoding a positive selection marker, and a polynucleotide encoding a cognate RS. In certain embodiments, the second population of cells comprises cells that were not eliminated by the negative selection. The polynucleotides are expressed in the cell and the cell is grown in the presence of a selection agent, e.g., ampicillin. tRNAs are then selected for their ability to be aminoacylated by the coexpressed cognate synthetase and to insert an amino acid in response to this selector codon. Typically, these cells show an enhancement in suppression efficiency compared to cells harboring non-functional tRNA(s), or tRNAs that cannot efficiently be recognized by the synthetase of interest. The cell harboring the non-functional tRNAs or tRNAs that are not efficiently recognized by the synthetase of interest, are sensitive to the antibiotic. Therefore, tRNAs that: (i) are not substrates for endogenous host, e.g., *Escherichia coli*, synthetases; (ii) can be aminoacylated by the synthetase of interest; and (iii) are functional in translation, survive both selections.

Accordingly, the same marker can be either a positive or negative marker, depending on the context in which it is screened. That is, the marker is a positive marker if it is screened for, but a negative marker if screened against.

The stringency of the selection, e.g., the positive selection, the negative selection or both the positive and negative selection, in the above described-methods, optionally includes varying the selection stringency. For example, because barnase is an extremely toxic protein, the stringency of the negative selection can be controlled by introducing different numbers of selector codons into the barnase gene and/or by using an inducible promoter. In another example, the concentration of the selection or screening agent is varied (e.g., ampicillin concentration). In some aspects of the invention, the stringency is varied because the desired activity can be low during early rounds. Thus, less stringent selection criteria are applied in early rounds and more stringent criteria are applied in later rounds of selection. In certain embodiments, the negative selection, the positive selection or both the negative and positive selection can be repeated multiple times. Multiple different negative selection markers, positive selection markers or both negative and positive selection markers can be used. In certain embodiments, the positive and negative selection marker can be the same.

Other types of selections/screening can be used in the invention for producing orthogonal translational components, e.g., an O-tRNA, an O—RS; and an O-tRNA/O—RS pair that loads an unnatural amino acid in response to a selector codon. For example, the negative selection marker, the positive selection marker or both the positive and negative selection markers can include a marker that fluoresces or catalyzes a luminescent reaction in the presence of a suitable reactant. In another embodiment, a product of the marker is detected by fluorescence-activated cell sorting (FACS) or by luminescence. Optionally, the marker includes an affinity based screening marker. See also, Francisco, J. A., et al., (1993) *Production and fluorescence-activated cell sorting of Escherichia coli expressing a functional antibody fragment on the external surface. Proc Natl Acad Sci USA.* 90:10444-8.

Additional methods for producing a recombinant orthogonal tRNA can be found, e.g., in International Application Publications WO 2002/086075, entitled "METHODS AND COMPOSITIONS FOR THE PRODUCTION OF ORTHOGONAL tRNA AMINOACYL-tRNA SYNTHETASE PAIRS;" WO 2004/094593, entitled "EXPANDING THE EUKARYOTIC GENETIC CODE;" and WO 2005/019415, filed Jul. 7, 2004. See also Forster et al., (2003) *Programming peptidomimetic synthetases by translating genetic codes designed de novo PNAS* 100(11):6353-6357; and, Feng et al., (2003), *Expanding tRNA recognition of a TRNA synthetase by a single amino acid change, PNAS* 100 (10): 5676-5681.

Orthogonal Aminoacyl-tRNA Synthetase (O—RS)

An O—RS of the invention preferentially aminoacylates an O-tRNA with an unnatural amino acid, in vitro or in vivo. An O—RS of the invention can be provided to the translation system, e.g., a cell, by a polypeptide that includes an O—RS and/or by a polynucleotide that encodes an O—RS or a portion thereof. For example, an example O—RS comprises an amino acid sequence as set forth in the sequence listing and examples herein, or a conservative variation thereof. In another example, an O—RS, or a portion thereof, is encoded by a polynucleotide sequence that encodes an amino acid comprising sequence in the sequence listing or examples herein, or a complementary polynucleotide sequence thereof. See, e.g., the tables and examples herein for sequences of exemplary O—RS molecules. See also, the section entitled "Nucleic Acid and Polypeptide Sequence and Variants" herein.

Methods for identifying an orthogonal aminoacyl-tRNA synthetase (O—RS), e.g., an O—RS, for use with an O-tRNA, are also a feature of the invention. For example, a method includes subjecting to selection, e.g., positive selection, a population of cells of a first species, where the cells individually comprise: 1) a member of a plurality of aminoacyl-tRNA synthetases (RSs), (e.g., the plurality of RSs can include mutant RSs, RSs derived from a species other than the first species or both mutant RSs and RSs derived from a species other than the first species); 2) the orthogonal tRNA (O-tRNA) (e.g., from one or more species); and 3) a polynucleotide that encodes an (e.g., positive) selection marker and comprises at least one selector codon. Cells are selected or screened for those that show an enhancement in suppression efficiency compared to cells lacking or with a reduced amount of the member of the plurality of RSs. Suppression efficiency can be measured by techniques known in the art and as described herein. Cells having an enhancement in suppression efficiency comprise an active RS that aminoacylates the O-tRNA. A level of aminoacylation (in vitro or in vivo) by the active RS of a first set of tRNAs from the first species is compared to the level of aminoacylation (in vitro or in vivo) by the active RS of a second set of tRNAs from the second species. The level of aminoacylation can be determined by a detectable substance (e.g., a labeled unnatural amino acid). The active RS that more efficiently aminoacylates the second set of tRNAs compared to the first set of tRNAs is typically selected, thereby providing an efficient (optimized) orthogonal aminoacyl-tRNA synthetase for use with the O-tRNA. An O—RS, identified by the method, is also a feature of the invention.

Any of a number of assays can be used to determine aminoacylation. These assays can be performed in vitro or in vivo. For example, in vitro aminoacylation assays are described in, e.g., Hoben and Soll (1985) *Methods Enzymol.* 113:55-59. Aminoacylation can also be determined by using a reporter along with orthogonal translation components and detecting the reporter in a cell expressing a polynucleotide comprising at least one selector codon that encodes a protein. See also, WO 2002/085923, entitled "IN VIVO INCORPORATION OF UNNATURAL AMINO ACIDS;" and WO 2004/094593, entitled "EXPANDING THE EUKARYOTIC GENETIC CODE."

Identified O—RS can be further manipulated to alter substrate specificity of the synthetase, so that only a desired unnatural amino acid, but not any of the common 20 amino acids, are charged to the O-tRNA. Methods to generate an orthogonal aminoacyl tRNA synthetase with a substrate specificity for an unnatural amino acid include mutating the synthetase, e.g., at the active site in the synthetase, at the editing mechanism site in the synthetase, at different sites by combining different domains of synthetases, or the like, and applying a selection process. A strategy is used, which is based on the combination of a positive selection followed by a negative selection. In the positive selection, suppression of the selector codon introduced at a nonessential position(s) of a positive marker allows cells to survive under positive selection pressure. In the presence of both natural and unnatural amino acids, survivors thus encode active synthetases charging the orthogonal suppressor tRNA with either a natural or unnatural amino acid. In the negative selection, suppression of a selector codon introduced at a nonessential position(s) of a negative marker removes synthetases with natural amino acid specificities. Survivors of the negative and positive selection encode synthetases that aminoacylate (charge) the orthogonal suppressor tRNA with unnatural amino acids only. These synthetases can then be subjected to further mutagenesis, e.g., DNA shuffling or other recursive mutagenesis methods.

A library of mutant O—RSs can be generated using various mutagenesis techniques known in the art. For example, the mutant RSs can be generated by site-specific mutations, random point mutations, homologous recombination, DNA shuffling or other recursive mutagenesis methods, chimeric construction or any combination thereof. For example, a library of mutant RSs can be produced from two or more other, e.g., smaller, less diverse "sub-libraries." Chimeric libraries of RSs are also included in the invention. It should be noted that libraries of tRNA synthetases from various organism (e.g., microorganisms such as eubacteria or archaebacteria) such as libraries that comprise natural diversity (see, e.g., U.S. Pat. No. 6,238,884 to Short et al; U.S. Pat. No. 5,756,316 to Schallenberger et al; U.S. Pat. No. 5,783,431 to Petersen et al; U.S. Pat. No. 5,824,485 to Thompson et al; U.S. Pat. No. 5,958,672 to Short et al), are optionally constructed and screened for orthogonal pairs.

Once the synthetases are subject to the positive and negative selection/screening strategy, these synthetases can then be subjected to further mutagenesis. For example, a nucleic acid that encodes the O—RS can be isolated; a set of polynucleotides that encode mutated O—RSs (e.g., by random mutagenesis, site-specific mutagenesis, recombination or any combination thereof) can be generated from the nucleic acid; and, these individual steps or a combination of these steps can be repeated until a mutated O—RS is obtained that preferentially aminoacylates the O-tRNA with the unnatural amino acid. In some aspects of the invention, the steps are performed multiple times, e.g., at least two times.

Additional levels of selection/screening stringency can also be used in the methods of the invention, for producing O-tRNA, O—RS, or pairs thereof. The selection or screening stringency can be varied on one or both steps of the method to produce an O—RS. This could include, e.g., varying the amount of selection/screening agent that is used, etc. Additional rounds of positive and/or negative selections can also be performed. Selecting or screening can also comprise one or more of a change in amino acid permeability, a change in translation efficiency, a change in translational fidelity, etc. Typically, the one or more change is based upon a mutation in one or more gene in an organism in which an orthogonal tRNA-tRNA synthetase pair is used to produce protein.

Additional general details for producing O—RS, and altering the substrate specificity of the synthetase can be found in Internal Publication Number WO 2002/086075, entitled "METHODS AND COMPOSITIONS FOR THE PRODUCTION OF ORTHOGONAL tRNA AMINOACYL-tRNA SYNTHETASE PAIRS;" and WO 2004/094593, entitled "EXPANDING THE EUKARYOTIC GENETIC CODE." See also, Wang and Schultz "Expanding the Genetic Code," Angewandte Chemie Int. Ed., 44(1):34-66 (2005), the content of which is incorporated by reference in its entirety.

Source and Host Organisms

The orthogonal translational components (O-tRNA and O—RS) of the invention can be derived from any organism (or a combination of organisms) for use in a host translation system from any other species, with the caveat that the O-tRNA/O—RS components and the host system work in an orthogonal manner. It is not a requirement that the O-tRNA and the O—RS from an orthogonal pair be derived from the same organism. In some aspects, the orthogonal components are derived from Archaea genes (i.e., archaebacteria) for use in a eubacterial host system.

For example, the orthogonal O-tRNA can be derived from an Archae organism, e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kan-* dleri, *Methanosarcina mazei* (Mm), *Pyrobaculum aerophilum, Pyrococcus abyssi, Sulfolobus solfataricus* (Ss), *Sulfolobus tokodaii, Themmoplasma acidophilum, Thermoplasma volcanium*, or the like, or a eubacterium, such as *Escherichia coli, Thermus thernophilus, Bacillus stearothenmphilus*, or the like, while the orthogonal O—RS can be derived from an organism or combination of organisms, e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei, Pyrobaculum aerophilum, Pyrococcus abyssi, Sulfolobus solfataricus, Sulfolobus tokodaii, Thermoplasma acidophilum, Thermoplasma volcanium*, or the like, or a eubacterium, such as *Escherichia coli, Thermus thermophilus, Bacillus stearothermphilus*, or the like. In one embodiment, eukaryotic sources, e.g., plants, algae, protists, fungi, yeasts, animals (e.g., mammals, insects, arthropods, etc.), or the like, can also be used as sources of O-tRNAs and O—RSs.

The individual components of an O-tRNA/O—RS pair can be derived from the same organism or different organisms. In one embodiment, the O-tRNA/O—RS pair is from the same organism. Alternatively, the O-tRNA and the O—RS of the O-tRNA/O—RS pair are from different organisms.

The O-tRNA, O—RS or O-tRNA/O—RS pair can be selected or screened in vivo or in vitro and/or used in a cell, e.g., a eubacterial cell, to produce a polypeptide with an unnatural amino acid. The eubacterial cell used is not limited, for example, *Escherichia coli, Thermus thermophilus, Bacillus stearothermphilus*, or the like. Compositions of eubacterial cells comprising translational components of the invention are also a feature of the invention.

See also, International Application Publication Number WO 2004/094593, entitled "EXPANDING THE EUKARYOTIC GENETIC CODE," filed Apr. 16, 2004, for screening O-tRNA and/or O—RS in one species for use in another species.

In some aspects, the O-tRNA, O—RS or O-tRNA/O—RS pair can be selected or screened in vivo or in vitro and/or used in a cell, e.g., a eukaryotic cell, to produce a polypeptide with an unnatural amino acid. The eukaryotic cell used is not limited; for example, any suitable yeast cell, such as *Saccharomyces cerevisiae* (*S. cerevisiae*) or the like, can be used. Compositions of eukaryotic cells comprising translational components of the invention are also a feature of the invention.

*Saccharomyces cerevisiae* can be chosen as a eukaryotic host species, as this organism provides various advantages. The species is unicellular, has a rapid generation time, and genetically well characterized. See, e.g., D. Burke, et al., (2000) *Methods in Yeast Genetics*. Cold Spring Harbor Laboratory Press, Cold Spring Harbor, N.Y. Moreover, since the translational machinery of eukaryotes is highly conserved (see, e.g., (1996) *Translational Control*. Cold Spring Harbor Laboratory, Cold Spring Harbor, N.Y.; Y. Kwok, & J. T. Wong, (1980), *Evolutionary relationship between Halobacterium cutirubrum and eukaryotes determined by use of aminoacyl-tRNA synthetases as phylogenetic probes, Canadian Journal of Biochemistry* 58:213-218; and, (2001) *The Ribosome*. Cold Spring Harbor Laboratory Press, Cold Spring Harbor, N.Y.), O—RS genes (e.g., O—RS genes derived from wild-type *E. coli* RS sequences) for the incorporation of unnatural amino acids discovered in *S. cerevisiae* can be introduced into higher eukaryotic organisms (e.g., in mammalian cells) and used, in partnership with cognate tRNAs (see, e.g., K. Sakamoto, et al., (2002) *Site-specific incorporation of an unnatural amino acid into proteins in mammalian cells, Nucleic Acids Res*. 30:4692-4699; and, C. Kohrer, et al., (2001), *Import of amber and ochre suppressor tRNAs into mammalian cells: a general approach to site-specific insertion of amino acid analogues into proteins, Proc. Natl. Acad. Sci. U.S.A.* 98:14310-14315) to incorporate unnatural amino acids.

Although orthogonal translation systems (e.g., comprising an O—RS, an O-tRNA and an unnatural amino acid) can utilize cultured host cells to produce proteins having unnatural amino acids, it is not intended that an orthogonal translation system of the invention require an intact, viable host cell. For example, a orthogonal translation system can utilize a cell-free system in the presence of a cell extract. Indeed, the use of cell free, in vitro transcription/translation systems for protein production is a well established technique. Adaptation of these in vitro systems to produce proteins having unnatural amino acids using orthogonal translation system components described herein is well within the scope of the invention.

Selector Codons

Selector codons of the invention expand the genetic codon framework of protein biosynthetic machinery. For example, a selector codon includes, e.g., a unique three base codon, a nonsense codon, such as a stop codon, e.g., an amber codon (UAG), or an opal codon (UGA), an unnatural codon, at least a four base codon, a rare codon, or the like. A number of selector codons can be introduced into a desired gene, e.g., one or more, two or more, more than three, etc. By using different selector codons, multiple orthogonal tRNA/synthetase pairs can be used that allow the simultaneous site-specific incorporation of multiple unnatural amino acids e.g., including at least one unnatural amino acid, using these different selector codons.

In one embodiment, the methods involve the use of a selector codon that is a stop codon for the incorporation of an unnatural amino acid in vivo in a cell. For example, an O-tRNA is produced that recognizes the stop codon and is aminoacylated by an O—RS with an unnatural amino acid. This O-tRNA is not recognized by the naturally occurring host's aminoacyl-tRNA synthetases. Conventional site-directed mutagenesis can be used to introduce the stop codon at the site of interest in a polynucleotide encoding a polypeptide of interest. See, e.g., Sayers, J. R., et al. (1988), 5',3' *Exonuclease in phosphorothioate-based oligonucleotide-directed mutagenesis. Nucleic Acids Res*, 791-802. When the O—RS, O-tRNA and the nucleic acid that encodes a polypeptide of interest are combined, e.g., in vivo, the unnatural amino acid is incorporated in response to the stop codon to give a polypeptide containing the unnatural amino acid at the specified position. In one embodiment of the invention, the stop codon used as a selector codon is an amber codon, UAG, and/or an opal codon, UGA. In one example, a genetic code in which UAG and UGA are both used as a selector codon can encode 22 amino acids while preserving the ochre nonsense codon, UAA, which is the most abundant termination signal.

The incorporation of unnatural amino acids in vivo can be done without significant perturbation of the host cell. For example in non-eukaryotic cells, such as *Escherichia coli*, because the suppression efficiency for the UAG codon depends upon the competition between the O-tRNA, e.g., the amber suppressor tRNA, and the release factor 1 (RF1) (which binds to the UAG codon and initiates release of the growing peptide from the ribosome), the suppression efficiency can be modulated by, e.g., either increasing the expression level of O-tRNA, e.g., the suppressor tRNA, or using an RF1 deficient strain. In eukaryotic cells, because the suppression efficiency for the UAG codon depends upon the competition between the O-tRNA, e.g., the amber suppressor tRNA, and a eukaryotic release factor (e.g., eRF) (which binds to a stop codon and initiates release of the growing peptide from the ribosome), the suppression efficiency can be modulated by, e.g., increasing the expression level of O-tRNA, e.g., the suppressor tRNA. In addition, additional compounds can also be present, e.g., reducing agents such as dithiothretiol (DTT).

Unnatural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., *Biochemistry,* 32:7939 (1993). In this case, the synthetic tRNA competes with the naturally occurring $tRNA^{Arg}$, which exists as a minor species in *Escherichia coli.* In addition, some organisms do not use all triplet codons. An unassigned codon AGA in *Micrococcus luteus* has been utilized for insertion of amino acids in an in vitro transcription/translation extract. See, e.g., Kowal and Oliver, *Nucl. Acid. Res.* 25:4685 (1997). Components of the invention can be generated to use these rare codons in vivo.

Selector codons can also comprise extended codons, e.g., four or more base codons, such as, four, five, six or more base codons. Examples of four base codons include, e.g., AGGA, CUAG, UAGA, CCCU, and the like. Examples of five base codons include, e.g., AGGAC, CCCCU, CCCUC, CUAGA, CUACU, UAGGC and the like. Methods of the invention include using extended codons based on frameshift suppression. Four or more base codons can insert, e.g., one or multiple unnatural amino acids, into the same protein. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using a four or more base codon. See also, Anderson et al., (2002) *Exploring the Limits of Codon and Anticodon Size, Chemistry and Biology,* 9:237-244; and, Magliery, (2001) *Expanding the Genetic Code: Selection of Efficient Suppressors of Four-base Codons and Identification of "Shifty" Four-base Codons with a Library Approach in Escherichia coli, J. Mol. Biol.* 307: 755-769.

For example, four-base codons have been used to incorporate unnatural amino acids into proteins using in vitro biosynthetic methods. See, e.g., Ma et al., (1993) *Biochemistry,* 32:7939; and Hohsaka et al., (1999) *J. Am. Chem. Soc.* 121: 34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.,* 121:12194. In an in vivo study, Moore et al. examined the ability of $tRNA^{Leu}$ derivatives with NCUA anticodons to suppress UAGN codons (N can be U, A, G, or C), and found that the quadruplet UAGA can be decoded by a $tRNA^{Leu}$ with a UCUA anticodon with an efficiency of 13 to 26% with little decoding in the 0 or −1 frame. See Moore et al., (2000) *J. Mol. Biol.,* 298:195. In one embodiment, extended codons based on rare codons or nonsense codons can be used in invention, which can reduce missense readthrough and frameshift suppression at other unwanted sites. Four base codons have been used as selector codons in a variety of orthogonal systems. See, e.g., WO 2005/019415; WO 2005/007870 and WO 2005/07624. See also, Wang and Schultz "Expanding the Genetic Code," *Angewandte Chemie Int. Ed.,* 44(1):34-66 (2005), the content of which is incorporated by reference in its entirety. While the examples below utilize an amber selector codon, four or more base codons can be used as well, by modifying the examples herein to include four-base O-tRNAs and synthetases modified to include mutations similar to those previously described for various unnatural amino acid O—RSs.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein, Nature Biotechnology,* 20:177-182. See also Wu, Y., et al., (2002) *J. Am. Chem. Soc.* 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.,* 111:8322; and Piccirilli et al., (1990) *Nature,* 343:33; Kool, (2000) *Curr. Opin. Chem. Biol.,* 4:602. These bases in general mispair to some degree with natural bases and cannot be enzymatically replicated. Kool and co-workers demonstrated that hydrophobic packing interactions between bases can replace hydrogen bonding to drive the formation of base pair. See Kool, (2000) *Curr. Opin. Chem. Biol.,* 4:602; and Guckian and Kool, (1998) *Angew. Chem. Int. Ed. Engl.,* 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.,* 121:11586; and Ogawa et al., (2000) *J. Am. Chem. Soc.,* 122:3274. A 3MN:3MN self-pair can be synthesized by KF with efficiency and selectivity sufficient for biological function. See, e.g., Ogawa et al., (2000) J. Am. Chem. Soc., 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.,* 123:7439. A novel metallobase pair, Dipic:Py, has also been developed, which forms a stable pair upon binding Cu(II). See Meggers et al., (2000) *J. Am. Chem. Soc.* 122:10714. Because extended codons and unnatural codons are intrinsically orthogonal to natural codons, the methods of the invention can take advantage of this property to generate orthogonal tRNAs for them.

A translational bypassing system can also be used to incorporate an unnatural amino acid in a desired polypeptide. In a translational bypassing system, a large sequence is inserted into a gene but is not translated into protein. The sequence contains a structure that serves as a cue to induce the ribosome to hop over the sequence and resume translation downstream of the insertion.

Unnatural Amino Acids

As used herein, an unnatural amino acid refers to any amino acid, modified amino acid, or amino acid analogue other than selenocysteine and/or pyrrolysine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

I

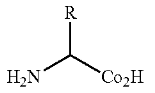

An unnatural amino acid is typically any structure having Formula I wherein the R group is any substituent other than one used in the twenty natural amino acids. See e.g., *Biochemistry by L. Stryer,* 3rd ed. 1988, Freeman and Company, New York, for structures of the twenty natural amino acids. Note that, the unnatural amino acids of the invention can be naturally occurring compounds other than the twenty alpha-amino acids above.

Because the unnatural amino acids of the invention typically differ from the natural amino acids in side chain, the unnatural amino acids form amide bonds with other amino acids, e.g., natural or unnatural, in the same manner in which they are formed in naturally occurring proteins. However, the unnatural amino acids have side chain groups that distinguish them from the natural amino acids.

Of particular interest herein are unnatural amino acids provided in FIG. 1. For example, these unnatural amino acids include but are not limited to p-ethylthiocarbonyl-L-phenylalanine, p-(3-oxobutanoyl)-L-phenylalanine, 1,5-dansyl-alanine, 7-amino-coumarin amino acid, 7-hydroxy-coumarin amino acid, nitrobenzyl-serine, O-(2-nitrobenzyl)-L-tyrosine, p-carboxymethyl-L-phenylalanine, p-cyano-L-phenylalanine, m-cyano-L-phenylalanine, biphenylalanine, 3-amino-L-tyrosine, bipyridyl alanine, p-(2-amino-1-hydroxyethyl)-L-phenylalanine, p-isopropyl thiocarbonyl-L-phenylalanine, 3-nitro-L-tyrosine and p-nitro-L-phenylalanine. Both the L and D-enantiomers of these unnatural amino acids find use with the invention In addition to the unnatural amino acids of FIG. 1, other unnatural amino acids can be simultaneously incorporated into a polypeptide of interest, e.g., using an appropriate second O—RS/O-tRNA pair in conjunction with an orthogonal pair provided by the present invention. Many such additional unnatural amino acids and suitable orthogonal pairs are known. See the references cited herein. For example, see Wang and Schultz "Expanding the Genetic Code," *Angewandte Chemie Int. Ed.,* 44(1):34-66 (2005), the content of which is incorporated by reference in its entirety.

In other unnatural amino acids, for example, R in Formula I optionally comprises an alkyl-, aryl-, acyl-, hydrazine, cyano-, halo-, hydrazide, alkenyl, ether, borate, boronate, phospho, phosphono, phosphine, enone, imine, ester, hydroxylamine, amine, and the like, or any combination thereof. Other unnatural amino acids of interest include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, biotin or biotin-analogue containing amino acids, keto containing amino acids, glycosylated amino acids, a saccharide moiety attached to the amino acid side chain, amino acids comprising polyethylene glycol or polyether, heavy atom substituted amino acids, chemically cleavable or photocleavable amino acids, amino acids with an elongated side chain as compared to natural amino acids (e.g., polyethers or long chain hydrocarbons, e.g., greater than about 5, greater than about 10 carbons, etc.), carbon-linked sugar-containing amino acids, amino thioacid containing amino acids, and amino acids containing one or more toxic moiety.

In another aspect, the invention provides unnatural amino acids having the general structure illustrated by Formula IV below:

IV

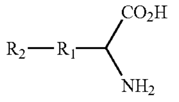

An unnatural amino acid having this structure is typically any structure where $R_1$ is a substituent used in one of the twenty natural amino acids (e.g., tyrosine or phenylalanine) and $R_2$ is a substituent. Thus, this type of unnatural amino acid can be viewed as a natural amino acid derivative.

In addition to unnatural amino acids that contain novel side chains such as those shown in FIG. 1, unnatural amino acids can also optionally comprise modified backbone structures, e.g., as illustrated by the structures of Formula II and III:

II

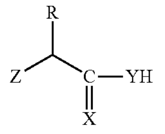

III

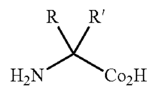

wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β, and γ amino acids such as substituted β-alanine and γ-amino butyric acid.

In some aspects, the invention utilizes unnatural amino acids in the L-configuration. However, it is not intended that the invention be limited to the use of L-configuration unnatural amino acids. It is contemplated that the D-enantiomers of these unnatural amino acids also find use with the invention.

Tyrosine analogs include para-substituted tyrosines, ortho-substituted tyrosines, and meta substituted tyrosines, wherein the substituted tyrosine comprises an alkynyl group, acetyl group, a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, γ-substituted derivatives, cyclic derivatives, and amide substituted glutamine derivatives. Example phenylalanine analogs include, but are not limited to, para-substituted phenylalanines, ortho-substituted phenyalanines, and meta-substituted phenylalanines, wherein the substituent comprises an alkynyl group, a hydroxy group, a methoxy group, a methyl group, an allyl group, an aldehyde, a nitro, a thiol group, or keto group, or the like. Specific examples of unnatural amino acids include, but are not limited to, p-ethylthiocarbonyl-L-phenylalanine, p-(3-oxobutanoyl)-L-phenylalanine, 1,5-dansyl-alanine, 7-amino-coumarin amino acid, 7-hydroxy-coumarin amino acid, nitrobenzyl-serine, O-(2-nitrobenzyl)-L-tyrosine, p-carboxymethyl-L-phenylalanine, p-cyano-L-phenylalanine, m-cyano-L-phenylalanine, biphenylalanine, 3-amino-L-tyrosine, bipyridyl alanine, p-(2-amino-1-hydroxyethyl)-L-phenylalanine, p-isopropylthiocarbonyl-L-phenylalanine, 3-nitro-L-tyrosine and p-nitro-L-phenylalanine. Also, a p-propargyloxyphenylalanine, a 3,4-dihydroxy-L-phenyalanine (DHP), a 3,4,6-trihydroxy-L-phenylalanine, a 3,4,5-trihydroxy-L-phenylalanine, 4-nitro-phenylalanine, a p-acetyl-L-phenylalanine, O-methyl-L-tyrosine, an L-3-(2-naphthyl) alanine, a 3-methyl-phenylalanine, an O-4-allyl-L-tyrosine, a 4-propyl-L-tyrosine, a 3-nitro-tyrosine, a 3-thiol-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like. The structures of a variety of unnatural amino acids are provided herein, see, for example, FIG. 1. See also, Published International Application WO 2004/094593, entitled "EXPANDING THE EUKARYOTIC GENETIC CODE."

Chemical Synthesis of Unnatural Amino Acids

Many of the unnatural amino acids provided above are commercially available, e.g., from Sigma (USA) or Aldrich (Milwaukee, Wis., USA). Those that are not commercially available are optionally synthesized as provided in various publications or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) *J. Med. Chem.*, 38, 4660-4669; King, F. E. & Kidd, D. A. A. (1949) *A New Synthesis of Glutamine and of γ-Dipeptides of Glutamic Acid from Phthylated Intermediates. J. Chem. Soc.* 3315-3319; Friedman, O. M. & Chatterrji, R. (1959) *Synthesis of Derivatives of Glutamine as Model Substrates for Anti-Tumor Agents. J. Am. Chem. Soc.* 81, 3750-3752; Craig, J. C. et al. (1988) Absolute Configuration of the Enantiomers of 7-Chloro-4 [[4-(diethylamino)-1-methylbutyl]amino]quinoline (Chloroquine). *J. Org. Chem.* 53, 1167-1170; Azoulay, M., Vilmont, M. & Frappier, F. (1991) *Glutamine analogues as Potential Antimalarials, Eur. J. Med. Chem.* 26, 201-5; Koskinen, A. M. P. & Rapoport, H. (1989) *Synthesis of 4-Substituted Prolines as Conformationally Constrained Amino Acid Analogues. J. Org. Chem.* 54, 1859-1866; Christie, B. D. & Rapoport, H. (1985) *Synthesis of Optically Pure Pipecolates from L-Asparagine. Application to the Total Synthesis of (+)-Apovincamime through Amino Acid Decarbonylation and Iminium Ion Cyclization. J. Org. Chem.* 1989: 1859-1866; Barton et al., (1987) *Synthesis of Novel α-Amino-Acids and Derivatives Using Radical Chemistry: Synthesis of L- and D-α-Amino-Adipic Acids, L-α-aminopimelic Acid and Appropriate Unsaturated Derivatives. Tetrahedron Lett.* 43:4297-4308; and, Subasinghe et al., (1992) *Quisqualic acid analogues: synthesis of beta-heterocyclic 2-aminopropanoic acid derivatives and their activity at a novel quisqualate-sensitized site. J. Med. Chem.* 35:4602-7. See also, International Publication WO 2004/058946, entitled "PROTEIN ARRAYS," filed on Dec. 22, 2003.

Cellular Uptake of Unnatural Amino Acids

Unnatural amino acid uptake by a cell is one issue that is typically considered when designing and selecting unnatural amino acids, e.g., for incorporation into a protein. For example, the high charge density of α-amino acids suggests that these compounds are unlikely to be cell permeable. Natural amino acids are taken up into the cell via a collection of protein-based transport systems often displaying varying degrees of amino acid specificity. A rapid screen can be done which assesses which unnatural amino acids, if any, are taken up by cells. See, e.g., the toxicity assays in, e.g., International Publication WO 2004/058946, entitled "PROTEIN ARRAYS," filed on Dec. 22, 2003; and Liu and Schultz (1999) *Progress toward the evolution of an organism with an expanded genetic code. PNAS* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, e.g., in a cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923, supra) relies on the addition of a combination of known enzymes from other organisms. The genes for these enzymes can be introduced into a cell by transforming the cell with a plasmid comprising the genes. The genes, when expressed in the cell, provide an enzymatic pathway to synthesize the desired compound.

Examples of the types of enzymes that are optionally added are provided in the examples below. Additional enzymes sequences are found, e.g., in Genbank. Artificially evolved enzymes are also optionally added into a cell in the same manner. In this manner, the cellular machinery and resources of a cell are manipulated to produce unnatural amino acids.

Indeed, any of a variety of methods can be used for producing novel enzymes for use in biosynthetic pathways, or for evolution of existing pathways, for the production of unnatural amino acids, in vitro or in vivo. Many available methods of evolving enzymes and other biosynthetic pathway components can be applied to the present invention to produce unnatural amino acids (or, indeed, to evolve synthetases to have new substrate specificities or other activities of interest). For example, DNA shuffling is optionally used to develop novel enzymes and/or pathways of such enzymes for the production of unnatural amino acids (or production of new synthetases), in vitro or in vivo. See, e.g., Stemmer (1994), *Rapid evolution of a protein in vitro by DNA shuffling, Nature* 370(4):389-391; and, Stemmer, (1994), *DNA shuffling by random fragmentation and reassembly: In vitro recombination for molecular evolution, Proc. Natl. Acad. Sci. USA.,* 91:10747-10751. A related approach shuffles families of related (e.g., homologous) genes to quickly evolve enzymes with desired characteristics. An example of such "family gene shuffling" methods is found in Crameri et al. (1998) "DNA shuffling of a family of genes from diverse species accelerates directed evolution" *Nature,* 391(6664): 288-291. New enzymes (whether biosynthetic pathway components or synthetases) can also be generated using a DNA recombination procedure known as "incremental truncation for the creation of hybrid enzymes" ("ITCHY"), e.g., as described in Ostermeier et al. (1999) "A combinatorial approach to hybrid enzymes independent of DNA homology" *Nature Biotech* 17:1205. This approach can also be used to generate a library of enzyme or other pathway variants which can serve as substrates for one or more in vitro or in vivo recombination methods. See, also, Ostermeier et al. (1999) "Combinatorial Protein Engineering by Incremental Truncation," *Proc. Natl. Acad. Sci. USA,* 96: 3562-67, and Ostermeier et al. (1999), "Incremental Truncation as a Strategy in the Engineering of Novel Biocatalysts," *Biological and Medicinal Chemistry,* 7: 2139-44. Another approach uses exponential ensemble mutagenesis to produce libraries of enzyme or other pathway variants that are, e.g., selected for an ability to catalyze a biosynthetic reaction relevant to producing an unnatural amino acid (or a new synthetase). In this approach, small groups of residues in a sequence of interest are randomized in parallel to identify, at each altered position, amino acids which lead to functional proteins. Examples of such procedures, which can be adapted to the present invention to produce new enzymes for the production of unnatural amino acids (or new synthetases) are found in Delegrave & Youvan (1993) *Biotechnology Research* 11: 1548-1552. In yet another approach, random or semi-random mutagenesis using doped or degenerate oligonucleotides for enzyme and/or pathway component engineering can be used, e.g., by using the general mutagenesis methods of e.g., Arkin and Youvan (1992) "Optimizing nucleotide mixtures to encode specific subsets of amino acids for semi-random mutagenesis" *Biotechnology* 10:297-300; or Reidhaar-Olson et al. (1991) "Random mutagenesis of protein sequences using oligonucleotide cassettes" *Methods Enzymol.* 208:564-86. Yet another approach, often termed a "non-stochastic" mutagenesis, which uses polynucleotide reassembly and site-saturation mutagenesis can be used to produce enzymes and/or pathway components, which can then be screened for an ability to perform one or more synthetase or biosynthetic pathway function (e.g., for the production of unnatural amino acids in vivo). See, e.g., Short "NON-STOCHASTIC GENERATION OF GENETIC VACCINES AND ENZYMES" WO 00/46344.

An alternative to such mutational methods involves recombining entire genomes of organisms and selecting resulting progeny for particular pathway functions (often referred to as "whole genome shuffling"). This approach can be applied to the present invention, e.g., by genomic recombination and selection of an organism (e.g., an *E. coli* or other cell) for an ability to produce an unnatural amino acid (or intermediate thereof). For example, methods taught in the following publications can be applied to pathway design for the evolution of existing and/or new pathways in cells to produce unnatural amino acids in vivo: Patnaik et al. (2002) "Genome shuffling of *lactobacillus* for improved acid tolerance" *Nature Biotechnology,* 20(7): 707-712; and Zhang et al. (2002) "Genome shuffling leads to rapid phenotypic improvement in bacteria" Nature, February 7, 415(6872): 644-646.

Other techniques for organism and metabolic pathway engineering, e.g., for the production of desired compounds are also available and can also be applied to the production of unnatural amino acids. Examples of publications teaching useful pathway engineering approaches include: Nakamura and White (2003) "Metabolic engineering for the microbial production of 1,3 propanediol" *Curr. Opin. Biotechnol.* 14(5):454-9; Berry et al. (2002) "Application of Metabolic Engineering to improve both the production and use of Biotech Indigo" *J. Industrial Microbiology and Biotechnology* 28:127-133; Banta et al. (2002) "Optimizing an artificial metabolic pathway: Engineering the cofactor specificity of Corynebacterium 2,5-diketo-D-gluconic acid reductase for use in vitamin C biosynthesis" *Biochemistry,* 41(20), 6226-36; Selivonova et al. (2001) "Rapid Evolution of Novel Traits in Microorganisms" *Applied and Environmental Microbiology,* 67:3645, and many others.

Regardless of the method used, typically, the unnatural amino acid produced with an engineered biosynthetic pathway of the invention is produced in a concentration sufficient for efficient protein biosynthesis, e.g., a natural cellular amount, but not to such a degree as to significantly affect the concentration of other cellular amino acids or to exhaust cellular resources. Typical concentrations produced in vivo in this manner are about 10 mM to about 0.05 mM. Once a cell is engineered to produce enzymes desired for a specific pathway and an unnatural amino acid is generated, in vivo selections are optionally used to further optimize the production of the unnatural amino acid for both ribosomal protein synthesis and cell growth.

Orthogonal Components for Incorporating Unnatural Amino Acids

The invention provides compositions and methods of producing orthogonal components for incorporating unnatural amino acids, e.g., the unnatural amino acids provided in FIG. 1, into a growing polypeptide chain in response to a selector codon, e.g., an amber stop codon, a nonsense codon, a four or more base codon, etc., e.g., in vivo. For example, the invention provides orthogonal-tRNAs (O-tRNAs), orthogonal aminoacyl-tRNA synthetases (O—RSs) and pairs thereof. These pairs can be used to incorporate an unnatural amino acid into growing polypeptide chains.

A composition of the invention includes an orthogonal aminoacyl-tRNA synthetase (O—RS), where the O—RS preferentially aminoacylates an O-tRNA with p-ethylthiocarbonyl-L-phenylalanine, p-(3-oxobutanoyl)-L-phenylalanine, 1,5-dansyl-alanine, 7-amino-coumarin alanine, 7-hydroxycoumarin alanine, o-nitrobenzyl-serine, O-(2-nitrobenzyl)-L-tyrosine, p-carboxymethyl-L-phenylalanine, p-cyano-L-phenylalanine, m-cyano-L-phenylalanine, biphenylalanine, 3-amino-L-tyrosine, bipyridylalanine, p-(2-amino-1-hydroxyethyl)-L-phenylalanine; p-isopropylthiocarbonyl-L-phenylalanine; 3-nitro-L-tyrosine or p-nitro-L-phenylalanine. In certain embodiments, the O—RS comprises an amino acid sequence comprising any one of SEQ ID NOS: 7-10, 12, 14, 16, 18, 20, 22, 24, 26, 28, 30, 32, 34, 36, 38, 40, 42, 44, 46, 50, 52-55, 57 and 59-63, and conservative variations thereof. In certain embodiments of the invention, the O—RS preferentially aminoacylates the O-tRNA over any endogenous tRNA with an the particular unnatural amino acid, where the O—RS has a bias for the O-tRNA, and where the ratio of O-tRNA charged with an unnatural amino acid to the endogenous tRNA charged with the same unnatural amino acid is greater than 1:1, and more preferably where the O—RS charges the O-tRNA exclusively or nearly exclusively.

A composition that includes an O—RS can optionally further include an orthogonal tRNA (O-tRNA), where the O-tRNA recognizes a selector codon. Typically, an O-tRNA of the invention includes at least about, e.g., a 45%, a 50%, a 60%, a 75%, an 80%, or a 90% or more suppression efficiency in the presence of a cognate synthetase in response to a selector codon as compared to the suppression efficiency of an O-tRNA comprising or encoded by a polynucleotide sequence as set forth in the sequence listings (e.g., SEQ ID NO: 1) and examples herein. In one embodiment, the suppression efficiency of the O—RS and the O-tRNA together is, e.g., 5 fold, 10 fold, 15 fold, 20 fold, 25 fold or more greater than the suppression efficiency of the O-tRNA in the absence of an O—RS. In some aspects, the suppression efficiency of the O—RS and the O-tRNA together is at least 45% of the suppression efficiency of an orthogonal tyrosyl-tRNA synthetase pair derived from *Methanococcus jannaschii*, or alternatively, an orthogonal leucyl-tRNA synthetase pair derived from *E. coli*.

A composition that includes an O-tRNA can optionally include a cell (e.g., a eubacterial cell, such as an *E. coli* cell and the like, or a eukaryotic cell such as a yeast cell), and/or a translation system.

A cell (e.g., a eubacterial cell or a yeast cell) comprising a translation system is also provided by the invention, where the translation system includes an orthogonal-tRNA (O-tRNA); an orthogonal aminoacyl-tRNA synthetase (O—RS); and, an unnatural amino acid, e.g., an amino acid shown in FIG. 1. Typically, the O—RS preferentially aminoacylates the O-tRNA over any endogenous tRNA with the unnatural amino acid, where the O—RS has a bias for the O-tRNA, and where the ratio of O-tRNA charged with the unnatural amino acid to the endogenous tRNA charged with the unnatural amino acid is greater than 1:1, and more preferably where the O—RS charges the O-tRNA exclusively or nearly exclusively. The O-tRNA recognizes the first selector codon, and the O—RS preferentially aminoacylates the O-tRNA with an unnatural amino acid. In one embodiment, the O-tRNA comprises or is encoded by a polynucleotide sequence as set forth in SEQ ID NO: 1, SEQ ID NO: 2, or a complementary polynucleotide sequence thereof. In one embodiment, the O—RS comprises an amino acid sequence as set forth in any one of SEQ ID NOS: 7-10, 12, 14, 16, 18, 20, 22, 24, 26, 28, 30, 32, 34, 36, 38, 40, 42, 44, 46, 50, 52-55, 57, 59-63, and conservative variations thereof.

A cell of the invention can optionally further comprise an additional different O-tRNA/O—RS pair and a second unnatural amino acid, e.g., where this O-tRNA recognizes a second selector codon and this O—RS preferentially aminoacylates the corresponding O-tRNA with the second unnatural amino acid, where the second amino acid is different from the first unnatural amino acid. Optionally, a cell of the invention includes a nucleic acid that comprises a polynucleotide that encodes a polypeptide of interest, where the polynucleotide comprises a selector codon that is recognized by the O-tRNA.

In certain embodiments, a cell of the invention is a eubacterial cell (such as *E. coli*) or a yeast cell, that includes an orthogonal-tRNA (O-tRNA), an orthogonal aminoacyl-tRNA synthetase (O—RS), an unnatural amino acid, and a nucleic acid that comprises a polynucleotide that encodes a polypeptide of interest, where the polynucleotide comprises the selector codon that is recognized by the O-tRNA. In certain embodiments of the invention, the O—RS preferentially aminoacylates the O-tRNA with the unnatural amino acid with an efficiency that is greater than the efficiency with which the O—RS aminoacylates any endogenous TRNA.

In certain embodiments of the invention, an O-tRNA of the invention comprises or is encoded by a polynucleotide sequence as set forth in the sequence listings (e.g., SEQ ID NO: 1 or SEQ ID NO: 2) or examples herein, or a complementary polynucleotide sequence thereof. In certain embodiments of the invention, an O—RS comprises an amino acid sequence as set forth in the sequence listings, or a conservative variation thereof. In one embodiment, the O—RS or a portion thereof is encoded by a polynucleotide sequence encoding an amino acid as set forth in the sequence listings or examples herein, or a complementary polynucleotide sequence thereof.

The O-tRNA and/or the O—RS of the invention can be derived from any of a variety of organisms (e.g., eukaryotic and/or non-eukaryotic organisms).

Polynucleotides are also a feature of the invention. A polynucleotide of the invention includes an artificial (e.g., man-made, and not naturally occurring) polynucleotide comprising a nucleotide sequence encoding a polypeptide as set forth in the sequence listings herein, and/or is complementary to or that polynucleotide sequence. A polynucleotide of the invention can also includes a nucleic acid that hybridizes to a polynucleotide described above, under highly stringent conditions, over substantially the entire length of the nucleic acid. A polynucleotide of the invention also includes a polynucleotide that is, e.g., at least 75%, at least 80%, at least 90%, at least 95%, at least 98% or more identical to that of a naturally occurring tRNA or corresponding coding nucleic acid (but a polynucleotide of the invention is other than a naturally occurring tRNA or corresponding coding nucleic acid), where the tRNA recognizes a selector codon, e.g., a four base codon. Artificial polynucleotides that are, e.g., at least 80%, at least 90%, at least 95%, at least 98% or more identical to any of the above and/or a polynucleotide comprising a conservative variation of any the above, are also included in polynucleotides of the invention.

Vectors comprising a polynucleotide of the invention are also a feature of the invention. For example, a vector of the invention can include a plasmid, a cosmid, a phage, a virus, an expression vector, and/or the like. A cell comprising a vector of the invention is also a feature of the invention.

Methods of producing components of an O-tRNA/O—RS pair are also features of the invention. Components produced by these methods are also a feature of the invention. For example, methods of producing at least one tRNA that is orthogonal to a cell (O-tRNA) include generating a library of mutant tRNAs; mutating an anticodon loop of each member of the library of mutant tRNAs to allow recognition of a selector codon, thereby providing a library of potential O-tR- NAs, and subjecting to negative selection a first population of cells of a first species, where the cells comprise a member of the library of potential O-tRNAs. The negative selection eliminates cells that comprise a member of the library of potential O-tRNAs that is aminoacylated by an aminoacyl-tRNA synthetase (RS) that is endogenous to the cell. This provides a pool of tRNAs that are orthogonal to the cell of the first species, thereby providing at least one O-tRNA. An O-tRNA produced by the methods of the invention is also provided.

In certain embodiments, the methods further comprise subjecting to positive selection a second population of cells of the first species, where the cells comprise a member of the pool of tRNAs that are orthogonal to the cell of the first species, a cognate aminoacyl-tRNA synthetase, and a positive selection marker. Using the positive selection, cells are selected or screened for those cells that comprise a member of the pool of tRNAs that is aminoacylated by the cognate aminoacyl-tRN A synthetase and that shows a desired response in the presence of the positive selection marker, thereby providing an O-tRNA. In certain embodiments, the second population of cells comprise cells that were not eliminated by the negative selection.

Methods for identifying an orthogonal-aminoacyl-tRNA synthetase that charges an O-tRNA with an unnatural amino acid are also provided. For example, methods include subjecting a population of cells of a first species to a selection, where the cells each comprise: 1) a member of a plurality of aminoacyl-tRNA synthetases (RSs), (e.g., the plurality of RSs can include mutant RSs, RSs derived from a species other than a first species or both mutant RSs and RSs derived from a species other than a first species); 2) the orthogonal-tRNA (O-tRNA) (e.g., from one or more species); and 3) a polynucleotide that encodes a positive selection marker and comprises at least one selector codon.

Cells (e.g., a host cell) are selected or screened for those that show an enhancement in suppression efficiency compared to cells lacking or having a reduced amount of the member of the plurality of RSs. These selected/screened cells comprise an active RS that aminoacylates the O-tRNA. An orthogonal aminoacyl-tRNA synthetase identified by the method is also a feature of the invention.

Methods of producing a protein in a cell (e.g., in a eubacterial cell such as an *E. coli* cell or the like, or in a yeast cell) having the unnatural amino acid at a selected position are also a feature of the invention. For example, a method includes growing, in an appropriate medium, a cell, where the cell comprises a nucleic acid that comprises at least one selector codon and encodes a protein, providing the unnatural amino acid, and incorporating the unnatural amino acid into the specified position in the protein during translation of the nucleic acid with the at least one selector codon, thereby producing the protein. The cell further comprises: an orthogonal-tRNA (O-tRNA) that functions in the cell and recognizes the selector codon; and, an orthogonal aminoacyl-tRNA synthetase (O—RS) that preferentially aminoacylates the O-tRNA with the unnatural amino acid. A protein produced by this method is also a feature of the invention.

The invention also provides compositions that include proteins, where the proteins comprise, e.g., p-ethylthiocarbonyl-L-phenylalanine, p-(3-oxobutanoyl)-L-phenylalanine, 1,5-dansyl-alanine, 7-amino-coumarin amino acid, 7-hydroxy-coumarin amino acid, nitrobenzyl-serine, O-(2-nitrobenzyl)-L-tyrosine, p-carboxymethyl-L-phenylalanine, p-cyano-L-phenylalanine, m-cyano-L-phenylalanine, biphenylalanine, 3-amino-L-tyrosine, bipyridyl alanine, p-(2-amino-1-hydroxyethyl)-L-phenylalanine, p-isopropylthiocarbonyl-L-phenylalanine, 3-nitro-L-tyrosine or p-nitro-L-phenylalanine. In certain embodiments, the protein comprises an amino acid sequence that is at least 75% identical to that of a known protein, e.g., a therapeutic protein, a diagnostic protein, an industrial enzyme, or portion thereof. Optionally, the composition comprises a pharmaceutically acceptable carrier.

Nucleic Acid and Polypeptide Sequence and Variants

As described herein, the invention provides for polynucleotide sequences encoding, e.g., O-tRNAs and O—RSs, and polypeptide amino acid sequences, e.g., O—RSs, and, e.g., compositions, systems and methods comprising said polynucleotide or polypeptide sequences. Examples of said sequences, e.g., O-tRNA and O—RS amino acid and nucleotide sequences are disclosed herein (see Table 5, e.g., SEQ ID NOS: 7-10, 12, 14, 16, 18, 20, 22, 24, 26, 28, 30, 32, 34, 36, 38, 40, 42, 44, 46, 50, 52-55, 57 and 59-63). However, one of skill in the art will appreciate that the invention is not limited to those sequences disclosed herein, e.g., in the Examples and sequence listing. One of skill will appreciate that the invention also provides many related sequences with the functions described herein, e.g., polynucleotides and polypeptides encoding conservative variants of an O—RS disclosed herein.

The construction and analysis of orthogonal synthetase species (O—RS) that are able to aminoacylate an O-tRNA with an unnatural amino acid, for example, an unnatural amino acid provided in FIG. 1, are described in Examples 1 through 16. These Examples describe the construction and analysis of O—RS species that are able to incorporate the unnatural amino acids p-ethylthiocarbonyl-L-phenylalanine, p-(3-oxobutanoyl)-L-phenylalanine, 1,5-dansyl-alanine, 7-amino-coumarin alanine, 7-hydroxy-coumarin alanine, o-nitrobenzyl-serine, O-(2-nitrobenzyl)-L-tyrosine, p-carboxymethyl-L-phenylalanine, p-cyano-L-phenylalanine, m-cyano-L-phenylalanine, biphenylalanine, 3-amino-L-tyrosine, bipyridylalanine, p-(2-amino-1-hydroxyethyl)-L-phenylalanine; p-isopropylthiocarbonyl-L-phenyl alanine; 3-nitro-L-tyrosine and p-nitro-L-phenylalanine.

The invention provides polypeptides (O—RSs) and polynucleotides, e.g., O-tRNA, polynucleotides that encode O—RSs or portions thereof, oligonucleotides used to isolate aminoacyl-tRNA synthetase clones, etc. Polynucleotides of the invention include those that encode proteins or polypeptides of interest of the invention with one or more selector codon. In addition, polynucleotides of the invention include, e.g., a polynucleotide comprising a nucleotide sequence as set forth in SEQ ID NO: 11, 13, 15, 17, 19, 21, 23, 25, 27, 29, 31, 33, 35, 37, 39, 41, 43, 45, 47, 51, 56 and 58, and a polynucleotide that is complementary to or that encodes a polynucleotide sequence thereof. A polynucleotide of the invention also includes any polynucleotide that encodes an O—RS amino acid sequence comprising SEQ ID NO: 7-10, 12, 14, 16, 18, 20, 22, 24, 26, 28, 30, 32, 34, 36, 38, 40, 42, 44, 46, 50, 52-55, 57 and 59-63. Similarly, an artificial nucleic acid that hybridizes to a polynucleotide indicated above under highly stringent conditions over substantially the entire length of the nucleic acid (and is other than a naturally occurring polynucleotide) is a polynucleotide of the invention. In one embodiment, a composition includes a polypeptide of the invention and an excipient (e.g., buffer, water, pharmaceutically acceptable excipient, etc.). The invention also provides an antibody or antisera specifically immunoreactive with a polypeptide of the invention. An artificial polynucleotide is a polynucleotide that is man made and is not naturally occurring.

A polynucleotide of the invention also includes an artificial polynucleotide that is, e.g., at least 75%, at least 80%, at least 90%, at least 95%, at least 98% or more identical to that of a naturally occurring tRNA, (but is other than a naturally occurring tRNA). A polynucleotide also includes an artificial polynucleotide that is, e.g., at least 75%, at least 80%, at least 90%, at least 95%, at least 98% or more identical (but not 100% identical) to that of a naturally occurring tRNA.

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid sequence. Similarly, "conservative amino acid substitutions," where one or a limited number of amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences which do not alter the encoded activity of a nucleic acid molecule, such as the addition of a non-functional sequence, is a conservative variation of the basic nucleic acid.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitutions within a group is a "conservative substitution".

TABLE 1

Conservative Amino Acid Substitutions

| Nonpolar and/or Aliphatic Side Chains | Polar, Uncharged Side Chains | Aromatic Side Chains | Positively Charged Side Chains | Negatively Charged Side Chains |
|---|---|---|---|---|
| Glycine | Serine | Phenylalanine | Lysine | Aspartate |
| Alanine | Threonine | Tyrosine | Arginine | Glutamate |
| Valine | Cysteine | Tryptophan | Histidine | |
| Leucine | Methionine | | | |
| Isoleucine | Asparagine | | | |
| Proline | Glutamine | | | |

Nucleic Acid Hybridization

Comparative hybridization can be used to identify nucleic acids of the invention, including conservative variations of nucleic acids of the invention, and this comparative hybridization method is a preferred method of distinguishing nucleic acids of the invention. In addition, target nucleic acids which hybridize to a nucleic acid represented by SEQ ID NOS: 11, 13, 15, 17, 19, 21, 23, 25, 27, 29, 31, 33, 35, 37, 39, 41, 43, 45, 47, 51, 56 and 58, under high, ultra-high and ultra-ultra high stringency conditions are a feature of the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least 50% as well to the probe as to the perfectly matched complementary target, i.e., with a signal to noise ratio at least half as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in *Current Protocols in Molecular Biology*, Ausubel et al., eds., *Current Protocols*, a joint venture between Greene Publishing Associates, Inc. and John Wiley & Sons, Inc., (supplemented through 2004) ("Ausubel"); Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher)

than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In some aspects, the invention provides a nucleic acid that comprises a unique subsequence in a nucleic acid selected from the sequences of O-tRNAs and O—RSs disclosed herein. The unique subsequence is unique as compared to a nucleic acid corresponding to any known O-tRNA or O—RS nucleic acid sequence. Alignment can be performed using, e.g., BLAST set to default parameters. Any unique subsequence is useful, e.g., as a probe to identify the nucleic acids of the invention.

Similarly, the invention includes a polypeptide which comprises a unique subsequence in a polypeptide selected from the sequences of O—RSs disclosed herein. Here, the unique subsequence is unique as compared to a polypeptide corresponding to any of known polypeptide sequence.

The invention also provides for target nucleic acids which hybridizes under stringent conditions to a unique coding oligonucleotide which encodes a unique subsequence in a polypeptide selected from the sequences of O—RSs wherein the unique subsequence is unique as compared to a polypeptide corresponding to any of the control polypeptides (e.g., parental sequences from which synthetases of the invention were derived, e.g., by mutation). Unique sequences are determined as noted above.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding an O-tRNA or O—RS, or the amino acid sequence of an O—RS) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more unnatural amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Current *Protocols in Molecular Biology*, Ausubel et al., eds., *Current Protocols*, a joint venture between Greene Publishing Associates, Inc. and John Wiley & Sons, Inc., supplemented through 2004).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Mutagenesis and Other Molecular Biology Techniques

Polynucleotide and polypeptides of the invention and used in the invention can be manipulated using molecular biological techniques. General texts which describe molecular biological techniques include Berger and Kimmel, *Guide to Molecular Cloning Techniques, Methods in Enzymology volume* 152 Academic Press, Inc., San Diego, Calif. (Berger); Sambrook et al., *Molecular Cloning—A Laboratory Manual* (*3rd Ed.*), *Vol.* 1-3, Cold Spring Harbor Laboratory, Cold Spring Harbor, N.Y., 2001 ("Sambrook") and *Current Protocols in Molecular Biology*, F. M. Ausubel et al., eds., *Current Protocols*, a joint venture between Greene Publishing Associates, Inc. and John Wiley & Sons, Inc., (supplemented through 2004) ("Ausubel"). These texts describe mutagenesis, the use of vectors, promoters and many other relevant topics related to, e.g., the generation of genes that include selector codons for production of proteins that include unnatural amino acids, orthogonal tRNAs, orthogonal synthetases, and pairs thereof.

Various types of mutagenesis are used in the invention, e.g., to mutate tRNA molecules, to produce libraries of tRNAs, to produce libraries of synthetases, to insert selector codons that encode an unnatural amino acids in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

Host cells are genetically engineered (e.g., transformed, transduced or transfected) with the polynucleotides of the invention or constructs which include a polynucleotide of the invention, e.g., a vector of the invention, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (e.g., shuttle vectors) and selection markers for both prokaryotic and eukaryotic systems. Vectors are suitable for replication and/or integration in prokaryotes, eukaryotes, or preferably both. See Giliman & Smith, *Gene* 8:81 (1979); Roberts, et al., *Nature,* 328:731 (1987); Schneider, B., et al., *Protein Expr. Purif.* 6435:10

(1995); Ausubel, Sambrook, Berger (all supra). The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70-73 (1987)), and/or the like.

A highly efficient and versatile single plasmid system was developed for site-specific incorporation of unnatural amino acids into proteins in response to the amber stop codon (UAG) in *E. coli*. In the new system, the pair of *M. jannaschii* suppresstor tRNAtyr(CUA) and tyrosyl-tRNA synthetase are encoded in a single plasmid, which is compatible with most *E. coli* expression vectors. Monocistronic tRNA operon under control of proK promoter and terminator was constructed for optimal secondary structure and tRNA processing. Introduction of a mutated form of glnS promoter for the synthetase resulted in a significant increase in both suppression efficiency and fidelity. Increases in suppression efficiency were also obtained by multiple copies of tRNA gene as well as by a specific mutation (D286R) on the synthetase (Kobayashi et al., "Structural basis for orthogonal tRNA specificities of tyrosyl-tRNA synthetases for genetic code expansion," Nat. Struct. Biol., 10(6):425-432 [2003]). The generality of the optimized system was also demonstrated by highly efficient and accurate incorporation of several different unnatural amino acids, whose unique utilities in studying protein function and structure were previously proven.

A catalogue of Bacteria and Bacteriophages useful for cloning is provided, e.g., by the ATCC, e.g., *The ATCC Catalogue of Bacteria and Bacteriophage* (1996) Gherna et al. (eds) published by the ATCC. Additional basic procedures for sequencing, cloning and other aspects of molecular biology and underlying theoretical considerations are also found in Sambrook (supra), Ausubel (supra), and in Watson et al. (1992) *Recombinant DNA Second Edition* Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex. mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

The engineered host cells can be cultured in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Proteins and Polypeptides of Interest

Methods of producing a protein in a cell with an unnatural amino acid at a specified position are also a feature of the invention. For example, a method includes growing, in an appropriate medium, the cell, where the cell comprises a nucleic acid that comprises at least one selector codon and encodes a protein; and, providing the unnatural amino acid; where the cell further comprises: an orthogonal-tRNA (O-tRNA) that functions in the cell and recognizes the selector codon; and, an orthogonal aminoacyl-tRNA synthetase (O—RS) that preferentially aminoacylates the O-tRNA with the unnatural amino acid. A protein produced by this method is also a feature of the invention.

In certain embodiments, the O—RS comprises a bias for the aminoacylation of the cognate O-tRNA over any endogenous tRNA in an expression system. The relative ratio between O-tRNA and endogenous tRNA that is charged by the O—RS, when the O-tRNA and O—RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

The invention also provides compositions that include proteins, where the proteins comprise an unnatural amino acid. In certain embodiments, the protein comprises an amino acid sequence that is at least 75% identical to that of a therapeutic protein, a diagnostic protein, an industrial enzyme, or portion thereof.

The compositions of the invention and compositions made by the methods of the invention optionally are in a cell. The O-tRNA/O—RS pairs or individual components of the invention can then be used in a host system's translation machinery, which results in an unnatural amino acid being incorporated into a protein. International Publication Numbers WO 2004/094593, filed Apr. 16, 2004, entitled "EXPANDING THE EUKARYOTIC GENETIC CODE," and WO 2002/085923, entitled "IN VIVO INCORPORATION OF UNNATURAL AMINO ACIDS," describe this process, and are incorporated herein by reference. For example, when an O-tRNA/O—RS pair is introduced into a host, e.g., an *Escherichia coli* cell or a yeast cell, the pair leads to the in vivo incorporation of an unnatural amino acid such as p-ethylthiocarbonyl-L-phenylalanine, p-(3-oxobutanoyl)-L-phenylalanine, 1,5-dansyl-alanine, 7-amino-coumarin alanine, 7-hydroxy-coumarin alanine, o-nitrobenzyl-serine, O-(2-nitrobenzyl)-L-tyrosine, p-carboxymethyl-L-phenylalanine, p-cyano-L-phenylalanine, m-cyano-L-phenylalanine, biphenylalanine, 3-amino-L-tyrosine, bipyridylalanine, p-(2-amino-1-hydroxyethyl)-L-phenyl alanine; p-isopropylthiocarbonyl-L-phenylalanine; 3-nitro-L-tyrosine or p-nitro-L-phenylalanine into a protein in response to a selector codon. The unnatural amino acid that is added to the system can a synthetic amino acid, such as a derivative of a phenylalanine or tyrosine, which can be exogenously added to the growth medium. Optionally, the compositions of the present invention can be in an in vitro translation system, or in an in vivo system(s).

A cell of the invention provides the ability to synthesize proteins that comprise unnatural amino acids in large useful quantities. In some aspects, the composition optionally includes, e.g., at least 10 micrograms, at least 50 micrograms, at least 75 micrograms, at least 100 micrograms, at least 200 micrograms, at least 250 micrograms, at least 500 micrograms, at least 1 milligram, at least 10 milligrams or more of the protein that comprises an unnatural amino acid, or an amount that can be achieved with in vivo protein production methods (details on recombinant protein production and purification are provided herein). In another aspect, the protein is optionally present in the composition at a concentration of, e.g., at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, e.g., a cell lysate, a buffer, a pharmaceutical buffer, or other liquid suspension (e.g., in a volume of, e.g., anywhere from about 1 mL to about 100 L). The production of large quantities (e.g., greater that that typically possible with other methods, e.g., in vitro translation) of a protein in a cell including at least one unnatural amino acid is a feature of the invention.

The incorporation of an unnatural amino acid can be done to, e.g., tailor changes in protein structure and/or function, e.g., to change size, acidity, nucleophilicity, hydrogen bonding, hydrophobicity, accessibility of protease target sites, target to a moiety (e.g., for a protein array), incorporation of labels or reactive groups, etc. Proteins that include an unnatural amino acid can have enhanced or even entirely new catalytic or physical properties. For example, the following properties are optionally modified by inclusion of an unnatural amino acid into a protein: toxicity, biodistribution, structural properties, spectroscopic properties, chemical and/or photochemical properties, catalytic ability, half-life (e.g., serum half-life), ability to react with other molecules, e.g., covalently or noncovalently, and the like. The compositions including proteins that include at least one unnatural amino acid are useful for, e.g., novel therapeutics, diagnostics, catalytic enzymes, industrial enzymes, binding proteins (e.g., antibodies), and e.g., the study of protein structure and function. See, e.g., Dougherty, (2000) *Unnatural Amino Acids as Probes of Protein Structure and Function, Current Opinion in Chemical Biology,* 4:645-652.

In some aspects of the invention, a composition includes at least one protein with at least one, e.g., at least two, at least three, at least four, at least five, at least six, at least seven, at least eight, at least nine, or at least ten or more unnatural amino acids. The unnatural amino acids can be the same or different, e.g., there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is an unnatural amino acid. For a given protein with more than one unnatural amino acids, the unnatural amino acids can be identical or different (e.g., the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Essentially any protein (or portion thereof) that includes an unnatural amino acid (and any corresponding coding nucleic acid, e.g., which includes one or more selector codons) can be produced using the compositions and methods herein. No attempt is made to identify the hundreds of thousands of known proteins, any of which can be modified to include one or more unnatural amino acid, e.g., by tailoring any available mutation methods to include one or more appropriate selector codon in a relevant translation system. Common sequence repositories for known proteins include GenBank EMBL, DDBJ and the NCBI. Other repositories can easily be identified by searching the internet.

Typically, the proteins are, e.g., at least 60%, at least 70%, at least 75%, at least 80%, at least 90%, at least 95%, or at least 99% or more identical to any available protein (e.g., a therapeutic protein, a diagnostic protein, an industrial enzyme, or portion thereof, and the like), and they comprise one or more unnatural amino acid. Examples of therapeutic, diagnostic, and other proteins that can be modified to comprise one or more unnatural amino acid can be found, but not limited to, those in International Publications WO 2004/094593, filed Apr. 16, 2004, entitled "Expanding the Eukaryotic Genetic Code;" and, WO 2002/085923, entitled "IN VIVO INCORPORATION OF UNNATURAL AMINO ACIDS." Examples of therapeutic, diagnostic, and other proteins that can be modified to comprise one or more unnatural amino acids include, but are not limited to, e.g., Alpha-1 antitrypsin, Angiostatin, Antihemolytic factor, antibodies (further details on antibodies are found below), Apolipoprotein, Apoprotein, Atrial natriuretic factor, Atrial natriuretic polypeptide, Atrial peptides, C—X—C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, 1309, R83915, R91733, HCC1, T58847, D31065, T64262), CD40 ligand, C-kit Ligand, Collagen, Colony stimulating factor (CSF), Complement factor 5a, Complement inhibitor, Complement receptor 1, cytokines, (e.g., epithelial Neutrophil Activating Peptide-78, GROα/MGSA, GROβ, GROγ, MIP-1α, MIP-1δ, MCP-1), Epidermal Growth Factor (EGF), Erythropoietin ("EPO"), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), Hirudin, Human serum albumin, Insulin, Insulin-like Growth Factor (IGF), interferons (e.g., IFN-α, IFN-β, IFN-γ), interleukins (e.g., IL-1, IL-2, IL-3, IL-4, IL-5, IL-6, IL-7, IL-8, IL-9, IL-10, IL-11, IL-12, etc.), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Pyrogenic exotoxins A, B, and C, Relaxin, Renin, SCF, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Superoxide dismutase (SOD), Toxic shock syndrome toxin (TSST-1), Thymosin alpha 1, Tissue plasminogen activator, Tumor necrosis factor beta (TNF beta), Tumor necrosis factor receptor (TNFR), Tumor necrosis factor-alpha (TNF alpha), Vascular Endothelial Growth Factor (VEGEF), Urokinase and many others.

One class of proteins that can be made using the compositions and methods for in vivo incorporation of unnatural amino acids described herein includes transcriptional modulators or a portion thereof. Example transcriptional modulators include genes and transcriptional modulator proteins that modulate cell growth, differentiation, regulation, or the like. Transcriptional modulators are found in prokaryotes, viruses, and eukaryotes, including fungi, plants, yeasts, insects, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA.

One class of proteins of the invention (e.g., proteins with one or more unnatural amino acids) include biologically active proteins such as cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Enzymes (e.g., industrial enzymes) or portions thereof with at least one unnatural amino acid are also provided by the invention. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Many of these proteins are commercially available (See, e.g., the Sigma BioSciences 2002 catalogue and price list), and the corresponding protein sequences and genes and, typically, many variants thereof, are well-known (see, e.g., Genbank). Any of them can be modified by the insertion of one or more unnatural amino acid according to the invention, e.g., to alter the protein with respect to one or more therapeutic, diagnostic or enzymatic properties of interest. Examples of therapeutically relevant properties include serum half-life, shelf half-life, stability, immunogenicity, therapeutic activity, detectability (e.g., by the inclusion of reporter groups (e.g., labels or label binding sites) in the unnatural amino acids), reduction of $LD_{50}$ or other side effects, ability to enter the body through the gastric tract (e.g., oral availability), or the like. Examples of diagnostic properties include shelf half-life, stability, diagnostic activity, detectability, or the like. Examples of relevant enzymatic properties include shelf half-life, stability, enzymatic activity, production capability, or the like.

A variety of other proteins can also be modified to include one or more unnatural amino acid using compositions and methods of the invention. For example, the invention can include substituting one or more natural amino acids in one or more vaccine proteins with an unnatural amino acid, e.g., in proteins from infectious fungi, e.g., *Aspergillus, Candida* species; bacteria, particularly *E. coli*, which serves a model for pathogenic bacteria, as well as medically important bacteria such as Staphylococci (e.g., *aureus*), or Streptococci (e.g., *pneumoniae*); protozoa such as sporozoa (e.g., *Plasmodia*), *rhizopods* (e.g., *Entamoeba*) and flagellates (*Trypanosoma, Leishmania, Trichomonas, Giardia*, etc.); viruses such as (+) RNA viruses (examples include Poxviruses e.g., vaccinia; Picornaviruses, e.g. polio; Togaviruses, e.g., rubella; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase are also suitable targets for unnatural amino acid modification.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein under "Mutagenesis and Other Molecular Biology Techniques" to include, e.g., one or more selector codon for the incorporation of an unnatural amino acid. For example, a nucleic acid for a protein of interest is mutagenized to include one or more selector codon, providing for the insertion of the one or more unnatural amino acids. The invention includes any such variant, e.g., mutant, versions of any protein, e.g., including at least one unnatural amino acid. Similarly, the invention also includes corresponding nucleic acids, i.e., any nucleic acid with one or more selector codon that encodes one or more unnatural amino acid.

To make a protein that includes an unnatural amino acid, one can use host cells and organisms that are adapted for the in vivo incorporation of the unnatural amino acid via orthogonal tRNA/RS pairs. Host cells are genetically engineered (e.g., transformed, transduced or transfected) with one or more vectors that express the orthogonal tRNA, the orthogonal tRNA synthetase, and a vector that encodes the protein to be derivatized. Each of these components can be on the same vector, or each can be on a separate vector, or two components can be on one vector and the third component on a second vector. The vector can be, for example, in the form of a plasmid, a bacterium, a virus, a naked polynucleotide, or a conjugated polynucleotide.

Defining Polypeptides by Immunoreactivity

Because the polypeptides of the invention provide a variety of new polypeptide sequences (e.g., polypeptides comprising unnatural amino acids in the case of proteins synthesized in the translation systems herein, or, e.g., in the case of the novel synthetases, novel sequences of standard amino acids), the polypeptides also provide new structural features which can be recognized, e.g., in immunological assays. The generation of antisera, which specifically bind the polypeptides of the invention, as well as the polypeptides which are bound by such antisera, are a feature of the invention. The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul, *Fundamental Immunology,* 4th Ed., 1999, Raven Press, New York, for antibody structure and terminology.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity. Additional details on proteins, antibodies, antisera, etc. can be found in International Publication Numbers WO 2004/094593, entitled "EXPANDING THE EUKARYOTIC GENETIC CODE;" WO 2002/085923, entitled "IN VIVO INCORPORATION OF UNNATURAL AMINO ACIDS;" WO 2004/035605, entitled "GLYCOPROTEIN SYNTHESIS;" and WO 2004/058946, entitled "PROTEIN ARRAYS."

Use of O-tRNA and O—RS and O-tRNA/O—RS Pairs

The compositions of the invention and compositions made by the methods of the invention optionally are in a cell. The O-tRNA/O—RS pairs or individual components of the invention can then be used in a host system's translation machinery, which results in an unnatural amino acid being incorporated into a protein. International Publication Number WO 2002/085923 by Schultz, et al., entitled "IN VIVO INCORPORATION OF UNNATURAL AMINO ACIDS," describes this process and is incorporated herein by reference. For example, when an O-tRNA/O—RS pair is introduced into a host, e.g., *Escherichia coli* or yeast, the pair leads to the in vivo incorporation of an unnatural amino acid, which can be exogenously added to the growth medium, into a protein, e.g., a myoglobin test protein or a therapeutic protein, in response to a selector codon, e.g., an amber nonsense codon. Optionally, the compositions of the invention can be in an in vitro translation system, or in a cellular in vivo system(s). Proteins with the unnatural amino acid can be used in any of a wide range of applications. For example, the unnatural moiety incorporated into a protein can serve as a target for any of a wide range of modifications, for example, crosslinking with other proteins, with small molecules such as labels or dyes and/or biomolecules. With these modifications, incorporation of the unnatural amino acid can result in improved therapeutic proteins and can be used to alter or improve the catalytic function of enzymes. In some aspects, the incorporation and subsequent modification of an unnatural amino acid in a protein can facilitate studies on protein structure, interactions with other proteins, and the like.

Photoregulation and Photocaging

Photoregulated amino acids (e.g., photochromic, photocleavable, photoisomerizable, etc.) can be used to spatially and temporally control a variety of biological process, e.g., by directly regulating the activity of enzymes, receptors, ion channels or the like, or by modulating the intracellular concentrations of various signaling molecules. See, e.g., Shigeri et al., *Pharmacol. Therapeut.,* 2001, 91:85; Curley, et al., *Pharmacol. Therapeut.,* 1999, 82:347; Curley, et al., *Curr. Op. Chem. Bio.,* 1999, 3:84; "Caged Compounds" *Methods in Enzymology*, Marriott, G., Ed, Academic Press, NY, 1998, V. 291; Adams, et al., *Annu. Rev. Physiol.,* 1993, 55:755+; and Bochet, et al., *J. Chem. Soc., Perkin* 1, 2002, 125. In various embodiments herein, the compositions and methods comprise photoregulated amino acids. For example, the invention provides orthogonal translation systems for the incorporation of the photoregulated unnatural amino acids o-nitrobenzyl-serine and O-(2-nitrobenzyl)-L-tyrosine (see, FIG. 1, and Examples 8 and 9).

"Photoregulated amino acids" are typically, e.g., photosensitive amino acids. Photoregulated amino acids in general are those that are controlled in some fashion by light (e.g., UV, IR, etc.). Thus, for example, if a photoregulated amino acid is incorporated into a polypeptide having biological activity, illumination can alter the amino acid, thereby changing the biological activity of the peptide. Some photoregulated amino acids can comprise "photocaged amino acids," "photosensitive amino acids," "photolabile amino acids," "photoisomerizable," etc. "Caged species," such as caged amino acids, or caged peptides, are those trapped inside a larger entity (e.g., molecule) and that are released upon specific illumination. See, e.g., Adams, et al., *Annu. Rev. Physiol.,* 1993, 55:755-784. "Caging" groups of amino acids can inhibit or conceal (e.g., by disrupting bonds which would usually stabilize interactions with target molecules, by changing the hydrophobicity or ionic character of a particular side chain, or by steric hindrance, etc.) biblogical activity in a molecule, e.g., a peptide comprising such amino acid. "Photoisomerizable" amino acids can switch isomer forms due to light exposure. The different isomers of such amino acids can end up having different interactions with other side chains in a protein upon incorporation. Photoregulated amino acids can thus control the biological activity (either through activation, partial activation, inactivation, partial inactivation, modified activation, etc.) of the peptides in which they are present. See Adams above and other references in this section for further definitions and examples of photoregulated amino acids and molecules.

A number of photoregulated amino acids are known to those in the art and many are available commercially. Methods of attaching and/or associating photoregulating moieties to amino acids are also known. Such photoregulated amino acids in general are amenable to various embodiments herein. It will be appreciated that while a number of possible photoregulating moieties, e.g., photocaging groups and the like, as well as a number of photoregulated amino acids are listed herein, such recitation should not be taken as limiting. Thus, the current invention is also amenable to photoregulating moieties and photoregulated amino acids that are not specifically recited herein.

As stated, a number of methods are optionally applicable to create a photoregulated amino acid. Thus, for example, a photoregulated amino acid, e.g., a photocaged amino acid can be created by protecting its α-amino group with compounds such as BOC (butyloxycarbonyl), and protecting the α-carboxyl group with compounds such as a t-butyl ester. Such protection can be followed by reaction of the amino acid side chain with a photolabile caging group such as 2-nitrobenzyl, in a reactive form such as 2-nitrobenzylchloroformate, α-carboxyl 2-nitrobenzyl bromide methyl ester, or 2-nitrobenzyl diazoethane. After the photolabile cage group is added, the protecting groups can be removed via standard procedures. See, e.g., U.S. Pat. No. 5,998,580.

As another example, lysine residues can be caged using 2-nitrobenzylchloroformate to derivatize the ϵ-lysine amino group, thus eliminating the positive charge. Alternatively, lysine can be caged by introducing a negative charge into a peptide (which has such lysine) by use of an α-carboxy 2-nitrobenzyloxycarbonyl caging group. Additionally, phosphoserine and phosphothreonine can be caged by treatment of the phosphoamino acid or the phosphopeptide with 1(2-nitrophenyl)diazoethane. See, e.g., Walker et al., *Meth Enzymol.* 172:288-301, 1989. A number of other amino acids are also easily amenable to standard caging chemistry, for example serine, threonine, histidine, glutamine, asparagine, aspartic acid and glutamic acid. See, e.g., Wilcox et al., *J. Org. Chem.* 55:1585-1589, 1990). Again, it will be appreciated that recitation of particular photoregulated (amino acids and/or those capable of being converted to photoregulated forms) should not necessarily be taken as limiting.

Amino acid residues can also be made photoregulated (e.g., photosensitive or photolabile) in other fashions. For example, certain amino acid residues can be created wherein irradiation causes cleavage of a peptide backbone that has the particular amino acid residue. For example a photolabile glycine, 2-nitrophenyl glycine, can function in such a manner. See, e.g., Davis, et al., 1973, *J. Med. Chem.,* 16:1043-1045. Irradiation of peptides containing 2-nitrophenylglycine will cleave the peptide backbone between the alpha carbon and the alpha amino group of 2-nitrophenylglycine. Such cleavage strategy is generally applicable to amino acids other than glycine, if the 2-nitrobenzyl group is inserted between the alpha carbon and the alpha amino group.

A large number of photoregulating groups, e.g., caging groups, and a number of reactive compounds used to covalently attach such groups to other molecules such as amino acids, are well known in the art. Examples of photoregulating (e.g., photolabile, caging) groups include, but are not limited to: o-nitrobenzyl-serine, O-(2-nitrobenzyl)-L-tyrosine, nitroindolines; N-acyl-7-nitroindolines; phenacyls; hydroxyphenacyl; brominated 7-hydroxycoumarin-4-ylmethyls (e.g., Bhc); benzoin esters; dimethoxybenzoin; meta-phenols; 2-nitrobenzyl; 1-(4,5-dimethoxy-2-nitrophenyl) ethyl (DMNPE); 4,5-dimethoxy-2-nitrobenzyl (DMNB); alpha-carboxy-2-nitrobenzyl (CNB); 1-(2-nitrophenyl)ethyl (NPE); 5-carboxymethoxy-2-nitrobenzyl (CMNB); (5-carboxymethoxy-2-nitrobenzyl)oxy) carbonyl; (4,5-dimethoxy-2-nitrobenzyl)oxy) carbonyl; desoxybenzoinyl; and the like. See, e.g., U.S. Pat. No. 5,635,608 to Haugland and Gee (Jun. 3, 1997) entitled. "α-carboxy caged compounds" *Neuro* 19, 465 (1997); *J Physiol* 508.3, 801 (1998); *Proc Natl Acad Sci USA* 1988 September, 85(17):6571-5; *J Biol Chem* 1997 Feb. 14, 272(7):4172-8; *Neuron* 20, 619-624, 1998; *Nature Genetics*, vol. 28:2001:317-325; *Nature*, vol. 392, 1998:936-941; Pan, P., and Bayley, H. "Caged cysteine and thiophosphoryl peptides" *FEBS Letters* 405:81-85 (1997); Pettit et al. (1997) "Chemical two-photon uncaging: a novel approach to mapping glutamate receptors" *Neuron* 19:465-471; Furuta et al. (1999) "Brominated 7-hydroxycoumarin-4-ylmethyls: novel photolabile protecting groups with biologically useful cross-sections for two photon photolysis" *Proc. Natl. Acad. Sci.* 96(4):1193-1200; Zou et al. "Catalytic subunit of protein kinase A caged at the activating phosphothreonine" *J. Amer. Chem. Soc.* (2002) 124:8220-8229; Zou et al. "Caged Thiophosphotyrosine Peptides" *Angew. Chem. Int. Ed.* (2001) 40:3049-3051; Conrad II et al. "p-Hydroxyphenacyl Phototriggers: The reactive Excited State of Phosphate Photorelease" *J. Am. Chem. Soc.* (2000) 122:9346-9347; Conrad II et al. "New Phototriggers 10: Extending the π,π* Absorption to Release Peptides in Biological Media" *Org. Lett.* (2000) 2:1545-1547; Givens et al. "A New Phototriggers 9: p-Hydroxyphenacyl as a C-Terminus Photoremovable Protecting Group for Oligopeptides" *J. Am. Chem. Soc.* (2000) 122:2687-2697; Bishop et al. "40-Aminomethyl-2,20-bipyridyl-4-carboxylic Acid (Abc) and Related Derivatives: Novel Bipyridine Amino Acids for the Solid-Phase Incorporation of a Metal Coordination Site Within a Peptide Backbone" *Tetrahedron* (2000) 56:4629-4638; Ching et al. "Polymers As Surface-Based Tethers with Photolytic triggers Enabling Laser-Induced Release/Desorption of Covalently Bound Molecules" *Bioconjugate Chemistry* (1996) 7:525-8; *BioProbes Handbook,* 2002 from Molecular Probes, Inc.; and *Handbook of Fluorescent Probes and Research Products*, Ninth Edition or Web Edition, from Molecular Probes, Inc, as well as the references herein. Many compounds, kits, etc. for use in caging various molecules are commercially available, e.g., from Molecular Probes, Inc. Additional references are found in, e.g., Merrifield, Science 232:341 (1986) and Corrie, J. E. T. and Trentham, D. R. (1993) In: Biological Applications of Photochemical Switches, ed., Morrison, H., John Wiley and Sons, Inc. New York, pp. 243-305. Examples of suitable photosensitive caging groups include, but are not limited to, 2-nitrobenzyl, benzoin esters, N-acyl-7-nitindolines, meta-phenols, and phenacyls.

In some embodiments, a photoregulating (e.g., caging) group can optionally comprise a first binding moiety, which can bind to a second binding moiety. For example, a commercially available caged phosphoramidite [1-N-(4,4'-Dimethoxytrityl)-5-(6-biotinamidocaproamidomethyl)-1-(2-nitrophenyl)-ethyl]-2-cyanoethyl-(N,N-diisopropyl)-phosphoramidite (PC Biotin Phosphoramadite, from Glen Research Corp., www.glenres.com) comprises a photolabile group and a biotin (the first binding moiety). A second binding moiety, e.g., streptavidin or avidin, can thus be bound to the caging group, increasing its bulkiness and its effectiveness at caging. In certain embodiments, a caged component comprises two or more caging groups each comprising a first binding moiety, and the second binding moiety can bind two or more first binding moieties simultaneously. For example, the caged component can comprise at least two biotinylated caging groups; binding of streptavidin to multiple biotin moieties on multiple caged component molecules links the caged components into a large network. Cleavage of the photolabile group attaching the biotin to the component results in dissociation of the network.

Traditional methods of creating caged polypeptides (including e.g. peptide substrates and proteins such as antibodies or transcription factors) include, e.g., by reacting a polypeptide with a caging compound or by incorporating a caged amino acid during synthesis of a polypeptide. See, e.g., U.S. Pat. No. 5,998,580 to Fay et al. (Dec. 7, 1999) entitled "Photosensitive caged macromolecules"; Kossel et al. (2001) *PNAS* 98:14702-14707; *Trends Plant Sci* (1999) 4:330-334; *PNAS* (1998) 95:1568-1573; *J. Am. Chem. Soc.* (2002) 124:8220-8229; *Pharmacology & Therapeutics* (2001) 91:85-92; and *Angew. Chem. Int. Ed. Engl.* (2001) 40:3049-3051. A photolabile polypeptide linker (e.g., for connecting a protein transduction domain and a sensor, or the like) can, for example, comprise a photolabile amino acid such as that described in U.S. Pat. No. 5,998,580.

Irradiation with light can, e.g., release a side chain residue of an amino acid that is important for activity of the peptide comprising such amino acid. Additionally, in some embodiments, uncaged amino acids can cleave the peptide backbone of the peptide comprising the amino acid and can thus, e.g., open a cyclic peptide to a linear peptide with different biological properties, etc.

Activation of a caged peptide can be done through destruction of a photosensitive caging group on a photoregulated amino acid by any standard method known to those skilled in the art. For example, a photosensitive amino acid can be uncaged or activated by exposure to a suitable conventional light source, such as lasers (e.g., emitting in the UV range or infrared range). Those of skill in the art will be aware of and familiar with a number of additional lasers of appropriate wavelengths and energies as well as appropriate application protocols (e.g., exposure duration, etc.) that are applicable to use with photoregulated amino acids such as those utilized herein. Release of photoregulated caged amino acids allows control of the peptides that comprise such amino acids. Such control can be both in terms of location and in terms of time. For example, focused laser exposure can uncage amino acids in one location, while not uncaging amino acids in other locations.

Those skilled in the art will appreciate a variety of assays can be used for evaluating the activity of a photoregulated amino acid, e.g., the assays described in the examples herein. A wide range of, e.g., cellular function, tissue function, etc. can be assayed before and after the introduction of a peptide comprising a photoregulated amino acid into the cell or tissue as well as after the release of the photoregulated molecule.

The compositions and methods herein can be utilized in a number of aspects. For example, photoregulated amino acids (e.g., in peptides) can deliver therapeutic compositions to discrete locations of a body since the release or activation/deactivation/etc. of the photoregulated amino acid can be localized through targeted light exposure, etc. It will also be appreciated that the methods, structures, and compositions of the invention are applicable to incorporation/use of photoregulated natural amino acids (e.g., ones with photoregulating moieties attached/associated with them).

Photochromic and photocleavable groups can be used to spatially and temporally control a variety of biological processes, either by directly regulating the activity of enzymes (see, e.g., Westmark, et al., *J. Am. Chem. Soc.* 1993, 115: 3416-19 and Hohsaka, et al., *J. Am. Chem. Soc.* 1994, 116: 413-4), receptors (see, e.g., Bartels, et al., *Proc. Natl. Acad. Sci. USA,* 1971, 68:1820-3; Lester, et al., *Nature* 1977, 266: 373-4: Cruz, et al., *J. Am. Chem. Soc.,* 2000, 122:8777-8; and, Pollitt, et al., *Angew. Chem. Int. Ed. Engl.,* 1998, 37:2104-7), or ion channels (see, e.g., Lien, et al., *J. Am. Chem. Soc.* 1996, 118:12222-3; Borisenko, et al., *J. Am. Chem. Soc.* 2000, 122:6364-70; and, Banghart, et al., *Nat. Neurosci.* 2004, 7:1381-6.), or by modulating the intracellular concentrations of various signaling molecules (see, e.g., Adams, et al., *Annu. Rev. Physiol.* 1993, 55:755-84). In general, this requires the chemical modification of either a protein or small molecule with a photoreactive ligand such as azobenzene or a nitrobenzyl group. The ability to genetically incorporate photoresponsive amino acids into proteins at defined sites directly in living organisms would significantly extend the scope of this technique. See, e.g., Wu, et al., *J. Am. Chem. Soc.* 2004, 126: 14306-7.

Kits

Kits are also a feature of the invention. For example, a kit for producing a protein that comprises at least one unnatural amino acid in a cell is provided, where the kit includes a container containing a polynucleotide sequence encoding an O-tRNA, and/or an O-tRNA, and/or a polynucleotide sequence encoding an O—RS, and/or an O—RS. In one embodiment, the kit further includes an unnatural amino acid such as p-ethylthiocarbonyl-L-phenylalanine, p-(3-oxobutanoyl)-L-phenylalanine, 1,5-dansyl-alanine, 7-amino-coumarin alanine, 7-hydroxy-coumarin alanine, o-nitrobenzyl-serine, O-(2-nitrobenzyl)-L-tyrosine, p-carboxymethyl-L-phenylalanine, p-cyano-L-phenylalanine, m-cyano-L-phenylalanine, biphenylalanine, 3-amino-L-tyrosine, bipyridylalanine, p-(2-amino-1-hydroxyethyl)-L-phenylalanine; p-isopropylthiocarbonyl-L-phenylalanine; 3-nitro-L-tyrosine or p-nitro-L-phenylalanine. In another embodiment, the kit further comprises instructional materials for producing the protein.

EXAMPLES

The following examples are offered to illustrate, but not to limit the claimed invention. One of skill will recognize a variety of non-critical parameters that may be altered without departing from the scope of the claimed invention.

Example 1

Orthogonal Translation Components for the in vivo Incorporation of 3-nitro-L-tyrosine into Proteins in *E. coli*

The present Example describes compositions and methods for the biosynthetic incorporation of 3-nitro-L-tyrosine (see, FIG. 1) into proteins using *E. coli* host cell translation machinery. Novel orthogonal tRNA/synthetase pairs derived from *M. jannaschii* were isolated that function in an *E. coli* host cell system.

Novel orthogonal synthetases were derived from *M. jannaschii* tyrosyl tRNA synthetase, and were used in conjunction with the previously described *M. jannaschii* suppressor tyrosyl-tRNA$_{CUA}$ (SEQ ID NO: 1). These new orthogonal pairs have no affinity or very low affinity for any of the common (i.e., naturally occurring) amino acids. The derived orthogonal tRNA synthetases selectively charge the amber suppressor tyrosyl-tRNA$_{CUA}$ with 3-nitro-L-tyrosine. The aminoacylated suppressor tRNA (i.e., the "charged" tRNA) is used as a substrate by endogenous *E. coli* translation apparatus to incorporate 3-nitro-L-tyrosine in response to a TAG amber stop codon (a selector codon) encountered in a transcript. The orthogonality of these tRNA/synthetase pairs ensures that neither the tRNA nor the synthetases cross react with endogenous *E. coli* tRNAs or synthetases and that the unnatural amino acid gets delivered only in response to TAG.

The novel synthetases were isolated using protocols previously described, see e.g., Alfonta et al., Journal of the American Chemical Society 125(48):14662-14663 (2003); and International Publication WO 2005/038002, published Apr. 28, 2005.

A library of *M. jannaschii* tyrosyl tRNA-synthetase mutants was generated by mutagenesis of the wild-type *M. jannaschii* tyrosyl tRNA-synthetase. The amino acid and polynucleotide sequences of the wild-type *M. jannaschii* tyrosyl tRNA-synthetase molecule are shown in Table 5 and provided in SEQ ID NOS: 3 and 4, respectively. The mutagenesis consisted of randomizing predicted active site residues based on the crystal structure of the homologous tyrosyl tRNA-synthetase from *Bacillus stearothermophilus.*

Following mutagenesis, the pool of synthetases in the mutant library was passed through five rounds of positive and negative selection. This selection yielded seven synthetase clones that had the ability to charge the O-tRNA with 3-nitro-L-tyrosine, denoted clones A through G. These selected synthetase clones were sequenced, and their amino acid sequences were determined, as follows.

TABLE 2

| *Methanococcus jannaschii* | Amino acid position | | | | | | |
|---|---|---|---|---|---|---|---|
| tyrosyl-tRNA synthetase | 32 | 67 | 70 | 155 | 158 | 167 | SEQ ID NO: |
| wild-type | Tyr | Ala | His | Gln | Asp | Ala | 3 |
| clone A | | Val | Val | | | | 7 |
| Clone B | | Val | Val | | | | 7 |
| Clone C | | Val | Val | | | | 7 |
| Clone D | Ser | Thr | Asn | | | Thr | 8 |
| Clone E | | Val | Val | | | | 7 |

TABLE 2-continued

| *Methanococcus jannaschii* tyrosyl-tRNA synthetase | Amino acid position 32 | 67 | 70 | 155 | 158 | 167 | SEQ ID NO: |
|---|---|---|---|---|---|---|---|
| Clone F | Ala | Pro | | | | Gly | 9 |
| Clone G | | Val | Val | | | | 7 |

Clones A, B, C, E and G all converged to the same mutant sequence. Clones D and F showed different sequences. The amino acid sequences of these mutant synthetases are provided in Table 5, SEQ ID NOS: 7-9).

Example 2

Orthogonal Translation Components for the In Vivo Incorporation of p-nitro-L-phenylalanine ($NO_2$-Phe) into Proteins in *E. coli*

This EXAMPLE describes the site-specific, genetically-programmed incorporation of p-nitro-L-phenylalanine (see, FIG. 1; also written $NO_2$-Phe) into proteins in *E. coli* using a novel orthogonal translation system.

The unnatural amino acid $NO_2$-Phe has been used as a photoaffinity labeling probe to study protein-receptor structure (Dong, *Mol. Pharmacol.* 2005, 69, 1892), and as a fluorescence quencher to investigate protease activity (Wang, *Biochem. Biophys. Res. Comm.* 1994, 201:835) and protein structure (Sisido, *J. Am. Chem. Soc.* 1998, 120:7520; 2002, 124:14586). This amino acid has been incorporated site-specifically into proteins with an in vitro biosynthetic method using three-base (Schultz, *Science* 1989, 244:182), four-base (M. Sisido) and five-base (M. Sisido, *Nucleic Acids Res.* 2001, 29, 3646) codons. However, this approach typically produces only small amounts of protein. Moreover, the method is limited due to the need of stoichiometric amounts of acylated tRNA and an inability to regenerate the aminoacyl tRNA. In view of these limitations, we developed a novel in vivo orthogonal translation system to incorporate the unnatural amino acid directly into proteins, as described below.

To genetically encode $NO_2$-Phe in *E. coli*, the specificity of an orthogonal *Methanococcus jannaschii* tyrosyl-tRNA synthetase (MjTyrRS) was altered so that the synthetase specifically charges the mutant tyrosine amber suppressor tRNA (mutRNA$_{CUA}^{Tyr}$) with the unnatural amino acid $NO_2$-Phe. The mutant synthetase was derived from the screening of a mutant MjTyrRS library. Positions for mutagenesis in that mutant library were chosen in view of the analysis of the crystal structure of a mutant MjTyrRS that selectively charges mutRNA$_{CUA}^{Tyr}$ with p-bromophenylalanine.

After several rounds of positive and negative selection using mutRNA$_{CUA}^{Tyr}$ and the mutant MjTyrRS library in the presence or absence of 1 mM of $NO_2$-Phe, respectively, a clone was evolved whose survival at high concentration of chloroamphenicol (90 μg/mL) was dependent on the presence of $NO_2$-Phe. Moreover, green fluorescence was only observed for the selected clone in the presence of $NO_2$-Phe with a T7/GFPuv reporter with an amber selector codon at sites within the reporter gene. This result suggests that the evolved synthetase has a higher specificity for $NO_2$-Phe than for any other natural amino acid. Sequencing of the clone revealed the following mutations in this evolved synthetase:

Tyr32→Leu
Glu107→Ser
Asp158→Pro
Ile159→Leu
His160→Asn
Leu162→Glu

The nucleotide sequence of this clone is provided in Table 5, SEQ ID NO: 11, and the corresponding amino acid sequence is provided in Table 5, SEQ ID NO: 10.

Figure 2:
FIG. 2 provides a photograph of a stained SDS-PAGE analysis of the Z-domain protein accumulated in the presence (lane 2) or absence (lane 3) of p-nitro-L-phenylalanine. Lane 1 contains molecular mass markers.
Figure 3:
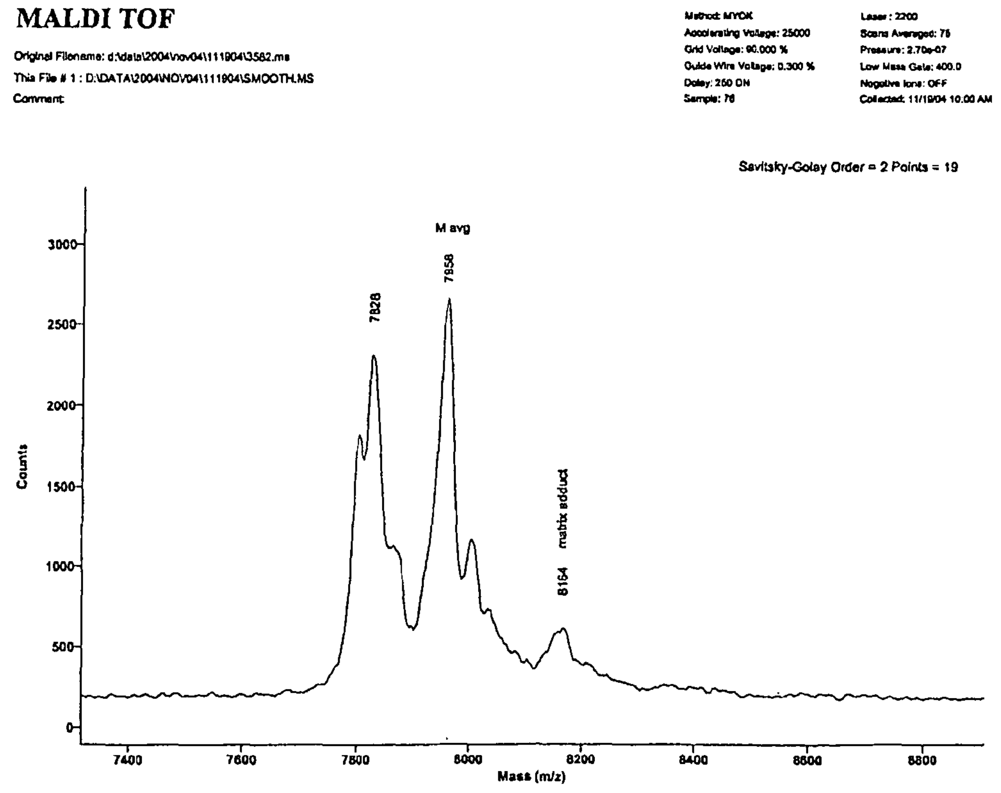
FIG. 3 provides a MALDI-TOF analysis of p-nitro-L-phenylalanine incorporated Z-domain protein. Expected mass: 7958, 7826 (exclusion of first methionine); observed: 7958, 7828.

To test the ability of the evolved synthetase (mut$NO_2$-PheRS) and mutRNA$_{CUA}^{Tyr}$ to selectively incorporate $NO_2$-Phe into proteins, an amber stop codon was substituted at a permissive site (Lys7) in the gene for the Z domain protein with a C-terminal hexameric His tag. Cells transformed with mut$NO_2$-PheRS, mutRNA$_{CUA}^{Tyr}$ and the Z domain gene were grown in the presence of 1 mM $NO_2$-Phe in GMML minimal media. The mutant protein was purified using an $Ni^{2+}$ affinity column and subsequently analysed by SDS-PAGE (see, FIG. 2) and MALDI-TOF (FIG. 3). The observed mass (m/e=7958) from MALDI-TOF analysis matches the expected mass (m/e=7958) for the $NO_2$-Phe incorporated Z-domain protein. No Z domain was obtained in the absence of $NO_2$-Phe (see, FIG. 1), indicating a very high fidelity in the incorporation of the unnatural amino acid.

Next, the feasibility of using the incorporated $NO_2$-Phe as a fluorescence quencher was examined. From the reported fluorophore counterparts of $NO_2$-Phe such as tyrosine, tryptophan, 1-pyrenylalanine, and β-anthraniloyl-l-α,β-diaminopropionic acid, the tryptophan/$NO_2$-Phe pair was picked to incorporate into a model GCN4 leucine zipper, which forms a parallel coiled-coil homodimer. The DNA binding region of the GCN4 gene (676-840 bp), which does not encode any tryptophan, was cloned from the yeast genome into the protein expression vector pET-26b. Subsequently, site-directed mutagenesis was utilized to substitute amino acids in this protein at specific sites with either tryptophan or the $NO_2$-Phe unnatural amino acid (encoded by the TAG selector codon). The GCN4 expression vector as well as a plasmid containing both mut$NO_2$-PheRS and mutRNA$_{CUA}^{Tyr}$ were cotransformed into *E. coli* BL21(DE3) cells, which were then grown in the presence of 1 mM $NO_2$-Phe in GMML minimal media. The accumulated GCN4p1 mutant proteins were purified using an $Ni^{2+}$ affinity column and confirmed by SDS-PAGE and MALDI-TOF analyses.

Figure 4A:
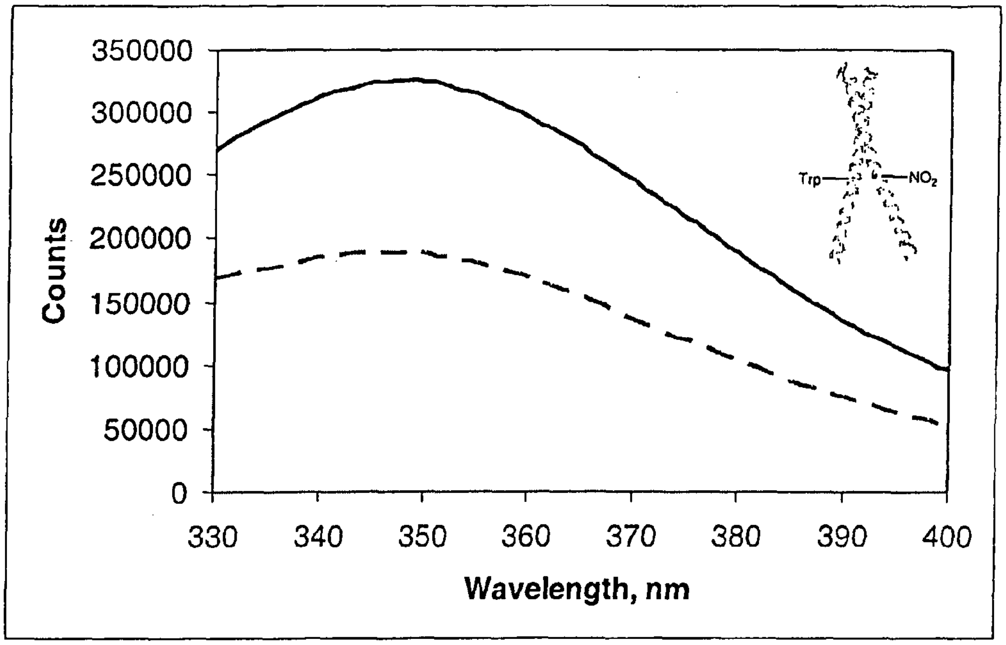
FIG. 4A provides a fluorescence spectra of the $^{22}$Trp GCN4p1 mutant (solid line) and the mixture of $^{22}$Trp and $^{22}$p-nitro-L-phenylalanine GCN4p1 mutants (broken line).
Figure 4B:
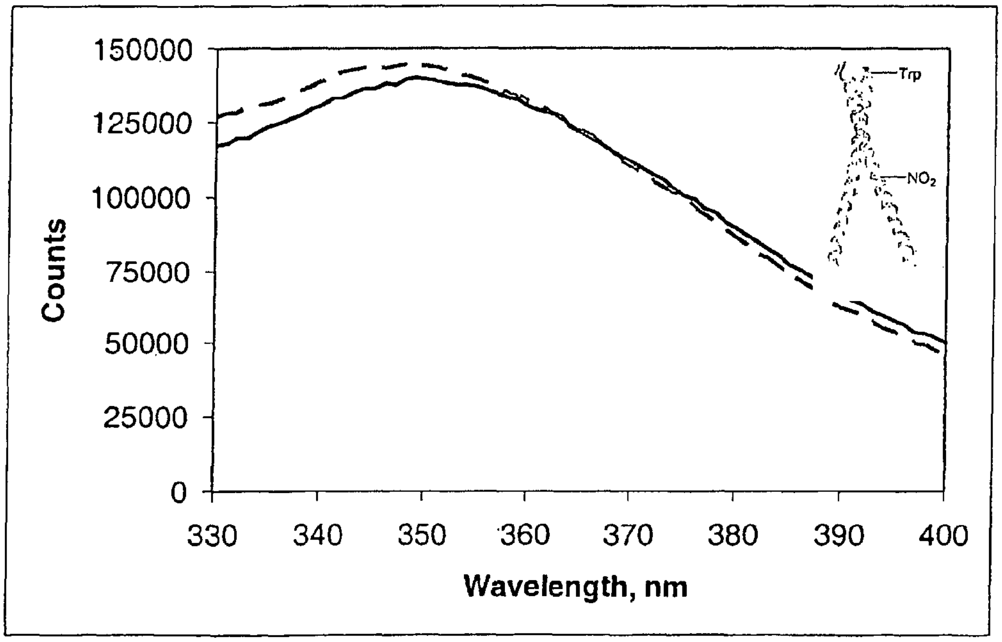
FIG. 4B provides a fluorescence spectra of the $^{55}$Trp GCN4 µl mutant (solid line) and the mixture of 55Trp and 22p-nitro-L-phenylalanine GCN4p1 mutants (broken line).

Steady-state fluorescence spectra were measured for the purified mutant proteins. FIG. 4A shows the fluorescence spectrum of the $^{22}$Trp mutant protein alone and that of the mixture of $^{22}$Trp and $^{22}NO_2$-Phe mutants, while FIG. 4B shows the fluorescence spectrum of the $^{55}$Trp mutant protein and the spectrum of the mixture of $^{55}$Trp and $^{22}NO_2$-Phe mutants. A distinct fluorescence quenching was observed in $^{22}$Trp/$^{22}NO_2$-Phe mutant pair; on the other hand, no significant fluorescence quenching was obtained for the $^{55}$Trp/$^{22}NO_2$-Phe mutant pair. This result clearly shows that the fluorophor/quencher interaction between Trp/$NO_2$-Phe pair is distance-dependant. Thus, this system can readily be applied to the study of protein folding and protein-protein as well as protein-ligand interactions.

Example 3

Orthogonal Translation Components for the in vivo Incorporation of the Redox Active Amino Acid 3-amino-L-tyrosine into Proteins in *E. coli*

The present Example describes compositions and methods for the biosynthetic incorporation of 3-amino-L-tyrosine (see, FIG. 1; also written $NH_2$—YRS) into proteins using *E. coli* host cell translation machinery. Novel orthogonal synthetase/tRNA pairs derived from *M. jannaschii* for incorporating this unnatural amino acid were isolated that function in an *E. coli* host cell system.

This unnatural amino acid side chain is readily oxidized to the corresponding semiquinone and quinone, thus can be used to both probe and manipulate electron transfer processes in proteins. The oxidized quinone form can efficiently conjugate with acrylamide through a hetero-Diels-Alder reaction. This last property provides another use, namely where the unnatural amino acid serves as a handle for chemical modification of proteins.

Novel orthogonal synthetase were derived from *M. jannaschii* tyrosyl tRNA synthetase, and were used in conjunction with the previously described *M. jannaschii* suppressor $tRNA_{CUA}$ (SEQ D NO: 1) This new orthogonal pair has no affinity or very low affinity for any of the common (i.e., naturally occurring) amino acids. The derived orthogonal tRNA synthetase selectively charges the amber suppressor $tRNA_{CUA}$ with 3-amino-L-tyrosine. The aminoacylated suppressor tRNA (i.e., the "charged" tRNA) is used as a substrate by endogenous *E. coli* translation apparatus to incorporate 3-amino-L-tyrosine in response to the TAG amber stop codon (a selector codon) encountered in a transcript. The orthogonality of these tRNA/synthetase pairs ensures that neither the tRNA nor the synthetases cross react with endogenous *E. coli* tRNAs or synthetases and that the unnatural amino acid gets delivered only in response to TAG.

The novel synthetases were isolated using protocols that have been previously described. A library of *M. jannaschii* tyrosyl tRNA-synthetase mutants was generated by mutagenesis of the wild-type *M. jannaschii* tyrosyl tRNA-synthetase. The mutagenesis consisted of randomizing predicted active site residues based on the crystal structure of other aminoacyl tRNA-synthetase molecules.

Following mutagenesis, the pool of synthetases in the mutant library was subjected to multiple rounds of positive and negative selection. This selection yielded one synthetase clone that had the ability to charge the O-tRNA with 3-amino-L-tyrosine. This selected synthetase clone has the amino acid sequence shown in Table 5, SEQ ID NO: 12; and has the polynucleotide sequence shown in Table 5, SEQ ID NO: 13.

Example 4

Orthogonal Translation Components for the in vivo Incorporation of the Phosphotyrosine mimic amino acid p-carboxymethyl-L-phenylalanine into Proteins in *E. coli*

The present Example describes compositions and methods for the biosynthetic incorporation of p-carboxymethyl-L-phenylalanine (see, FIG. 1; also written pCMF) into proteins using *E. coli* host cell translation machinery. Novel orthogonal synthetase/tRNA pairs derived from *M. jannaschii* for incorporating this unnatural amino acid were isolated that function in an *E. coli* host cell system.

This unnatural amino acid side chain can be used as a stable mimic for tyrosine phosphorylation. Tyrosine phosphorylation plays an important role in regulating cellular signal transduction in a broad range of cellular processes, such as cell growth, metabolic regulation, transcriptional regulation, and proliferation. Tyrosine phosphorylation is a reversible process in vivo. The tendency to dephosphorylate tyrosine by endogenous tyrosine phosphatases interferes with studies of the effects of tyrosine phosphorylation, thus hindering the interpretation of those studies. The amino acid p-carboxymethyl-L-phenylalanine is a phosphotyrosine mimic, is cell permeable, and furthermore, does not serve as a substrate for tyrosine phosphatases. This unnatural amino acid, when incorporated into proteins, can be used to generate protein mutants that are constitutively active. This unnatural amino acid can also be used in the context of phage display to select for inhibitors to protein tyrosine phosphatase from libraries of peptides containing p-carboxymethyl-L-phenylalanine.

Novel orthogonal synthetases were derived from *M. jannaschii* tyrosyl tRNA synthetase, and were used in conjunction with the previously described *M. jannaschii* suppressor $tRNA_{CUA}$. These new orthogonal pairs have no affinity or very low affinity for any of the common (i.e., naturally occurring) amino acids. The derived orthogonal tRNA synthetases selectively charge the amber suppressor $tRNA_{CUA}$ with p-carboxymethyl-L-phenylalanine. The aminoacylated suppressor tRNA (i.e., the "charged" tRNA) is used as a substrate by the endogenous *E. coli* translation apparatus to incorporate p-carboxymethyl-L-phenylalanine in response to a TAG amber stop codon (a selector codon) encountered in a transcript. The orthogonality of these tRNA/synthetase pairs ensures that neither the tRNA nor the synthetases cross react with endogenous *E. coli* tRNAs or synthetases and that the unnatural amino acid gets delivered only in response to TAG.

A search for orthogonal synthetases that have the ability to specifically charge an orthogonal tRNA with p-carboxymethyl-L-phenylalanine was undertaken. This search used protocols that have been previously described. A library of *M. jannaschii* tyrosyl tRNA-synthetase mutants was generated by mutagenesis of the wild-type *M. jannaschii* tyrosyl tRNA-synthetase, where the mutagenesis consisted of randomizing predicted active site residues based on the crystal structure of other aminoacyl tRNA-synthetase molecules.

Following mutagenesis, the mutant synthetase library was passed through multiple rounds of positive and negative selection. This selection yielded five synthetase clones that had the ability to charge the O-tRNA with p-carboxymethyl-L-phenylalanine. These synthetase clones were sequenced, and the amino acid sequences were determined, as shown in Table 5. The amino acid sequences of these O—RS clones is provided in SEQ ID NOS: 14, 16, 18, 20 and 22. The nucleotide sequences of these same O—RS clones is provided in SEQ ID NOS: 15, 17, 19, 21 and 23.

Example 5

Orthogonal Translation Components for in vivo Incorporation of the Hydrophobic Unnatural amino acid Biphenylalanine into Proteins in *E. coli*

The present Example describes compositions and methods for the biosynthetic incorporation of biphenylalanine (see, FIG. 1) into proteins using *E. coli* host cell translation machinery. Novel orthogonal synthetase/tRNA pairs derived from *M. jannaschii* for incorporating this unnatural amino acid were isolated that function in an *E. coli* host cell system.

The biphenylalanine unnatural amino acid has a large aromatic side chain. Hydrophobic interactions are one of the major forces that drive protein folding and protein-protein interactions (the other major forces are electrostatic interactions, hydrogen bonds, and van der waals forces). Hydrophobic interactions are involved in many biological events, such as protein transport across cell membranes, protein aggregation, and enzyme catalysis. The hydrophobicity of biphenylalanine is higher than any of the common 20 amino acids. Incorporation of biphenylalanine into proteins is a useful tool in studying and modulating intramolecular and intermolecular hydrophobic packing interactions in proteins.

Novel orthogonal synthetases were derived from *M. jannaschii* tyrosyl tRNA synthetase, and are used in conjunction with the previously described *M. jannaschii* suppressor $tRNA_{CUA}$. Theses new orthogonal pairs have no affinity or very low affinity for any of the common (i.e., naturally occurring) amino acids. The derived orthogonal tRNA synthetases selectively charge the amber suppressor $tRNA_{CUA}$ with biphenylalanine. The aminoacylated suppressor tRNA (i.e., the "charged" tRNA) is used as a substrate by the endogenous *E. coli* translation apparatus to incorporate biphenylalanine in response to the TAG amber stop codon (a selector codon) encountered in a transcript. The orthogonality of these tRNA/synthetase pairs ensures that neither the tRNA nor the synthetases cross react with endogenous *E. coli* tRNAs or synthetases and that the unnatural amino acid gets delivered only in response to TAG.

A search for orthogonal synthetases that have the ability to specifically charge an orthogonal tRNA with biphenylalanine was undertaken. This search used protocols that have been previously described. A library of *M. jannaschii* tyrosyl tRNA-synthetase mutants was generated by mutagenesis of the wild-type *M. jannaschii* tyrosyl tANA-synthetase, where the mutagenesis consisted of randomizing predicted active site residues based on the crystal structure of other aminoacyl tRNA-synthetase molecules.

Following mutagenesis, the mutant synthetase library was passed through multiple rounds of positive and negative selection. This selection yielded seven synthetase clones that had the ability to charge the O-tRNA with biphenylalanine. These synthetase clones were sequenced, as shown in Table 5. The amino acid sequences of these O—RS clones is provided in SEQ ID NOS: 24, 26, 28, 30, 32, 34 and 36. The corresponding nucleotide sequences of these same O—RS clones is provided in SEQ ID NOS: 25, 27, 29, 31, 33, 35 and 37.

Example 6

Orthogonal Translation Components for In Vivo Incorporation of the Metal-Chelating Unnatural Amino Acid Bipyridylalanine into Proteins in *E. coli*

The present Example describes compositions and methods for the biosynthetic incorporation of bipyridylalanine (see, FIG. 1) into proteins using the *E. coli* host cell translation machinery. Novel orthogonal synthetase/tRNA pairs derived from *M. jannaschii* for incorporating this unnatural amino acid were isolated that function in an *E. coli* host cell system.

The bipyridylalanine unnatural amino acid has the ability to chelate metal ions. The N,N-bidentate moiety of this amino acid side chain is a strong chelator to transition metal ions, such as $Cu^{2+}$, $Fe^{2+}$, $Ni^{2+}$, $Zn^{2+}$ and $Ru^{2+}$, etc. This metal chelating amino acid can be used to (1) introduce redox active or electrophilic metal ions into proteins, (2) form fluorescent metal ion complexes such as $Ru(bpy)_3$, or (3) mediate the metal ion dependent dimerization of proteins containing bipyridylalanine.

Novel orthogonal synthetases were derived from *M. jannaschii* tyrosyl tRNA synthetase, and were used in conjunction with the previously described *M. jannaschii* suppressor $tRNA_{CUA}$. The new orthogonal pairs have no affinity or very low affinity for any of the common (i.e., naturally occurring) amino acids. The derived orthogonal tRNA synthetase selectively charged the amber suppressor $tRNA_{CUA}$ with bipyridylalanine. The aminoacylated suppressor tRNA (i.e., the "charged" tRNA) is used as a substrate by the endogenous *E. coli* translation apparatus to incorporate bipyridylalanine in response to the TAG amber stop codon (a selector codon) encountered in a transcript. The orthogonality of these tRNA/synthetase pairs ensures that neither the tRNA nor the synthetases cross react with endogenous *E. coli* tRNAs or synthetases and that the unnatural amino acid gets delivered only in response to TAG.

A search for orthogonal synthetases that have the ability to specifically charge an orthogonal tRNA with bipyridylalanine was undertaken. This search used protocols that have been previously described. A library of *M. jannaschii* tyrosyl tRNA-synthetase mutants was generated by mutagenesis of the wild-type *M. jannaschii* tyrosyl tRNA-synthetase, where the mutagenesis consisted of randomizing predicted active site residues based on the crystal structure of other aminoacyl tRNA-synthetase molecules.

Following mutagenesis, the mutant synthetase library was passed through multiple rounds of positive and negative selection. This selection yielded two synthetase clones that had the ability to charge the O-tRNA with bipyridylalanine. These synthetase clones were sequenced, as shown in Table 5. The amino acid sequences of these O—RS clones is provided in SEQ ID NOS: 38 and 40. The corresponding nucleotide sequences of these same O—RS clones is provided in SEQ ID NOS: 39 and 41.

Example 7

Orthogonal Translation Components for In Vivo Incorporation of the Fluorescent Unnatural Amino Acid 1,5-Dansylalanine into Proteins in Yeast Host Cells The present Example describes compositions and methods for the biosynthetic incorporation of 1,5-dansylalanine (see, FIG. 1) into proteins using yeast host cell translation machinery. Novel orthogonal synthetase/tRNA pairs derived from *E. coli* for incorporating this unnatural amino acid were isolated that function in the yeast host cell system.

Fluorescence has become one of the most important detection signals in biotechnology due to its high sensitivity and safety of handling. Moreover, processes like fluorescence resonance energy transfer (FRET) or fluorescence polarization make possible the real time analysis of biomolecular binding events, movements or conformational changes. Current fluorescent methodology to study proteins in vivo often rely on fusion constructs with large fluorescent proteins. Alternatively, small organic labels can be used to minimize structural perturbation, but exhibit poor regioselectivity, are cytotoxic or demand introduction of dye binding protein motifs and are rather restricted to the protein surface. In contrast, a fluorescent amino acid does not necessarily contain groups with cytotoxic potential, its introduction is only a minor alteration of protein structure and specific labeling is possible at any position of the protein in vivo.

Figure 5:
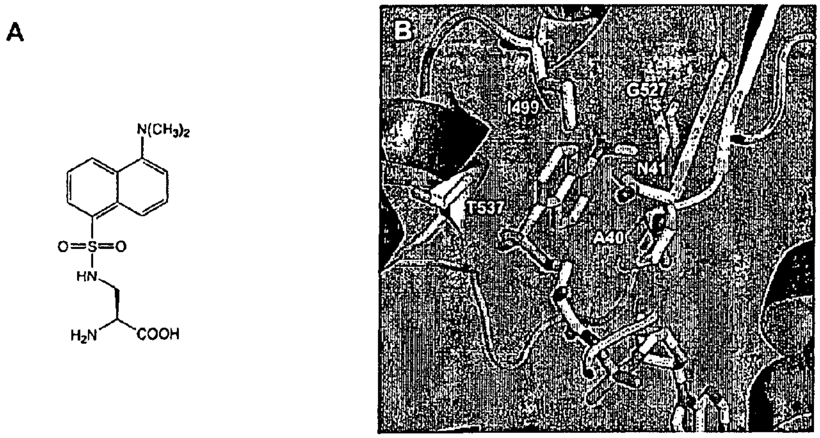
FIG. 5A provides the chemical structure of 1,5-dansylalanine.
FIG. 5B provides a model of the *Thermus thermophilus* leucyl-tRNA synthetase (LRS) active site with bound 1,5-dansylalanine-AMP-amide. Active site residues of mutant LRS clone B8 that are part of the randomized region are shown as sticks. The numbering corresponds to *E. coli* LRS.

The present invention provides orthogonal translation system components that incorporate the fluorescent amino acid 1,5-dansyl-modified alanine (see, FIG. 5A) in growing polypeptide chains in yeast. This unnatural amino acid can also be identified by its IUPAC nomenclature: 2-amino-3-(5-dimethylamino-naphthalene-1-sulfonylamino)-propionic acid. The dansyl chromophore has interesting spectral properties, including an exceptionally high separation of excitation and emission maxima (>200 nm) and a high dependence of emission intensity on the polarity of the environment. This makes it well suited to study protein conformational changes or binding events where the local protein environment and thus polarity is affected. Synthesis of the unnatural amino acid was achieved in a two-step procedure including coupling of N-Boc-aminoalanine to dansylchloride using triethylamine in dichloromethane and subsequent acidic deprotection with TFA in dichloromethane.

Novel synthetases for incorporating 1,5-dansylalanine were isolated using protocols previously described, see e.g., Wu et al., Journal of the American Chemical Society 126:14306-14307 (2004); and International Application No. PCT/US 2005/034002, filed Sep. 21, 2005, by Deiters et al. A mutant *E. coli* leucyl-tRNA synthetase clone (clone B8) that displayed initial charging activity was isolated from a randomized *E. coli* leucyl-tRNA synthetase library in a yeast host cell system. See, Table 5 and SEQ ID NOS: 42 and 43. The sites in the mutant *E. coli* leucyl-tRNA synthetase library were M40, L41, Y499, Y527 and H537. Additional mutations (caused during library construction) found in all clones throughout the library were H67R, N196T, R262A and S497C.

However, the B8 mutant *E. coli* synthetase exhibited background activity towards one or more natural amino acids with a weight similar to leucine as judged by MALDI TOF MS of the expressed model protein human superoxide dismutase bearing a permissive amber codon at position 33 (hSOD-33TAG-His6). Theoretical docking studies with dansylalanine-AMP amide and a crystal structure of the homologous leucyl-tRNA synthetase from *Thermus thermophilus* (*T. th.*) suggested formation of an enlarged binding pocket that binds the ligand by mainly hydrophobic interactions without participation of s-stacking to the naphtyl moiety (see, FIG. 5B).

A proofreading activity is present in *E. coli* leucyl-tRNA synthetase, and since activating and charging activity towards 1,5-dansylalanine was already evolved in the selected mutant, a strategy was devised that targeted the selective removal of activated or charged natural amino acids by remodelling the editing site. It was contemplated that the observed background was due to incorporation of leucine as suggested by MALDI TOF MS. Crystal structures of the homologous leucyl-tRNA synthetase from *T. th.* and mutational studies suggest that a simple steric block of unpolar amino acids towards the γ-methyl side chain prevents activated or charged leucine from binding to the hydrolytic site (Lincecum et al., Mol. Cell., 4:951-963 [2003]).

Figure 6:
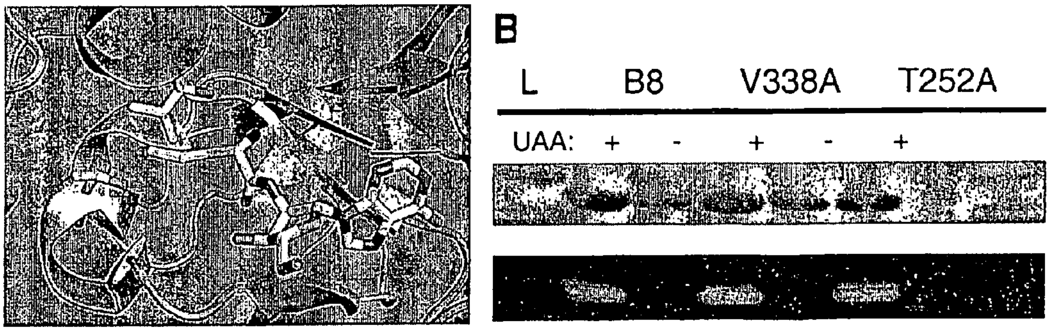
FIGS. 6A and 6B describe the redesign strategy of the mutant B8 leucyl-tRNA synthetase editing site.

To increase hydrolytic activity towards leucine, residues T252 and V338 in the *E. coli* synthetase editing domain were exchanged to alanine by Quikchange mutagenesis in order to enlarge the binding pocket (see, FIG. 6A). The V338A synthetase (see, Table 5, SEQ ID NOS: 46 and 47) did not exhibit significant difference in expression studies using the model protein human superoxide dismutase (hSOD), whereas the T252A synthetase (see, Table 5, SEQ ID NOS: 44 and 45) showed a marked reduction in background (see, FIG. 6B). High selectivity of this mutant was further confirmed by MALDI TOF MS of hSOD-33TAG-His6.

Thus, the invention provides novel mutant tRNA-synthetases derived from *E. coli* leucyl-tRNA synthetase that have the ability to biosynthetically incorporate 1,5-dansylalanine into proteins using yeast (e.g., *Saccharomyces cerevisiae*) host cell translation machinery.

Example 8

Orthogonal Translation Components for in vivo Incorporation of the Photocaged Unnatural Amino Acid o-nitrobenzylserine into Proteins in Yeast Host Cells The present Example describes compositions and methods for the biosynthetic incorporation of o-nitrobenzylserine (see, FIG. 1) into proteins using yeast host cell translation machinery. Novel orthogonal synthetase/tRNA pairs derived from *E. coli* for incorporating this unnatural amino acid were isolated that function in the yeast host cell system.

The investigation of function of a specific gene in living organisms mostly relies on its deactivation or activation and studying of the resulting effects. Classic genetic knockout studies target the gene on the DNA level, leading to inactivation of the production of all encoded protein variants and do not allow real time investigation of resulting effects. In recent years, the use of small organic molecules has dramatically increased the specificity of gene deactivation. Using such tools, a single protein variant (or a single domain of that variant) can be targeted and effects can be investigated in real time after addition of the molecule.

The introduction of photocaged amino acids into proteins as transient, activatable knockouts can further increase the accuracy of such studies. Using chemical knockout strategies, diffusion time of the compound to its target protein can be rate limiting and it is only possible to investigate a whole cell. In contrast, photouncaging of specific amino acids can be performed on a rapid timescale and specific compartments of a cell can be investigated using pulsed and highly focused laser light.

A mutant *E. coli* leucyl-tRNA synthetase has previously been evolved from a mutant *E. coli* leucyl-tRNA synthetase library in yeast host cells that specifically recognizes the caged cysteine derivative o-nitrobenzylcysteine, also written o-NBC (see, Wu et al., Journal of the American Chemical Society 126:14306-14307 (2004); and International Application No. PCT/US 2005/034002, filed Sep. 21, 2005, by Deiters et al.). To expand the applicability of this approach, the evolution of an aminoacyl-tRNA synthetase specifically incorporating o-nitrobenzylserine (oNBS) was contemplated. When genetically incorporated into proteins, this photocaged unnatural amino acid could be used to photoregulate any function involving serine residues, for example but not limited to, serine phosphorylation by kinases, representing one of the most important chemical markers in signal transduction pathways. The oNBS amino acid can be synthesized by coupling o-nitrobenzylic bromide to Boc-N-Ser-O-tBu in DMF using NaH as base and subsequent acidic deprotection with TFA in methylenechloride under presence of triethylsilane as scavenger with 52% overall yield.

The mutant *E. coli* leucyl-tRNA synthetase evolved for oNBC incorporation (clone 3H11; see Table 5, SEQ ID NOS: 48 and 49) already exhibited some limited activity for incorporating oNBS, but with about twofold reduced efficiency compared to an oNBC amino acid. To evolve a more efficient oNBS translation system, the selected clone 3H11 synthetase was diversified by error prone PCR, again using three different mutagenicities, to introduce one, two or five mutations per gene, yielding an overall diversity of $1\times10^7$ clones. The positions in the leucyl-tRNA-synthetase enzyme that were targeted for randomization were M40, 141, Y499, Y527 and H537. The protocols used herein follow the general methodologies described in the art, e.g., Wu et al., Journal of the American Chemical Society 126:14306-14307 (2004); and International Application No. PCT/US 2005/034002, filed Sep. 21, 2005, by Deiters et al.

Figure 7:
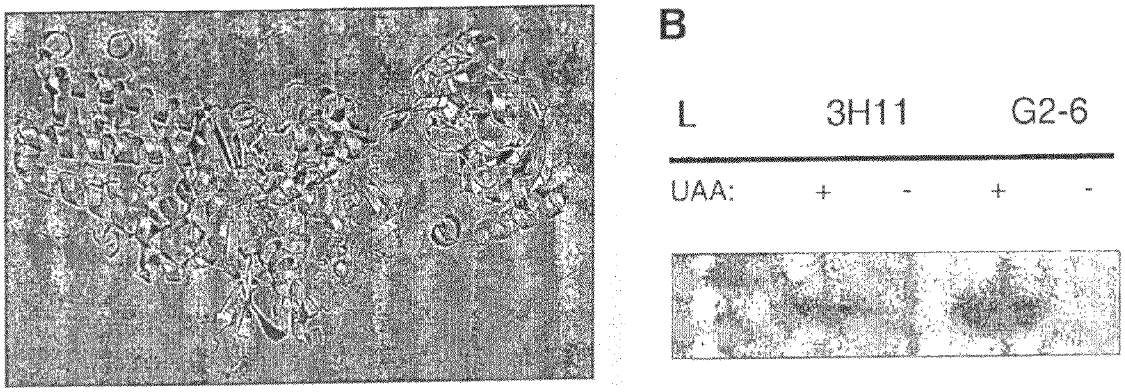
FIGS. 7A and 7B describe the enhanced amber suppression efficiency of *E. coli* leucyl-tRNA synthetase clone G2-6, generated by error prone PCR and selection.

Screening of the new mutant synthetase library yielded an improved synthetase (clone G2-6) with twofold enhanced oNBS incorporation efficiency. Sequencing of the G2-6 clone identified five additional mutations throughout the enzyme in comparison to the initial 3H11 synthetase starting material (positions S31G, T247A, T248S, M617I and V673A). Additional mutations (caused during library construction) found in all clones throughout the library were also observed as follows: H67R, N196T, R262A and S497C. The complete amino acid and nucleotide sequences of this synthetase isolate are provided in Table 5, SEQ ID NOs: 50 and 51. This improved mutant synthetase is illustrated schematically in FIG. 7A, and the improvement in oNBS incorporation activity in the G2-6 synthetase mutant is illustrated experimentally in FIG. 7B. The selective incorporation of oNBS was further confirmed by MALDI MS again using hSOD as model system for expression studies.

Thus, the invention provides a novel mutant tRNA-synthetase derived from *E. coli* leucyl-tRNA synthetase that has the ability to biosynthetically incorporate oNBS into proteins using yeast (e.g., *Saccharomyces cerevisiae*) host cell translation machinery.

Example 9

Orthogonal Translation Components for in vivo Incorporation of the Photocaged Unnatural Amino Acid O-(2-nitrobenzyl)-L-tyrosine into Proteins in *E. coli*

The present Example describes compositions and methods for the biosynthetic incorporation of O-(2-nitrobenzyl)-L-tyrosine (see, FIG. 1) into proteins using Archae synthetase species and *E. coli* host cell translation machinery. Novel orthogonal synthetase/tRNA pairs derived from *M. jannaschii* for incorporating this unnatural amino acid were isolated that function in the *E. coli* host cell system.

"Caged proteins" are modified proteins whose biological activity can be controlled by light, usually by photolytic conversion from an inactive to an active form. This is particularly useful since irradiation can be easily controlled in timing, location and amplitude, enabling detailed studies of protein function (for reviews, see Shigeri et al., *Pharmacol. Therapeut.* 2001, 91:85; Curley and Lawrence *Pharmacol. Therapeut.* 1999, 82:347; Curley and Lawrence, *Curr. Op. Chem. Bio.* 1999, 3:84; "Caged Compounds", *Methods in Enzymology*; Marriott, G., Ed.; Academic Press: New York, 1998; V. 291; and Adams and Tsien, *Annu. Rev. Physiol.* 1993, 55:755).

The most common caging groups are 2-nitrobenzyl groups (see, Bochet, *J. Chem. Soc., Perkin* 12002, 125; Givens et al., *Methods in Enzymology* 1998, 291, 1; and Pillai, *Synthesis* 1980, 1), which are installed on hydroxy, carboxy, thio, or amino groups of polypeptides or proteins and are readily cleaved upon irradiation with non-photodamaging UV light. Previously, caged proteins were produced by chemical modification of isolated proteins without positional control on the caging group installation and also mostly resulting in the incorporation of multiple caging groups (e.g., Self and Thompson, *Nature Med.* 1996, 2, 817). Other examples employ the in vitro incorporation of a caged amino acid using a nonsense codon suppression technique (see, Philipson et al., *Am. J. Physiol. Cell. Physiol.* 2001, 281, C195; Pollitt and Schultz *Angew. Chem. Int. Ed.* 1998, 37, 2105; Cook et al., *Angew. Chem. Int. Ed.* 1995, 34, 1629). Since the aminoacylated-tRNA has to be synthesized chemically, only small quantities of protein are accessible and in vivo studies are limited.

The use of orthogonal translation system technology has overcome the inherent limitations in these technologies. Using cellular systems, non-natural amino acids can be site-specifically incorporated with high translational fidelity into proteins in vivo by addition of new components to the translational machinery of *E. coli* (for review, see, for example, Wang and Schultz, *Angew. Chem. Int. Ed.* 2004, 44, 34; Cropp and Schultz, *Trend. Gen.* 2004, 20, 625; and Wang and Schultz, *Chem. Commun.* 2002, 1).

The present Example describes the addition of a photocaged tyrosine, O-(2-nitrobenzyl)-L-tyrosine (see FIG. 1), to the genetic code of *E. coli*. Tyrosine is an important amino acid in protein tyrosine kinase and phosphatase substrates, it is an essential residue in several enzyme active sites, and it is often located at protein-protein interfaces.

Figure 8:
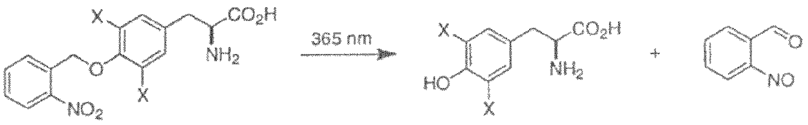
FIG. 8 provides a schematic representation of the photo-decaging (photoactivation) of the caged tyrosine molecule O-(2-nitrobenzyl)-L-tyrosine by irradiation at 365 nm, resulting in cleavage of the benzylic CO-bond and rapid formation of the decaged amino acid.

Irradiation of O-(2-nitrobenzyl)-L-tyrosine (synthesized from L-tyrosine as described in Miller et al., *Neuron* 1998, 20, 619) at 365 nm induces cleavage of the benzylic CO-bond and rapid formation of the decaged amino acid ($t_{1/2}$=4 min, see supporting information), as illustrated schematically in FIG. 8.

Figure 9:
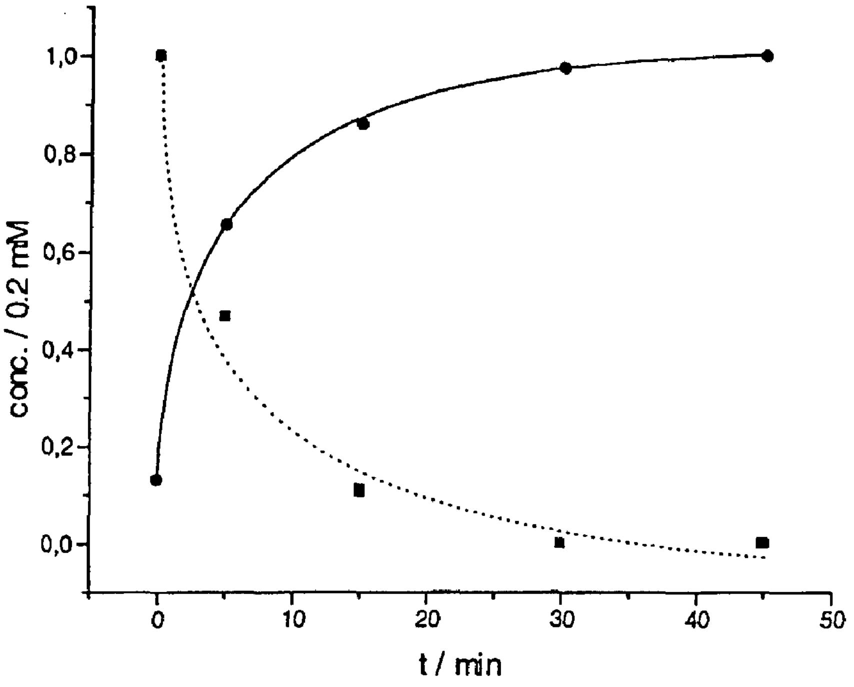
FIG. 9 provides concentration curve assays illustrating the experimentally observed photodecaging (photoactivation) of the caged tyrosine molecule O-(2-nitrobenzyl)-L-tyrosine. Photodecaging of O-(2-nitrobenzyl)-L-tyrosine was illustrated by irradiation of a 0.2 mM amino acid solution in water using a handheld UV lamp (365 nm at 10 mm distance). Aliquots were taken at specific time points and analyzed by LC/MS. The concentrations of O-(2-nitrobenzyl)-L-tyrosine (squares) and the corresponding decaged species (circles) are shown.

Photodecaging of O-(2-nitrobenzyl)-L-tyrosine can be experimentally observed, as illustrated in the experimental results shown in FIG. 9. As shown in this figure, the photodecaging of O-(2-nitrobenzyl)-L-tyrosine was studied by irradiation of a 0.2 mM solution in water (one well of a six-well plate) using a handheld UV lamp (365 nm at 10 mm distance). Aliquots were taken at specific time points and analyzed by LC/MS. The concentrations of O-(2-nitrobenzyl)-L-tyrosine (squares) and the decaged species (circles) are shown in the figure. 50% decaging was achieved after approximately four minutes.

The *Methanococcus jannaschii* tyrosyl tRNA-synthetase (MjYRS) was used as a starting point for the generation of an orthogonal synthetase that accepts O-(2-nitrobenzyl)-L-tyrosine, but not any of the 20 common amino acids as a substrate. MjYRS does not aminoacylate any endogenous *E. coli* tRNAs with tyrosine, but aminoacylates a mutant tyrosine amber suppressor ($mutRNA_{CUA}$). To alter the specificity of the MjYRS to selectively recognize O-(2-nitrobenzyl)-L-tyrosine, a library of approximately $10^9$ YRS mutants was generated by randomizing six residues (Tyr32, Leu65, Phe108, Gln109, Asp158 and Leu162) in the tyrosine binding pocket, based on the crystal structure of the *M. jannaschii* YRS/$tRNA^{Tyr}$-tyrosine complex (Zhang et al., *Prot. Sci.* 2005, 14, 1340; Kobayashi et al., *Nat. Struct. Biol.* 2003, 10, 425). These six residues were chosen based on their close proximity to the para position of the phenyl ring of tyrosine, among which Tyr32 and Asp158 form hydrogen bonds with the hydroxyl group of tyrosine. Mutations of these residues are expected to expand the substrate binding pocket of the synthetase to specifically recognize O-(2-nitrobenzyl)-L-tyrosine and other unnatural amino acids.

Active synthetase variants were screened from the mutant MjYRS library using chloramphenicol acetyl transferase (CAT) and barnase reporter systems for positive and negative selections, respectively. After five rounds of alternating positive and negative selection, 96 clones were screened for a phenotype in the presence and absence of O-(2-nitrobenzyl)-L-tyrosine. Three synthetases were further characterized using an in vivo assay based on suppression of the Asp112TAG codon in the CAT gene. *E. coli* expressing the three MjYRS/$mutRNA_{CUA}$ pairs survived on chloramphenicol with $IC_{50}$ values of 110 mg/L and less than 10 mg/L in the presence and absence of O-(2-nitrobenzyl)-L-tyrosine (1 mM), respectively. The large difference in chloramphenicol resistance suggests a substantial in vivo specificity of the selected synthetase/tRNA pairs for insertion of O-(2-nitrobenzyl)-L-tyrosine over all 20 natural amino acids in response to an amber codon.

Nucleic acids encoding these three O-(2-nitrobenzyl)-L-tyrosine-tRNA synthetases were sequenced, and their amino acid sequences were deduced. The complete amino acid sequences of the three ONBY synthetase clones is provided in Table 5, SEQ ID NOs: 52-54. The results of this sequencing are shown in Table 3.

TABLE 3

| synthetase species | Amino Acid Position (mutant codon) | | | | | |
|---|---|---|---|---|---|---|
| MjYRS | 32 | 65 | 108 | 109 | 158 | 162 |
| wild-type RS | Tyr | Leu | Phe | Gln | Asp | Leu |
| ONBY RS-1 | Gly (GGG) | Gly (GGT) | Ala (GCG) | Arg (CGT) | Glu (GAG) | Tyr (TAT) |
| ONBY RS-2 | Ala (GCT) | Gly (GGG) | Cys (TGT) | Asp (GAT) | Ala (GCG) | Gly (GGT) |
| ONBY RS-3 | Gly (GGG) | Gly (GGT) | Glu (GAG) | Gln (CAG) | Ser (TCG) | Glu (GAG) |

Conceivably, the mutations Tyr324Gly32/Ala32 and Asp158→Glu158, Ala158, or Ser158 result in the loss of hydrogen bonds between Tyr32, Asp158, and the natural substrate tyrosine, thus disfavoring its binding.

To measure the fidelity and efficiency of the three ONB-MjYRSs, O-(2-nitrobenzyl)-L-tyrosine was incorporated in response to an amber codon at position four in a C-terminally hexahistidine tagged mutant sperm whale myoglobin gene. To express recombinant protein, plasmid pBAD/JYAMB-4TAG (which encodes the mutant sperm whale myoglobin gene with an arabinose promoter and an rrnB terminator; the tyrosyl $tRNA_{CUA}$ on an lpp promoter and an rrnC terminator; and a tetracycline resistance marker) was co-transformed with a pBK vector (encoding the mutant synthetase and a kanamycin resistance gene) into DH10B *E. coli* in the presence of both the synthetase/$mutRNA_{CUA}$ pair and O-(2-nitrobenzyl)-L-tyrosine (1 mM). Cells were amplified in Luria-Bertani media (5 mL) supplemented with tetracycline (25 mg/L) and kanamycin (30 mg/L), washed with phosphate buffer, and used to innoculate 500 mL of liquid glycerol minimal media (GMML; glycerol minimal media supplemented with 0.3 mM leucine) containing the appropriate antibiotics, photocaged tyrosine (1 mM), and arabinose (0.002%). Cells were grown to saturation and then harvested by centrifugation.

Figure 10:
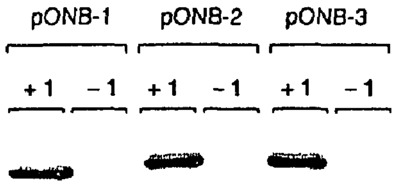
FIG. 10 provides a Gelcode Blue stained SDS-PAGE of myoglobin 74TAG expressed in the presence or absence of O-(2-nitrobenzyl)-L-tyrosine using three different mutant synthetases.

Purified mutant myoglobin protein was obtained by Ni-NTA affinity chromatography with a yield of approximately 2-3 mg/L and judged to be >90% homogeneous by SDS-PAGE and Gelcode Blue staining. The yield is comparable to myoglobin expression using the wild type MjYRS/mutR-$NA_{CUA}$ pair suppressing the same amber codon. No myoglobin was detectable if the unnatural amino acid was withheld or in the presence of 1 mM tyrosine, revealing a very high selectivity of all three synthetases for O-(2-nitrobenzyl)-L-tyrosine (see, FIG. 10).

Figures 11A, 11B:
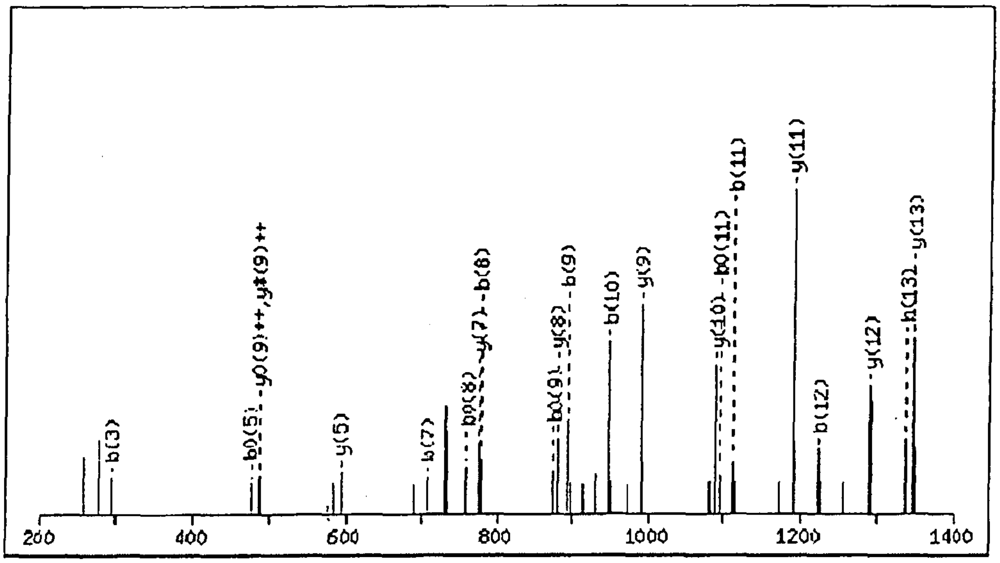
FIGS. 11A and 11B provide an LC-MS/MS analysis of 74TAG mutant myoglobin protein showing tyrosine at position 74 (tryptic peptide HGVTVLTALGYILK).

To further confirm the identity of the site-specifically photocaged protein, a different myoglobin mutant with an amber codon at Gly74 (due to superior mass spectrometry properties) was expressed in the presence of pONB-MjYRS-1, $tRNA_{CUA}$, and O-(2-nitrobenzyl)-L-tyrosine (1 mM). The myoglobin mutant 74TAG was expressed, under the same conditions as the 4TAG mutant, using the synthetase pONB-1 in presence of O-(2-nitrobenzyl)-L-tyrosine (1 mM) and purified by nickel affinity column. Protein bands were visualized by Gelcode Blue staining of an SDS-PAGE gel and excised from the polyacrylamide gel. The gel pieces were sliced into 1.5-mm cubes and subjected to trypsin hydrolysis essentially as described (Shevchenko et al., *Anal. Chem.* 1996, 68, 850-858). Tryptic peptides were analyzed by liquid chromatography tandem mass spectrometry (LC-MS/MS) analysis performed on a Finnigan LCQ Deca ion trap mass spectrometer (Thermo Finnigan) fitted with a Nanospray HPLC (Agilent 1100 series). The precursor ions corresponding to the singly and doubly charged ions of the peptide HGVTVLTALGJILK containing the unnatural amino acid (denoted J) were separated and fragmented with an ion trap mass spectrometer. The LC-MS/MS analysis shows Tyrosine at position 74 (tryptic peptide HGVTVLTALGYILK). The fragment ion masses could be assigned, indicating the site-specific incorporation of tyrosine (3) at position 74 (see, FIGS. 11A and 11B). The detection of Tyr74 is most likely due to a fragmentation of the labile benzylether in O-(2-nitrobenzyl)-L-tyrosine during MS analysis.

Figures 12A, 12B:
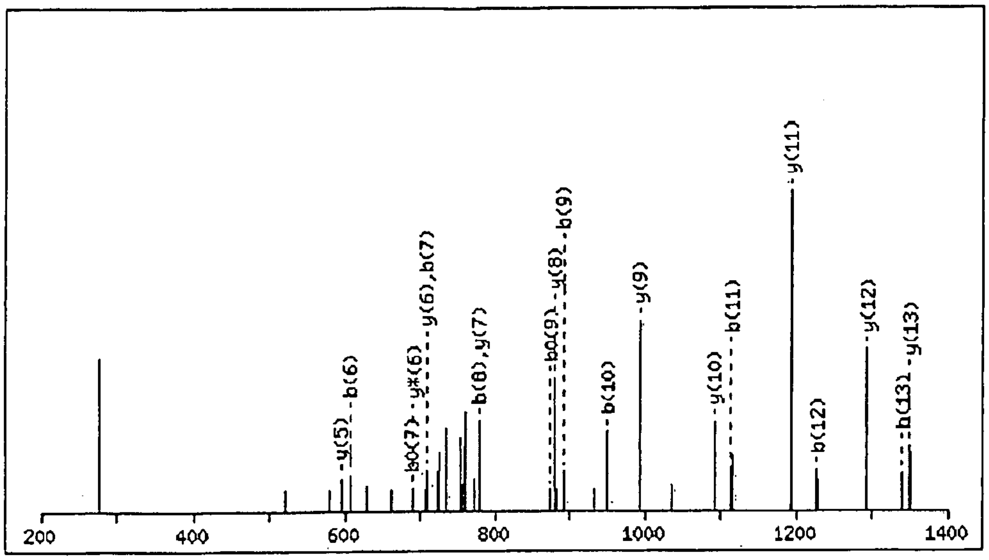
FIGS. 12A and 12B provide an LC-MS/MS analysis similar to that described in FIGS. 11A and 11B, except where the analysis uses a deuterated O-(2-nitrobenzyl)-L-tyrosine, where J denotes the deuterated amino acid (tryptic peptide HGVTVLTALGJILK).

To confirm the previous incorporation of the caged amino acid O-(2-nitrobenzyl)-L-tyrosine, the deuterated derivative was synthesized and used in an expression of the same myoglobin mutant under identical conditions. The protein was then trypsinized and subjected to an analysis by mass spectrometry. An assignment of the fragment ion masses revealed $d_2$-tyrosine incorporation at position 74 of myoglobin, unambiguously demonstrating the incorporation of the unnatural amino acid 2 (see FIGS. 12A and 12B). The LC MS/MS analysis did not indicate incorporation of any natural amino acid at this position, providing additional evidence for the high fidelity of the evolved synthetase.

Additionally, the in vivo photochemical activation of a protein having O-(2-nitrobenzyl)-L-tyrosine incorporated can be demonstrated by employing lacZ as a reporter gene. *E. coli* β-galactosidase displays an essential tyrosine at position 503 (Juers et al., *Biochemistry* 2001, 40, 14781; Penner et al., *Biochem. Cell Biol.* 1999, 77, 229). The corresponding codon was mutated to an amber stop codon TAG for the incorporation of the caged O-(2-nitrobenzyl)-L-tyrosine. The β-galactosidase is monitored before and after tyrosine decaging. The β-galactosidase activity is restored following irradiation in vivo.

Example 10

Orthogonal Translation Components for In Vivo Incorporation of the Unnatural Amino Acid p-cyanophenylalanine into Proteins in *E. coli*

The present Example describes compositions and methods for the biosynthetic incorporation of p-cyanophenylalanine (see, FIG. 1; also written 4-cyanophenylalanine) into proteins using *E. coli* host cell translation machinery. Novel orthogonal synthetase/tRNA pairs derived from *M. jannaschii* for incorporating this unnatural amino acid were isolated that function in an *E. coli* host cell system.

The cyano group is an excellent local environment IR probe, as its CN stretching vibration ($\nu_2$) undergoes a frequency shift on the order of ten wave numbers when moved from hydrophobic to hydrophilic surroundings (Getahun et al., "Using Nitrile-Derivatized Amino Acids as Infrared Probes of Local Environment," *JACS* 125, 405-411 [2003]). Para (4-position) and meta (3-position) cyanophenylalanine are thus useful in studying an assortment of protein properties including protein-protein binding, protein conformation, and hydrophobic collapse.

Para and meta forms of cyanophenylalanine can exist in both polar and hydrophobic environments while in a peptide chain, and their effects on conformation are negligible. Thus, either is likely to reside in the same environment as the wild-type residue it replaces in a protein or peptide. Further, the compounds' CN stretching vibration is narrow, does not overlap with any other protein absorptions, is largely decoupled from the protein's other vibrations, and is quite sensitive to changes in solvent polarity. For these reasons, both are excellent tools for peptide conformational studies.

Aromatic Nitriles as Local Environment IR Probes in Small Peptides

Figure 13:
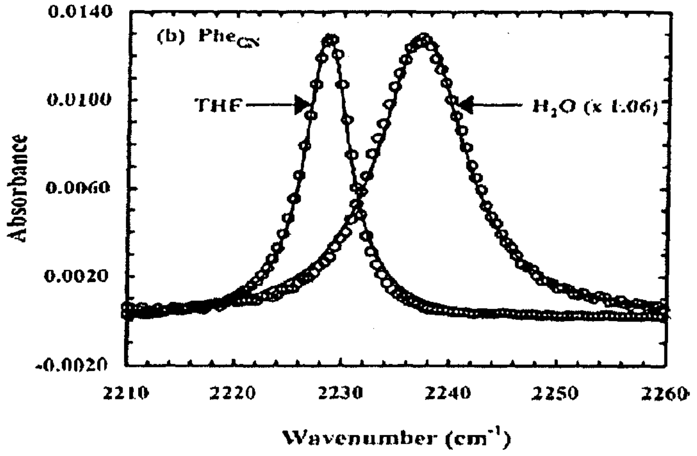
FIG. 13 provides superposition graphs of a para-cyanophenylalanine IR spectra taken in THF and water.

Getahun and coworkers (Getahun et al., "Using Nitrile-Derivatized Amino Acids as Infrared Probes of Local Environment," *JACS* 125, 405-411 [2003]) have shown (see, FIG. 13) that the cyano stretching vibration of para-cyanophenylalanine is ten wavenumbers higher in water than in THF. When the 14-residue amphipathic peptide mastoparan x (MPx) is mutated to incorporate para-cyanophenylalanine into its lipid binding portion, the cyano stretch is at 2229.6 $cm^{-1}$ when MPx is bound to a POPC lipid bilayer. In water, the MPx PheCN mutant's CN stretching vibration occurs at 2235.7 $cm^{-1}$. In sum, the cyano stretch in a hydrated peptide is similar to the free para-cyanophenylalanine cyano stretch in water, while the PheCN cyano stretch in a buried peptide is similar to the free PheCN cyano stretch THF (Tucker et al., "A New Method for Determining the Local Environment and Orientation of Individual Side Chains of Membrane-Binding Peptides," *JACS* 126 5078-5079 [2004]).

A novel orthogonal synthetase was derived from *M. jannaschii* tyrosyl tRNA synthetase, and are used in conjunction with the previously described *M. jannaschii* suppressor $tRNA_{CUA}$. This new orthogonal pair has no affinity or very low affinity for any of the common (i.e., naturally occurring) amino acids. The derived orthogonal tRNA synthetase selectively charges the amber suppressor $tRNA_{CUA}$ with p-cyanophenylalanine. The aminoacylated suppressor tRNA (i.e., the "charged" tRNA) is used as a substrate by the endogenous *E. coli* translation apparatus to incorporate p-cyanophenylalanine in response to the TAG amber stop codon (a selector codon) encountered in a transcript. The orthogonality of these tRNA/synthetase pairs ensures that neither the tRNA nor the synthetases cross react with endogenous *E. coli* tRNAs or synthetases and that the unnatural amino acid gets delivered only in response to TAG.

A search for orthogonal synthetases that have the ability to specifically charge an orthogonal tRNA with p-cyanophenylalanine was undertaken. This search used protocols that have been previously described. A library of *M. jannaschii* tyrosyl tRNA-synthetase mutants was generated by mutagenesis of the wild-type *M. jannaschii* tyrosyl tRNA-synthetase, where the mutagenesis consisted of randomizing predicted active site residues based on the crystal structure of other aminoacyl tRNA-synthetase molecules.

Following mutagenesis, the mutant synthetase library was passed through multiple rounds of positive and negative selection. This selection yielded one synthetase clone that had the ability to charge the O-tRNA with p-cyanophenylalanine. This synthetase clone was sequenced, and the amino acid sequence was determined, as shown in Table 5, SEQ ID NOs: 55 and 56). This synthetase mutant shows the follow substitutions relative to the wild-type synthetase sequence: Tyr32Leu, Leu65Val, Phe108Trp, Gln109Met, Asp158Gly and Ile159Ala.

Example 11

Orthogonal Translation Components for In Vivo Incorporation of the Unnatural Amino Acid m-cyanophenylalanine into Proteins in *E. coli*

The present Example describes compositions and methods for the biosynthetic incorporation of m-cyanophenylalanine (see, FIG. 1; also written 3-cyanophenylalanine) into proteins using *E. coli* host cell translation machinery. Novel orthogonal synthetase/tRNA pairs derived from *M. jannaschii* for incorporating this unnatural amino acid were isolated that function in an *E. coli* host cell system.

The cyano group is an excellent local environment IR probe, as its CN stretching vibration ($\nu_2$) undergoes a frequency shift on the order of ten wave numbers when moved from hydrophobic to hydrophilic surroundings (Getahun et al., "Using Nitrile-Derivatized Amino Acids as Infrared Probes of Local Environment," *JACS* 125, 405-411 [2003]). Para (4-position) and meta (3-position) cyanophenylalanine are thus useful in studying an assortment of protein properties including protein-protein binding, protein conformation, and hydrophobic collapse.

Para and meta forms of cyanophenylalanine can exist in both polar and hydrophobic environments while in a peptide chain, and their effects on conformation are negligible. Thus, either is likely to reside in the same environment as the wild-type residue it replaces in a protein or peptide. Further, the compounds' CN stretching vibration is narrow, does not overlap with any other protein absorptions, is largely decoupled from the protein's other vibrations, and is quite sensitive to changes in solvent polarity. For these reasons, both are excellent tools for peptide conformational studies.

Aromatic Nitriles in Proteins

Following established directed evolution protocols, a novel *Methanococcus jannaschii* tRNATyrCUA-tyrosyl-tRNA synthetase (TyrRS) pair was evolved that site specifically incorporates meta-cyanophenylalanine with high fidelity in response to an amber TAG codon. This new orthogonal pair has no affinity or very low affinity for any of the common (i.e., naturally occurring) amino acids. The derived orthogonal tRNA synthetase selectively charges the amber suppressor $tRNA_{CUA}$ with m-cyanophenylalanine. The aminoacylated suppressor tRNA (i.e., the "charged" tRNA) is used as a substrate by endogenous *E. coli* translation apparatus to incorporate m-cyanophenylalanine in response to the TAG amber stop codon (a selector codon) encountered in a transcript. The orthogonality of these tRNA/synthetase pairs ensures that neither the tRNA nor the synthetases cross react with endogenous *E. coli* tRNAs or synthetases and that the unnatural amino acid gets delivered only in response to an amber nonsense codon, TAG.

Construction of the orthogonal synthetase that has the ability to specifically charge an orthogonal tRNA with m-cyanophenylalanine used protocols that have been previously described. A library of *M. jannaschii* tyrosyl tRNA-synthetase mutants was generated by mutagenesis of the wild-type *M. jannaschii* tyrosyl tRNA-synthetase, where the mutagenesis consisted of randomizing predicted active site residues based on the crystal structure of other aminoacyl tRNA-synthetase molecules.

Following mutagenesis, the mutant synthetase library was passed through multiple rounds of positive and negative selection. This selection yielded a synthetase clone that had the ability to charge the O-tRNA with m-cyanophenylalanine. This synthetase clone was sequenced, and the amino acid sequence was determined (see, Table 5, SEQ ID NOs: 57 and 58). This synthetase mutant shows the follow substitutions relative to the wild-type synthetase sequence: Tyr32His, His70Ser, Asp158Ser, Ile159Ser and Leu162Pro.

We attempted to suppress a Tyr7→TAG mutant of the c-terminal $HiS_6$-tagged Z-domain protein in both the presence and absence of m-cyanophenylalanine and p-cyanophenylalanine, using their respective orthogonal tRNA/synthetase pair. In both cases, full length protein was produced in the presence of unnatural amino acid, while no product was detectable by Coomasssie blue staining on an SDS-PAGE gel in the absence of the respective unnatural amino acid.

Figure 14:
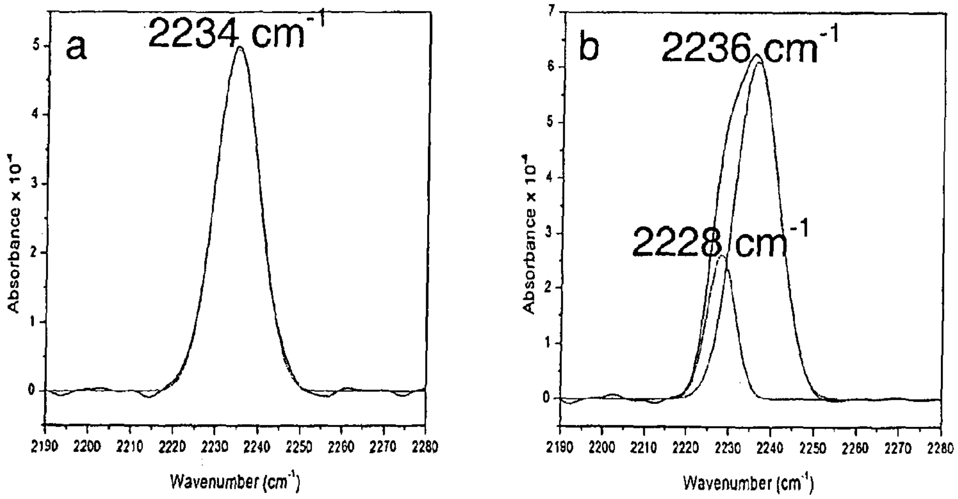
FIG. 14A provides the background-subtracted spectrum of para-cyanophenylalanine (solid) fit to a Gaussian curve (dashed).
FIG. 14B provides the background-subtracted spectrum of meta-cyanophenylalanine (solid) fit to two Gaussian curves (dashed).

Further, we have obtained IR spectra of this protein with both meta and para-cyanophenylalanine incorporated into position 7. After background subtraction of the wild-type z-domain IR spectrum, we obtained the spectra shown in FIGS. 14A and 14B. FIG. 14A shows that para-cyanophenylalanine has a single absorbance between the extremes shown in FIG. 13, suggesting that residue number seven lies along the surface of the protein, but does not point directly into solution. FIG. 14B shows the spectrum of meta-cyanophenylalanine as the sum of two Gaussian, distributions with peaks at 2236 and 2228 $cm^{-1}$. The $R^2$ value for the curves is greater than 0.99, an excellent curve-fit, and data in FIG. 14B thus suggest that m-cyanophenylalanine has two conformations. As evidenced by the peak at 2228 $cm^{-1}$, one conformation places the cyano group in a hydrophobic region of the protein. The peak at 2236 $cm^{-1}$ suggests that the other conformation places it in a hydrated environment.

Example 12

Orthogonal Translation Components for In Vivo Incorporation of the Unnatural Amino Acid p-(2-amino-1-hydroxyethyl)-L-phenylalanine into Proteins in *E. coli*

The present Example describes compositions and methods for the biosynthetic incorporation of p-(2-amino-1-hydroxyethyl)-L-phenylalanine (see, FIG. 1) into proteins using *E. coli* host cell translation machinery. Novel orthogonal synthetase/tRNA pairs derived from *M. jannaschii* for incorporating this unnatural amino acid were isolated that function in an *E. coli* host cell system.

The site-specific modification of proteins with biophysical probes, cytotoxic-agents, cross-linking agents, and other agents has been widely used to analyze protein structure and function, and in the development of diagnostics, therapeutic agents, and high-throughput screening. One approach to the selective modification of proteins involves the oxidation of an N-terminal serine or threonine to the corresponding aldehyde and subsequent coupling with hydrazine, alkoxyamine, or hydrazide derivatives. Unfortunately, this method is limited since it can only be used to modify the N-terminal position of a protein. Our approach of placing the aminoalcohol critical functional group of 2-amino-1-hydroxyethyl onto a target protein's side chain will remove the limitation of selective protein modification on the N-terminus only with the added benefit of controlling the position of the aminoalcohol group in protein.

A novel orthogonal synthetase was derived from *M. jannaschii* tyrosyl tRNA synthetase, and is used in conjunction with the previously described *M. jannaschii* suppressor $tRNA_{CUA}$. This new orthogonal pair has no affinity or very low affinity for any of the common (i.e., naturally occurring) amino acids. The derived orthogonal tRNA synthetase selectively charges the amber suppressor $tRNA_{CUA}$ with p-(2-amino-1-hydroxyethyl)-L-phenylalanine. The aminoacylated suppressor tRNA (i.e., the "charged" tRNA) is used as a substrate by endogenous *E. coli* translation apparatus to incorporate p-(2-amino-1-hydroxyethyl)-L-phenylalanine in response to the TAG amber stop codon (a selector codon) encountered in a transcript. The orthogonality of this tRNA/synthetase pair ensures that neither the tRNA nor the synthetase cross reacts with endogenous *E. coli* tRNAs or synthetases and that the unnatural amino acid gets incorporated only in response to an amber nonsense codon, TAG.

A search for orthogonal synthetases that have the ability to specifically charge an orthogonal tRNA with p-(2-amino-1-hydroxyethyl)-L-phenylalanine was undertaken. This search used protocols that have been previously described. A library of *M. jannaschii* tyrosyl tRNA-synthetase mutants was generated by mutagenesis of the wild-type *M. jannaschii* tyrosyl tRNA-synthetase, where the mutagenesis consisted of randomizing predicted active site residues based on the crystal structure of other aminoacyl tRNA-synthetase molecules.

Following mutagenesis, the mutant synthetase library was passed through multiple rounds of positive and negative selection. This selection yielded one synthetase clone that had the ability to charge the O-tRNA with p-(2-amino-1-hydroxyethyl)-L-phenylalanine. That synthetase clone was sequenced, and the amino acid sequence was determined (see, Table 5, SEQ ID NO: 59). This synthetase mutant shows the follow substitutions relative to the wild-type *M. janaschii* synthetase sequence:

| | | | | | | |
|---|---|---|---|---|---|---|
| wild-type *M. janaschii* tyrosyl-tRNA synthetase | Tyr 32 | Leu 65 | Phe 108 | Gln 109 | Asp 158 | Leu 162 |
| mutant synthetase specific for p-(2-amino-1-hydroxyethyl)-L-phenylalanine (mutant codon) | Asp (GAT) | Glu (GAG) | Arg (CGT) | Gln (CAG) | Gly (GGG) | Asn (AAT) |

Example 13

Orthogonal Translation Components for in vivo Incorporation of the Unnatural Amino Acid p-ethylthiocarbonyl-L-phenylalanine into Proteins in *E. coli*

The present Example describes compositions and methods for the biosynthetic incorporation of p-ethylthiocarbonyl-L-phenylalanine (see, FIG. 1) into proteins using *E. coli* host cell translation machinery. Novel orthogonal synthetase/tRNA pairs derived from *M. jannaschii* for incorporating this unnatural amino acid were isolated that function in an *E. coli* host cell system.

A useful method for the generation of semisynthetic proteins is native chemical ligation in which two fully unprotected peptide fragments can be coupled by an amide bond under mild physiological conditions at room temperature (Nilsson et al., *Annu. Rev. Biophys. Biomol. Struct.* 2005, 34, 91-118; Dawson et al., *Science* 1994, 266, 776-779). A variation of this method, termed expressed protein ligation in which one or both reaction partners have been produced by recombinant means, is useful for the synthesis of proteins consisting of greater than 100 residues (Muir, *Annu. Rev. Biochem* 2003, 72, 249-289; David et al. *Eur. J. Biochem.*

2004, 271, 663-677). In practice, both techniques require the presence of a C-terminal α-thioester, limiting these methods to modification at the C-terminus of a peptide fragment. The placement of a reactive thioester group at any residue in a bacterially expressed peptide/protein would significantly expand the scope of these techniques, allowing, for example, the synthesis of cyclic or branched structures or the selective modification of side chains with biophysical probes, polyethylene glycols or various tags. Methods for the generation of proteins having thioester-containing side chains find use in that the thioester-containing side chains can participate in subsequent chemical ligation reactions in vitro and possibly in vivo (Camarero and Muir, *J. Am. Chem. Soc.* 1999, 121, 5597-5598; Camarero et al., Bioorg Med. Chem. 2001, 9, 2479-2484; Scott et al., *Proc. Natl. Acad. Sci. USA* 1999, 96, 13638-13643; Evans et al., *J. Biol. Chem.* 2000, 275, 9091-9094; Yeo et al., *Chem. Commun.* 2003, 2870-2871).

Figure 15:
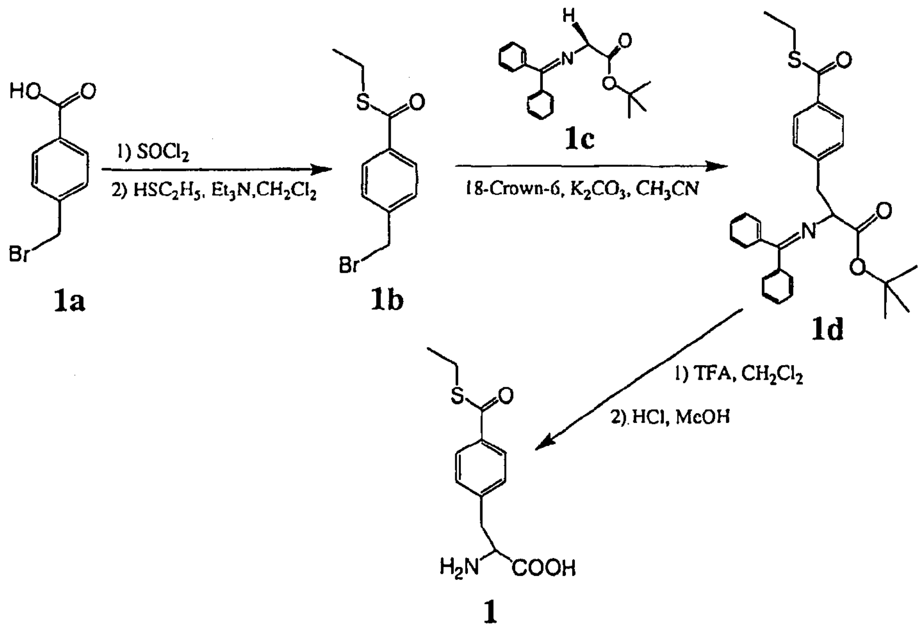
FIG. 15 provides a schematic describing the synthesis of p-ethyl thiocarbonyl-L-phenylalanine FIG. 16 provides a MALDI-TOF mass spectrum analysis result of mutant Z domain proteins containing unnatural amino acid at the seventh position. All the experimentally obtained mass data are in excellent agreement with those calculated masses of intact proteins containing either thioester or carboxylic acid groups.

Synthesis of p-Ethylthiocarbonyl-L-Phenylalanine p-ethylthiocarbonyl-L-phenylalanine (structure 1; also termed 4-(ethylthiocarbonyl)-L-phenylalanine) was synthesized in four steps (see, FIG. 15) starting from commercially available α-bromo-p-toluic acid (1a) and N-(diphenylmethylene) glycine tert-butyl ester (1c). These steps are outlined below.

Synthesis of S-ethyl 4-(bromomethyl)benzothioate (structure 1b): To a solution of 1a (2.15 g, 10.0 mmol) in THF (50 ml) was added thionyl chloride (2 ml, 28 mmol), followed by addition of DMF (50 μl) and the reaction mixture was stirred for 5 hours at room temperature. The organic solvents were removed under reduced pressure until a white solid appeared, which was then dissolved in THF (50 ml) and the solution was cooled to 0° C. A solution of ethanethiol (0.78 ml, 10.0 mmol) and triethylamine (2 ml, 14 mmol) in THF (10 ml) was added dropwise over a course of 30 minutes. The reaction mixture was stirred for another four hours and solvent was removed. Water (100 ml) and ether (200 ml) were added. The organic phase was washed with $H_2O$ (2×50 mL), dried over $NaSO_4$, and removed under reduced pressure. The crude product was purified by flash chromatography on silica gel (8% ethyl acetate in hexane), yielding 1b (2.18 g, 78%) as a colorless oil. $^1H$ NMR (400 MHz, $CDCl_3$) δ7.94 (d, J=8.0 Hz, 2H), 7.46 (d, J=8.0 Hz, 2H), 4.50 (s, 2H), 3.07 (q, J=7.6, 15.2 Hz, 2H), 1.35 (t, J=9.2 Hz, 3H). Exact mass m/z calculated for $C_{10}H_{11}BrOS$ 258.0/260.0, found (LC/MS) 259.1/260.1.

Synthesis of tert-butyl 2-(diphenylmethyleneamino)-3-(4-(ethylthiocarbonyl)phenyl)propanoate (structure 1d): A solution containing 1b (0.455 g, 1.76 mmol), 1c (0.47 g, 1.60 mmol), 18-crown-6 (0.42 g, 1.59 mmol) and anhydrous $K_2CO_3$ (0.344 g, 2.50 mmol) in anhydrous $CH_3CN$ (10 ml) was stirred for 24 hours at room temperature. The organic solvents were removed under reduced pressure. Water (100 ml) and $CH_2Cl_2$ (200 ml) were added. The organic phase was washed with $H_2O$ (2×50 mL), dried over $NaSO_4$, and removed under reduced pressure. The crude product was used directly in the next step without purification. Exact mass m/z calculated for $C_{29}H_{31}NO_3S$ 473.2, found (LC/MS) 474.3.

Synthesis of (4-(ethylthiocarbonyl))phenylalanine (1): A solution of 1d (0.94 g, 2.0 mmol) from the previous step in trifluoroacetic acid (8 ml) and $CH_2Cl_2$ (2 ml) was stirred for one hour at room temperature. After the organic solvents were completely removed under reduced pressure, concentrated HCl solution (0.8 ml) and MeOH (10 ml) were added and the resulting solution was stirred for 1 hour at room temperature, after which time all solvent was removed and anhydrous acetone (10 ml) was added. The solution was filtered and the recovered solid was triturated with anhydrous MeOH (2 ml). After filtration, the methanolic filtrate was subjected to reduced pressure to afford 1 as a white solid (>0.55 g, 95%). $^1H$ NMR (400 NMz, DMSO-$d_6$) δ 7.85 (d, J=8.0 Hz, 2H), 7.44 (d, J=8.0 Hz, 2H), 4.21 (t, J=6.4 Hz, 1H), 3.06 (q, J=14.8, 17.2 Hz, 2H), 3.00 (s, 2H), 1.26 (t, J=7.2 Hz, 3H). Exact mass m/z calculated for $C_{12}H_{15}NO_3S$ 253.1, found (LC/MS) 254.2.

Genetic Programming of p-Ethylthiocarbonyl-L-Phenylalanine Incorporation

To genetically encode p-ethylthiocarbonyl-L-phenylalanine in *E. coli*, it was necessary to generate an orthogonal aminoacyl-tRNA synthetase/tRNA pair specific for this amino acid. On the basis of a crystal structure of the *M. jannaschii* TyrRS-tRNA L-tyrosine complex (Kobayashi et al., *Nat. Struct. Biol.* 2003, 10, 425-432), six residues ($Tyr^{32}$, $Leu^{65}$, $Phe^{108}$, $Gln^{109}$, $Asp^{158}$ and $Leu^{162}$) in the tyrosine-binding site of *M. jannaschii* TyrRS were randomly mutated. A library of $10^9$ TyrRS mutants was passed through three rounds of positive selection (based on the suppression of an amber codon in chloramphenicol acetyltransferase) alternated with two rounds of negative selection (based on suppression of three amber codons in the barnase gene) in the presence and absence of p-ethylthiocarbonyl-L-phenylalanine, respectively, and a number of clones emerged whose survival in chloramphenicol was dependent on p-ethylthiocarbonyl-L-phenylalanine. One of these mutants was found to support cell growth in 120 μg $mL^{-1}$ chloramphenicol in the presence of p-ethylthiocarbonyl-L-phenylalanine, and 10 μg $mL^{-1}$ chloramphenicol in its absence.

Sequencing of this clone revealed the following mutations: Tyr32Ala, Leu65Phe, Phe108Trp, Gln109Ser, Asp158Ser and Leu162His (see, Table 5, SEQ ID NO: 60). The mutation of $Tyr^{32}$ to $Ala^{32}$ likely removes the hydrogen bond between the phenolic hydroxyl group of bound tyrosine and $Tyr^{32}$.

| wild-type *M. janaschii* tyrosyl-tRNA synthetase | Tyr 32 | Leu 65 | Phe 108 | Gln 109 | Asp 158 | Leu 162 |
|---|---|---|---|---|---|---|
| mutant synthetase specific for p-ethylthiocarbonyl-L-phenylalanine (mutant codon) | Ala (GCT) | Phe (TTT) | Trp (TGG) | Ser (AGT) | Ser (TCG) | His (CAT) |

To confirm that the observed phenotype is caused by the site-specific incorporation of p-ethylthiocarbonyl-L-phenylalanine by the $mutRNA_{CUA}$-mutTyrRS pair, an amber codon was substituted for the seventh position (Tyr) in the gene encoding the Z domain protein (Nilsson et al., *Protein Eng.* 1987, 1, 107-113) fused to a C-terminal $HiS_6$ tag. Protein was expressed in the presence or absence of 1 mM p-ethylthiocarbonyl-L-phenylalanine and purified by Ni-NTA chromatography. Analysis by SDS-PAGE showed that expression of the mutant Z domain protein was completely dependent on the presence of p-ethylthiocarbonyl-L-phenylalanine. The mutant protein was expressed in approximately 10-30% yield relative to the wide-type Z domain protein (~8 mg/L in minimal medium containing 1% glycerol, 0.3 mM leucine and 1 mM p-ethylthiocarbonyl-L-phenylalanine with appropriate antibiotics).

Figure 16:
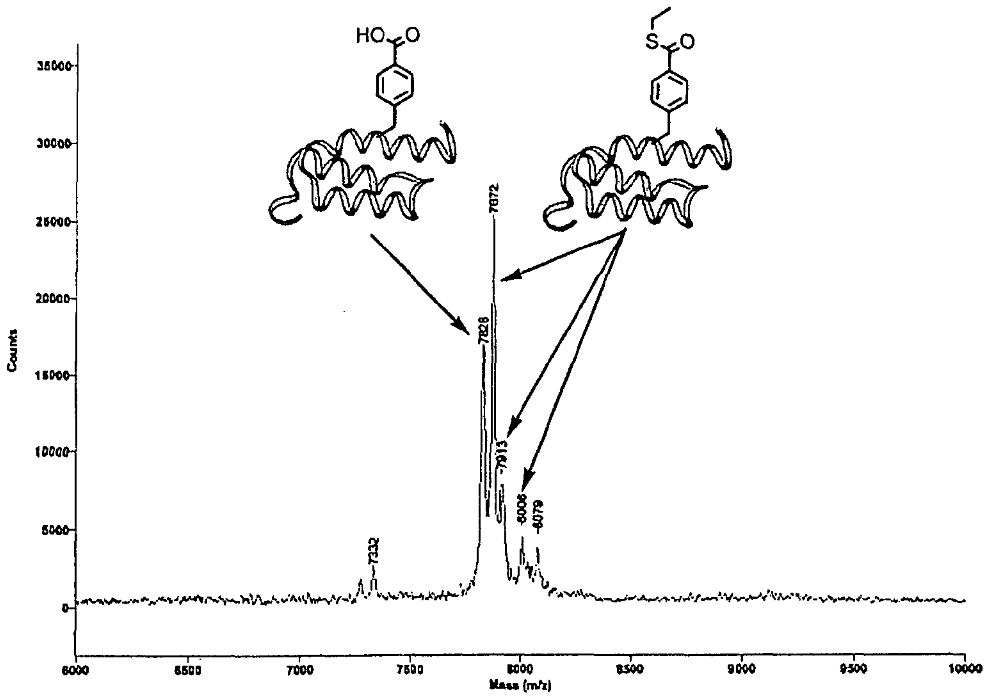

Additional evidence for the site specific incorporation of p-ethylthiocarbonyl-L-phenylalanine was obtained by matrix-assisted laser desorption/ionization time-of-flight mass spectrometry (MALDI-TOF MS). In addition to the observation of an experimental average mass of 8006 Da for the intact Tyr→p-ethylthiocarbonyl-L-phenylalanine protein ($M_{theoretical}$=8002 Da, see, FIG. 16), a minor peak corresponding to the mutant protein without the first methionine moiety in acetylated form ($M_{Experimental}$=7913 Da vs. $M_{Theoretical}$=7913 Da) and a major peak corresponding to the mutant protein without the first methionine moiety ($M_{Experimental}$=7871 Da vs. $M_{Theoretical}$=7871 Da) were also detected (FIG. 16). Another major peak of 7828 Da was present that corresponds to Z domain protein containing a free carboxylic acid group instead of a thioester moiety at position 7, which has a calculated mass of 7827 Da in its protonated form. With the assumption that both acid and thioester-containing mutant proteins have comparable ionization efficiencies under mass detection conditions, the integration of their corresponding mass peak areas suggests that around 40% thioester-containing mutant protein is hydrolyzed. The fact that the mutant synthetase does not incorporate unnatural amino acid p-ethylthiocarbonyl-L-phenylalanine in its hydrolysized form in vivo and that p-ethylthiocarbonyl-L-phenylalanine appears to be stable both in vitro and in vivo, suggest that the hydrolysis of the thioester into the acid occurs after its incorporation into Z domain protein by the thioester-specific mutant synthetase.

Figure 17:
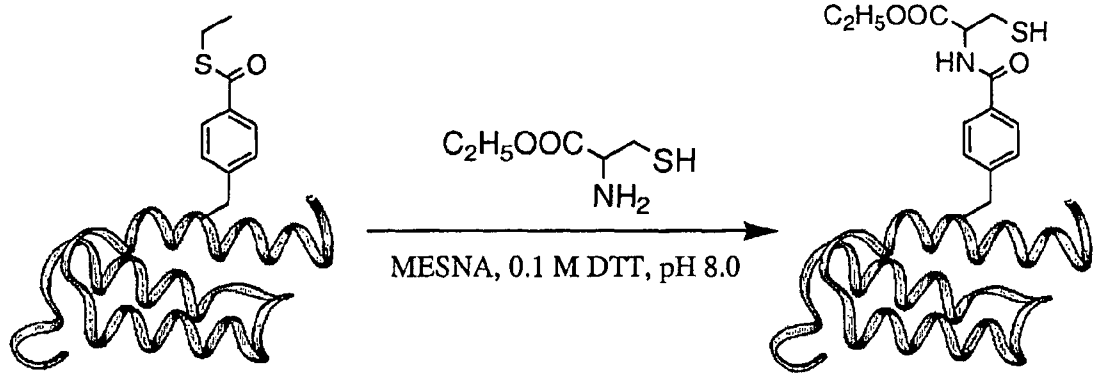
FIG. 17 provides a schematic of protein labeling by chemical ligation.

To determine whether the thioester side chain of the mutant proteins can be selectively modified, an in vitro chemical ligation was performed with 20-60 μg/ml crude thioester-containing mutant protein and 10 mM cysteine ethyl ester in a phosphate buffered solution containing 100 mM dithiothreitol (DTT) and 2 M guanidinium chloride at a pH 8.0. The resulting modified protein was then purified and analyzed by MALDI-TOF MS. Experimental average masses of 7956 Da and 7998 Da, corresponding to thioester-containing proteins modified with one cysteine molecule ($M_{Theoretical}$=7958 Da and 8000 Da for proteins without the first methionine moiety and without the first methionine moiety in acetylated form, respectively), were obtained (FIG. 17). The labeling efficiency could be qualitatively estimated to be greater than 85% by the integration of their mass peak areas.

As shown in FIG. 16, Z domain proteins are predominantly expressed without the first methionine residue. In this form, unmodified thioester-containing mutant protein has a molecular weight of 7872, which may overlap with the acid-containing proteins in acetylated form ($M_{Theoretical}$=7869 Da). Therefore, in calculating the labeling efficiency, the peak area at 7867 Da was taken as the upper-limit value for unmodified thioester-containing proteins, leading to an estimate of greater than 85% labeling efficiency.

The peaks at 7825 Da and 7867 Da ($M_{Theoretical}$=7827 Da and 7869 Da) are indicative of the presence of Z domain proteins containing a carboxylic acid group at position 7, which is not reactive toward cysteine ethyl ester. As expected, no labeling products were detected for WT Z domain proteins, indicating that the labeling reaction occurred only between the cysteine molecule and the thioester group but not any existing functional groups in the WT protein. On the other hand, neither intramolecular side chain cyclization nor self-dimerization involving the thioester group and any ϵ-amino group of the five lysine residues in thioester-containing mutant proteins were observed. These data, therefore, demonstrate the excellent selectivity and reactivity of the thioester handle for the reliable and selective in vitro modification of proteins.

Chemical Ligation Between Cysteine Ethyl Ester and Thioester-Containing Domain Proteins

*E. coli* DH10B cells (60 ml) harboring plasmid encoding the mutant tRNA synthetase and expression vector pLEIZ encoding Z domain gene with an amber codon at the $7^{th}$ position and a COOH-terminal His-6 tag were grown at 37° C., induced for four hours at an $OD_{600}$ of 0.5 by the addition of 1 mM isopropyl-β-D-thiogalactopyranoside (IPTG) and pelleted. To the pelleted cells was added 1 ml buffer solution (6M guanidinium chloride, 100 mM sodium phosphate, 200 mM sodium chloride, pH=8.0). The solution was shaken for 1 hour at room temperature, sonicated for three minutes and centrifuged to remove any cell debris. To the clear supernatant was added 2 ml of phosphate buffered solution (100 mM sodium phosphate, 200 mM sodium chloride, 0.01 M cysteine ethyl ester, pH=8.0), 150 μl dithiothreitol solution (2 M) and 60 mg of sodium 2-mercaptoethenesulfonate (MESNA). The solution mixture was shaken for 12 hours at room temperature. The solution containing modified proteins was exchanged and concentrated into 500 μl buffer solution (8 M urea, 100 mM sodium phosphate, 10 mM Trizma, pH 8.0). Modified proteins were purified by $Ni^{2+}$ affinity chromatography according to manufacturer's protocol (Qiagen, Chatsworth, Calif.), dialyzed against distilled water and analyzed by MALDI-TOF MS.

Conclusion

In conclusion, we have provided a novel orthogonal synthetase derived from *M. jannaschii* tyrosyl tRNA synthetase. When used in conjunction with an *M. jannaschii* suppressor $tRNA_{CUA}$, these reagents allow the in vivo incorporation of the unnatural amino acid p-ethylthiocarbonyl-L-phenylalanine in polypeptide chains. This work illustrates a biosynthetic protocol for bacterial production of proteins containing a side chain thioester handle at defined sites. This allows the highly selective and efficient chemical ligation of a wide variety of ligands to the reactive group on the p-ethylthiocarbonyl-L-phenylalanine amino acid residue following incorporation of the amino acid into a protein.

Example 14

Orthogonal Translation Components for In Vivo Incorporation of the Diketone Unnatural Amino Acid p-(3-oxobutanoyl)-L-phenylalanine into Proteins in *E. coli*

The present Example describes compositions and methods for the biosynthetic incorporation of the diketone unnatural amino acid p-(3-oxobutanoyl)-L-phenylalanine (see, FIG. 1) into proteins using *E. coli* host cell translation machinery. Novel orthogonal synthetase/tRNA pairs derived from *M. jannaschii* for incorporating this unnatural amino acid were isolated that function in an *E. coli* host cell system.

The comparative studies on the ability of simple monoketone or β-diketone functional groups to form imines with butylamine and the stabilities of thus formed imines in phosphate buffer at different pHs demonstrate the facile production of enol imine formed from the β-diketone moiety at pHs ranging from 6.5 to 10.5, as well as its superior stability toward the acidic hydrolysis down to pH 3.9. In comparison, at a pH up to 10.5 under the identical conditions, the monoketone group essentially remains as a free form with no detectable imine formation. Accordingly, an unnatural amino acid bearing a β-diketone moiety on its side chain was synthesized and the identification of an orthogonal tRNA-synthetase pair capable of incorporating this unnatural amino acid was undertaken. The invention provides a successfully evolved mutant synthetase that specifically incorporation of this diketone-containing amino acid into proteins in vivo with high translational efficiency and fidelity. As described more fully below, a biotin hydroxylamine derivative was then selectively coupled to this diketone group that was genetically encoded into a Z domain protein, suggesting that the diketone moiety could serve as a powerful chemical handle whose reactivity is orthogonal to normal biological chemistries for bringing a variety of external properties into the target proteins.

Figure 21:
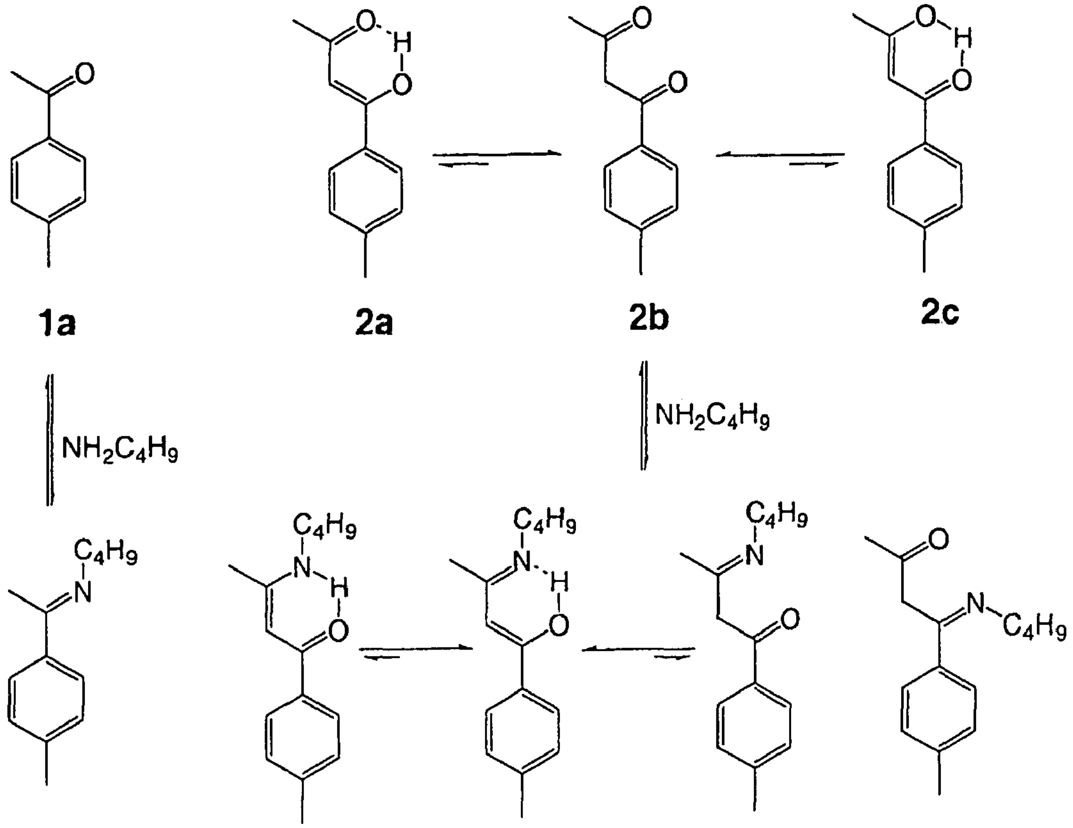
FIG. 21 provides a scheme describing the synthesis of various adducts of the diketone-containing moiety.

It has been previously demonstrated that by adding new components to the translational machinery of *Escherichia coli* or yeast, noncanonical amino acids could be site-specifically incorporated with high translational fidelity and efficiency into proteins in vitro or in vivo using orthogonal translation components. This approach has been used to genetically incorporate ketone-containing amino acids into proteins, which could subsequently be conjugated with non-peptidic molecules with diverse biological and/or physical properties (e.g., polyethylene glycol, biotin, glycomimetics, etc) through the formation of hydrazone and oxime bonds. Although these hydrazone and oxime bonds are stable at the physiological conditions, they are disadvantaged by the requirement for the simultaneous presence of two functional groups that are not found among the common twenty amino acids. If one had a reactive functional group such as a thioester or β-diketone that directly formed stable adducts with ε-amino group of lysines or α-amino groups, one could form intermolecular or intramolecular protein crosslinks. To this end, we now report the genetic encoding of the diketone-containing amino acid 2 in *Escherichia coli*. See, FIG. 21.

It was contemplated that the conjugated product of an aryl diketone 2 with an aliphatic amine may lead to the formation of imine adducts 3 (see, FIG. 21), which can tautomerize to the corresponding enamines stabilized by a six-membered intramolecular hydrogen bond. This may result in a stable adduct at physiological pH. To experimentally verify this rationale, we began by measuring the relative reactivity of a simple model system that includes a series of imine formations between butylamine and the aryl monoketone 1a and the aryl diketone 2 in 100 mM phosphate buffer at different pHs ranging from 6.5 to 10.5. The various adducts (1b and 3a-3d) were assayed using liquid chromatography mass spectrometry (LC/MS). See, Table 4. This Table describes the results of the imine formation between butylamine (10 mM) and either aryl monoketone 1 (1 mM) or 2 (1 mM) in PBS buffer (100 mM $K(PO_4)_i$, 500 mM NaCl) at different pHs. Reactions were conducted for one week at room temperature.

TABLE 4

| | Conversion percentage to their respective imine adducts at different pHs | | | | | 75% MeOH |
|---|---|---|---|---|---|---|
| Substrate | pH 6.5 | pH 7.4 | pH 8.4 | pH 9.5 | pH 10.5 | in H2O ** |
| 1 | 0% | 0% | 0% | 0% | 0% | >90% |
| 2 | 30% | 50% | 50% | 57% | 75% | >90% |

** 12 hours reaction time at room temperature

This analysis showed that, at pH up to 10.5, 1a essentially remains as a free form with no detectable formation of 1b. In contrast, at a pH of 7.4, 50% of 2 have already been converted into 3 and this percentage increases to an impressive value of 75% at pH 10.5.

This, taken together with the previous observations that keto form 2b and enol-imine form 3b dominates over other corresponding taumers in aqueous medium (Iglesias, *Curr. Org. Chem.* 2004, 8, 1-24; Patteux et al., *Org. Lett.* 2003, 5, 3061-3063; Aly, *Tetrahedron* 2003, 50, 1739-1747; Lopez et al., *Tetrahedron: Asymmetry* 1998, 9, 3741-3744; Mazzone et al., S. *Eur. J. Med. Chem.* 1986, 21, 277-284; and Kim and Ryu, *Bull. Korean. Chem. Soc.* 1992, 13, 184-187), thereby confirming that the hydrogen-bonding induced stabilization does significantly facilitate the production of 3 (predominantly 3b) when compared to 1a.

Figure 18:
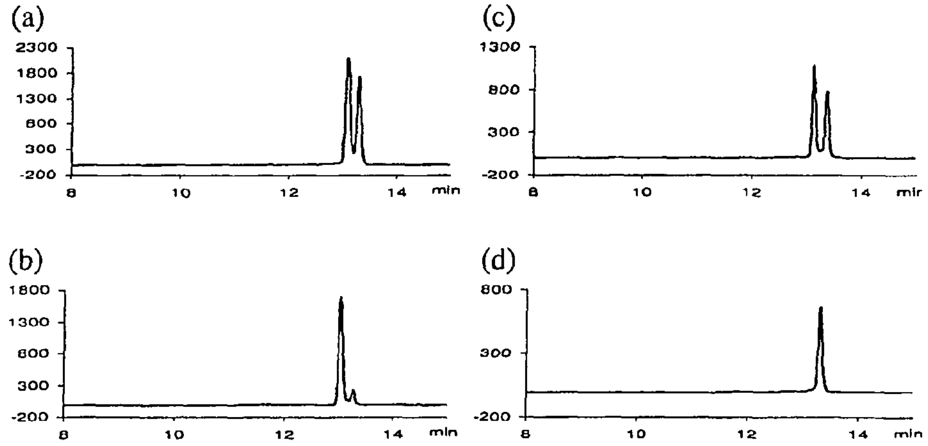
FIGS. 18A-18D provide LC/MS elution profiles (first peak: 3; second peak: 2) monitored at 340 nm.

To further corroborate that the stabilized intramolecular H-bond renders 3a greater stability toward the hydrolysis than simple imine 1b, LC/MS analysis were also performed on both 1b and 3 at pH ranging from 1.9 to 9.4. As demonstrated in FIG. 1, 3 (presumably 3b) essentially remain intact at the physiological pH of 7.4 or above. Only ~40% conversion of 3 to 2 occurs at a pH down to 3.9 after 4 days at room temperature. A more acidic treatment of 3 led to the complete uninstallation of the amino group (FIG. 18). In sharp contrast but as expected, 1b is readily hydrolyzed even at a pH 10.5 after overnight stirring (data not shown).

Unnatural Amino Acid Synthesis

Figure 19:
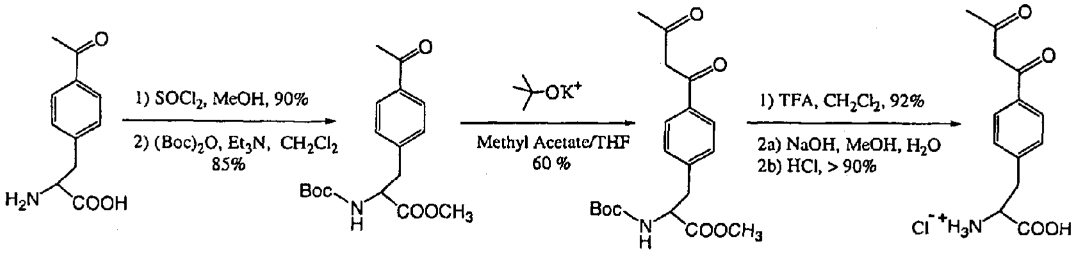
FIG. 19 provides a schematic describing the synthesis of the diketone-containing unnatural amino acid p-(3-oxobutanoyl)-L-phenylalanine.

Encouraged by these findings, we wished to establish the chemistry for derivatizing an unnatural amino acid p-(3-oxobutanoyl)-L-phenylalanine containing a diketone moiety in its side chain. Our synthesis strategy (see, FIG. 19) starts from readily accessible p-acetyl-(±)-L-phenylalanine by protecting the backbone amino and acid groups by Boc chemistry and esterification, respectively. The addition of a second carbonyl group was accomplished under reaction conditions involving potassium tert-butoxide in a mixed solvent (2:3 [v/v] methyl acetate:THF). The removal of Boc group with TFA, followed by alkaline hydrolysis, delivered the desired p-(3-oxobutanoyl)-L-phenylalanine with an overall yield of 40%.

Identification of Orthogonal Translation Components

Novel orthogonal aminoacyl-tRNA synthetase/tRNA pairs were constructed for in vivo incorporation of p-(3-oxobutanoyl)-L-phenylalanine into proteins using established protocols. On the basis of the crystal structure of the *M. jannaschii* TyrRS-tRNA(Tyr) L-tyrosine complex (Kobayashi et al., *Nat. Struct. Biol.* 2003, 10, 425-432), six residues ($Tyr^{32}$, $Leu^{65}$, $Phe^{108}$, $Gln^{109}$, $Asp^{158}$ and $Leu^{162}$) around the tyrosine-binding site of *M. jannaschii* TyrRS were randomly mutated. After sequentially passing the generated library of approximately $10^9$ mutants through three rounds of positive selection, alternated with two rounds of negative selection according to our published protocol, a number of clones emerged whose survival in chloramphenicol was dependent on the presence of p-(3-oxobutanoyl)-L-phenylalanine. Two TyrRS mutants were identified by using an in vivo assay based on the suppression of the $Asp^{112}$ TAG codon in the CAT gene. These two mutants can support cell growth in 120 μg mL-1 chloramphenicol in the presence of p-(3-oxobutanoyl)-L-phenylalanine, and up to 10 μg $mL^{-1}$ chloramphenicol without p-(3-oxobutanoyl)-L-phenylalanine. This result suggests that the two evolved synthetases both have higher activity for p-(3-oxobutanoyl)-L-phenylalanine than for any natural amino acid. Sequencing the DNA of these mutants revealed that they converged to the same sequence (see, Table 5, SEQ ID NO: 61).

Both hydrogen bonds between the phenolic hydroxy group of bound tyrosine and $Tyr^{32}$ and $Asp^{158}$ are disrupted by mutations to Gly. $Leu^{65}$ is converted to $Val^{65}$, possibly providing more space to accommodate the extended backbone of the β-diketone. The mutations of Phe108Thr and Leu162Ser as well as a conserved $Gln^{109}$ may thus indicate their involvement in H-bonding to the carbonyl oxygen in β-diketone moiety. The sequences of these synthetase clones is summarized below.

| | | | | | | |
|---|---|---|---|---|---|---|
| wild-type *M. janaschii* tyrosyl-tRNA synthetase | Tyr 32 | Leu 65 | Phe 108 | Gln 109 | Asp 158 | Leu 162 |
| mutant synthetase specific for p-(3-oxobutanoyl)-L-phenylalanine (mutant codon) | Gly (GGT) | Val (GTT) | Thr (ACT) | Gln (CAG) | Gly (GGG) | Ser (AGT) |

Figure 20:
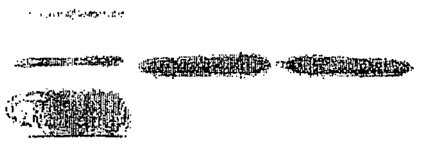
FIG. 20 provides a Gelcode Blue stained SDS-PAGE analysis of expressed Z domain protein in the presence or absence of p-(3-oxobutanoyl)-L-phenylalanine. The analysis shows the in vitro labeling of mutant Z domain protein containing p-(3-oxobutanoyl)-L-phenylalanine with fluorescein hydrazide. wt=wild type.

To confirm that the observed phenotype is caused by the site-specific incorporation of p-(3-oxobutanoyl)-L-phenylalanine by the $mutRNA_{CUA}^{Tyr}$-mutTyrRS pair, an amber codon was introduced in place of the codon for tyrosine at the seventh position in the gene encoding the Z domain protein (Nilsson et al., *Protein Eng.* 1987, 1, 107-113) fused to a C-terminal $HiS_6$ tag. Protein was expressed in the presence or absence of 1 mM p-(3-oxobutanoyl)-L-phenylalanine and purified by Ni-NTA chromatography. Analysis by SDS-PAGE revealed unnatural amino acid dependent protein expression (FIG. 20). The volume of mutant protein loaded into the gel is three times the wide type (WT) protein where diketone-containing unnatural amino acid is replaced with a tyrosine residue, indicating around 30% incorporation efficiency of p-(3-oxobutanoyl)-L-phenylalanine compared to tyrosine.

More convincing evidence for the unambiguous incorporation of p-(3-oxobutanoyl)-L-phenylalanine was obtained by matrix-assisted laser desorption/ionization time-of-flight mass spectrometry (MA11-TOF MS). In addition to the observation of an experimental average mass of 7991 Da ($M_{Theoretical}$=7997 Da) for the intact protein, a major peak corresponding to the protein without the first methionine moiety ($M_{Experimental}$=7867 Da, $M_{Theoretical}$=7866 Da) was also detected. The signal-to-noise ratio was >400, suggesting a fidelity for the incorporation of p-(3-oxobutanoyl)-L-phenylalanine of better than 99% using evolved $mutRNA_{CUA}^{Tyr}$-mutTyrRS pair.

The possibility of using a diketone moiety as a chemical handle for site-specific modification of protein with external properties was tested by carrying out in vitro labeling of expressed diketone-containing proteins with biotin hydroxylamine derivative (MW=331.39, purchased from Molecular Probes). The purified mutant and WT Z domain proteins were treated with 2 mM biotin hydroxylamine in phosphate buffer at a pH 4.0 at 25° C. for 12 hours. After dialysis against water to remove excess biotin hydroxylamine, the proteins were analyzed by MALDI-TOF MS. Experimental average masses of 8315 Da ($M_{Theoretical}$=8310 Da, biotin-labeled intact mutant protein), 8182 Da ($M_{Theoretical}$=8179 Da, biotin-labeled mutant protein without the first methionine residue), and 8225 Da ($M_{Theoretical}$=8221 Da, biotin-labeled mutant protein without the first methionine residue in its acetylated form) were obtained, confirming that biotin hydroxylamine reacted with the mutant Z domain proteins in a molar ratio of 1:1. As expected, no labeling products were detected for WT Z domain proteins, indicating that the labeling reaction occurred only between the hydroxylamine and the diketone group, but not any existing functional groups in the WT protein. Taken together with no observation of unlabeled diketone-containing mutant proteins in the mass spectrum, these data demonstrate the excellent specificity and high reactivity of the diketone handle for the selective in vitro modification of proteins.

The present Example demonstrates that the incorporation of a β-diketone handle into protein in vivo using an evolved and highly specific orthogonal translation system occurs site specifically with a high fidelity and efficiency that is comparable with its natural counterpart. Given both the high stability and facile production of 3 over a broad pH range, the modulation of protein-protein interactions through the formation of Schiff base between the β-diketone moiety and the amino group of a lysine residue is highly possible, especially when p-(3-oxobutanoyl)-L-phenylalanine is placed in a favorable hydrophobic environment.

Example 15

Orthogonal Translation Components for in vivo Incorporation of the Unnatural Amino Acid p-isopropylthiocarbonyl-L-phenylalanine into Proteins in *E. coli*

The present Example describes compositions and methods for the biosynthetic incorporation of p-isopropylthiocarbonyl-L-phenylalanine (see, FIG. 1) into proteins using *E. coli* host cell translation machinery. Novel orthogonal synthetase/tRNA pairs derived from *M. jannaschii* for incorporating this unnatural amino acid were isolated that function in an *E. coli* host cell system. This unnatural amino acid finds use as a target for port-translational modifications when incorporated into proteins, and is further advantageous because the chemically reactive moiety on the unnatural amino acid is resistant to the hydrolysis activities of cellular enzymes.

A novel orthogonal synthetase was derived from *M. jannaschii* tyrosyl tRNA synthetase, and is used in conjunction with the previously described *M. jannaschii* suppressor $tRNA_{CUA}$. This new orthogonal pair has no affinity or very low affinity for any of the common (i.e., naturally occurring) amino acids. The derived orthogonal tRNA synthetase selectively charges the amber suppressor $tRNA_{CUA}$ with p-isopropylthiocarbonyl-L-phenylalanine. The aminoacylated suppressor tRNA (i.e., the "charged" tRNA) is used as a substrate by endogenous *E. coli* translation apparatus to incorporate p-isopropylthiocarbonyl-L-phenylalanine in response to the TAG amber stop codon (a selector codon) encountered in a transcript. The orthogonality of this tRNA/synthetase pair ensures that neither the tRNA nor the synthetase cross reacts with endogenous *E. coli* tRNAs or synthetases and that the unnatural amino acid gets incorporated only in response to an amber nonsense codon, TAG.

A search for orthogonal synthetases that have the ability to specifically charge an orthogonal tRNA with p-isopropylthiocarbonyl-L-phenylalanine was undertaken. This search used protocols that have been previously described. A library of *M. jannaschii* tyrosyl tRNA-synthetase mutants was generated by mutagenesis of the wild-type *M. jannaschii* tyrosyl tRNA-synthetase, where the mutagenesis consisted of randomizing predicted active site residues based on the crystal structure of other aminoacyl tRNA-synthetase molecules.

Following mutagenesis, the mutant synthetase library was passed through multiple rounds of positive and negative selection. This selection yielded one synthetase clone that had the ability to charge the O-tRNA with p-isopropylthiocarbonyl-L-phenylalanine. That synthetase clone was sequenced, and the amino acid sequence was determined (see, Table 5, SEQ ID NO: 62). This synthetase mutant shows the follow substitutions relative to the wild-type *M. janaschii* synthetase sequence:

| | | | | | | |
|---|---|---|---|---|---|---|
| wild-type *M. janaschii* tyrosyl-tRNA synthetase | Tyr 32 | Leu 65 | Phe 108 | Gln 109 | Asp 158 | Leu 162 |
| mutant synthetase specific for p-isopropylthiocarbonyl-L-phenylalanine (mutant codon) | Gly (GGG) | Cys (TGT) | Cys (TGT) | Met (ATG) | Gly (GGT) | Tyr (TAT) |

one tryptophan residue, and specific chemical labeling of proteins with fluorescent probes is extremely difficult.

The coumarin alanines shown in FIG. 1 have been chemically synthesized. A novel orthogonal synthetase was derived from *M. jannaschii* tyrosyl tRNA synthetase, and is used in conjunction with the previously described *M. jannaschii* suppressor $tRNA_{CUA}$ to incorporate these coumarin amino acids. This new orthogonal pair has no affinity or very low affinity for any of the common (i.e., naturally occurring) amino acids. The derived orthogonal tRNA synthetase selectively charges the amber suppressor $TRNA_{CUA}$ with 7-amino-coumarin alanine and 7-hydroxy-coumarin alanine. The aminoacylated suppressor tRNA (i.e., the "charged" tRNA) is used as a substrate by the endogenous *E. coli* translation apparatus to

Example 16

Orthogonal Translation Components for In Vivo Incorporation of Fluorescent Unnatural Amino Acids containing Coumarin into Proteins in *E. coli*

The present Example describes compositions and methods for the biosynthetic incorporation of 7-amino-coumarin alanine and 7-hydroxy-coumarin alanine (see, FIG. 1) into proteins using *E. coli* host cell translation machinery. Novel orthogonal synthetase/tRNA pairs derived from *M. jannaschii* for incorporating this unnatural amino acid were isolated that function in an *E. coli* host cell system.

Fluorescence is one of the most sensitive and useful techniques in molecular biology. The discovery of Green Fluorescent Protein (GFP) has led to a dramatic revolution in cell biology, allowing the study of protein expression, localization, dynamics and interaction in living cells by direct visualization (Lippincott-Schwartz et al., *Nat. Rev. Mol. Cell. Bio.* (2001) 2:444-456). However, the protein interaction and dynamics cannot be pinpointed at atomic resolution due to the size of GFP. GFP also requires many transcripts to achieve a suitable signal, and required a lag-time for its folding and fluorophore maturation.

The incorporation of fluorescent amino acids, as opposed to an entire fluorescent protein moiety, would overcome some of the limitations in the GFP fluorescence system. The site-specific incorporation of fluorescent amino acids would introduce minimum perturbation to the host protein, which permits the measurement of fluorescence resonance energy transfer (FRET) with much greater precision (Truong and Ikura, *Curr. Opin. Struct. Bio.* 2001, 11:573-578). In addition, the use of a fluorescent amino acid will permit the probing of the local environment of each amino acid position, and pinpoint the residues that mediate interaction with other cellular components by varying the position of the fluorescent amino acid in the protein. This would also be very useful to study protein folding in vitro (Lakowicz, J. R. Principles of Fluorescence Spectroscopy Ed. 2; Kluwer Academic/Plenum Publishers: New York, 1999), especially in a single-molecular system (Lipman et al., *Science* 2003, 301:1233-1235), because one protein molecule normally contains more than incorporate 7-amino-coumarin alanine and 7-hydroxy-coumarin alanine in response to the TAG amber stop codon (a selector codon) encountered in a transcript. The orthogonality of this tRNA/synthetase pair ensures that neither the tRNA nor the synthetase cross reacts with endogenous *E. coli* tRNAs or synthetases and that the unnatural amino acid gets incorporated only in response to TAG.

A search for orthogonal synthetases that have the ability to specifically charge an orthogonal tRNA with 7-amino-coumarin alanine or 7-hydroxy-coumarin alanine was undertaken. This search used protocols that have been previously described. A library of *M. jannaschii* tyrosyl tRNA-synthetase mutants was generated by mutagenesis of the wild-type *M. jannaschii* tyrosyl tRNA-synthetase, where the mutagenesis consisted of randomizing six predicted active site residues based on the crystal structure of other aminoacyl tRNA-synthetase molecules. The library has a diversity of approximately $10^9$ species.

Following mutagenesis, the mutant synthetase library was passed through multiple rounds of positive and negative selection. This selection yielded one synthetase clone that had the ability to charge the O-tRNA with 7-amino-coumarin alanine or 7-hydroxy-coumarin alanine. That synthetase clone was sequenced, and the amino acid sequence was determined (see, Table 5, SEQ ID NO: 63). This synthetase mutant shows the follow substitutions relative to the wild-type *M. janaschii* tyrosyl-tRNA synthetase sequence: Y32R, L65A, H70M, D158N and L162T.

Additional data has been obtained demonstrating the selective incorporation of the coumarin alanine amino acids into proteins in response to a selector codon in an orthogonal translation system comprising the isolated synthetase species. This data includes, (a) expression studies where a myoglobin gene having a TAG selector codon at position 4 is expressed only in the presence of the unnatural amino acid; (b) the mutant myoglobin synthesized in the presence of the unnatural amino acid appears as a fluorescent band in an SDS-PAGE gel analysis; and (c) the isolated mutant synthetase has been crystallized, and the co-crystal structure of the mutant synthetase in the presence of the unnatural amino acid is fluorescent.

Example 17

O—RS and O-tRNA Species for the Incorporation of Unnatural Amino Acids

A variety of O-tRNA species can be used with the present invention, and the invention is not limited to the use of any particular O-tRNA. For example, O-tRNA species that comprise the nucleotide sequence of SEQ ID NO: 1 or SEQ ID NO: 2 find use with the invention. With the teaching provided herein, additional O-tRNA species can be constructed for use with the invention.

Similarly, O—RS species are also provided (see, Table 5) for use in protocols for the incorporation of unnatural amino acids, e.g., an unnatural amino acid selected from p-ethylthiocarbonyl-L-phenylalanine, p-(3-oxobutanoyl)-L-phenylalanine, 1,5-dansyl-alanine, 7-amino-coumarin alanine, 7-hydroxy-coumarin alanine, o-nitrobenzyl-serine, O-(2-nitrobenzyl)-L-tyrosine, p-carboxymethyl-L-phenylalanine, p-cyano-L-phenylalanine, m-cyano-L-phenylalanine, biphenylalanine, 3-amino-L-tyrosine, bipyridylalanine, p-(2-amino-1-hydroxyethyl)-L-phenylalanine; p-isopropylthiocarbonyl-L-phenylalanine; 3-nitro-L-tyrosine and p-nitro-L-phenylalanine. The O—RS polypeptides of the invention include those polypeptides that comprise the amino acid sequences provided in Table 5, SEQ ID NOS: 7-10, 12, 14, 16, 18, 20, 22, 24, 26, 28, 30, 32, 34, 36, 38, 40, 42, 44, 46, 50, 52-55, 57 and 59-63.

Examples of polynucleotides that encode O—RSs or portions thereof are also provided. For example, polynucleotides that encode O—RS molecules of the invention include SEQ ID NOS: 11, 13, 15, 17, 19, 21, 23, 25, 27, 29, 31, 33, 35, 37, 39, 41, 43, 45, 47, 51, 56, 58. However, it is not intended that the polynucleotides of the invention be limited to those provided in Table 5. Indeed, any polynucleotide that encodes an O—RS amino acid sequence of the invention, e.g., SEQ ID NOS: 7-10, 12, 14, 16, 18, 20, 22, 24, 26, 28, 30, 32, 34, 36, 38, 40, 42, 44, 46, 50, 52-55, 57 and 59-63, is also a feature of the invention.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

Example 18

Nucleotide and Amino Acid Sequences

This Example provides nucleotide and amino acid sequences for various polynucleotides and polypeptides, respectively. The sequences provided in Table 5 below are meant to provide examples only, and it is not intended that the invention be limited in any way by the sequences provided Table 5.

TABLE 5

Nucleotide and Amino Acid Sequences

| SEQ ID NO: | Description | SEQUENCE |
|---|---|---|
| 1 | Methanococcus jannaschii-suppressor tyrosyl-tRNA$_{CUA}$ mutRNA$_{CUA}^{Tyr}$ | CCGGCGGUAGUUCAGCAGGGCAGAACGGCGGACUCUAAAUCCG CAUGGCGCUGGUUCAAAUCCGGCCCGCCGGACCA |
| 2 | E. coli suppressor tRNA$^{Leu5}{}_{CUA}$ | GCCCGGAUGGUGGAAUCGGUAGACACAAGGGAUUCUAAAUCCC UCGGCGUUCGCGCUGUGCGGGUUCAAGUCCCGCUCCGGGUACC A |
| 3 | Wild-type Methanococcus jannaschii tyrosyl-tRNA synthetase (MjTyrRS) amino acid sequence | MDEFEMIKRNTSEIISEEELREVLKKDEKSAYIGFEPSGKIHL GHYLQIKKMIDLQNAGFDIIILLADLHAYLNQKGELDEIRKIG DYNKKVFEAMGLKAKYVYGSEFQLDKDYTLNVYRLALKTTLKR ARRSMELIAREDENPKVAEVIYPIMQVNDIHYLGVDVAVGGME QRKIHMLARELLPKKVVCIHNPVLTGLDGEGKMSSSKGNFIAV DDSPEEIRAKIKKAYCPAGVVEGNPIMEIAKYFLEYPLTIKRP EKFGGDLTVNSYEELESLFKNKELHPMDLKNAVAEELIKILEP IRKRL |
| 4 | Wild-type Methanococcus jannaschii tyrosyl-LRNA synthetase (MjTyrRS) nucleotide sequence | ATGGACGAATTTGAAATGATAAAGAGAAACACATCTGAAATTATCAGC GAGGAAGAGTTAAGAGAGGTTTTAAAAAAAGATGAAAAATCTGCTTAC ATAGGTTTTGAACCAAGTGGTAAAATACATTTAGGGCATTATCTCCAA ATAAAAAAGATGATTGATTTACAAAATGCTGGATTTGATATAATTATA TTGTTGGCTGATTTACACGCCTATTTAAACCAGAAAGGAGAGTTGGAT GAGATTAGAAAATAGGAGATTATAACAAAAAAGTTTTTGAAGCAAATG GGGTTAAAGGCAAAATATGTTTATGGAAGTGAATTCCAGCTTGATAAG GATTATACACTGAATGTCTATAGATTGGCTTTAAAAACTACCTTAAAA AGAGCAAGAAGGAGTATGGAACTTATAGCAAGAGAGGATGAAAATCCA AAGGTTGCTGAAGTTATCTATCCAATAATGCAGGTTAATGATATTCAT TATTTAGGCGTTGATGTTGCAGTTGGAGGGATGGAGCAGAGAAAAATA CACATGTTAGCAAGGGAGCTTTTACCAAAAAAGGTTGTTTGTATTCAC AACCCTGTCTTAACGGGTTTGGATGGAGAAGGAAAGATGAGTTCTTCA AAAGGGAATTTTATAGCTGTTGATGACTCTCCAGAAGAGATTAGGGCT |

TABLE 5-continued

| SEQ ID NO: | Description | SEQUENCE |
|---|---|---|
| | | AAGATAAAGAAAGCATACTGCCCAGCTGGAGTTGTTGAAGGAAATCCA ATAATGGAGATAGCTAAATACTTCCTTGAATATCCTTTAACCATAAAA AGGCCAGAAAAATTTGGTGGAGATTTGACAGTTAATAGCTATGAGGAG TTAGAGAGTTTATTTAAAAATAAGGAATTGCATCCAATGGATTTAAAA AATGCTGTAGCTGAAGAACTTATAAAGATTTTAGAGCCAATTAGAAAG AGATTA |
| 5 | Wild-type *E. coli* leucyl-tRNA synthetase (EcLeuRS) amino acid seqeunce | MQEQYRPEEIESKVQLHWDEKRTFEVTEDESKEKYYCLSMLPY PSGRLHMGHVRNYTIGDVIARYQRMLGKNVLQPIGWDAFGLPA EGAAVKNNTAPAPWTYDNIAYMKNQLKMLGFGYDWSRELATCT PEYYRWEQKFFTELYKKGLVYKKTSAVNWCPNDQTVLANEQVI DGCCWRCDTKVERKEIPQWFIKITAYADELLNDLDKLDHWPDT VKTMQRNWIGRSEGVEITFNVNDYDNTLTVYTTRPDTFMGCTY LAVAAGHPLAQKAAENNPELAAFIDECRNTKVAEAEMATMEKK GVDTGFKAVHPLTGEEIPVWAANFVLMEYGTGAVMAVPGHDQR DYEFASKYGLNIKPVILAADGSEPDLSQQALTEKGVLFNSGEF NGLDHEAAFNAIADKLTAMGVGERKVNYRLRDWGVSRQRYWGA PIPMVTLEDGTVMPTPDDQLPVILPEDVVMDGITSPIKADPEW AKTTVNGMPALRETDTFDTFMESSWYYARYTCPQYKEGMLDSE AANYWLPVDIYIGGIEHAIMHLLYFRFFHKLMRDAGMVNSDEP AKQLLCQGMVLADAFYYVGENGERNWVSPVDAIVERDEKGRIV KAKDAAGHELVYTGMSKMSKSKNNGIDPQVMVERYGADTVRLF MNFASPADMTLEWQESGVEGANRFLKRVWKLVYEHTAKGDVAA LNVDALTENQKALRRDVHKTIAKVTDDIGRRQTFNTAIAAIME LMNKLAKAPTDGEQDRALMQEALLAVVRMLNPFTPHICFTLWQ ELKGEGDIDNAPWPVADEKAMVEDSTLVVVQVNGKVRAKITVP VDATEEQVRERAGQEHLVAKYLDGVTVRKVIYVPGKLLNLVVG |
| 6 | Wild-type *E. coli* leucyl-tRNA synthetase (EcLeuRS) nucleotide sequence | ATGCAAGAGCAATACCGCCCGGAAGAGATAGAATCCAAAGTAC AGCTTCATTGGGATGAGAAGCGCACATTTGAAGTAACCGAAGA CGAGAGCAAAGAGAAGTATTACTGCCTGTCTATGCTTCCCTAT CCTTCTGGTCGACTACACATGGGCTACGTACGTAACTACACCA TCGGTGACGTGATCGCCCGCTACCAGCATATGCTGGGCAAAAA CGTCCTGCAGCCGATCGGCTGGGACGCGTTTGGTCTGCCTGCG GAAGGCGCGGCGGTGAAAAACAACACCGCTCCGGCACCGTGGA CGTACGACAACATCGCGTATATGAAAAACCAGCTCAAAATGCT GGGCTTTGGTTATGACTGGAGCCGCGAGCTGGCAACCTGTACG CCGGAATACTACCGTTGGGAACAGAAATTCTTCACCGAGCTGT ATAAAAAAGGCCTGGTATATAAGAAGACTTCTGCGGTCAACTG GTGCCCGAACGACCAGACCGTACTGGCGAACGAACAAGTTATC CACGGCTGCTGCTGGCGCTGCGATACCAAAGTTGAACGTAAAG AGATCCCGCAGTGGTTTATCAAAATCAATGCTTACGCTGACGA GCTGCTCAACGATCTGGATAAACTGGATCACTGGCCACACACC GTTAAAACCATGCAGCGTAACTGGATCGGTCGTTCCGAAGGCG TGGAGATCACCTTCAACGTTAACGACTATGACAACACGCTGAC CGTTTACACTACCCGCCCGGACACCTTTATGGGTTGTACCTAC CTGGCGGTACGTGCGGGTCATCCGCTGGCGCAGAAAGCGGCGG AAAATAATCCTGAACTGGCCGCCTTTATTGACGAATGCCGTAA CACCAAAGTTGCCGAAGCTGAAATGGCGACGATGGAGAAAAAA GGCGTCGATACTGGCTTTAAAGCGGTTCACCCATTAACGGGCG AAGAAATTCCCGTTTGGGCAGCAAACTTCGTATTGATGGAGTA CCGCACGGGCGCACTTATGGCGGTACCGGGGCACGACCAGCGC GACTACGAGTTTGCCTCTAAATACGGCCTGAACATCAAACCGG TTATCCTGGCAGCTGACGGCTCTGAGCCAGATCTTTCTCAGCA AGCCCTGACTGAAAAAGGCGTGCTGTTCAACTCTGGCGAGTTC AACGGTCTTGACCATGAAGCGGCCTTCAACGCCATCGCCGATA AACTGACTGCGATGGGCGTTGGCGAGCGTAAAGTGAACTACCG CCTGCGCGACTGGGGTGTTTCCCGTCAGCGTTACTGGGGCGCG CCGATTCCGATGGTGACGCTGGAAGACGGTACCGTAATGCCGA CCCCGGACGACCAGCTGCCGGTGATCCTGCCGGAAGATGTGGT AATGGACGGCATTACCAGCCCGATTAAAGCAGATCCGGAGTGC GCGAAAACTACCGTTAACGGTATGCCAGCACTGCGTGAAACCG ACACTTTCGACACCTTTATGGAGTCCTCCTGGTACTATGCGCG CTACACTTGCCCGCAGTACAAAGAAGGTATGCTGGATTCCGAA GCGGCTAACTACTGGCTGCCGGTGGATATCTACATTGGTGGTA TTGAACACGCCATTATGCACCTGCTCTACTTCCGCTTCTTCCA CAAACTGATGCGTGATGCAGGCATGGTGAACTCTGACGAACCA GCGAAACAGTTGCTGTGTCAGGGTATGGTGCTGGCAGATGCCT TCTACTATGTTGGCGAAAACGGCGAACGTAACTGGGTTTCCCC GGTTGATGCTATCGTTGAACGTGACGAGAAAGGCCGTATCGTG AAAGCGAAAGATGCGGCAGCCCATGAACTGGTTTATACCGCCA TGACCAAAATGTCCAAGTCGAAGAACAACGGTATCGACCCGCA GGTGATGGTTGAACGTTACGGCGCGGACACCGTTCGTCTGTTT ATGATGTTTGCTTCTCCGGCTGATATGACTCTCGAATGGCAGG |

TABLE 5-continued

Nucleotide and Amino Acid Sequences

| SEQ ID NO: | Description | SEQUENCE |
|---|---|---|
| | | AATCCGGTGTGGAAGGGGCTAACCGCTTCCTGAAACGTGTCTG<br>GAAACTGGTTTACGAGCACACAGCAAAAGGTGATGTTGCGGCA<br>CTGAACGTTGATGCGCTGACTGAAAATCAGAAAGCGCTGCGTC<br>GCGATGTGCATAAAACGATCGCTAAAGTGACCGATGATATCGG<br>CCGTCGTCAGACCTTCAACACCGCAATTGCGGCGATTATGGAG<br>CTGATGAACAAACTGGCGAAAGCACCAACCGATGGCGAGCAGG<br>ACCGCGCTCTGATGCAGGAAGCACTGCTGGCCGTTGTCCGTAT<br>GCTTAACCCCTTCACCCCGCACATCTGCTTCACGCTGTGGCAG<br>GAACTGAAAGGCGAAGGCGATATCGACAACGCGCCGTGGCCGG<br>TTGCTGACGAAAAAGCGATGGTGGAAGACTCCACGCTGGTCGT<br>GGTGCAGGTTAACGGTAAAGTCCGTGCCAAAATCACCGTTCCG<br>GTGGACGCAACGGAAGAACAGGTTCGCGAACGTGCTGGCCAGG<br>AACATCTGGTAGCAAAATATCTTGATGGCGTTACTGTACGTAA<br>AGTGATTTACGTACCACGTAAACTCCTCAATCTGGTCGTTGGC<br>TAA |
| 7 | 3-nitro-L-tyrosine aminoacyl-tRNA synthetase isolates-A, B, C, E and G amino acid sequence (derived from wild-type *Methannococcus jannaschii* tyrosyl tRNA-synthetase), each having amino acid changes:<br>A67V, H70V | MDEFEMIKRNTSEIISEEELREVLKKDEKSAYIGFEPSGKIHL<br>GHYLQIKKMIDLQNAGFDIIILL**V**DL**V**AYLNQKGELDEIRKI<br>GDYNKKVFEAMGLKAKYVYGSEFQLDKDYTLNVYRLALKTTLK<br>RARRSMELIAREDENPKVAEVIYPIMQVNDIHYLGVDVAVGGM<br>EQRKIHMLARELLPKKVVCIHNPVLTGLDGEGKMSSSKGNFIA<br>VDDSPEEIRAKIKKAYCPAGVVEGNPIMEIAKYFLEYPLTIKR<br>PEKFGGDLTVNSYEELESLFKNKELHPMDLKNAVAEELIKILE<br>PIRKRL |
| 8 | 3-nitro-L-tyrosine aminoacyl-tRNA synthetase isolate-D amino acid sequence (derived from wild-type *Methanococcus jannaschii* tyrosyl tRNA-synthetase), having amino acid changes:<br>Y32S, A67T, H70N, A167T | MDEFEMIKRNTSEIISEEELREVLKKDEKSA**S**IGFEPSGKIHL<br>GHYLQIKKMIDLQNAGFDIIILL**T**DL**N**AYLNQKGELDEIRKI<br>GDYNKKVFEAMGLKAKYVYGSEFQLDKDYTLNVYRLALKTTLK<br>RARRSMELIAREDENPKVAEVIYPIMQVNDIHYLGVDV**T**VGGM<br>EQRKIHMLARELLPKKVVCTHNPVLTGLDGEGKMSSSKGNFIA<br>VDDSPEEIRAKIKKAYCPAGVVEGNPIMEIAKYFLEYPLTIKR<br>PEKFGGDLTVNSYEELESLFKNKELHPMDLKNAVAEELTKILE<br>PIRKRL |
| 9 | 3-nitro-L-tyrosine aminoacyl-tRNA synthetase isolate-F amino acid sequence (derived from wild-type *Methanococcus jannaschii* tyrosyl tRNA-synthetase), having amino acid changes:<br>Y32A, A67P, A167G | MDEFEMIKRNTSEIISEEELREVLKKDEKSA**Y**IGFEPSGKIHL<br>GHYLQIKKMIDLQNAGFDIIILL**P**DLHAYLNQKGELDEIRKIG<br>DYNKKVFEAMGLKAKYVYGSEFQLDKDYTLNVYRLALKTTLKR<br>ARRSMELIAREDENPKVAEVIYPIMQVNDIHYLGVDV**G**VGGME<br>QRKIHMLARELLPKKVVCIHNPVLTGLDGEGKMSSSKGNFTAV<br>DDSPEEIRAKIKKAYCPAGVVEGNPIMEIAKYFLEYPLTIKRP<br>EKFGGDLTVNSYEELESLFKNKELHPMDLKNAVAEELIKILEP<br>IRKRL |
| 10 | p-nitro-L-phenylalanine aminoacyl-tRNA synthetase amino acid sequence (derived from wild-type *Methanococcus jannaschii* tyrosyl tRNA-synthetase), having amino acid changes:<br>Tyr32Leu, Glu107Ser,<br>Asp158Pro, Ile159Leu,<br>His160Asn, Leu162Glu | MDEFEMIKRNTSEIISEEELREVLKKDEKSA**L**IGFEPSGKIHL<br>GHYLQIKKIDLQNAGFDIIILLADLHAYLNQKGELDEIRKIG<br>DYNKKVFEAMGLKAKYVYGS**S**FQLDKDYTLNVYRLALKTTLKR<br>ARRSMELIAREDENPKVAEVIYPIMQVN**PLN**Y**E**GVDVAVGGM<br>EQRKIHMLARELLPKKVVCIHNPVLTGLDGEGKMSSSKGNFIA<br>VDDSPEEIRAKIKKAYCPAGVVEGNPIMEIAKYFLEYPLTIKR<br>PEKFGGDLTVNSYEELESLFKNKELHPMDLKNAVAEELIKILE<br>PIRKRL |
| 11 | p-nitro-L-phenylalanine aminoacyl-tRNA synthetase nucleotide sequence | ATGGACGAATTTGAAATGATAAAGAGAAACACATCTGAAATTA<br>TCAGCGAGGAAGAGTTAAGAGAGGTTTTAAAAAAAGATGAAAA<br>ATCTGCTCTGATAGGTTTTGAACCAAGTGGTAAAATACATTTA<br>GGGCATTATCTCCAAATAAAAAAGATGATTGATTTACAAAATG<br>CTGGATTTGATATAATTATATTGTTGGCTGATTTACACGCCTA<br>TTTAAACCAGAAAGGAGAGTTGGATGAGATTAGAAAAATAGGA<br>GATTATAACAAAAAAGTTTTTGAAGCAATGGGGTTAAAGGCAA<br>AATATGTTTATGGAAGTTCGTTCCAGCTTGATAAGGATTATAC<br>ACTGAATGTCTATAGATTGGCTTTAAAAACTACCTTAAAAAGA<br>GCAAGAAGGAGTATGGAACTTATAGCAAGAGAGGATGAAAATC<br>CAAAGGTTGCTGAAGTTATCTATCCAATAATGCAGGTTAATCC<br>TCTTAATTATGAGGGCGTTGATGTTGCAGTTGGAGGGATGGAG<br>CAGAGAAAAATACACATGTTAGCAAGGGAGCTTTTACCAAAAA<br>AGGTTGTTTGTATTCACAACCCTGTCTTAACGGGTTTGGATGG<br>AGAAGGAAAGATGAGTTCTTCAAAAGGGAATTTTATAGCTGTT<br>GATGACTCTCCAGAAGAGATTAGGGCTAAGATAAAGAAAGCAT<br>ACTGCCCAGCTGGAGTTGTTGAAGGAAATCCAATAATGGAGAT<br>AGCTAAATACTTCCTTGAATATCCTTTAACCATAAAAAGGCCA<br>GAAAAATTTGGTGGAGATTTGACAGTTAATAGCTATGAGGAGT |

TABLE 5-continued

Nucleotide and Amino Acid Sequences

| SEQ ID NO: | Description | SEQUENCE |
|---|---|---|
| | | TAGAGAGTTTATTTAAAAATAAGGAATTGCATCCAATGGATTT AAAAAATGCTGTAGCTGAAGAACTTATAAAGATTTTAGAGCCA ATTAGAAAGAGATTATAA |
| 12 | 3-amino-L-tyrosine aminoacyl tRNA synthetase amino acid sequence (derived from wild-type *Methanococcus jannaschii* tyrosyl tRNA-synthetase) | MDEFEMIKRNTSEIISEEELREVLKKDEKSAQIGFEPSGKIHL GHYLQIKKMIDLQNAGFDIIIELADLHAYLNQKGELDEIRKIG DYNKKVPEAMGLKAKYVYGSEGLLDKDYTLNVYRLALKTTLKR ARRSMELIAREDENPKVAEVIYPIMQVNSIHYTGVDVAVGGME QRKIHMLARELLPKKVVCIHNPVLTGLDGEGKMSSSKGNFIAV DDSPEEIRAKIKKAYCPAGVVEGNPIMEIAKYFLEYPLTIKRP EKFGGDLTVNSYEELESLFKNKELHPMDLKNAVAEELIKILEP IRKRL |
| 13 | 3-amino-L-tyrosine aminoacyl-tRNA synthetase nucleotide sequence | ATGGACGAATTTGAAATGATAAAGAGAAACACATCTGAAATTA TCAGCGAGGAAGAGTTAAGAGAGGTTTTAAAAAAAGATGAAAA ATCTGCTCAGATAGGTTTTGAACCAAGTGGTAAAATACATTTA GGGCATTATCTCCAAATAAAAAAGATGATTGATTTACAAAATG CTGGATTTGATATAATTATAGAGTTGGCTGATTTACACGCCTA TTTAAACCAGAAAGGAGAGTTGGATGAGATTAGAAAAATAGGA GATTATAACAAAAAAACTTTTTGAAGCAATGGGGTTAAAGGCAA AATATGTTTATGGAAGTGAAGGTTTGCTTGATAAGGATTATAC ACTGAATGTCTATAGATTGGCTTTAAAAACTACCTTAAAAAGA GCAAGAAGGAGTATGGAACTTATAGCAAGAGAGGATGAAAATC CAAAGGTTGCTGAAGTTATCTATCCAATAATGCAGGTTAATTC TATTCATTATACTGGCGTTGATGTTGCAGTTGGAGGGATGGAG CAGAGAAAAATACACATGTTAGCAAGGGAGCTTTTACCAAAAA AGGTTGTTTGTATTCACAACCCTGTCTTAACGGGTTTGGATGG AGAAGGAAAGATGAGTTCTTCAAAAGGGAATTTTATAGCTGTT GATGACTCTCCAGAAGAGATTAGGGCTAAGATAAAGAAAGCAT ACTGCCCAGCTGGAGTTGTTGAAGGAAATCCAATAATGGAGAT AGCTAAATACTTCCTTGAATATCCTTTAACCATAAAAAGGCCA GAAAAATTTGGTGGAGATTTGACAGTTAATAGCTATGAGGAGT TAGAGAGTTTATTTAAAAATAAGGAATTGCATCCAATGGATTT AAAAAATGCTGTAGCTGAAGAACTTATAAACATTTTACAGCCA ATTAGAAAGAGATTATAA |
| 14 | p-carboxymethyl-L-phenylalanine aminoacyl-tRNA synthetase clone #1 amino acid sequence (derived from wild-type *Methanococcus jannaschii* tyrosyl tRNA-synthetase) | MDEFEMIKRNTSEIISEEELREVLKKDEKSAAIGFEPSGKIHL GHYLQIKKMIDLQNAGFDIIISLADLHAYLNQKGELDEIRKIG DYNKKVFEAMGLKAKYVYGSERNLDKDYTLNVYRLALKTTLKR ARRSMELIAREDENPKVAEVIYPIMQVNSIHYHGVDVAVGGME QRKIHMLARELLPKKVVCIHNPVLTGLDGEGKMSSSKGNFIAV DDSPEEIRAKIKKAYCPACVVEGNPIMEIAKYFLEYPLTIKRP EKFGGDLTVNSYEELESLFKNKELHPMDLKNAVAEELIKILEP IRKRL |
| 15 | p-carboxymethyl-L-phenylalanine aminoacyl-tRNA synthetase clone #1 nucleotide sequence | ATGGACGAATTTGAAATGATAAAGAGAAACACATCTGAAATTA TCAGCGAGGAAGAGTTAAGAGAGGTTTTAAAAAAAGATGAAAA ATCTGCTGCGATAGGTTTTGAACCAAGTGGTAAAATACATTTA GGGCATTATCTCCAAATAAAAAAGATGATTGATTTACAAAATG CTGGATTTGATATAATTATATCGTTGGCTGATTTACACGCCTA TTTAAACCAGAAAGGAGAGTTGGATGAGATTAGAAAAATAGGA GATTATAACAAAAAAGTTTTTGAAGCAATGGGGTTAAAGGCAA AATATGTTTATGGAAGTGAACGTAATCTTCATAAGGATTATAC ACTGAATGTCTATAGATTGGCTTTAAAAACTACCTTAAAAAGA GCAAGAAGCAGTATGGAACTTATAGCAAGAGAGGATGAAAATC CAAAGGTTGCTGAAGTTATCTATCCAATAATGCAGGTTAATTC TATTCATTATCATGGCGTTGATGTTGCAGTTGGAGGGATGGAG CAGAGAAAAATACACATGTTAGCAAGGGAGCTTTTACCAAAAA AGGTTGTTTGTATTCACAACCCTGTCTTAACGGGTTTGGATGG AGAAGGAAAGATGAGTTCTTCAAAAGGGAATTTTATAGCTGTT GATGACTCTCCAGAAGAGATTAGGGCTAAGATAAAGAAAGCAT ACTGCCCAGCTGGAGTTGTTGAAGGAAATCCAATAATGGAGAT AGCTAAATACTTCCTTGAATATCCTTTAACCATAAAAAGGCCA GAAAAATTTGGTGGAGATTTGACAGTTAATAGCTATGAGGAGT TAGAGAGTTTATTTAAAAATAAGGAATTGCATCCAATGGATTT AAAAAATGCTGTAGCTGAACAACTTATAAAGATTTTACAGCCA ATTAGAAAGAGATTATAA |
| 16 | p-carboxymethyl-L-phenylalanine aminoacyl-tRNA synthetase clone #2 amino acid sequence (derived from wild-type *Methanococcus* | MDEFEMIKRNTSEIISEEELREVLKKDEKSASIGFEPSGKIHL GHYLQIKKNIDLQNAGFDIIIALADLHAYLNQKGELDEIRKIG DYNKKVFEAMGLKAKYVYGSENYLDKDYTLNVYRLALKTTLKR ARRSMELIAREDENPKVAEVIYPIMQVNGIHYKGVDVAVGGME |

TABLE 5-continued

Nucleotide and Amino Acid Sequences

| SEQ ID NO: | Description | SEQUENCE |
|---|---|---|
| | *jannaschii* tyrosyl tRNA-synthetase) | QRKIHMLARELLPKKVVCIHNPVLTGLDGEGKMSSSKGNFIAV<br>DDSPEEIRAKIKKAYCPAGVVEGNPIMEIAKYFLEYPLTIKRP<br>EKFGGDLTVMSYEELESLFKNKELHPMDLKNAVAEELIKILEP<br>IRKRL |
| 17 | p-carboxymethyl-L-phenylalanine aminoacyl-tRNA synthetase clone #2 nucleotide sequence | ATGGACGAATTTGAAATGATAAAGAGAAACACATCTGAAATTA<br>TCAGCGAGGAAGAGTTAAGAGAGGTTTTAAAAAAAGATGAAAA<br>ATCTGCTTCTATAGGTTTTGAACCAAGTGGTAAAATACATTTA<br>GGGCATTATCTCCAAATAAAAAGATGATTGATTTACAAAATG<br>CTGGATTTGATATAATTATAGCTTTGGCTGATTTACACGCCTA<br>TTTAAACCAGAAAGGAGAGTTGGATGAGATTAGAAAAATAGGA<br>GATTATAACAAAAAAGTTTTTGAAGCAATGGGGTTAAAGGCAA<br>AATATGTTTATGGAAGTGAAAATTATCTTGATAAGGATTATAC<br>ACTGAATGTCTATAGATTGGCTTTAAAAACTACCTTAAAAAGA<br>GCAAGAAGGAGTATGGAACTTATAGCAAGAGAGGATGAAAATC<br>CAAAGGTTGCTGAAGTTATCTATCCAATAATGCAGGTTAATGG<br>TATTCATTATAAGGGCGTTGATGTTGCAGTTGGAGGGATGGAG<br>CAGAGAAAAATACACATGTTAGCAAGGGAGCTTTTACCAAAAA<br>AGGTTGTTTGTATTCACAACCCTGTCTTAACGGGTTTGGATGG<br>AGAAGGAAAGATGAGTTCTTCAAAAGGGAATTTTATAGCTGTT<br>GATGACTCTCCAGAAGAGATTAGGGCTAAGATAAAGAAAGCAT<br>ACTGCCCAGCTGGAGTTGTTGAAGGAAATCCAATAATGGAGAT<br>AGCTAAATACTTCCTTGAATATCCTTTAACCATAAAAAGGCCA<br>GAAAAATTTGGTGGAGATTTGACAGTTAATAGCTATGAGGAGT<br>TAGAGAGTTTATTTAAAAATAAGGAATTGCATCCAATGGATTT<br>AAAAAATGCTGTAGCTGAAGAACTTATAAAGATTTTAGAGCCA<br>ATTAGAAAGAGATTATAA |
| 18 | p-carboxymethyl-L-phenylalanine aminoacyl-tRNA synthetase clone #3 amino acid sequence (derived from wild-type *Methanococcus jannaschii* tyrosyl tRNA-synthetase) | MDEFEMIKRNTSEIISEEELREVLKKDEKSASIGFEPSGKIHL<br>GHYLQIKKMIDLQNAGFDIIIALADLHAYLNQKGELDEIRKIG<br>DYNKKVFEAMGLKAKYVYGSERQLDKDYTLNVYRLALKTTLKR<br>ARRSMELIAREDENPKVAEVIYPIMQVNGIHYKGVDVAVGGME<br>QRKIHMLARELLPKKVVCIHNPVLTGLDGEGKMSSSKGNFIAV<br>DDSPEEIRAKIKKAYCPAGVVEGNPIMEIAKYFLEYPLTIKRP<br>EKFGGDLTVNSYEELESLFKNKELHPMDLKNAVAEELIKILEP<br>IRKRL |
| 19 | p-carboxymethyl-L-phenylalanine aminoacyl-tRNA synthetase clone #3 nucleotide sequence | ATGGACGAATTTGAAATGATAAAGAGAAACACATCTGAAATTA<br>TCAGCGAGGAAGAGTTAAGAGAGGTTTTAAAAAAAGATGAAAA<br>ATCTGCTTCGATAGGTTTTGAACCAAGTGGTAAAATACATTTA<br>GGGCATTATCTCCAAATAAAAAGATGATTGATTTACAAAATG<br>CTGGATTTGATATAATTATAGCGTTGGCTGATTTACACGCCTA<br>TTTAAACCAGAAAGGAGAGTTGGATGAGATTAGAAAAATAGGA<br>GATTATAACAAAAAAGTTTTTGAAGCAATGGGGTTAAAGGCAA<br>AATATGTTTATGGAAGTGAACGTCAGCTTGATAAGGATTATAC<br>ACTGAATGTCTATAGATTGGCTTTAAAAACTACCTTAAAAAGA<br>GCAAGAAGGAGTATGGAACTTATAGCAAGAGAGGATGAAAATC<br>CAAAGGTTGCTGAAGTTATCTATCCAATAATGCAGGTTAATGG<br>TATTCATTATAAGGGCGTTGATGTTGCAGTTGGAGGGATGGAG<br>CAGAGAAAAATACACATGTTAGCAAGGGAGCTTTTACCAAAAA<br>AGGTTGTTTGTATTCACAACCCTGTCTTAACGGGTTTGGATGG<br>AGAAGGAAAGATGAGTTCTTCAAAAGGGAATTTTATAGCTGTT<br>GATGACTCTCCAGAAGAGATTAGGGCTAAGATAAAGAAACCAT<br>ACTGCCCAGCTGGAGTTGTTGAAGGAAATCCAATAATGGAGAT<br>AGCTAAATACTTCCTTGAATATCCTTTAACCATAAAAAGGCCA<br>GAAAAATTTGGTGGAGATTTGACAGTTAATAGCTATGAGGAGT<br>TAGAGAGTTTATTTAAAAATAAGGAATTGCATCCAATGGATTT<br>AAAAAATGCTGTAGCTGAAGAACTTATAAAGATTTTAGAGCCA<br>ATTAGAAAGAGATTATAA |
| 20 | p-carboxymethyl-L-phenylalanine aminoacyl-tRNA synthetase clone #4 amino acid sequence (derived from wild-type *Methanococcus jannaschii* tyrosyl tRNA-synthetase) | MDEFEMIKRNTSEIISEEELREVLKKDEKSASIGFEPSGKIHL<br>GHYLQIKKMIDLQNAGFDIIIALADLHAYLNQKGELDEIRKIG<br>DYNKKVFEAMGLKAKYVYGSEAQLDKDYTLNVYRLALKTTLKR<br>ARRSMELIAREDENPKVAEVIYPIMQVNGIHYKGVDVAVGGME<br>QRKIHMLARELLPKKVVCIHNPVLTGLDGEGKMSSSKGNFIAV<br>DDSPEEIRAKIKKAYCPAGVVEGNPIMEIAKYFLEYPLTIKRP<br>EKFGGDLTVNSYEELESLFKNKELHPMDLKNAVAEELIKILEP<br>IRKRL |
| 21 | p-carboxymethyl-L-phenylalanine aminoacyl-tRNA synthetase clone #4 nucleotide sequence | ATGGACGAATTTGAAATGATAAAGAGAAACACATCTGAAATTA<br>TCAGCGAGGAAGAGTTAAGAGAGGTTTTAAAAAAAGATGAAAA<br>ATCTGCTTCGATAGGTTTTGAACCAAGTGGTAAAATACATTTA<br>GGGCATTATCTCCAAATAAAAAGATGATTGATTTACAAAATG<br>CTGGATTTGATATAATTATAGCGTTGGCTGATTTACACGCCTA |

TABLE 5-continued

| SEQ ID NO: | Description | SEQUENCE |
|---|---|---|
| | | TTTAAACCAGAAAGGAGAGTTGGATGAGATTAGAAAAATAGGA GATTATAACAAAAAAGTTTTTGAAGCAATGGGGTTAAAGGCAA AATATGTTTATGGAAGTGAAGCGCAGCTTGATAAGGATTATAC ACTGAATGTCTATAGATTGGCTTTAAAAACTACCTTAAAAAGA GCAAGAAGGAGTATGGAACTTATAGCAAGAGAGGATGAAAATC CAAAGGTTGCTGAAGTTATCTATCCAATAATGCAGGTTAATGG TATTCATTATAAGGGCGTTGATGTTGCAGTTGGAGCGATGGAG CAGAGAAAAATACACATGTTACCAAGGGAGCTTTTACCAAAAA AGGTTGTTTGTATTCACAACCCTGTCTTAACCCGTTTGGATGG AGAAGGAAAGATGAGTTCTTCAAAAGGGAATTTTATAGCTGTT GATGACTCTCCAGAAGAGATTAGGGCTAAGATAAAGAAAGCAT ACTGCCCAGCTGGAGTTGTTGAAGGAAATCCAATAATGGAGAT AGCTAAATACTTCCTTGAATATCCTTTAACCATAAAAAGGCCA GAAAAATTTGGTGGAGATTTGACAGTTAATAGCTATGAGGAGT TAGAGAGTTTATTTAAAAATAAGGAATTGCATCCAATGGATTT AAAAAATGCTGTAGCTGAAGAACTTATAAAGATTTTAGAGCCA ATTAGAAAGAGATTATAA |
| 22 | p-carboxymethyl-L-phenylalanine aminoacyl-tRNA synthetase clone #5 amino acid sequence (derived from wild-type *Methanococcus jannaschii* tyrosyl tRNA-synthetase) | MDEFEMIKRNTSEIISEEELREVLKKDEKSASIGFEPSGKIHL GHYLQIKKMIDLQNAGFDIIIALADLHAYLNQKGELDEIRKIG DYNKKVFEAMGLKAKYVYGSEKHLDKDYTLNVYRLALKTTLKR ARRSMELIAREDENPKVAEVIYPIMQVNGIHYKGVDVAVGGME QRKIHMLARELLPKKVVCIHNPVLTGLDGEGKMSSSKGNFIAV DDSPEEIRAKIKKAYCPAGVVEGNPIMEIAKYFLEYPLTIKRP EKFGGDLTVNSYEELESLFKNKELHPMDLKNAVAEELIKILEP IRKRL |
| 23 | p-carboxymethyl-L-phenylalanine aminoacyl-tRNA synthetase clone #5 nucleotide sequence | ATGGACGAATTTGAAATGATAAAGAGAAACACATCTGAAATTA TCAGCGAGGAAGAGTTAAGAGAGGTTTTAAAAAAAGATGAAAA ATCTGCTTCTATAGGTTTTGAACCAAGTGGTAAAATACATTTA GGGCATTATCTCCAAATAAAAAAGATGATTGATTTACAAAATG CTGGATTTGATATAATTATAGCGTTGGCTCATTTACACGCCTA TTTAAACCAGAAAGGAGAGTTGGATGAGATTAGAAAAATAGGA GATTATAACAAAAAAGTTTTTGAAGCAATGGGGTTAAAGGCAA AATATGTTTATGGAAGTGAAAAGCATCTTGATAAGGATTATAC ACTGAATGTCTATAGATTGGCTTTAAAAACTACCTTAAAAAGA GCAAGAAGGAGTATGGAACTTATAGCAAGAGAGGATGAAAATC CAAAGGTTGCTGAAGTTATCTATCCAATAATGCAGGTTAATGG TATTCATTATAAGGGCGTTGATGTTGCAGTTGGAGGGATGGAG CAGAGAAAAATACACATGTTAGCAAGGGAGCTTTTACCAAAAA AGGTTGTTTGTATTCACAACCCTGTCTTAACGGGTTTGGATGG AGAAGGAAAGATGAGTTCTTCAAAAGGGAATTTTATAGCTGTT GATGACTCTCCAGAAGAGATTAGGGCTAAGATAAAGAAAGCAT ACTGCCCAGCTGGAGTTGTTGAAGGAAATCCAATAATGGAGAT AGCTAAATACTTCCTTGAATATCCTTTAACCATAAAAAGGCCA GAAAAATTTGGTGGAGATTTGACAGTTAATAGCTATGAGGAGT TAGAGAGTTTATTTAAAAATAAGGAATTGCATCCAATGGATTT AAAAAATGCTGTAGCTGAAGAACTTATAAAGATTTTAGAGCCA ATTAGAAAGAGATTATAA |
| 24 | biphenylalanine aminoacyl-tRNA synthetase clone #1 amino acid sequence (derived from wild-type *Methanococcus jannaschii* tyrosyl tRNA-synthetase) | MDEFEMIKRNTSEIISEEELREVLKKDEKSAAIGFEPSGKIHL GHYLQIKKMIDLQNAGFDIIIGLADLHAYLNQKGELDEIRKIG DYNKKVFEAMGLKAKYVYGSEEPLDKDYTLNVYRLALKTTLKR ARRSMELIAREDENPKVAEVIYPIMQVNCIHYHGVPVAVGGME QRKIHMLARELLPKKVVCIHNPVLTGLDGEGKMSSSKGNFIAV DDSPEEIRAKIKKAYCPAGVVEGNPIMEIAKYFLEYPLTIKRP EKFGGDLTVNSYEELESLFKNKELHPMDLKNAVAEELIKILEP IRKRL |
| 25 | biphenylalanine aminoacyl-tRNA synthetase clone #1 nucleotide sequence | ATGGACGAATTTGAAATGATAAAGAGAAACACATCTGAAATTA TCAGCGAGGAAGAGTTAAGAGAGGTTTTAAAAAAAGATGAAAA ATCTGCTGCTATAGGTTTTGAACCAAGTGGTAAAATACATTTA GGGCATTATCTCCAAATAAAAAAGATGATTGATTTACAAAATG CTGGATTTGATATAATTATAGGGTTGGCTGATTTACACGCCTA TTTAAACCAGAAAGGAGAGTTGGATGAGATTAGAAAAATAGGA GATTATAACAAAAAAGTTTTTGAAGCAATGGGGTTAAAGGCAA AATATGTTTATGGAAGTGAAGAGCCGCTTGATAAGGATTATAC ACTGAATGTCTATAGATTGGCTTTAAAAACTACCTTAAAAAGA GCAAGAAGGAGTATGGAACTTATAGCAAGAGAGGATGAAAATC CAAAGGTTGCTGAAGTTATCTATCCAATAATGCAGGTTAATTG TATTCATTATCATGGCGTTGATGTTGCAGTTGGAGGGATGGAG CAGAGAAAAATACACATGTTAGCAAGGGAGCTTTTACCAAAAA AGGTTGTTTGTATTCACAACCCTGTCTTAACGGGTTTGGATGG AGAAGGAAAGATGAGTTCTTCAAAAGGGAATTTTATAGCTGTT |

TABLE 5-continued

Nucleotide and Amino Acid Sequences

| SEQ ID NO: | Description | SEQUENCE |
|---|---|---|
| | | GATGACTCTCCAGAAGAGATTAGGGCTAAGATAAAGAAAGCAT<br>ACTGCCCAGCTGGAGTTGTTGAAGCAAATCCAATAATGGAGAT<br>AGCTAAATACTTCCTTGAATATCCTTTAACCATAAAAAGGCCA<br>GAAAAATTTGGTGGAGATTTGACAGTTAATAGCTATGAGGAGT<br>TAGAGAGTTTATTTAAAAATAAGGAATTGCATCCAATGGATTT<br>AAAAAATGCTGTAGCTGAAGAACTTATAAAGATTTTAGAGCCA<br>ATTAGAAAGAGATTATAA |
| 26 | biphenylalanine aminoacyl-tRNA synthetase clone #2 amino acid sequence (derived from wild-type *Methanococcus jannaschii* tyrosyl tRNA-synthetase) | MDEFEMIKRNTSEIISEEELREVLKKDEKSALIGFEPSGKIHL<br>GHYLQIKKMIDLQNAGFDIIITLADLSAYLNQKGELDEIRKIG<br>DYNKKVFEAMGLKAKYVYGSEFQLDKDYTLNVYRLALKTTLKR<br>ARRSMELIAREDENPKVAEVIYPIMGVNVIHYHGVDVAVGGME<br>QRKIHMLARELLPKKVVCIHNPVLTGLDGEGKMSSSKGNFIAV<br>DDSPEEIRAKIKKAYCPAGVVEGNPIMEIAKYFLEYPLTIKRP<br>EKFGGDLTVNSYEELESLFKNKELHPMDLKNAVAEELIKILEP<br>IRKRL |
| 27 | biphenylalanine aminoacyl-tRNA synthetase clone #2 nucleotide sequence | ATGGACGAATTTGAAATGATAAAGAGAAACACATCTGAAATTA<br>TCAGCGAGGAAGAGTTAAGAGAGGTTTTAAAAAAAGATGAAAA<br>ATCTGCTCTGATAGGTTTTGAACCAAGTGGTAAAATACATTTA<br>GGGCATTATCTCCAAATAAAAAAGATGATTGATTTACAAAATG<br>CTGGATTTGATATAATTATAACTTTGGCTGATTTATCTGCCTA<br>TTTAAACCAGAAAGGAGAGTTGGATGAGATTAGAAAAATAGGA<br>GATTATAACAAAAAAGTTTTTGAAGCAATGGGGTTAAAGGCAA<br>AATATGTTTATGGAAGTGAATTCCAGCTTGATAAGCATTATAC<br>ACTGAATGTCTATAGATTGGCTTTAAAAACTACCTTAAAAAGA<br>GCAAGAAGGAGTATGGAACTTATAGCAAGAGAGGATGAAAATC<br>CAAAGGTTCCTGAAGTTATCTATCCAATAATGGGTGTTAATGT<br>TATTCATTATCATGGCGTTGATGTTGCAGTTGGAGGGATGGAG<br>CAGAGAAAAATACACATGTTAGCAAGGGACCTTTTACCAAAAA<br>AGGTTGTTTGTATTCACAACCCTGTCTTAACGGGTTTGGATGG<br>AGAAGGAAAGATGAGTTCTTCAAAAGGGAATTTTATAGCTGTT<br>GATGACTCTCCAGAAGAGATTAGCGCTAAGATAAAGAAAGCAT<br>ACTGCCCAGCTGGAGTTGTTGAAGGAAATCCAATAATGGAGAT<br>AGCTAAATACTTCCTTGAATATCCTTTAACCATAAAAAGGCCA<br>GAAAAATTTGGTGGAGATTTGACAGTTAATAGCTATGAGGAGT<br>TAGAGAGTTTATTTAAAAATAAGGAATTGCATCCAATGGATTT<br>AAAAAATGCTGTAGCTGAAGAACTTATAAAGATTTTAGAGCCA<br>ATTAGAAACAGATTATAA |
| 28 | biphenylalanine aminoacyl-tRNA synthetase clone #3 amino acid sequence (derived from wild-type *Methanococcus jannaschii* tyrosyl tRNA-synthetase) | MDEFEMIKRNTSEIISEEELREVLKKDEKSAAIGFEPSGKIHL<br>GHYLQIKKMIDLQNAGFDIIISLADLHAYLNQKGELDEIRKIG<br>DYNKKVFEAMGLKAKYVYGSERELDKDYTLNVYRLALKTTLKR<br>ARRSMELIAREDENPKVAEVIYPIMQVNSIHYSGVDVAVGGME<br>QRKIHMLARELLPKKVVCIHNPVLTGLDGEGKMSSSKGNFIAV<br>DDSPEEIRAKIKKAYCPAGVVEGNPIMEIAKYFLEYPLTIKRP<br>EKFGGDLTVNSYEELESLFKNKELHPMDLKNAVAEELIKILEP<br>IRKRL |
| 29 | biphenylalanine aminoacyl-tRNA synthetase clone #3 nucleotide sequence | ATGGACGAATTTGAAATGATAAAGAGAAACACATCTGAAATTA<br>TCAGCGAGGAAGAGTTAAGAGAGGTTTTAAAAAAAGATGAAAA<br>ATCTGCTGCTATAGGTTTTGAACCAAGTGGTAAAATACATTTA<br>GGGCATTATCTCCAAATAAAAAAGATGATTGATTTACAAAATG<br>CTGGATTTGATATAATTATATCGTTGGCTGATTTACACGCCTA<br>TTTAAACCAGAAAGGAGAGTTGGATGAGATTAGAAAAATAGGA<br>GATTATAACAAAAAAGTTTTTGAAGCAATGGGGTTAAAGGCAA<br>AATATGTTTATGGAAGTGAAAGGGAGCTTGATAAGGATTATAC<br>ACTGAATGTCTATAGATTGGCTTTAAAAACTACCTTAAAAAGA<br>GCAAGAAGGAGTATGGAACTTATAGCAAGAGACGATGAAAATC<br>CAAAGGTTGCTGAAGTTATCTATCCAATAATGCAGGTTAATAG<br>TATTCATTATAGTGGCGTTGATGTTGCAGTTGGAGGGATGGAG<br>CAGAGAAAAATACACATGTTAGCAAGGGAGCTTTTACCAAAAA<br>AGGTTGTTTGTATTCACAACCCTGTCTTAACGGGTTTGGATGG<br>AGAAGGAAAGATGAGTTCTTCAAAAGGGAATTTTATAGCTGTT<br>GATGACTCTCCAGAAGAGATTAGGGCTAAGATAAAGAAAGCAT<br>ACTGCCCAGCTGGAGTTGTTGAAGGAAATCCAATAATGGAGAT<br>AGCTAAATACTTCCTTGAATATCCTTTAACCATAAAAACGCCA<br>GAAAAATTTGGTGGAGATTTGACAGTTAATAGCTATGAGGAGT<br>TAGAGAGTTTATTTAAAAATAAGGAATTGCATCCAATGGATTT<br>AAAAAATGCTGTAGCTGAAGAACTTATAAAGATTTTAGAGCCA<br>ATTAGAAAGAGATTATAA |

TABLE 5-continued

Nucleotide and Amino Acid Sequences

| SEQ ID NO: | Description | SEQUENCE |
|---|---|---|
| 30 | biphenylalanine aminoacyl-tRNA synthetase clone #4 amino acid sequence (derived from wild-type *Methanococcus jannaschii* tyrosyl tRNA-synthetase) | MDEFEMTKRNTSEIISEEELREVLKKDEKSAHIGFEPSGKIHL GHYLQIKKMIDLQNAGFDIIIVLADLHAYLNQKGELDEIRKIG DYNKKVFEAMGLKAKYVYGSESKLDKDYTLNVYRLALKTTLKR ARRSMELIAREDENPKVAEVIYPIMQVNGIHYLGVDVAVGGME QRKIHMLARELLPKKVVCIHNPVLTGLDGEGKMSSSKGNFIAV DDSPEEIRAKIKKAYCPAGVVEGNPIMEIAKYFLEYPLTIKRP EKFGGDLTVNSYEELESLFKNKELHPMDLKNAVAEELIKILEP IRKRL |
| 31 | biphenylalanine aminoacyl-tRNA synthetase clone #4 nucleotide sequence | ATGGACGAATTTGAAATGATAAAGAGAAACACATCTGAAATTA TCAGCGAGGAAGAGTTAAGAGAGGTTTTAAAAAAACATGAAAA ATCTGCTCATATAGGTTTTGAACCAAGTGGTAAAATACATTTA GGGCATTATCTCCAAATAAAAAAGATGATTGATTTACAAAATG CTGGATTTGATATAATTATAGTTTTGGCTGATTTACACGCCTA TTTAAACCAGAAAGGAGAGTTGGATGAGATTAGAAAAATAGGA GATTATAACAAAAAAGTTTTTGAAGCAATGGGGTTAAAGGCAA AATATGTTTATGGAAGTGAATCGAAGCTTGATAAGGATTATAC ACTGAATGTCTATAGATTGGCTTTAAAAACTACCTTAAAAAGA GCAAGAAGGAGTATGGAACTTATAGCAAGAGAGGATGAAAATC CAAAGGTTGCTGAAGTTATCTATCCAATAATGCAGGTTAATGG TATTCATTATCTTGGCGTTGATGTTGCAGTTGGAGGGATGGAG CAGAGAAAAATACACATGTTAGCAAGGGAGCTTTTACCAAAAA AGGTTGTTTGTATTCACAACCCTGTCTTAACGGGTTTGGATGG AGAAGGAAAGATGAGTTCTTCAAAAGGGAATTTTATAGCTGTT GATGACTCTCCAGAAGAGATTAGGGCTAAGATAAAGAAAGCAT ACTGCCCAGCTGGAGTTGTTGAAGGAAATCCAATAATGGAGAT AGCTAAATACTTCCTTGAATATCCTTTAACCATAAAAAGGCCA GAAAAATTTGGTGGAGATTTGACAGTTAATAGCTATGAGGAGT TAGAGAGTTTATTTAAAAATAAGGAATTGCATCCAATGGATTT AAAAAATGCTGTAGCTGAAGAACTTATAAAGATTTTAGAGCCA ATTAGAAAGAGATTATAA |
| 32 | biphenylalanine aminoacyl-tRNA synthetase clone #5 amino acid sequence (derived from wild-type *Methanococcus jannaschii* tyrosyl tRNA-synthetase) | MDEFEMIKRNTSEIISEEELREVLKKDEKSAGIGFEPSGKIHL GHYLQIKKMIDLQNAGFDIIIVLADLHAYLNQKGELDEIRKIG DYNKKVFEAMGLKAKYVYGSEADLDKDYTLNVYRLALKTTLKR ARRSMELIAREDENPKVAEVIYPIMQVNSIHYRGVDVAVGGME QRKIHMLARELLPKKVVCIHNPVLTGLDGEGKMSSSKGNFIAV DDSPEEIRAKIKKAYCPAGVVEGNPIMEIAKYFLEYPLTIKRP EKFGGDLTVNSYEELESLFKNKELHPMDLKNAVAEELIKILEP IRKRL |
| 33 | biphenylalanine aminoacyl-tRNA synthetase clone #5 nucleotide sequence | ATGGACGAATTTGAAATGATAAAGAGAAACACATCTGAAATTA TCAGCGAGGAAGAGTTAAGAGAGGTTTTAAAAAAAGATGAAAA ATCTGCTGGGATAGGTTTTGAACCAAGTGGTAAAATACATTTA GGGCATTATCTCCAAATAAAAAAGATGATTGATTTACAAAATG CTGGATTTGATATAATTATAGTTTTGGCTGATTTACACGCCTA TTTAAACCAGAAAGGAGAGTTGGATGAGATTAGAAAAATAGGA GATTATAACAAAAAAGTTTTTGAAGCAATGGGGTTAAAGGCAA AATATGTTTATGGAAGTGAAGCGGATCTTGATAAGGATTATAC ACTGAATGTCTATAGATTGGCTTTAAAAACTACCTTAAAAAGA GCAAGAAGGAGTATGGAACTTATAGCAAGAGAGGATGAAAATC CAAAGGTTGCTGAAGTTATCTATCCAATAATGCAGGTTAATTC GATTCATTATCGTGGCGTTGATGTTGCAGTTGGAGGGATGGAG CAGAGAAAAATACACATGTTAGCAAGGGAGCTTTTACCAAAAA AGGTTGTTTGTATTCACAACCCTGTCTTAACGGGTTTCGATGG AGAAGGAAAGATGAGTTCTTCAAAAGGGAATTTTATAGCTGTT GATGACTCTCCAGAAGAGATTAGGGCTAAGATAAAGAAAGCAT ACTGCCCAGCTGGAGTTGTTGAAGGAAATCCAATAATGGAGAT AGCTAAATACTTCCTTGAATATCCTTTAACCATAAAAAGGCCA GAAAAATTTGGTGGAGATTTGACAGTTAATAGCTATGAGGAGT TAGAGAGTTTATTTAAAAATAAGGAATTGCATCCAATGGATTT AAAAAATGCTGTAGCTGAAGAACTTATAAAGATTTTAGAGCCA ATTAGAAAGACATTATAA |
| 34 | biphenylalanine aminoacyl-tRNA synthetase clone #6 amino acid sequence (derived from wild-type *Methanococcus jannaschii* tyrosyl tRNA-synthetase) | MDEFEMIKRNTSEIISEEELREVLKKDEKSAHIGFEPSGKIHL GHYLQIKKMIDLQNAGFDIIIVLADLHAYLNQKGELDEIRKIG DYNKKVFEAMGLKAKYVYGSERPLDKDYTLNVYRLALKTTLKR ARRSMELIAREDENPKVAEVIYPIMQVNGIHYLGVDVAVGGME QRKIHMLARELLPKKVVCIHNPVLTGLDGEGKMSSSKGNFIAV DDSPEEIRAKIKKAYCPAGVVEGNPIMEIAKYFLEYPLTIKRP EKFGGDLTVNSYEELESLFKNKELHPMDLKNAVAEELIKILEP IRKRL |

TABLE 5-continued

| Nucleotide and Amino Acid Sequences | | |
|---|---|---|
| SEQ ID NO: | Description | SEQUENCE |
| 35 | biphenylalanine aminoacyl-tRNA synthetase clone #6 nucleotide sequence | ATGGACGAATTTGAAATGATAAAGAGAAACACATCTGAAATTA<br>TCAGCGAGGAACAGTTAAGAGAGGTTTTAAAAAAAGATGAAAA<br>ATCTGCTCATATAGGTTTTGAACCAAGTGGTAAAATACATTTA<br>GGGCATTATCTCCAAATAAAAAAGATGATTGATTTACAAAATG<br>CTGGATTTGATATAATTATAGTTTTGGCTGATTTACACGCCTA<br>TTTAAACCAGAAAGGAGAGTTGGATGAGATTAGAAAAATAGGA<br>GATTATAACAAAAAAGTTTTTGAAGCAATGGGGTTAAAGGCAA<br>AATATGTTTATGGAAGTGAAAGGCCTCTTGATAAGGATTATAC<br>ACTGAATGTCTATAGATTGGCTTTAAAAACTACCTTAAAAAGA<br>GCAAGAAGGAGTATGGAACTTATAGCAAGAGAGGATGAAAATC<br>TATTCATTATCTGGGCGTTGATGTTGCAGTTGGAGGGATGGAG<br>CAGAGAAAAATACACATGTTAGCAAGGGAGCTTTTACCAAAAA<br>AGGTTGTTTGTATTCACAACCCTGTCTTAACGGGTTTGGATGG<br>AGAAGGAAAGATGAGTTCTTCAAAAGGGAATTTTATAGCTGTT<br>GATGACTCTCCAGAAGAGATTAGGGCTAAGATAAAGAAAGCAT<br>ACTGCCCAGCTGGAGTTGTTGAAGGAAATCCAATAATGGAGAT<br>AGCTAAATACTTCCTTGAATATCCTTTAACCATAAAAAGGGCA<br>GAAAAATTTGGTGGAGATTTGACAGTTAATAGCTATGAGGAGT<br>TAGAGAGTTTATTTAAAAATAAGGAATTGCATCCAATGGATTT<br>AAAAAATGCTGTAGCTGAAGAACTTATAAAGATTTTAGAGCCA<br>ATTAGAAAGAGATTATAA |
| 36 | biphenylalanine aminoacyl-tRNA synthetase clone #7 amino acid sequence (derived from wild-type *Methanococcus jannaschii* tyrosyl tRNA-synthetase) | MDEFEMIKRNTSEIISEEELREVLKKDEKSAHIGFEPSGKIHL<br>GHYLQIKKMIDLQNAGFDIIIHLADLHAYLNQKGELDEIRKIG<br>DYNKKVFEAMGLKAKYVYGSEWMLDKDYTLNVYRLALKTTLKR<br>ARRSMELIAREDENPKVAEVIYPIMQVNGIHYKGVDVAVGGME<br>QRKIHMLARELLPKKVVCIHNPVLTGLDGEGKMSSSKGNFIAV<br>DDSPEEIRAKIKKAYCPAGVVEGNPIMEIAKYFLEYPLTIKRP<br>EKFGGDLTVNSYEELESLFKNKELHPMDLKNAVAEELIKILEP<br>IRKRL |
| 37 | biphenylalanine aminoacyl-tRNA synthetase clone #7 nucleotide sequence | ATGGACGAATTTGAAATGATAAAGAGAAACACATCTGAAATTA<br>TCAGCGAGGAAGAGTTAAGAGAGGTTTTAAAAAAAGATGAAAA<br>ATCTGCTCATATAGGTTTTGAACCAAGTGGTAAAATACATTTA<br>GGGCATTATCTCCAAATAAAAAAGATGATTGATTTACAAAATG<br>CTGGATTTGATATAATTATACATTTGGCTGATTTACACGCCTA<br>TTTAAACCAGAAAGGAGAGTTGGATGAGATTAGAAAAATAGGA<br>GATTATAACAAAAAAGTTTTTGAAGCAATGGGGTTAAAGGCAA<br>AATATGTTTATGGAAGTGAATGGATGCTTGATAAGCATTATAC<br>ACTGAATGTCTATAGATTGGCTTTAAAAACTACCTTAAAAAGA<br>GCAAGAAGGAGTATGGAACTTATAGCAAGAGAGGATGAAAATC<br>CAAAGGTTGCTGAAGTTATCTATCCAATAATGCAGGTTAATGG<br>GATTCATTATAAGGGCGTTGATGTTGCAGTTGGAGGCATGGAG<br>CAGAGAAAAATACACATGTTAGCAAGGGAGCTTTTACCAAAAA<br>AGGTTGTTTGTATTCACAACCCTGTCTTAACGGGTTTGGATGG<br>AGAAGGAAAGATGAGTTCTTCAAAAGGGAATTTTATAGCTGTT<br>GATGACTCTCCAGAAGAGATTAGGGCTAAGATAAAGAAAGCAT<br>ACTGCCCAGCTGGAGTTGTTGAAGGAAATCCAATAATGGAGAT<br>AGCTAAATACTTCCTTGAATATCCTTTAACCATAAAAACGCCA<br>GAAAAATTTGGTGGAGATTTGACAGTTAATAGCTATCAGGAGT<br>TAGAGAGTTTATTTAAAAATAAGGAATTGCATCCAATGGATTT<br>AAAAAATGCTGTAGCTGAAGAACTTATAAAGATTTTAGAGCCA<br>ATTAGAAACACATTATAA |
| 38 | bipyridylalanine aminoacyl-tRNA synthetase clone #1 amino acid sequence (derived from wild-type *Methanococcus jannaschii* tyrosyl tRNA-synthetase) | MDEFEMIKRNTSEIISEEELREVLKKDEKSAEIGFEPSGKIHL<br>GHYLQIKKMIDLQNAGFDIIIHLADLHAYLNQKGELDEIRKIG<br>DYNKKVFEANGLKAKYVYGSEWMLDKDYTLNVYRLALKTTLKR<br>ARRSMELIAREDENPKVAEVIYPIMQVNGHHYHGVDVAVGGME<br>QRKIHMLARELLPKKVVCIHNPVLTGLDGEGKMSSSKGNFIAV<br>DDSPEEIRAKIKKAYCPAGVVEGNPIMEIAKYFLEYPLTIKRP<br>EKFGGDLTVNSYEELESLFKNKELHPMDLKNAVAEELIKILEP<br>IRKRL |
| 39 | bipyridylalanine aminoacyl-tRNA synthetase clone #1 nucleotide sequence | ATGGACGAATTTGAAATGATAAAGAGAAACACATCTGAAATTA<br>TCAGCGAGGAAGAGTTAAGACAGGTTTTAAAAAAAGATGAAAA<br>ATCTGCTGAGATAGGTTTTGAACCAAGTCGTAAAATACATTTA<br>GGGCATTATCTCCAAATAAAAAAGATGATTGATTTACAAAATG<br>CTGGATTTGATATAATTATACATTTGGCTGATTTACACGCCTA<br>TTTAAACCAGAAAGGAGAGTTGGATGAGATTAGAAAAATAGGA<br>GATTATAACAAAAAAGTTTTTGAAGCAATGGGGTTAAAGGCAA<br>AATATGTTTATGGAAGTGAATGGATGCTTGATAAGGATTATAC<br>ACTGAATGTCTATAGATTGGCTTTAAAAACTACCTTAAAAAGA<br>GCAAGAAGGAGTATGGAACTTATAGCAAGAGAGGATGAAAATC<br>CAAAGGTTGCTGAAGTTATCTATCCAATAATGCAGGTTAATGG |

TABLE 5-continued

Nucleotide and Amino Acid Sequences

| SEQ ID NO: | Description | SEQUENCE |
|---|---|---|
| | | TCATCATTATCATGGCGTTGATGTTGCAGTTGGAGGGATGGAG CAGAGAAAAATACACATGTTAGCAAGGGAGCTTTTACCAAAAA AGGTTGTTTGTATTCACAACCCTGTCTTAACGGCTTTGGATGG AGAAGGAAAGATGAGTTCTTCAAAAGGGAATTTTATAGCTGTT GATGACTCTCCAGAAGAGATTAGGGCTAAGATAAAGAAAGCAT ACTGCCCAGCTGGAGTTGTTGAAGGAAATCCAATAATGGAGAT AGCTAAATACTTCCTTGAATATCCTTTAACCATAAAAAGGCCA GAAAAATTTGGTGGAGATTTGACAGTTAATAGCTATGAGGAGT TAGAGAGTTTATTTAAAAATAAGGAATTGCATCCAATGGATTT AAAAAATGCTGTAGCTGAAGAACTTATAAAGATTTTAGAGCCA ATTAGAAAGAGATTATAA |
| 40 | bipyridylalanine aminoacyl-tRNA synthetase clone #2 amino acid sequence (derived from wild-type *Methanococcus jannaschii* tyrosyl tRNA-synthetase) | MDEFEMIKRNTSEIISEEELREVLKKDEKSAGIGFEPSGKIHL GHYLQIKKMIDLQNAGFDIIIYLADLAAYLNQKGELDEIRKIG DYNKKVFEAMGLKAKYVYGSEFQLDKDYTLNVYRLALKTTLKR ARRSMELIAREDENPKVAEVIYPIMEVNGWHYSGVDVAVGGME QRKIHMLARELLPKKVVCIHNPVLTGLDGEGKMSSSKGNFIAV DDSPEEIRAKIKKAYCPAGVVEGNPIMEIAKYFLEYPLTIKRP EKFGGDLTVNSYEELESLFKNKELHPMDLKNAVAEELIKILEP IRKRL |
| 41 | bipyridylalanine aminoacyl-tRNA synthetase clone #2 nucleotide sequence | ATGGACGAATTTGAAATGATAAAGAGAAACACATCTGAAATTA TCAGCGAGGAAGAGTTAAGAGAGGTTTTAAAAAAAGATGAAAA ATCTGCTGGTATAGGTTTTGAACCAAGTGGTAAAATACATTTA GGGCATTATCTCCAAATAAAAAAGATGATTGATTTACAAAATG CTGGATTTGATATAATTATATATTTGGCTGATTTAGCTGCCTA TTTAAACCAGAAAGGAGAGTTGGATGAGATTAGAAAAATAGGA GATTATAACAAAAAAGTTTTTGAAGCAATGGGGTTAAAGGCAA AATATGTTTATGGAAGTGAATTCCAGCTTGATAAGGATTATAC ACTGAATCTCTATAGATTGGCTTTAAAAACTACCTTAAAAAGA GCAAGAAGGAGTATGGAACTTATAGCAAGAGAGGATGAAAATC CAAAGGTTGCTGAAGTTATCTATCCAATAATGGAGGTTAATGC TTGGCATTATAGTGGCGTTGATGTTGCAGTTGGAGGGATGGAG CAGAGAAAAATACACATGTTAGCAAGGGAGCTTTTACCAAAAA AGGTTGTTTGTATTCACAACCCTGTCTTAACGGGTTTGGATGG AGAAGGAAAGATGAGTTCTTCAAAAGGGAATTTTATAGCTGTT GATGACTCTCCAGAAGAGATTAGGGCTAAGATAAAGAAAGCAT ACTGCCCAGCTGGAGTTGTTGAAGGAAATCCAATAATGGAGAT AGCTAAATACTTCCTTGAATATCCTTTAACCATAAAAAGGCCA GAAAAATTTGGTGGAGATTTGACAGTTAATAGCTATGAGGAGT TAGACAGTTTATTTAAAAATAAGGAATTGCATCCAATGGATTT AAAAAATGCTGTAGCTGAAGAACTTATAAAGATTTTAGAGCCA ATTACAAAGAGATTATAA |
| 42 | 1,5-dansylalanine aminoacyl-tRNA synthetase clone B8 amino acid sequence (derived from wild-type *E. coli* leucyl-tRNA synthetase) | MEEQYRPEEIESKVQLHWDEKRTFEVTEDESKEKYYCLSANPY PSGRLNMGHVRNYTIGDVIARYQRMLGKNVLQPIGWDAFGLPA EGAAVKNNTAPAPWTYDNIAYMKNQLKMLGFGYDWSRELATCT PEYYRWEQKFFTELYKKGLVYKKTSAVNWCPNDQTVLANEQVI DGCCWRCDTKVERKEIPQWFIKITAYADELLNDLDKLDHWPDT VKTMQRNWIGRSEGVEITFNVNDYDNTLTVYTTRPDTFMGCTY LAVAAGHPLAQKAAENNPELAAFIDECRNTKVAEAEMATMEKK GVDTGPKAVHPLTGEEIPVWAANFVLMEYGTGAVMAVPGHDQR DYEFASKYGLNIKPVILAADGSEPDLSQQALTEKGVLFNSGEF NGLDHEAAFNAIADKLTAMGVGERKVNYRLRDWGVSRQRYWGA PIPMVTLEDGTVMPTPDDQLPVILPEDVVMDGITSPIKADPEW AKTTVNGMPALRETDTFDTFMESCWIYARYTCPQYKEGMLDSE AANYWLPVDIGIGGIEHAIMTLLYFRFFHKLMRDAGMVNSDEP AKQLLCQGMVLADAFYYVGENGERNWVSPVDAIVERDEKGRIV KAKDAAGHELVYTGMSKMSKSKNNGIDPQVMVERYGADTVRLF MMFASPADMTLEWQESGVEGANRFLKRVWKLVYEHTAKGDVAA LNVDALTENQKALRRDVHKTIAKVTDDIGRRQTFNTAIAAIME LMNKLAKAPTDGEQDRALMQEALLAVVRMLNPFTPHICFTLWQ ELKGEGDIDNAPWPVADEKAMVEDSTLVVVQVNGKVRAKITVP VDATEEQVREPAGQEHLVAKYLDGVTVRKVIYVPGKLLNLVVG |
| 43 | 1,5-dansylalanine aminoacyl-tRNA synthetase clone B8 nucleotide sequence | ATGGAAGAGCAATACCGCCCGGAAGAGATAGAATCCAAAGTAC AGCTTCATTGGGATGAGAAGCGCACATTTGAAGTAACCGAAGA CGAGAGCAAAGAGAAGTATTACTGCCTGTCTGCTAATCCCTAT CCTTCTGGTCGACTACACATGGGCCACGTACGTAACTACACCA TCGGTGACGTGATCGCCCGCTACCAGCGTATGCTGGGCAAAAA CGTCCTGCAGCCGATCGGCTGGGACGCCTTTGGTCTGCCTGCG GAAGGCGCGGCGGTGAAAAACAACACCGCTCCGGCACCGTGGA CGTACGACAACATCGCGTATATGAAAAACCACCTCAAAATGCT GGGCTTTGGTTATGACTGGACCCGCGAGCTGGCAACCTGTACG |

TABLE 5-continued

Nucleotide and Amino Acid Sequences

| SEQ ID NO: | Description | SEQUENCE |
|---|---|---|
| | | CCGGAATACTACCGTTGGGAACAGAAATTCTTCACCGAGCTGT<br>ATAAAAAAGGCCTGGTATATAAGAAGACTTCTGCGGTCAACTG<br>GTGTCCGAACGACCAGACCGTACTGGCGAACGAACAAGTTATC<br>GACGGCTGCTGCTGGCGCTGCGATACCAAAGTTGAACGTAAAG<br>AGATCCCGCAGTGGTTTATCAAAATCACTGCTTACGCTGACGA<br>GCTGCTCAACGATCTGGATAAACTGGATCACTGGCCAGACACC<br>GTTAAAACCATGCAGCGTAACTCGATCGGTCGTTCCGAAGGCG<br>TGGAGATCACCTTCAACGTTAACGACTATGACAACACGCTGAC<br>CGTTTACACTACCCGCCCGGACACCTTTATGGGTTGTACCTAC<br>CTGGCGGTAGCTGCGGGTCATCCGCTGGCGCAGAAAGCGGCGG<br>AAAATAATCCTGAACTGGCGGCCTTTATTGACGAATGCCGTAA<br>CACCAAAGTTGCCGAAGCTGAAATGGCGACGATGCAGAAAAAA<br>GGCGTCGATACTGGCTTTAAAGCGGTTCACCCATTAACGGGCG<br>AAGAAATTCCCGTTTGGGCAGCAAACTTCGTATTGATGGAGTA<br>CGGCACGGGCGCAGTTATGGCGGTACCGGGGCACGACCAGCGC<br>GACTACGAGTTTGCCTCTAAATACGGCCTGAACATCAAACCGG<br>TTATCCTGGCAGCTGACGGCTCTGAGCCAGATCTTTCTCAGCA<br>AGCCCTGACTGAAAAAGGCGTGCTGTTCAACTCTGGCGAGTTC<br>AACGGTCTTGACCATGAAGCGGCCTTCAACGCCATCGCCGATA<br>AACTGACTGCGATGGGCGTTGGCGAGCGTAAAGTGAACTACCG<br>CCTGCGCGACTGGGGTGTTTCCCGTCAGCGTTACTGGGGCGCG<br>CCGATTCCGATGGTGACTCTAGAAGACGGTACCGTAATGCCGA<br>CCCCGGACGACCAGCTGCCGGTGATCCTGCCGGAAGATGTGGT<br>AATGGACGGCATTACCAGCCCGATTAAAGCAGATCCGGAGTGG<br>GCGAAAACTACCGTTAACGGTATGCCAGCACTGCGTGAAACCG<br>ACACTTTCGACACCTTTATGGAGTCCTGCTGGATTTATGCGCG<br>CTACACTTGCCCGCAGTACAAAGAAGGTATGCTGCATTCCGAA<br>GCGGCTAACTACTGGCTGCCGGTGGATATCGGTATTGGTGGTA<br>TTGAACACGCCATTATGACGCTGCTCTACTTCCGCTTCTTCCA<br>CAAACTGATGCGTGATGCAGGCATGGTGAACTCTGACGAACCA<br>GCGAAACAGTTGCTGTGTCAGGGTATGGTGCTGGCAGATGCCT<br>TCTACTATGTTGGCGAAAACGGCGAACGTAACTGGGTTTCCCC<br>GGTTGATGCTATCGTTGAACGTGACGAGAAAGGCCGTATCGTG<br>AAAGCGAAAGATGCGGCAGGCCATGAACTGGTTTATACCGGCA<br>TGAGCAAAATGTCCAAGTCCAAGAACAACCGTATCGACCCGCA<br>GGTGATGGTTGAACGTTACGGCGCGGACACCGTTCGTCTGTTT<br>ATGATGTTTGCTTCTCCGGCTGATATGACTCTCGAATGGCAGG<br>AATCCGGTGTGGAAGGGGCTAACCGCTTCCTGAAACGTGTCTG<br>CAAACTGGTTTACGAGCACACAGCAAAAGGTGATGTTGCGGCA<br>CTGAACGTTGATGCGCTCACTGAAAATCAGAAAGCGCTGCGTC<br>GCGATGTGCATAAAACGATCGCTAAAGTGACCGATGATATCGG<br>CCGTCGTCAGACCTTCAACACCGCAATTGCGGCGATTATGGAG<br>CTGATGAACAAACTGGCGAAAGCACCAACCGATGGCGAGCAGG<br>ATCGCGCTCTGATGCAGGAAGCACTGCTGGCCGTTGTCCGTAT<br>GCTTAACCCGTTCACCCCGCACATCTCCTTCACGCTGTGGCAG<br>GAACTGAAAGGCGAAGGCGATATCGACAACCCGCCGTGGCCGG<br>TTGCTGACGAAAAAGCGATGGTGGAAGACTCCACGCTGGTCGT<br>GGTGCAGGTTAACGGTAAAGTCCGTGCCAAAATCACCGTTCCG<br>GTGGACGCAACGGAAGAACAGGTTCGCGAACGTGCTGGCCAGG<br>AACATCTGGTAGCAAAATATCTTGATGCCGTTACTGTACGTAA<br>AGTGATTTACGTACCAGGTAAACTCCTCAATCTGGTCGTTGGC<br>TAA |
| 44 | 1,5-dansylalanine aminoacyl-tRNA synthetase T252A amino acid sequence (derived from wild-type *E. coli* leucyl-tRNA synthetase) | MEEQYRPEEIESKVQLHWDEKRTFEVTEDESKEKYYCLSANPY<br>PSGRLHMGHVRNYTIGDVIARYQRMLGKNVLQPIGWDAFGLPA<br>EGAAVKNNTAPAPWTYDNIAYMKNQLKMLGFGYDWSRELATCT<br>PEYYRWEQKFFTELYKKGLVYKKTSAVNWCPNDQTVANEQVI<br>DGCCWRCDTKVERKEIPQWFIKITAYADELLNDLDKLDHWPDT<br>VKTMQRNWIGRSEGVEITFNVNDYDNTLTVYTTRPDAFMGCTY<br>LAVAAGHPLAQKAAENNPELAAFIDECRNTKVAEAEMATMEKK<br>GVDTGFKAVHPLTGEEIPVWAANFVLMEYGTGAVMAVPGHDQR<br>DYEFASKYGLNIKPVILAADGSEPDLSQQALTEKGVLFNSGEF<br>NGLDHEAAFNAIADKLTAMGVGERKVNYRLRDWGVSRQRYWGA<br>PIPMVTLEDGTVMPTPDDQLPVILPEDVVMDGITSPIKADPEW<br>AKTTVNGMPALRETDTFDTFMESCWIYARYTCPQYKEGMLDSE<br>AANYWLPVDIGIGGIEHAIMTLLYFRFFHKLMRDAGMVNSDEP<br>AKQLLCQGMVLADAFYYVGENGERNWVSPVDAIVERDEKGRIV<br>KAKDAAGHELVYTGMSKMSKSKNNGIDPQVMVERYGADTVRLF<br>MMFASPADMTLEWQESGVEGANRFLKRVWKLVYEHTAKGDVAA<br>LNVDALTENQKALRRDVHKTIAKVTDDIGRRQTFNTAIAAIME<br>LMNKLAKAPTDGEQDRALMQEALLAVVRMLNPFTPHICFTLWQ<br>ELKGEGDIDNAPWPVADEKAMVEDSTLVVVQVNGKVRAKITVP<br>VDATEEQVRERAGQEHLVAKYLDGVTVRKVIYVPGKLLNLVVG |

TABLE 5-continued

Nucleotide and Amino Acid Sequences

| SEQ ID NO: | Description | SEQUENCE |
|---|---|---|
| 45 | 1,5-dansylalanine aminoacyl-tRNA synthetase T252A nucleotide sequence | ATGGAAGAGCAATACCGCCCGGAAGAGATAGAATCCAAAGTAC AGCTTCATTGGGATGAGAAGCGCACATTTGAAGTAACCGAAGA CGACAGCAAAGAGAAGTATTACTGCCTGTCTGCTAATCCCTAT CCTTCTGGTCGACTACACATGGGCCACGTACGTAACTACACCA TCGGTGACGTGATCGCCCGCTACCAGCGTATGCTGGGCAAAAA CGTCCTGCAGCCGATCGGCTGGGACGCGTTTGGTCTGCCTGCG GAAGGCGCGGCCGTGAAAAACAACACCGCTCCGGCACCGTGGA CGTACGACAACATCGCGTATATGAAAAACCACCTCAAAATGCT GGGCTTTGGTTATGACTGGAGCCGCGAGCTGGCAACCTGTACG CCCGAATACTACCGTTGGGAACAGAAATTCTTCACCGAGCTGT ATAAAAAAGGCCTGGTATATAAGAAGACTTCTGCGCTCAACTG GTGTCCGAACGACCAGACCGTACTGGCGAACGAACAAGTTATC GACGGCTGCTGCTGGCGCTGCGATACCAAAGTTGAACGTAAAG AGATCCCGCAGTGGTTTATCAAAATCACTGCTTACGCTGACGA GCTGCTCAACGATCTGGATAAACTGGATCACTGGCCAGACACC GTTAAAACCATGCAGCGTAACTGGATCGGTCCTTCCGAAGGCG TGGACATCACCTTCAACGTTAACGACTATGACAACACGCTGAC CGTTTACACTACCCGCCCGGACGCGTTTATGGGTTGTACCTAC CTGGCGGTAGCTGCGGGTCATCCGCTGGCGCAGAAAGCGGCGG AAAATAATCCTGAACTGGCGGCCTTTATTGACGAATGCCGTAA CACCAAAGTTGCCGAAGCTGAAATGGCGACGATGGAGAAAAAA GGCCTCGATACTGGCTTTAAAGCGGTTCACCCATTAACGGGCG AAGAAATTCCCGTTTGGGCAGCAAACTTCGTATTGATGGAGTA CGGCACGGGCGCAGTTATGGCGGTACCGGGGCACGACCAGCGC GACTACGAGTTTGCCTCTAAATACGGCCTGAACATCAAACCGG TTATCCTGGCACCTGACGGCTCTGAGCCAGATCTTTCTCAGCA AGCCCTGACTGAAAAAGGCGTGCTGTTCAACTCTGGCGAGTTC AACGGTCTTGACCATGAAGCGGCCTTCAACGCCATCGCCGATA AACTGACTGCGATGGGCGTTGGCGAGCGTAAAGTGAACTACCG CCTGCGCGACTGGGGTGTTTCCCGTCAGCGTTACTGGGGCGCG CCGATTCCGATGGTGACTCTAGAAGACGGTACCGTAATGCCGA CCCCGGACGACCAGCTGCCGGTGATCCTGCCGGAAGATGTGGT AATGGACGGCATTACCACCCCCATTAAAGCAGATCCGGAGTGG GCGAAAACTACCGTTAACGGTATGCCAGCACTGCGTGAAACCG ACACTTTCGACACCTTTATGGAGTCCTGCTGGATTTATGCGCG CTACACTTGCCCGCAGTACAAAGAAGGTATGCTGGATTCCGAA GCGGCTAACTACTGGCTGCCGGTGGATATCGGTATTGGTGGTA TTGAACACGCCATTATGACGCTGCTCTACTTCCGCTTCTTCCA CAAACTGATGCGTGATGCAGGCATGGTGAACTCTGACGAACCA GCGAAACAGTTGCTGTGTCAGGGTATGGTGCTGGCAGATGCCT TCTACTATGTTGGCGAAAACGGCGAACCTAACTGGGTTTCCCC GGTTGATGCTATCGTTGAACGTGACGAGAAAGGCCGTATCGTG AAAGCGAAAGATGCGGCAGGCCATGAACTGGTTTATACCGGCA TGAGCAAAATGTCCAAGTCGAAGAACAACGGTATCGACCCGCA CGTGATGGTTGAACGTTACGGCGCGGACACCGTTCGTCTGTTT ATGATGTTTGCTTCTCCGGCTGATATGACTCTCGAATGGCAGG AATCCGGTGTGGAAGGGGCTAACCGCTTCCTGAAACGTGTCTG GAAACTGGTTTACGAGCACACAGCAAAAGGTGATGTTGCGGCA CTGAACGTTGATGCGCTGACTCAAAATCAGAAACCGCTGCGTC GCGATGTGCATAAAACGATCGCTAAAGTGACCGATGATATCGG CCGTCGTCAGACCTTCAACACCGCAATTGCGGCGATTATGGAC CTGATGAACAAACTGGCGAAAGCACCAACCGATGGCGAGCAGC ATCGCGCTCTGATGCAGCAAGCACTGCTGGCCGTTGTCCGTAT GCTTAACCCGTTCACCCCGCACATCTGCTTCACGCTGTGGCAG GAACTCAAAGGCGAAGGCGATATCGACAACGCGCCGTGCCCGG TTGCTGACGAAAAAGCGATGGTGGAAGACTCCACGCTGGTCGT GGTGCAGGTTAACGGTAAAGTCCGTGCCAAAATCACCGTTCCG GTGGACGCAACGGAAGAACAGGTTCGCGAACGTGCTGGCCAGG AACATCTGGTAGCAAAATATCTTGATGGCGTTACTGTACGTAA AGTGATTTACGTACCAGCTAAACTCCTCAATCTGGTCGTTGGC TAAGCGGCC |
| 46 | 1,5-dansylalanine aminoacyl-tRNA synthetase V338A amino acid sequence (derived from wild-type *E. coli* leucyl-tRNA synthetase) | MEEQYRPEEIESKVQLHWDEKRTFEVTEDESKEKYYCLSANPY PSGRLHMGHVRNYTIGDVIARYQRMLGKNVLQPIGWDAFGLPA EGAAVKNNTAPAPWTYDNIAYMKNQLKMLCFGYDWSRELATCT PEYYRWEQKFFTELYKKGLVYKKTSAVNWCPNDQTVLANEQVI DGCCWRCDTKVERKEIPQWFIKITAYADELLNDLDKLDHWPDT VKTMQRNWIGRSEGVEITFNVNDYDNTLTVYTTRPDTFMGCTY LAVAAGHPLAQKAAENNPELAAFIDECRNTKVAEAEMATMEKK GVDTGFKAVHPLTGEEIPVWAANFVLMEYGTGAVMAAPGHDQR DYEFASKYGLNIKPVILAADGSEPDLSQQALTEKGVLFNSGEF NGLDHEAAFNAIADKLTAMGVGERKVNYRLRDWGVSRQRYWGA PIPMVTLEDGTVMPTPDDQLPVILPEDVVMDGITSPIKADPEW |

TABLE 5-continued

| Nucleotide and Amino Acid Sequences | |
|---|---|
| SEQ ID NO: Description | SEQUENCE |
| | AKTTVNGMPALRETDTFDTFMESCWIYARYTCPQYKEGMLDSE AANYWLPVDIGIGGIEHAIMTLLYFRFFHKLMRDAGMVNSDEP AKQLLCQGMVLADAFYYVGENGERNWVSPVDAIVERDEKGRIV KAKDAAGHELVYTGMSKMSKSKNNGIDPQVMVERYGADTVRLF MMFASPADMTLEWQESGVEGANRFLKRVWKLVYEHTAKGDVAA LNVDALTENQKALRRDVHKTIAKVTDDIGRRQTFNTAIAAIME LMNKLAKAPTDGEQDRALMQEALLAVVRMLNPFTPHICFTLWQ ELKGEGDIDNAPWPVADEKAMVEDSTLVVVQVNGKVRAKITVP VDATEEQVRERAGQEHLVAKYLDGVTVRKVIYVPGKLLNLVVG |
| 47 1,5-dansylalanine aminoacyl-tRNA synthetase V338A nucleotide sequence | ATGGAAGAGCAATACCGCCCGGAAGAGATAGAATCCAAAGTAC ACCTTCATTGGGATGAGAAGCGCACATTTGAAGTAACCGAACA CCAGAGCAAAGAGAAGTATTACTGCCTGTCTGCTAATCCCTAT CCTTCTGGTCGACTACACATGGGCCACGTACGTAACTACACCA TCGGTGACGTGATCGCCCGCTACCAGCGTATGCTGGGCAAAAA CGTCCTGCAGCCGATCGGCTGGCACGCGTTTGGTCTGCCTGCG GAAGGCGCGGCGGTGAAAAACAACACCGCTCCGGCACCGTGGA CGTACGACAACATCGCGTATATGAAAAACCACCTCAAAATGCT GGGCTTTGGTTATGACTGGAGCCGCGAGCTGGCAACCTGTACG CCGGAATACTACCGTTGGGAACAGAAATTCTTCACCGAGCTGT ATAAAAAAGGCCTGGTATATAAGAAGACTTCTGCGGTCAACTG GTGTCCGAACGACCAGACCGTACTGGCGAACGAACAAGTTATC GACGGCTGCTGCTGGCGCTGCGATACCAAAGTTGAACGTAAAG AGATCCCGCAGTGGTTTATCAAAATCACTGCTTACGCTGACGA GCTGCTCAACGATCTGCATAAACTGGATCACTGGCCAGACACC GTTAAAACCATGCAGCGTAACTGGATCGGTCGTTCCGAAGGCG TGGAGATCACCTTCAACGTTAACGACTATGACAACACGCTGAC CGTTTACACTACCCCCCCGGACACCTTTATGGGTTGTACCTAC CTGGCGGTAGCTGCGGGTCATCCGCTGGCGCAGAAAGCGGCGG AAAATAATCCTGAACTGGCGGCCTTTATTGACGAATGCCGTAA CACCAAAGTTGCCGAAGCTGAAATGGCGACGATGGAGAAAAAA GGCGTCGATACTGGCTTTAAAGCGGTTCACCCATTAACGGGCG AAGAAATTCCCGTTTGGGCACCAAACTTCGTATTGATGGAGTA CGGCACGGGCGCAGTTATGGCGGCGCCGGGGCACGACCAGCGC GACTACGAGTTTGCCTCTAAATACGGCCTGAACATCAAACCGG TTATCCTGGCAGCTGACGGCTCTGAGCCAGATCTTTCTCAGCA AGCCCTGACTGAAAAAGGCGTGCTGTTCAACTCTGGCGAGTTC AACGGTCTTGACCATGAAGCGGCCTTCAACGCCATCGCCGATA AACTGACTGCGATGGGCGTTGGCGAGCGTAAAGTGAACTACCG CCTGCGCGACTGGGGTGTTTCCCGTCAGCGTTACTGGGGCGCG CCGATTCCGATGGTGACTCTAGAAGACGGTACCGTAATGCCGA CCCCGGACGACCAGCTGCCGGTGATCCTGCCGGAAGATGTGGT AATGGACGGCATTACCAGCCCGATTAAAGCAGATCCGGAGTGG GCGAAAACTACCGTTAACGGTATGCCAGCACTGCGTGAAACCG ACACTTTCGACACCTTTATGGAGTCCTGCTGGATTTATGCGCG CTACACTTGCCCGCAGTACAAAGAAGGTATGCTGGATTCCGAA GCGGCTAACTACTGGCTGCCGGTGGATATCGGTATTGGTGGTA TTGAACACGCCATTATGACGCTGCTCTACTTCCCCTTCTTCCA CAAACTGATGCGTGATGCAGGCATGCTGAACTCTGACGAACCA GCGAAACAGTTGCTGTGTCAGGGTATGGTGCTGGCAGATGCCT TCTACTATGTTGGCGAAAACGGCGAACGTAACTGGCTTTCCCC GGTTGATGCTATCGTTGAACGTGACGAGAAAGGCCGTATCGTG AAAGCGAAAGATGCGGCAGGCCATGAACTGGTTTATACCGGCA TCAGCAAAATGTCCAAGTCGAAGAACAACGGTATCGACCCGCA GGTGATGGTTGAACGTTACGGCGCGGACACCGTTCGTCTGTTT ATGATGTTTGCTTCTCCGGCTGATATGACTCTCGAATGGCAGG AATCCGGTGTGGAAGGGGCTAACCGCTTCCTGAAACGTGTCTG GAAACTGGTTTACGAGCACACAGCAAAAGGTGATGTTGCGGCA CTGAACGTTGATGCGCTGACTGAAAATCAGAAAGCGCTGCGTC GCGATGTGCATAAAACGATCGCTAAAGTGACCGATGATATCGG CCGTCGTCAGACCTTCAACACCGCAATTGCGGCGATTATGGAG CTGATGAACAAACTGGCGAAAGCACCAACCGATGGCGAGCAGG ATCGCGCTCTGATGCAGGAAGCACTGCTGGCCGTTCTCCGTAT GCTTAACCCGTTCACCCCGCACATCTGCTTCACGCTGTGGCAG GAACTGAAAGGCGAAGGCGATATCGACAACGCGCCGTGGCCGG TTGCTGACGAAAAAGCGATGGTGGAAGACTCCACGCTGGTCGT GGTGCAGGTTAACGGTAAAGTCCGTGCCAAAATCACCGTTCCG GTGGACGCAACGGAAGAACAGGTTCGCGAACGTGCTGGCCAGG AACATCTGGTAGCAAAATATCTTGATGGCGTTACTGTACGTAA AGTGATTTACGTACCAGGTAAACTCCTCAATCTGGTCGTTGGC TAAGCGGCC |

TABLE 5-continued

Nucleotide and Amino Acid Sequences

| SEQ ID NO: | Description | SEQUENCE |
|---|---|---|
| 48 | o-nitrobenzylcysteine aminoacyl-tRNA synthetase clone 3H11 amino acid sequence (derived from wild-type *E. coli* leucyl-tRNA synthetase) | MEEQYRPEEIESKVQLHWDEKRTFEVTEDESKEKYYCLSWSPY<br>PSGRLHMGHVRNYTIGDVIARYQRMLGKNVLQPIGWDAFGLPA<br>EGAAVKNNTAPAPWTYDNIAYMKNQLKMLGFGYDWSRELATCT<br>PEYYRWEQKFFTELYKKGLVYKKTSAVNWCPNDQTVLANEQVI<br>DGCCWRCDTKVERKEIPQWFTKITAYADELLNDLDKLDHWPDT<br>VKTMQRNWIGRSEGVEITFNVNDYDNTLTVYTTRPDTFMGCTY<br>LAVAAGHPLAQKAAENNPELAAFIDECPNTKVAEAEMATMEKK<br>GVDTGFKAVHPLTGEEIPVWAANFVLMEYGTGAVMAVPGHDQR<br>DYEFASKYGLNIKPVILAADGSEPDLSQQALTEKGVLFNSGEF<br>NGLDHEAAFNAIADKLTAMGVGERKVNYRLRDWGVSRQRYWGA<br>PIPMVTLEDGTVMPTPDDQLPVILPEDVVMDGITSPIKADPEW<br>AKTTVNGMPALRETDTFDTFMESCWIYARYTCPQYKECMLDSE<br>AANYWLPVDIAIGGIEHAIMGLLYFRPFHKLMRDAGMVNSDEP<br>AKQLLCQGMVLADAFYYVGENGERNWVSPVDAIVERDEKGRIV<br>KAKDAAGHELVYTGMSKMSKSKNNGIDPQVMVERYGADTVRLF<br>MMFASPADMTLEWQESGVEGANRFLKRVWKLVYEHTAKGDVAA<br>LNVDALTENQKALRRDVHKTIAKVTDDIGRRQTFNTAIAAIME<br>LMNRLAKAPTDGEQDRALMQEALLAVVRMLNPFTPHICFTLWQ<br>ELKGEGDIDNAPWPVADEKAMVEDSTLVVVQVNGKVRAKITVP<br>VDATEEQVRERAGQEHLVAKYLDGVTVRKVIYVPGKLLNLVVG |
| 49 | o-nitrobenzylcysteine aminoacyl-tRNA synthetase clone 3H11 nucleotide sequence | ATGGAAGAGCAATACCGCCCGGAAGAGATAGAATCCAAAGTAC<br>AGCTTCATTGGGATGAGAAGCGCACATTTGAAGTAACCGAAGA<br>CGAGAGCAAAGAGAAGTATTACTGCCTGTCTTGGTCGCCCTAT<br>CCTTCTGGTCGACTACACATGGCCCACGTACGTAACTACACCA<br>TCGGTGACGTGATCGCCCGCTACCAGCGTATGCTGGGCAAAAA<br>CGTCCTGCAGCCGATCGGCTGGGACGCGTTTCGTCTGCCTGCG<br>GAAGGCGCGCCGGTGAAAAACAACACCGCTCCGGCACCGTGGA<br>CGTACGACAACATCCCGTATATGAAAAACCACCTCAAAATGCT<br>GGGCTTTGGTTATGACTGGAGCCGCGAGCTGGCAACCTGTACG<br>CCGGAATACTACCGTTGGGAACAGAAATTCTTCACCGAGCTGT<br>ATAAAAAAGGCCTCGTATATAAGAAGACTTCTGCGGTCAACTG<br>GTGCCCGAACGACCAGACCGTACTGGCGAACGAACAAGTTATC<br>GACGGCTGCTGCTGGCGCTGCGATACCAAAGTTGAACGTAAAG<br>AGATCCCGCAGTGGTTTATCAAAATCACTGCTTACGCTGACGA<br>GCTGCTCAACGATCTGGATAAACTGGATCACTGGCCAGACACC<br>GTTAAAACCATGCAGCGTAACTGGATCGGTCGTTCCGAAGGCG<br>TGGAGATCACCTTCAACGTTAACGACTATGACAACACGCTGAC<br>CGTTTACACTACCCGCCCGGACACCTTTATGGGTTGTACCTAC<br>CTGGCGGTAGCTGCGGGTCATCCGCTGGCCCAGAAAGCGGCGG<br>AAAATAATCCTGAACTGGCGGCCTTTATTGACGAATGCCGTAA<br>CACCAAAGTTGCCGAAGCTGAAATGGCGACGATGGACAAAAAA<br>GGCGTCGATACTGGGTTTAAAGCGGTTCACCCATTAACGGGCG<br>AAGAAATTCCCGTTTGGGCAGCAAACTTCGTATTGATGGAGTA<br>CGGCACGGGCGCAGTTATGGCGGTACCGGGGCACGACCAGCGC<br>GACTACGAGTTTGCCTCTAAATACGGCCTGAACATCAAACCGG<br>TTATCCTGGCAGCTGACGGCTCTGAGCCAGATCTTTCTCAGCA<br>AGCCCTGACTGAAAAAGGCGTGCTGTTCAACTCTGGCGAGTTC<br>AACGGTCTTGACCATGAAGCGGCCTTCAACGCCATCGCCGATA<br>AACTGACTGCGATGGGCGTTGGCGAGCGTAAACTGAACTACCG<br>CCTGCGCGACTGCGGTGTTTCCCGTCAGCGTTACTGGGGCGCG<br>CCGATTCCGATGGTGACGCTGGAAGACGGTACCGTAATGCCGA<br>CCCCGGACGACCAGCTGCCGGTGATCCTGCCGGAAGATGTGGT<br>AATGGACGGCATTACCAGCCCGATTAAAGCAGATCCGGAGTGG<br>GCGAAAACTACCGTTAACGGTATGCCAGCACTGCGTGAAACCG<br>ACACTTTCGACACCTTTATGGAGTCCTGCTGGATTTATGCGCG<br>CTACACTTGCCCGCAGTACAAAGAAGGTATGCTGGATTCCGAA<br>GCGGCTAACTACTGGCTGCCGGTGGATATCGCGATTGGTGGTA<br>TTGAACACGCCATTATGGGGCTGCTCTACTTCCGCTTCTTCCA<br>CAAACTGATGCGTGATGCAGGCATGGTGAACTCTGACGAACCA<br>GCGAAACAGTTGCTGTGTCAGGGTATGGTGCTGGCAGATGCCT<br>TCTACTATGTTCGCGAAAACGGCGAACGTAACTGGGTTTCCCC<br>GGTTGATGCTATCGTTGAACGTGACGAGAAAGGCCGTATCGTG<br>AAAGCGAAAGATGCGGCAGGCCATGAACTGGTTTATACCGGCA<br>TGAGCAAAATGTCCAAGTCGAAGAACAACGGTATCGACCCGCA<br>GGTGATGGTTGAACGTTACGGCGCGCACACCGTTCGTCTGTTT<br>ATGATGTTTGCTTCTCCGGCTGATATGACTCTCGAATGGCAGG<br>AATCCGGTGTGGAAGGGGCTAACCGCTTCCTGAAACGTGTCTG<br>GAAACTGGTTTACGAGCACACAGCAAAAGGTGATGTTGCGGCA<br>CTGAACGTTGATGCGCTGACTGAAAATCACAAAGCGCTGCGTC<br>GCGATGTGCATAAAACGATCGCTAAAGTGACCGATGATATCGG<br>CCGTCGTCAGACCTTCAACACCGCAATTGCGGCGATTATGGAG<br>CTGATGAACAAACTGGCGAAAGCACCAACCGATGGCGACCAGG |

TABLE 5-continued

Nucleotide and Amino Acid Sequences

| SEQ ID NO: | Description | SEQUENCE |
|---|---|---|
| | | ACCGCGCTCTGATGCAGGAAGCACTGCTGGCCGTTGTCCGTAT GCTTAACCCGTTCACCCCGCACATCTGCTTCACGCTGTGGCAG GAACTGAAAGGCGAAGGCGATATCGACAACGCGCCGTGGCCGC TTGCTGACGAAAAAGCGATGGTGGAAGACTCCACGCTGGTCGT GGTGCAGGTTAACGGTAAAGTCCGTGCCAAAATCACCGTTCCG GTGGACGCAACGGAAGAACAGGTTCGCGAACGTGCTGGCCAGG AACATCTGGTAGCAAAATATCTTGATGGCGTTACTGTACGTAA AGTGATTTACGTACCAGGTAAACTCCTCAATCTGGTCGTTGGC TAA |
| 50 | o-nitrobenzylserine aminoacyl-tRNA synthetase clone G2-6 amino acid sequence (derived from wild-type *E. coli* leucyl-tRNA synthetase) | MEEQYRPEEIESKVQLHWDEKRTFEVTEDEGKEKYYCLSWSPY PSGRLHMGHVRNYTIGDVIARYQRMLGKNVLQPIGWDAFGLPA EGAAVKNNTAPAPWTYDNIAYMKNQLKMLGFGYDWSRELATCT PEYYRWEQKFFTELYKKGLVYKKTSAVNWCPNDQTVLANEQVI DGCCWRCDTKVERKEIPQWFIKITAYADELLNDLDKLDHWPDT VKTMQRNWIGRSEGVEITFNVNDYDNTLTVYASRPDTFMGCTY LAVAAGHPLAQKAAENNPELAAFIDECRNTKVAEAEMATMEKK GVDTGFKAVHPLTGEEIPVWAANFVLMEYGTGAVMAVPGHDQR DYEFASKYGLNIKPVILAADGSEPDLSQQALTEKGVLFNSGEF NGLDHEAAFNAIADKLTAMGVGERKVNYRLRDWGVSRQRYWGA PIPMVTLEDGTVMPTPDDQLPVILPEDVVMDGITSPIKADPEW AKTTVWGMPALRETDTFDTFMESCWIYARYTCPQYKEGMLDSE AANYWLPVDIAIGGIEHAIMGLLYFRFFHKLMRDAGMVNSDEP AKQLLCQGMVLADAFYYVGEWGERNWVSPVDAIVERDEKGRIV KAKDAAGHELVYTGISKMSKSKNNGIDPQVNVERYGADTVRLF MMFASPADMTLEWQESGVEGANRFLKRAWKLVYEHTAKGDVAA LNVDALTENQKALRRDVHKTIAKVTDDIGRRQTFNTAIAAIME LMNKLAKAPTDGEQDRALMQEALLAVVRMLNPFTPHICFTLWQ ELKGEGDIDNAPWPVADEKAMVEDSTLVVVQVNGKVRAKITVP VDATEEQVRERAGQEHLVAKYLDGVTVRKVIYVPGKLLNLVVG |
| 51 | o-nitrobenzylserine aminoacyl-tRNA synthetase clone G2-6 nucleotide sequence | ATCTCGAAGCACACGAAACTTTTTCCTTCCTTCATTCACGCAC ACTACTCTCTAATGAGCAACGGTATACGGCCTTCCTTCCAGTT ACTTGAATTTGAAATAAAAAAAAGTTTGCTGTCTTGCTATCAA GTATAAATAGACCTGCAATTATTAATCTTTTGTTTCCTCGTCA TTGTTCTCGTTCCCTTTCTTCCTTGTTTCTTTTTCTGCACAAT ATTTCAAGCTATACCAAGCATACAATCAACTGAATTCAGTATG GAACAGCAATACCGCCCGGAAGAGATAGAATCCAAAGTACAGC TTCATTGGCATGAGAAGCGCACATTTGAAGTAACCGAAGACGA GGGCAAAGAGAAGTATTACTGCCTGTCTTGGTCGCCCTATCCT TCTGGTCGACTACACATGGGCCACGTACGTAACTACACCATCG GTGACGTGATCGCCCGCTACCAGCGTATGCTGGGCAAAAACGT CCTGCAGCCGATCGGCTGGGACGCGTTTGGTCTGCCTGCGGAA GGCGCGGCGGTGAAAAACAACACCGCTCCGGCACCGTGGACGT ACGACAACATCGCGTATATGAAAAACCAGCTCAAAATGCTGGG CTTTGCTTATGACTGGAGCCGCGAGCTGGCAACCTGTACGCCG GAATACTACCGTTGGGAACAGAAATTCTTCACCGAGCTGTATA AAAAAGGCCTGGTATATAAGAAGACTTCTGCGGTCAACTGGTG TCCGAACGACCAGACCGTACTGGCGAACGAACAAGTTATCGAC GGCTGCTGCTGGCGCTCCGATACCAAAGTTGAACGTAAAGAGA TCCCGCAGTGGTTTATCAAAATCACTGCTTACGCTGACGAGCT GCTCAACGATCTGGATAAACTCGATCACTGGCCAGACACCGTT AAAACCATCCAGCGTAACTGGATCGGTCGTTCCGAAGGCGTGG AGATCACCTTCAACGTTAACCACTATGACAACACGCTGACCGT TTACGCTTCCCGCCCGGACACCTTTATGGGTTGTACCTACCTG GCGGTAGCTGCGGGTCATCCGCTGGCGCAGAAAGCGGCGGAAA ATAATCCTGAACTGGCGGCCTTTATTGACCAATGGCGTAACAC CAAAGTTGCCGAAGCTGAAATGGCGACGATGGAGAAAAAAGGC GTCGATACTGGCTTTAAAGCGGTTCACCCATTAACGGGCGAAG AAATTCCCGTTTGGGCAGCAAACTTCGTATTGATGGAGTACGG CACGGGCGCAGTTATGGCGGTACCGGGGCACGACCAGCGCGAC TACGAGTTTGCCTCTAAATACGGCCTGAACATCAAACCGGTTA TCCTGGCAGCTGACGGCTCTGAGCCAGATCTTTCTCAGCAAGC CCTGACTGAAAAAGGCGTCCTGTTCAACTCTGGCGAGTTCAAC GGTCTTGACCATGAAGCGGCCTTCAACGCCATCGCCGATAAAC TGACTGCGATGGGCGTTGGCGAGCGTAAAGTGAACTACCGCCT GCGCGACTGGGGTGTTTCCCGTCAGCGTTACTGGGGCGCGCCG ATTCCGATGGTGACTCTAGAAGACGGTACCGTAATGCCGACCC CCGACCACCAGCTGCCCGTGATCCTGCCGGAAGATGTGGTAAT CGACGGCATTACCAGCCCGATTAAAGCAGATCCGGAGTGGGCG AAAACTACCGTTAACGGTATGCCAGCACTGCGTGAAACCGACA CTTTCGACACCTTTATGGAGTCCTGCTGGATTTATGCGCGCTA CACTTGCCCGCAGTACAAAGAAGGTATGCTGGATTCCGAAGCG GCTAACTACTGGCTGCCGGTGGATATCGCGATTGGTGGTATTG |

TABLE 5-continued

| Nucleotide and Amino Acid Sequences | | |
|---|---|---|
| SEQ ID NO: | Description | SEQUENCE |
| | | AACACGCCATTATGGGGCTGCTCTACTTCCGCTTCTTCCACAA<br>ACTGATGCCTGATGCAGGCATGGTGAACTGTGACGAACCAGCG<br>AAACAGTTGCTGTGTCAGGGTATGGTGCTGGCAGATGCCTTCT<br>ACTATGTTGGCGAAAACGGCGAACGTAACTGGGTTTCCCCGGT<br>TGATGCTATCGTTGAACGTGACGAGAAAGGCCGTATCGTGAAA<br>GCGAAAGATGCGGCAGGCCATGAACTGGTTTATACCGGCATAA<br>GCAAAATGTCCAAGTCGAAGAACAACGGTATCGACCCGCAGGT<br>GATGGTTGAACGTTACGGCGCGGACACCGTTCGTCTGTTTATG<br>ATGTTTGCTTCTCCGGCTCATATGACTCTCGAATGGCAGGAAT<br>CCGGTGTGGAAGGGGCTAACCGCTTCCTGAAACGTGCCTGGAA<br>ACTGGTTTACGAGCACACAGCAAAAGGTGATGTTGCGGCACTG<br>AACGTTGATGCGCTGACTGAAAATCAGAAACCGCTGCGTCGCG<br>ATGTGCATAAAACGATCGCTAAAGTGACCGATGATATCGGCCG<br>TCGTCAGACCTTCAACACCGCAATTGCGGCGATTATGGAGCTG<br>ATGAACAAACTGGCGAAAGCACCAACCGATGGCGAGCAGGATC<br>GCGCTCTGATGCAGGAAGCACTGCTGGCCGTTGTCCGTATGCT<br>TAACCCGTTCACCCCGCACATCTGCTTCACGCTGTGGCAGGAA<br>CTGAAAGGCGAAGGCGATATCGACAACGCGCCGTGGCCGGTTG<br>CTGACGAAAAAGCGATGGTGGAAGACTCCACGCTGGTCGTGGT<br>GCAGGTTAACGGTAAAGTCCGTGCCAAAATCACCGTTCCGGTG<br>GACGCAACGGAAGAACAGGTTCGCGAACGTGCTGGCCAGGAAC<br>ATCTGGTAGCAAAATATCTTGATGGCGTTACTGTACGTAAAGT<br>GATTTACGTACCAGGTAAACTCCTCAATCTGGTCGTTGGCTAA<br>GCGGCC |
| 52 | O-(2-nitrobenzyl)-L-tyrosine aminoacyl-tRNA synthetase clone ONBY-1 amino acid sequence (derived from wild-type *Methanococcus jannaschii* tyrosyl tRNA-synthetase) | MDEFEMIKRNTSEIISEEELREVLKKDEKSA**G**IGFEPSGKIHL<br>GHYLQIKKMIDLQNAGFDIII**G**LADLHAYLNQKGELDEIRKIG<br>DYNKKVFEAMGLKAKYVYGSE**AR**LDKDYTLNVYRLALKTTLK<br>RARRSMELIAREDENPKVAEVIYPIMQVN**E**IHY**Y**GVDVAVGG<br>MEQRKIHMLARELLPKKVVCIHNPVLTGLDGEGKMSSSKGNFI<br>AVDDSPEEIRAKIKKAYCPAGVVEGNPIMEIAKYFLEYPLTIK<br>RPEKFGGDLTVNSYEELESLFKNKELHFMDLKNAVAEELIKIL<br>EPIRKRL |
| 53 | O-(2-nitrobenzyl)-L-tyrosine aminoacyl-tRNA synthetase clone ONBY-2 amino acid sequence (derived from wild-type *Methanococcus jannaschii* tyrosyl tRNA-synthetase) | MDEFEMIKRNTSEIISEEELREVLKKDEKSA**A**IGFEPSGKIHL<br>GHYLQIKKMIDLQNAGFDIII**G**LADLHAYLNQKCELDEIRKIG<br>DYNKKVFEAMGLKAKYVYGSE**CD**LDKDYTLNVYRLALKTTLK<br>RARRSMELIAREDENPKVAEVIYPIMQVN**A**IHY**G**GVDVAVGG<br>MEQRKIHMLARELLPKKVVCIHMPVLTGLDGEGKMSSSKGNFI<br>AVDDSPEEIRAKIKKAYCPAGVVEGNPIMEIAKYFLEYPLTIK<br>RPEKFGGDLTVNSYEELESLFKNKELHPMDLKNAVAEELIKIL<br>EPIRKRL |
| 54 | O-(2-nitrobenzyl)-L-tyrosine aminoacyl-tRNA synthetase clone ONBY-3 amino acid sequence (derived from wild-type *Methanococcus jannaschii* tyrosyl tRNA-synthetase) | MDEFEMIKRNTSEIISEEELREVLKKDEKSA**G**IGFEPSGKIHL<br>GHYLQIKKMIDLQNAGFDIII**G**LADLHAYLNQKGELDEIRKIG<br>DYNKKVFEAMGLKAKYVYGSE**E**QLDKDYTLNVYRLALKTTLKR<br>ARRSMELIAREDENPKVAEVIYPIMQVN**S**IHY**E**GVDVAVGGM<br>EQRKIHMLARELLPKKVVCIHNPVLTGLDGEGKMSSSKGNFIA<br>VDDSPEEIRAKIKKAYCPAGVVEGNPIMEIAKYFLEYPLTIKR<br>PEKFGGDLTVNSYEELESLFKNKELHPMDLKNAVAEELIKILE<br>PIRKRL |
| 55 | p-cyanophenylalanine aminoacyl-tRNA synthetase amino acid sequence (derived from wild-type *Methanococcus jannaschii* Lyrosyl tRNA-synthetase), having the substitutions:<br>Tyr32Leu, Leu65Val, Phe108Trp, Gln109Met, Asp158Gly, Ile159Ala | MDEFEMIKRNTSEIISEEELREVLKKDEKSA**L**IGFEPSGKIHL<br>GHYLQIKKMIDLQNAGFDIII**V**LADLHAYLNQKGELDEIRKIG<br>DYNKKVFEAMGLKAKYVYGSE**WM**LDKDYTLNVYRLALKTTLKR<br>ARRSMELIAREDENPKVAEVIYPIMQVN**GA**HYLGVDVAVGGME<br>QRKIHMLARELLPKKVVCIHNPVLTGLDGEGKMSSSKGNFIAV<br>DDSPEEIRAKIKKAYCPAGVVEGNPIMEIAKYFLEYPLTIKRP<br>EKFGGDLTVNSYEELESLFKNKELHPMDLKNAVAEELIKILEP<br>IRKRL |
| 56 | p-cyanophenylalanine aminoacyl-tRNA synthetase nucleotide sequence | ATGGACGAATTTGAAATGATAAAGAGAAACACATCTGAAATTA<br>TCAGCGAGGAAGAGTTAAGAGAGGTTTTAAAAAAAGATGAAAA<br>ATCTGCTCTGATAGGTTTTGAACCAAGTGGTAAAATACATTTA<br>GGGCATTATCTCCAAATAAAAAAGATGATTGATTTACAAAATG<br>CTGGATTTGATATAATTATAGTTTTGGCTGATTTACATGCCTA<br>TTTAAACCAGAAAGGAGAGTTGGATCAGATTAGAAAAATAGGA<br>GATTATAACAAAAAAGTTTTTGAACCAATGGGGTTAAAGGCAA<br>AATATGTTTATGGAAGTCAATGGATGCTTGATAAGGATTATAC<br>ACTGAATGTCTATAGATTGGCTTTAAAAACTACCTTAAAAAGA<br>GCAAGAAGGAGTATGGAACTTATAGCAAGAGAGGATGAAAATC<br>CAAAGGTTGCTGAAGTTATCTATCCAATAATGCAGGTTAATGG<br>TGCTCATTATCTTGGCGTTGATGTTGCAGTTGGGGGGATGGAG |

TABLE 5-continued

Nucleotide and Amino Acid Sequences

| SEQ ID NO: | Description | SEQUENCE |
|---|---|---|
| | | CAGAGAAAAATACACATGTTAGCAAGGGAGCTTTTACCAAAAA<br>AGGTTGTTTGTATTCACAACCCTGTCTTAACGGGTTTGGATGG<br>AGAAGGAAAGATGAGTTCTTCAAAAGGGAATTTTATAGCTGTT<br>GATGACTCTCCAGAAGAGATTAGGGCTAACATAAAGAAAGCAT<br>ACTGCCCAGCTGGAGTTGTTGAAGGAAATCCAATAATGGAGAT<br>AGCTAAATACTTCCTTGAATATCCTTTAACCATAAAAAGGCCA<br>GAAAAATTTGGTGGAGATTTGACAGTTAATAGCTATGAGGAGT<br>TAGAGAGTTTATTTAAAAATAAGGAATTGCATCCAATGGATTT<br>AAAAAATGCTCTAGCTGAAGAACTTATAAAGATTTTAGAGCCA<br>ATTAGAAAGAGATTATAA |
| 57 | m-cyanophenylalanine aminoacyl-tRNA synthetase amino acid sequence (derived from wild-type *Methanococcus jannaschii* tyrosyl tRNA-synthetase), having the substitutions:<br>Tyr32His, His70Ser, Asp158Ser, Ile159Ser, Leu162Pro | MDEFEMIKRNTSEIISEEELREVLKKDEKSA**H**IGFEPSGKIHL<br>GHYLQIKKMIDLQNAGFDIIILLADL**S**AYLNQKGELDEIRKIG<br>DYNKKVFEAMCLKAKYVYGSEFQLDKDYTLNVYRLALKTTLKR<br>ARRSMELIAREDENPKVAEVIYPIMQVN**SS**HY**P**GVDVAVGGME<br>QRKIHMLARELLPKKVVCIHNPVLTGLDGEGKMSSSKGNFIAV<br>DDSPEEIRAKIKKAYCPAGVVEGNPIMEIAKYFLEYPLTIKRP<br>EKFGGDLTVNSYEELESLFKNKELHPMDLKNAVAEELIKILEP<br>IRKRL |
| 58 | m-cyanophenylalanine aminoacyl-tRNA synthetase nucleotide sequence | ATGGACGAATTTGAAATGATAAAGAGAAACACATCTGAAATTA<br>TCAGCGAGGAAGAGTTAAGACACGTTTTAAAAAAAGATGAAAA<br>ATCTGCTCATATAGGTTTTGAACCAAGTGGTAAAATACATTTA<br>GGGCATTATCTCCAAATAAAAAAGATGATTGATTTACAAAATG<br>CTGGATTTGATATAATTATATTGTTGGCTGATTTATCTGCCTA<br>TTTAAACCAGAAAGGAGAGTTGGATGACATTAGAAAAATAGGA<br>GATTATAACAAAAAAGTTTTTGAAGCAATGGGGTTAAAGGCAA<br>AATATGTTTATGGAAGTGAATTCCAGCTTGATAAGGATTATAC<br>ACTGAATGTCTATAGATTGGCTTTAAAAACTACCTTAAAAAGA<br>GCAAGAAGGAGTATGGAACTTATAGCAAGAGAGGATGAAAATC<br>CAAAGGTTGCTGAAGTTATCTATCCAATAATGCAGGTTAATAG<br>TTCGCATTATCCTGGCGTTGATGTTGCAGTTGGAGGGATGGAG<br>CAGAGAAAAATACACATGTTAGCAAGGGAGCTTTTACCAAAAA<br>AGGTTGTTTGTATTCACAACCCTGTCTTAACGGGTTTGGATGG<br>AGAAGGAAAGATGAGTTCTTCAAAAGGGAATTTTATAGCTGTT<br>GATGACTCTCCAGAAGAGATTAGGGCTAAGATAAAGAAAGCAT<br>ACTGCCCAGCTCGAGTTGTTGAAGGAAATCCAATAATGGAGAT<br>AGCTAAATACTTCCTTGAATATCCTTTAACCATAAAAAGGCCA<br>GAAAAATTTGGTGGAGATTTGACAGTTAATAGCTATGAGGAGT<br>TAGAGAGTTTATTTAAAAATAAGGAATTGCATCCAATGGATTT<br>AAAAAATGCTGTAGCTGAAGAACTTATAAAGATTTTACAGCCA<br>ATTAGAAAGAGATTATAA |
| 59 | p-(2-amino-1-hydroxyethyl)-L-phenylalanine aminoacyl-tRNA synthetase amino acid sequence (derived from wild-type *Methanococcus jannaschii* tyrosyl tRNA-synthetase), having the substitutions:<br>Tyr32Asp, Leu65Glu,<br>Phe108Arg, Asp158Gly,<br>Leu162Asn | MDEFEMIKRNTSEIISEEELREVLKKDEKSA**D**IGFEPSGKIHL<br>GHYLQIKKMIDLQNAGFDIII**E**LADLHAYLNQKGELDEIRKIG<br>DYNKKVFEAMGLKAKYVYGSE**R**QLDKDYTLNVYRLALKTTLKR<br>ARRSMELIAREDENPKVAEVIYPIMQVN**G**IHY**N**GVDVAVGGME<br>QRKIHMLARELLPKKVVCIHNPVLTGLDGEGKMSSSKGNFIAV<br>DDSPEEIRAKIKKAYCPAGVVEGNPIMEIAKYFLEYPLTIKRP<br>EKFGGDLTVNSYEELESLFKNKELHPMDLKNAVAEELIKILEP<br>IRKRL |
| 60 | p-ethylthiocarbonyl-L-phenylalanine aminoacyl-tRNA synthetase amino acid sequence (derived from wild-type *Methanococcus jannaschii* tyrosyl tRNA-synthetase), having the substitutions:<br>Leu65Phe, Phe108Trp,<br>Tyr32Ala,<br>Gln109Ser, Asp158Ser,<br>Leu162His | MDEFEMIKRNTSEIISEEELREVLKKDEKSA**A**IGFEPSGKIHL<br>GHYLQIKKMIDLQNAGFDIII**F**LADLHAYLNQKGELDEIRKIG<br>DYNKKVFEAMGLKAKYVYGSE**WS**LDKDYTLNVYRLALKTTLKR<br>ARRSMELIAREDENPKVAEVIYPIMQVN**S**IHY**H**GVDVAVGGME<br>QRKIHMLARELLPKKVVCIHNPVLTGLDGEGKMSSSKGNFIAV<br>DDSPEEIRAKIKKAYCPAGVVEGNPIMEIAKYFLEYPLTIKRP<br>EKFGGDLTVNSYEELESLFKNKELHPMDLKNAVAEELIKILEP<br>IRKRL |
| 61 | p-(3-oxobutanoyl)-L-phenylalanine aminoacyl-tRNA synthetase amino acid sequence (derived from wild-type *Methanococcus jannaschii* tyrosyl tRNA-synthetase), having the substitutions: | MDEFEMIKRNTSEIISEEELREVLKKDEKSA**G**IGFEPSGKIHL<br>GHYLQIKKMIDLQNAGFDIII**V**LADLHAYLNQKGELDEIRKIG<br>DYNKKVFEAMGLKAKYVYGSE**T**QLDKDYTLNVYRLALKTTLKR<br>ARRSMELIAREDENPKVAEVIYPIMQVN**G**IHY**S**GVDVAVGGME<br>QRKIHMLARELLPKKVVCIHNPVLTGLDGEGKMSSSKGNFIAV<br>DDSPEEIRAKIKKAYCPAGVVEGNPIMEIAKYFLEYPLTIKRP<br>EKFGGDLTVNSYEELESLFKNKELHPMDLKNAVAEELIKILEP |

TABLE 5-continued

| Nucleotide and Amino Acid Sequences | | |
|---|---|---|
| SEQ ID NO: | Description | SEQUENCE |
| | Tyr32Gly, Leu65Val, Phe108Thr, Asp158Gly, Leu162Ser | IRKRL |
| 62 | p-isopropylthiocarbonyl-L-phenylalanine aminoacyl-tRNA synthetase amino acid sequence (derived from wild-type *Methanococcus jannaschii* tyrosyl tRNA-synthetase), having the substitutions:<br>Tyr32Gly, Leu65Cys, Phe108Cys, Gln109Met, Asp158Gly, Leu162Tyr | MDEFEMIKRNTSEIISEEELREVLKKDEKSA**G**IGFEPSGKTHL<br>GHYLQIKKMIDLQNAGFDIII**C**LADLHAYLNQKGELDEIRKIG<br>DYNKKVFEAMGLKAKYVYGSE**CM**LDKDYTLNVYRLALKTTLKR<br>ARRSMELIAREDENPKVAEVIYPIMQVN**G**IHY**Y**GVDVAVGGME<br>QRKIHMLARELLPKKVVCIHNPVLTGLDGEGKMSSSKGNFIAV<br>DDSPEEIRAKIKKAYCPAGVVEGNPIMEIAKYFLEYPLTIKRP<br>EKFGGDLTVNSYEELESLPKNKELHPMDLKNAVAEELIKILEP<br>IRKRL |
| 63 | 7-amino-coumarin alanine and 7-hydroxy-coumarin alanine aminoacyl-tRNA synthetase amino acid sequence (derived from wild-type *Methanococcus jannaschii* tyrosyl tRNA-synthetase), having the substitutions:<br>Y32R, L65A, H70M, D158N and L162T | MDEFEMIKRNTSEIISEEELREVLKKDEKSA**R**IGFEPSGKIHL<br>GHYLQIKKMIDLQNAGFDIII**A**LADL**M**AYLNQKGELDEIRKIG<br>DYNKKVFEAMGLKAKYVYGSEFQLDKDYTLNVYRLALKTTLKR<br>ARRSMELIAREDENPKVAEVIYPIMQVN**N**IHY**T**GVDVAVGGME<br>QRKIHMLARELLPKKVVCIHNPVLTGLDGEGKMSSSKGNFIAV<br>DDSPEEIRAKIKKAYCPAGVVEGNPIMEIAKYFLEYPLTIKRP<br>EKFGGDLTVNSYEELESLFKNKELHPMDLKNAVAEELIKILEP<br>IRKRL |

What is claimed is:

1. A translation system comprising:

(a) a first unnatural amino acid selected from 3-nitro-L-tyrosine and p-nitro-L-phenylalanine;

(b) a first orthogonal aminoacyl-tRNA synthetase (O—RS); and (c) a first orthogonal tRNA (O-tRNA);

wherein said first O—RS aminoacylates said first O-tRNA with said first unnatural amino acid with an efficiency that is at least 50% of the efficiency observed for a translation system comprising said first unnatural amino acid, said first O-tRNA, and an O—RS comprising an amino acid sequence selected from SEQ ID NOs: 7-10.

2. The translation system of claim 1, wherein said first O—RS comprises an amino acid sequence selected from the amino acids sequences set forth in SEQ ID NOs: 7-10, and conservative variants thereof.

3. The translation system of claim 1, wherein said first O-tRNA is an amber suppressor tRNA.

4. The translation system of claim 1, wherein said first O-tRNA comprises or is encoded by a polynucleotide sequence set forth in SEQ ID NO: 1.

5. The translation system of claim 1, further comprising a nucleic acid encoding a protein of interest, said nucleic acid comprising at least one selector codon, wherein said selector codon is recognized by said first O-tRNA.

6. The translation system of claim 5, further comprising a second O—RS and a second O-tRNA, wherein the second O—RS preferentially aminoacylates the second O-tRNA with a second unnatural amino acid that is different from the first unnatural amino acid, and wherein the second O-tRNA recognizes a selector codon that is different from the selector codon recognized by the first O-tRNA.

7. The translation system of claim 1, wherein said system comprises a host cell wherein said host cell comprises said first unnatural amino acid, said first O—RS and said first O-tRNA.

8. The translation system of claim 7, wherein said host cell is a eubacterial cell.

9. The translation system of claim 8, wherein said eubacterial cell is an *E. coli* cell.

10. The translation system of claim 7, wherein said host cell comprises a polynucleotide encoding said first O—RS.

11. The translation system of claim 10, wherein said polynucleotide comprises a nucleotide sequence set forth in SEQ ID NO: 11.

12. The translation system of claim 7, wherein said host cell comprises a polynucleotide encoding said first O-tRNA.

13. A method for producing in a host cell a protein comprising an unnatural amino acid at a specified position, the method comprising:

(a) providing a host cell comprising:

(i) a first unnatural amino acid selected from 3-nitro-L-tyrosine and p-nitro-L-phenylalanine;

(ii) a first orthogonal tRNA (O-tRNA);

(iii) a first orthogonal aminoacyl-tRNA synthetase (O—RS), wherein said first O—RS preferentially aminoacylates said first O-tRNA with said unnatural amino acid with an efficiency that is at least 50% of the efficiency observed for said host cell comprising said first unnatural amino acid, said first O-tRNA, and an O—RS comprising an amino acid sequence selected from SEQ ID NOs: 7-10; and, (iv) a nucleic acid encoding said protein, wherein said nucleic acid comprises at least one selector codon that is recognized by said first O-tRNA; and, (b) growing said host cell; and (c) incorporating said unnatural amino acid at said selected position in said protein during translation of said protein, wherein said selected position in said protein corresponds to the position of the selector codon in said nucleic acid, thereby producing said protein comprising said unnatural amino acid at the selected position.

14. The method of claim 13, wherein said host cell comprises a polynucleotide encoding said O—RS.

15. The method of claim 13, wherein said host cell comprises an O—RS comprising an amino acid sequence selected from the amino acid sequences set forth in SEQ ID NOs: 7-10, and conservative variants thereof.

16. The method of claim 13, wherein said O—RS is produced by (A) mutating an amino acid binding pocket of a wild-type aminoacyl-tRNA synthetase by site-directed mutagenesis, and (B) selecting a resulting O—RS that preferentially aminoacylates said O-tRNA with said unnatural amino acid.

17. The method of claim 16, wherein said selecting step comprises positively selecting and negatively selecting for said O—RS from a pool comprising a plurality of resulting aminoacyl-tRNA synthetase molecules following site-directed mutagenesis.

18. The method of claim 13, wherein said host cell comprises a polynucleotide encoding said O-tRNA.

19. The method of claim 13, wherein said O-tRNA is an amber suppressor tRNA.

20. The method of claim 13, wherein said O-tRNA comprises or is encoded by a polynucleotide sequence set forth in SEQ ID NO: 1.

21. The method of claim 13, wherein said selector codon is an amber selector codon.

22. The method of claim 13, further wherein said protein comprises a second unnatural amino acid that is different from the first unnatural amino acid, wherein said host cell comprises a second O—RS and a second O-tRNA, wherein the second O—RS preferentially aminoacylates the second O-tRNA with a second unnatural amino acid that is different from the first unnatural amino acid, and wherein the second O-tRNA recognizes a selector codon in the nucleic acid that is different from the selector codon recognized by the first O-tRNA.

23. The method of claim 13, wherein said incorporating step comprises culturing said host cell.

24. The method of claim 13, wherein said providing a host cell comprises providing a eubacterial host cell or a yeast host cell.

25. The method of claim 24, wherein said providing a eubacterial host cell comprises providing an *E. coli* host cell.

26. The method of claim 13, wherein said providing a host cell comprises providing a host cell comprising a polynucleotide encoding said O—RS.

27. The method of claim 26, wherein said polynucleotide encoding said O—RS comprises a nucleotide sequence set forth in SEQ ID NO: 11.

* * * * *

SEQUENCE LISTING

<160> NUMBER OF SEQ ID NOS: 65

<210> SEQ ID NO 1
<211> LENGTH: 77
<212> TYPE: RNA
<213> ORGANISM: Artificial
<220> FEATURE:
<223> OTHER INFORMATION: mutant suppressor tyrosyl-tRNA CUA derived from Methanococcus jannaschii

<400> SEQUENCE: 1
ccggcgguag uucagcaggg cagaacggcg gacucuaaau ccgcauggcg cugguucaaa 60
uccggcccgc cggacca 77

<210> SEQ ID NO 2
<211> LENGTH: 87
<212> TYPE: RNA
<213> ORGANISM: Artificial
<220> FEATURE:
<223> OTHER INFORMATION: mutant suppressor tRNALeu5CUA derived from E. coli

<400> SEQUENCE: 2
gcccggaugg uggaaucggu agacacaagg gauucuaaau cccucggcgu ucgcgcugug 60
cggguucaag ucccgcuccg gguacca 87

<210> SEQ ID NO 3
<211> LENGTH: 306
<212> TYPE: PRT
<213> ORGANISM: Methanococcus jannaschii

<400> SEQUENCE: 3

Met Asp Glu Phe Glu Met Ile Lys Arg Asn Thr Ser Glu Ile Ile Ser
1 5 10 15

```
Glu Glu Glu Leu Arg Glu Val Leu Lys Lys Asp Glu Lys Ser Ala Tyr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 4
<211> LENGTH: 918
<212> TYPE: DNA
<213> ORGANISM: Methanococcus jannaschii

<400> SEQUENCE: 4

atggacgaat ttgaaatgat aaagagaaac acatctgaaa ttatcagcga ggaagagtta     60

agagaggttt taaaaaaaga tgaaaaatct gcttacatag gttttgaacc aagtggtaaa    120

atacatttag ggcattatct ccaaataaaa aagatgattg atttacaaaa tgctggattt    180

gatataatta tattgttggc tgatttacac gcctatttaa accagaaagg agagttggat    240

gagattagaa aaataggaga ttataacaaa aaagtttttg aagcaatggg gttaaaggca    300

aaatatgttt atggaagtga attccagctt gataaggatt atacactgaa tgtctataga    360

ttggctttaa aaactacctt aaaaagagca agaaggagta tggaacttat agcaagagag    420
```

-continued

```
gatgaaaatc caaaggttgc tgaagttatc tatccaataa tgcaggttaa tgatattcat    480

tatttaggcg ttgatgttgc agttggaggg atggagcaga gaaaaataca catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatggattt aaaaaatgct gtagctgaag aacttataaa gattttagag    900

ccaattagaa agagatta                                                  918
```

```
<210> SEQ ID NO 5
<211> LENGTH: 860
<212> TYPE: PRT
<213> ORGANISM: Escherichia coli

<400> SEQUENCE: 5

Met Gln Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Ser Lys
            20                  25                  30

Glu Lys Tyr Tyr Cys Leu Ser Met Leu Pro Tyr Pro Ser Gly Arg Leu
        35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Thr Phe Met Gly Cys
                245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
        275                 280                 285
```

-continued

```
Lys Val Ala Glu Ala Glu Met Ala Thr Met Glu Lys Lys Gly Val Asp
    290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
        355                 360                 365

Asp Leu Ser Gln Gln Ala Leu Thr Glu Lys Gly Val Leu Phe Asn Ser
    370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
            420                 425                 430

Pro Met Val Thr Leu Glu Asp Gly Thr Val Met Pro Thr Pro Asp Asp
        435                 440                 445

Gln Leu Pro Val Ile Leu Pro Glu Asp Val Val Met Asp Gly Ile Thr
    450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Ser Trp Tyr Tyr Ala Arg Tyr Thr Cys Pro Gln Tyr Lys Glu Gly Met
            500                 505                 510

Leu Asp Ser Glu Ala Ala Asn Tyr Trp Leu Pro Val Asp Ile Tyr Ile
        515                 520                 525

Gly Gly Ile Glu His Ala Ile Met His Leu Leu Tyr Phe Arg Phe Phe
    530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
            580                 585                 590

Val Glu Arg Asp Glu Lys Gly Arg Ile Val Lys Ala Lys Asp Ala Ala
        595                 600                 605

Gly His Glu Leu Val Tyr Thr Gly Met Ser Lys Met Ser Lys Ser Lys
    610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
            660                 665                 670

Val Trp Lys Leu Val Tyr Glu His Thr Ala Lys Gly Asp Val Ala Ala
        675                 680                 685

Leu Asn Val Asp Ala Leu Thr Glu Asn Gln Lys Ala Leu Arg Arg Asp
    690                 695                 700

Val His Lys Thr Ile Ala Lys Val Thr Asp Asp Ile Gly Arg Arg Gln
705                 710                 715                 720
```

Thr Phe Asn Thr Ala Ile Ala Ala Ile Met Glu Leu Met Asn Lys Leu
725 730 735

Ala Lys Ala Pro Thr Asp Gly Glu Gln Asp Arg Ala Leu Met Gln Glu
740 745 750

Ala Leu Leu Ala Val Val Arg Met Leu Asn Pro Phe Thr Pro His Ile
755 760 765

Cys Phe Thr Leu Trp Gln Glu Leu Lys Gly Glu Gly Asp Ile Asp Asn
770 775 780

Ala Pro Trp Pro Val Ala Asp Glu Lys Ala Met Val Glu Asp Ser Thr
785 790 795 800

Leu Val Val Val Gln Val Asn Gly Lys Val Arg Ala Lys Ile Thr Val
805 810 815

Pro Val Asp Ala Thr Glu Glu Gln Val Arg Glu Arg Ala Gly Gln Glu
820 825 830

His Leu Val Ala Lys Tyr Leu Asp Gly Val Thr Val Arg Lys Val Ile
835 840 845

Tyr Val Pro Gly Lys Leu Leu Asn Leu Val Val Gly
850 855 860

<210> SEQ ID NO 6
<211> LENGTH: 2583
<212> TYPE: DNA
<213> ORGANISM: Escherichia coli

<400> SEQUENCE: 6
atgcaagagc aataccgccc ggaagagata gaatccaaag tacagcttca ttgggatgag 60
aagcgcacat ttgaagtaac cgaagacgag agcaaagaga agtattactg cctgtctatg 120
cttccctatc cttctggtcg actacacatg ggccacgtac gtaactacac catcggtgac 180
gtgatcgccc gctaccagca tatgctgggc aaaaacgtcc tgcagccgat cggctgggac 240
gcgtttggtc tgcctgcgga aggcgcggcg gtgaaaaaca acaccgctcc ggcaccgtgg 300
acgtacgaca acatcgcgta tatgaaaaac cagctcaaaa tgctgggctt tggttatgac 360
tggagccgcg agctggcaac ctgtacgccg gaatactacc gttgggaaca gaaattcttc 420
accgagctgt ataaaaaagg cctggtatat aagaagactt ctgcggtcaa ctggtgcccg 480
aacgaccaga ccgtactggc gaacgaacaa gttatcgacg gctgctgctg gcgctgcgat 540
accaaagttg aacgtaaaga gatcccgcag tggtttatca aaatcaatgc ttacgctgac 600
gagctgctca acgatctgga taaactggat cactggccag acaccgttaa aaccatgcag 660
cgtaactgga tcggtcgttc cgaaggcgtg gagatcacct tcaacgttaa cgactatgac 720
aacacgctga ccgtttacac tacccgcccg gacaccttta tgggttgtac ctacctggcg 780
gtacgtgcgg gtcatccgct ggcgcagaaa gcggcggaaa ataatcctga actggcggcc 840
tttattgacg aatgccgtaa caccaaagtt gccgaagctg aaatggcgac gatggagaaa 900
aaaggcgtcg atactggctt taaagcggtt cacccattaa cgggcgaaga aattcccgtt 960
tgggcagcaa acttcgtatt gatggagtac ggcacgggcg cagttatggc ggtaccgggg 1020
cacgaccagc gcgactacga gtttgcctct aaatacggcc tgaacatcaa accggttatc 1080
ctggcagctg acggctctga gccagatctt tctcagcaag ccctgactga aaaaggcgtg 1140
ctgttcaact ctggcgagtt caacggtctt gaccatgaag cggccttcaa cgccatcgcc 1200
gataaactga ctgcgatggg cgttggcgag cgtaaagtga actaccgcct gcgcgactgg 1260
ggtgtttccc gtcagcgtta ctggggcgcg ccgattccga tggtgacgct ggaagacggt 1320
accgtaatgc cgaccccgga cgaccagctg ccggtgatcc tgccggaaga tgtggtaatg 1380
gacggcatta ccagcccgat taaagcagat ccggagtggg cgaaaactac cgttaacggt 1440
atgccagcac tgcgtgaaac cgacactttc gacaccttta tggagtcctc ctggtactat 1500
gcgcgctaca cttgcccgca gtacaaagaa ggtatgctgg attccgaagc ggctaactac 1560
tggctgccgg tggatatcta cattggtggt attgaacacg ccattatgca cctgctctac 1620
ttccgcttct tccacaaact gatgcgtgat gcaggcatgg tgaactctga cgaaccagcg 1680
aaacagttgc tgtgtcaggg tatggtgctg gcagatgcct tctactatgt tggcgaaaac 1740
ggcgaacgta actgggtttc cccggttgat gctatcgttg aacgtgacga gaaaggccgt 1800
atcgtgaaag cgaaagatgc ggcaggccat gaactggttt ataccggcat gagcaaaatg 1860
tccaagtcga agaacaacgg tatcgacccg caggtgatgg ttgaacgtta cggcgcggac 1920
accgttcgtc tgtttatgat gtttgcttct ccggctgata tgactctcga atggcaggaa 1980
tccggtgtgg aaggggctaa ccgcttcctg aaacgtgtct ggaaactggt ttacgagcac 2040
acagcaaaag gtgatgttgc ggcactgaac gttgatgcgc tgactgaaaa tcagaaagcg 2100
ctgcgtcgcg atgtgcataa aacgatcgct aaagtgaccg atgatatcgg ccgtcgtcag 2160
accttcaaca ccgcaattgc ggcgattatg gagctgatga acaaactggc gaaagcacca 2220
accgatggcg agcaggaccg cgctctgatg caggaagcac tgctggccgt tgtccgtatg 2280
cttaacccgt tcaccccgca catctgcttc acgctgtggc aggaactgaa aggcgaaggc 2340
gatatcgaca acgcgccgtg gccggttgct gacgaaaaag cgatggtgga agactccacg 2400
ctggtcgtgg tgcaggttaa cggtaaagtc cgtgccaaaa tcaccgttcc ggtggacgca 2460
acggaagaac aggttcgcga acgtgctggc caggaacatc tggtagcaaa atatcttgat 2520
ggcgttactg tacgtaaagt gatttacgta ccaggtaaac tcctcaatct ggtcgttggc 2580
taa 2583

<210> SEQ ID NO 7
<211> LENGTH: 306
<212> TYPE: PRT
<213> ORGANISM: Artificial
<220> FEATURE:
<223> OTHER INFORMATION: 3-nitro-L-tyrosine aminoacyl-tRNA synthetase

<400> SEQUENCE: 7

Met Asp Glu Phe Glu Met Ile Lys Arg Asn Thr Ser Glu Ile Ile Ser
1 5 10 15

Glu Glu Glu Leu Arg Glu Val Leu Lys Lys Asp Glu Lys Ser Ala Tyr
20 25 30

Ile Gly Phe Glu Pro Ser Gly Lys Ile His Leu Gly His Tyr Leu Gln
35 40 45

Ile Lys Lys Met Ile Asp Leu Gln Asn Ala Gly Phe Asp Ile Ile Ile
50 55 60

Leu Leu Val Asp Leu Val Ala Tyr Leu Asn Gln Lys Gly Glu Leu Asp
65 70 75 80

Glu Ile Arg Lys Ile Gly Asp Tyr Asn Lys Lys Val Phe Glu Ala Met
85 90 95

Gly Leu Lys Ala Lys Tyr Val Tyr Gly Ser Glu Phe Gln Leu Asp Lys
100 105 110

Asp Tyr Thr Leu Asn Val Tyr Arg Leu Ala Leu Lys Thr Thr Leu Lys
115 120 125

Arg Ala Arg Arg Ser Met Glu Leu Ile Ala Arg Glu Asp Glu Asn Pro
130 135 140

```
Lys Val Ala Glu Val Ile Tyr Pro Ile Met Gln Val Asn Asp Ile His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 8
<211> LENGTH: 306
<212> TYPE: PRT
<213> ORGANISM: Artificial
<220> FEATURE:
<223> OTHER INFORMATION: 3-nitro-L-tyrosine aminoacyl-tRNA synthetase

<400> SEQUENCE: 8

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ser
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Thr Asp Leu Asn Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Thr Val Gly Gly Met Glu Gln Arg Lys Ile
                165                 170                 175

His Met Leu Ala Arg Glu Leu Leu Pro Lys Lys Val Val Cys Ile His
            180                 185                 190
```

Asn Pro Val Leu Thr Gly Leu Asp Gly Glu Gly Lys Met Ser Ser Ser
195 200 205

Lys Gly Asn Phe Ile Ala Val Asp Asp Ser Pro Glu Glu Ile Arg Ala
210 215 220

Lys Ile Lys Lys Ala Tyr Cys Pro Ala Gly Val Val Glu Gly Asn Pro
225 230 235 240

Ile Met Glu Ile Ala Lys Tyr Phe Leu Glu Tyr Pro Leu Thr Ile Lys
245 250 255

Arg Pro Glu Lys Phe Gly Gly Asp Leu Thr Val Asn Ser Tyr Glu Glu
260 265 270

Leu Glu Ser Leu Phe Lys Asn Lys Glu Leu His Pro Met Asp Leu Lys
275 280 285

Asn Ala Val Ala Glu Glu Leu Ile Lys Ile Leu Glu Pro Ile Arg Lys
290 295 300

Arg Leu
305

<210> SEQ ID NO 9
<211> LENGTH: 306
<212> TYPE: PRT
<213> ORGANISM: Artificial
<220> FEATURE:
<223> OTHER INFORMATION: 3-nitro-L-tyrosine aminoacyl-tRNA synthetase

<400> SEQUENCE: 9

Met Asp Glu Phe Glu Met Ile Lys Arg Asn Thr Ser Glu Ile Ile Ser
1 5 10 15

Glu Glu Glu Leu Arg Glu Val Leu Lys Lys Asp Glu Lys Ser Ala Tyr
20 25 30

Ile Gly Phe Glu Pro Ser Gly Lys Ile His Leu Gly His Tyr Leu Gln
35 40 45

Ile Lys Lys Met Ile Asp Leu Gln Asn Ala Gly Phe Asp Ile Ile Ile
50 55 60

Leu Leu Pro Asp Leu His Ala Tyr Leu Asn Gln Lys Gly Glu Leu Asp
65 70 75 80

Glu Ile Arg Lys Ile Gly Asp Tyr Asn Lys Lys Val Phe Glu Ala Met
85 90 95

Gly Leu Lys Ala Lys Tyr Val Tyr Gly Ser Glu Phe Gln Leu Asp Lys
100 105 110

Asp Tyr Thr Leu Asn Val Tyr Arg Leu Ala Leu Lys Thr Thr Leu Lys
115 120 125

Arg Ala Arg Arg Ser Met Glu Leu Ile Ala Arg Glu Asp Glu Asn Pro
130 135 140

Lys Val Ala Glu Val Ile Tyr Pro Ile Met Gln Val Asn Asp Ile His
145 150 155 160

Tyr Leu Gly Val Asp Val Gly Val Gly Gly Met Glu Gln Arg Lys Ile
165 170 175

His Met Leu Ala Arg Glu Leu Leu Pro Lys Lys Val Val Cys Ile His
180 185 190

Asn Pro Val Leu Thr Gly Leu Asp Gly Glu Gly Lys Met Ser Ser Ser
195 200 205

Lys Gly Asn Phe Ile Ala Val Asp Asp Ser Pro Glu Glu Ile Arg Ala
210 215 220

Lys Ile Lys Lys Ala Tyr Cys Pro Ala Gly Val Val Glu Gly Asn Pro
225 230 235 240

Ile Met Glu Ile Ala Lys Tyr Phe Leu Glu Tyr Pro Leu Thr Ile Lys

```
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 10
<211> LENGTH: 306
<212> TYPE: PRT
<213> ORGANISM: Artificial
<220> FEATURE:
<223> OTHER INFORMATION: p-nitro-L-phenylalanine aminoacyl-tRNA
      synthetase

<400> SEQUENCE: 10

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu Asn
145                 150                 155                 160

Tyr Glu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
```

290 295 300

Arg Leu
305

<210> SEQ ID NO 11
<211> LENGTH: 921
<212> TYPE: DNA
<213> ORGANISM: Artificial
<220> FEATURE:
<223> OTHER INFORMATION: p-nitro-L-phenylalanine aminoacyl-tRNA synthetase

<400> SEQUENCE: 11
atggacgaat ttgaaatgat aaagagaaac acatctgaaa ttatcagcga ggaagagtta 60
agagaggttt taaaaaaaga tgaaaaatct gctctgatag gttttgaacc aagtggtaaa 120
atacatttag ggcattatct ccaaataaaa aagatgattg atttacaaaa tgctggattt 180
gatataatta tattgttggc tgatttacac gcctatttaa accagaaagg agagttggat 240
gagattagaa aaataggaga ttataacaaa aaagtttttg aagcaatggg gttaaaggca 300
aaatatgttt atggaagttc gttccagctt gataaggatt atacactgaa tgtctataga 360
ttggctttaa aaactacctt aaaaagagca agaaggagta tggaacttat agcaagagag 420
gatgaaaatc caaaggttgc tgaagttatc tatccaataa tgcaggttaa tcctcttaat 480
tatgagggcg ttgatgttgc agttggaggg atggagcaga gaaaaataca catgttagca 540
agggagcttt taccaaaaaa ggttgtttgt attcacaacc ctgtcttaac gggtttggat 600
ggagaaggaa agatgagttc ttcaaaaggg aattttatag ctgttgatga ctctccagaa 660
gagattaggg ctaagataaa gaaagcatac tgcccagctg gagttgttga aggaaatcca 720
ataatggaga tagctaaata cttccttgaa tatcctttaa ccataaaaag gccagaaaaa 780
tttggtggag atttgacagt taatagctat gaggagttag agagtttatt taaaaataag 840
gaattgcatc caatggattt aaaaaatgct gtagctgaag aacttataaa gattttagag 900
ccaattagaa agagattata a 921

<210> SEQ ID NO 12
<211> LENGTH: 306
<212> TYPE: PRT
<213> ORGANISM: Artificial
<220> FEATURE:
<223> OTHER INFORMATION: 3-amino-L-tyrosine aminoacyl-tRNA synthetase

<400> SEQUENCE: 12

Met Asp Glu Phe Glu Met Ile Lys Arg Asn Thr Ser Glu Ile Ile Ser
1 5 10 15

Glu Glu Glu Leu Arg Glu Val Leu Lys Lys Asp Glu Lys Ser Ala Gln
20 25 30

Ile Gly Phe Glu Pro Ser Gly Lys Ile His Leu Gly His Tyr Leu Gln
35 40 45

Ile Lys Lys Met Ile Asp Leu Gln Asn Ala Gly Phe Asp Ile Ile Ile
50 55 60

Glu Leu Ala Asp Leu His Ala Tyr Leu Asn Gln Lys Gly Glu Leu Asp
65 70 75 80

Glu Ile Arg Lys Ile Gly Asp Tyr Asn Lys Lys Val Phe Glu Ala Met
85 90 95

Gly Leu Lys Ala Lys Tyr Val Tyr Gly Ser Glu Gly Leu Leu Asp Lys
100 105 110

Asp Tyr Thr Leu Asn Val Tyr Arg Leu Ala Leu Lys Thr Thr Leu Lys

-continued

```
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ser Ile His
145                 150                 155                 160

Tyr Thr Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 13
<211> LENGTH: 921
<212> TYPE: DNA
<213> ORGANISM: Artificial
<220> FEATURE:
<223> OTHER INFORMATION: 3-amino-L-tyrosine aminoacyl-tRNA synthetase

<400> SEQUENCE: 13

atggacgaat ttgaaatgat aaagagaaac acatctgaaa ttatcagcga ggaagagtta     60

agagaggttt taaaaaaaga tgaaaaatct gctcagatag gttttgaacc aagtggtaaa    120

atacatttag ggcattatct ccaaataaaa aagatgattg atttacaaaa tgctggattt    180

gatataatta tagagttggc tgatttacac gcctatttaa accagaaagg agagttggat    240

gagattagaa aaataggaga ttataacaaa aaagtttttg aagcaatggg gttaaaggca    300

aaatatgttt atggaagtga aggtttgctt gataaggatt atacactgaa tgtctataga    360

ttggctttaa aaactacctt aaaaagagca agaaggagta tggaacttat agcaagagag    420

gatgaaaatc caaaggttgc tgaagttatc tatccaataa tgcaggttaa ttctattcat    480

tatactggcg ttgatgttgc agttggaggg atggagcaga gaaaaataca catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatggattt aaaaaatgct gtagctgaag aacttataaa gattttagag    900

ccaattagaa agagattata a                                              921
```

<210> SEQ ID NO 14
<211> LENGTH: 306
<212> TYPE: PRT
<213> ORGANISM: Artificial
<220> FEATURE:
<223> OTHER INFORMATION: p-carboxymethyl-L-phenylalanine aminoacyl-tRNA synthetase

<400> SEQUENCE: 14

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Ser Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Arg Asn Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ser Ile His
145                 150                 155                 160

Tyr His Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 15
<211> LENGTH: 921
<212> TYPE: DNA
<213> ORGANISM: Artificial
<220> FEATURE:
<223> OTHER INFORMATION: p-carboxymethyl-L-phenylalanine aminoacyl-tRNA synthetase -continued

<400> SEQUENCE: 15

```
atggacgaat ttgaaatgat aaagagaaac acatctgaaa ttatcagcga ggaagagtta     60

agagaggttt taaaaaaaga tgaaaaatct gctgcgatag gttttgaacc aagtggtaaa    120

atacatttag ggcattatct ccaaataaaa aagatgattg atttacaaaa tgctggattt    180

gatataatta tatcgttggc tgatttacac gcctatttaa accagaaagg agagttggat    240

gagattagaa aaataggaga ttataacaaa aaagtttttg aagcaatggg gttaaaggca    300

aaatatgttt atggaagtga acgtaatctt gataaggatt atacactgaa tgtctataga    360

ttggctttaa aaactacctt aaaaagagca agaaggagta tggaacttat agcaagagag    420

gatgaaaatc caaaggttgc tgaagttatc tatccaataa tgcaggttaa ttctattcat    480

tatcatggcg ttgatgttgc agttggaggg atggagcaga gaaaaataca catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatggattt aaaaaatgct gtagctgaag aacttataaa gattttagag    900

ccaattagaa agagattata a                                              921
```

<210> SEQ ID NO 16
<211> LENGTH: 306
<212> TYPE: PRT
<213> ORGANISM: Artificial
<220> FEATURE:
<223> OTHER INFORMATION: p-carboxymethyl-L-phenylalanine aminoacyl-tRNA
      synthetase

<400> SEQUENCE: 16

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ser
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Ala Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Asn Tyr Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Ile His
145                 150                 155                 160

Tyr Lys Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190
```

```
Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 17
<211> LENGTH: 921
<212> TYPE: DNA
<213> ORGANISM: Artificial
<220> FEATURE:
<223> OTHER INFORMATION: p-carboxymethyl-L-phenylalanine aminoacyl-tRNA synthetase

<400> SEQUENCE: 17

```
atggacgaat ttgaaatgat aaagagaaac acatctgaaa ttatcagcga ggaagagtta      60

agagaggttt taaaaaaaga tgaaaaatct gcttctatag gttttgaacc aagtggtaaa     120

atacatttag ggcattatct ccaaataaaa aagatgattg atttacaaaa tgctggattt     180

gatataatta tagctttggc tgatttacac gcctatttaa accagaaagg agagttggat     240

gagattagaa aaataggaga ttataacaaa aaagtttttg aagcaatggg gttaaaggca     300

aaatatgttt atggaagtga aaattatctt gataaggatt atacactgaa tgtctataga     360

ttggctttaa aaactacctt aaaaagagca agaaggagta tggaacttat agcaagagag     420

gatgaaaatc caaaggttgc tgaagttatc tatccaataa tgcaggttaa tggtattcat     480

tataagggcg ttgatgttgc agttggaggg atggagcaga gaaaaataca catgttagca     540

agggagcttt taccaaaaaa ggttgtttgt attcacaacc ctgtcttaac gggtttggat     600

ggagaaggaa agatgagttc ttcaaaaggg aattttatag ctgttgatga ctctccagaa     660

gagattaggg ctaagataaa gaaagcatac tgcccagctg gagttgttga aggaaatcca     720

ataatggaga tagctaaata cttccttgaa tatcctttaa ccataaaaag gccagaaaaa     780

tttggtggag atttgacagt taatagctat gaggagttag agagtttatt taaaaataag     840

gaattgcatc caatggattt aaaaaatgct gtagctgaag aacttataaa gattttagag     900

ccaattagaa agagattata a                                               921
```

<210> SEQ ID NO 18
<211> LENGTH: 306
<212> TYPE: PRT
<213> ORGANISM: Artificial
<220> FEATURE:
<223> OTHER INFORMATION: p-carboxymethyl-L-phenylalanine aminoacyl-tRNA synthetase

<400> SEQUENCE: 18

```
Met Asp Glu Phe Glu Met Ile Lys Arg Asn Thr Ser Glu Ile Ile Ser
```

```
1               5                   10                  15

Glu Glu Glu Leu Arg Glu Val Leu Lys Lys Asp Glu Lys Ser Ala Ser
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Ala Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Arg Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Ile His
145                 150                 155                 160

Tyr Lys Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 19
<211> LENGTH: 921
<212> TYPE: DNA
<213> ORGANISM: Artificial
<220> FEATURE:
<223> OTHER INFORMATION: p-carboxymethyl-L-phenylalanine aminoacyl-tRNA synthetase

<400> SEQUENCE: 19

```
atggacgaat ttgaaatgat aaagagaaac acatctgaaa ttatcagcga ggaagagtta      60

agagaggttt taaaaaaaga tgaaaaatct gcttcgatag gttttgaacc aagtggtaaa     120

atacatttag ggcattatct ccaaataaaa aagatgattg atttacaaaa tgctggattt     180

gatataatta tagcgttggc tgatttacac gcctatttaa accagaaagg agagttggat     240

gagattagaa aaataggaga ttataacaaa aaagtttttg aagcaatggg gttaaaggca     300
```

```
aaatatgttt atggaagtga acgtcagctt gataaggatt atacactgaa tgtctataga    360

ttggctttaa aaactacctt aaaaagagca agaaggagta tggaacttat agcaagagag    420

gatgaaaatc caaaggttgc tgaagttatc tatccaataa tgcaggttaa tggtattcat    480

tataagggcg ttgatgttgc agttggaggg atggagcaga gaaaaataca catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatggattt aaaaaatgct gtagctgaag aacttataaa gattttagag    900

ccaattagaa agagattata a                                              921


<210> SEQ ID NO 20
<211> LENGTH: 306
<212> TYPE: PRT
<213> ORGANISM: Artificial
<220> FEATURE:
<223> OTHER INFORMATION: p-carboxymethyl-L-phenylalanine aminoacyl-tRNA
      synthetase

<400> SEQUENCE: 20

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ser
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Ala Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Ala Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Ile His
145                 150                 155                 160

Tyr Lys Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255
```

Arg Pro Glu Lys Phe Gly Gly Asp Leu Thr Val Asn Ser Tyr Glu Glu
260 265 270

Leu Glu Ser Leu Phe Lys Asn Lys Glu Leu His Pro Met Asp Leu Lys
275 280 285

Asn Ala Val Ala Glu Glu Leu Ile Lys Ile Leu Glu Pro Ile Arg Lys
290 295 300

Arg Leu
305

<210> SEQ ID NO 21
<211> LENGTH: 921
<212> TYPE: DNA
<213> ORGANISM: Artificial
<220> FEATURE:
<223> OTHER INFORMATION: p-carboxymethyl-L-phenylalanine aminoacyl-tRNA synthetase

<400> SEQUENCE: 21
atggacgaat ttgaaatgat aaagagaaac acatctgaaa ttatcagcga ggaagagtta 60
agagaggttt taaaaaaaga tgaaaaatct gcttcgatag gttttgaacc aagtggtaaa 120
atacatttag ggcattatct ccaaataaaa aagatgattg atttacaaaa tgctggattt 180
gatataatta tagcgttggc tgatttacac gcctatttaa accagaaagg agagttggat 240
gagattagaa aaataggaga ttataacaaa aaagtttttg aagcaatggg gttaaaggca 300
aaatatgttt atggaagtga agcgcagctt gataaggatt atacactgaa tgtctataga 360
ttggctttaa aaactacctt aaaaagagca agaaggagta tggaacttat agcaagagag 420
gatgaaaatc caaaggttgc tgaagttatc tatccaataa tgcaggttaa tggtattcat 480
tataagggcg ttgatgttgc agttggaggg atggagcaga gaaaaataca catgttagca 540
agggagcttt taccaaaaaa ggttgtttgt attcacaacc ctgtcttaac gggtttggat 600
ggagaaggaa agatgagttc ttcaaaaggg aattttatag ctgttgatga ctctccagaa 660
gagattaggg ctaagataaa gaaagcatac tgcccagctg gagttgttga aggaaatcca 720
ataatggaga tagctaaata cttccttgaa tatcctttaa ccataaaaag gccagaaaaa 780
tttggtggag atttgacagt taatagctat gaggagttag agagtttatt taaaaataag 840
gaattgcatc caatggattt aaaaaatgct gtagctgaag aacttataaa gattttagag 900
ccaattagaa agagattata a 921

<210> SEQ ID NO 22
<211> LENGTH: 306
<212> TYPE: PRT
<213> ORGANISM: Artificial
<220> FEATURE:
<223> OTHER INFORMATION: p-carboxymethyl-L-phenylalanine aminoacyl-tRNA synthetase

<400> SEQUENCE: 22

Met Asp Glu Phe Glu Met Ile Lys Arg Asn Thr Ser Glu Ile Ile Ser
1 5 10 15

Glu Glu Glu Leu Arg Glu Val Leu Lys Lys Asp Glu Lys Ser Ala Ser
20 25 30

Ile Gly Phe Glu Pro Ser Gly Lys Ile His Leu Gly His Tyr Leu Gln
35 40 45

Ile Lys Lys Met Ile Asp Leu Gln Asn Ala Gly Phe Asp Ile Ile Ile
50 55 60

Ala Leu Ala Asp Leu His Ala Tyr Leu Asn Gln Lys Gly Glu Leu Asp

-continued 65 70 75 80

Glu Ile Arg Lys Ile Gly Asp Tyr Asn Lys Lys Val Phe Glu Ala Met
85 90 95

Gly Leu Lys Ala Lys Tyr Val Tyr Gly Ser Glu Lys His Leu Asp Lys
100 105 110

Asp Tyr Thr Leu Asn Val Tyr Arg Leu Ala Leu Lys Thr Thr Leu Lys
115 120 125

Arg Ala Arg Arg Ser Met Glu Leu Ile Ala Arg Glu Asp Glu Asn Pro
130 135 140

Lys Val Ala Glu Val Ile Tyr Pro Ile Met Gln Val Asn Gly Ile His
145 150 155 160

Tyr Lys Gly Val Asp Val Ala Val Gly Gly Met Glu Gln Arg Lys Ile
165 170 175

His Met Leu Ala Arg Glu Leu Leu Pro Lys Lys Val Val Cys Ile His
180 185 190

Asn Pro Val Leu Thr Gly Leu Asp Gly Glu Gly Lys Met Ser Ser Ser
195 200 205

Lys Gly Asn Phe Ile Ala Val Asp Asp Ser Pro Glu Glu Ile Arg Ala
210 215 220

Lys Ile Lys Lys Ala Tyr Cys Pro Ala Gly Val Val Glu Gly Asn Pro
225 230 235 240

Ile Met Glu Ile Ala Lys Tyr Phe Leu Glu Tyr Pro Leu Thr Ile Lys
245 250 255

Arg Pro Glu Lys Phe Gly Gly Asp Leu Thr Val Asn Ser Tyr Glu Glu
260 265 270

Leu Glu Ser Leu Phe Lys Asn Lys Glu Leu His Pro Met Asp Leu Lys
275 280 285

Asn Ala Val Ala Glu Glu Leu Ile Lys Ile Leu Glu Pro Ile Arg Lys
290 295 300

Arg Leu
305

<210> SEQ ID NO 23
<211> LENGTH: 921
<212> TYPE: DNA
<213> ORGANISM: Artificial
<220> FEATURE:
<223> OTHER INFORMATION: p-carboxymethyl-L-phenylalanine aminoacyl-tRNA
synthetase

<400> SEQUENCE: 23
atggacgaat ttgaaatgat aaagagaaac acatctgaaa ttatcagcga ggaagagtta 60
agagaggttt taaaaaaaga tgaaaaatct gcttctatag gttttgaacc aagtggtaaa 120
atacatttag ggcattatct ccaaataaaa aagatgattg atttacaaaa tgctggattt 180
gatataatta tagcgttggc tgatttacac gcctatttaa accagaaagg agagttggat 240
gagattagaa aaataggaga ttataacaaa aaagtttttg aagcaatggg gttaaaggca 300
aaatatgttt atggaagtga aaagcatctt gataaggatt atacactgaa tgtctataga 360
ttggctttaa aaactacctt aaaaagagca agaaggagta tggaacttat agcaagagag 420
gatgaaaatc caaaggttgc tgaagttatc tatccaataa tgcaggttaa tggtattcat 480
tataagggcg ttgatgttgc agttggaggg atggagcaga gaaaaataca catgttagca 540
agggagcttt taccaaaaaa ggttgtttgt attcacaacc ctgtcttaac gggtttggat 600
ggagaaggaa agatgagttc ttcaaaaggg aattttatag ctgttgatga ctctccagaa 660

-continued

```
gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatggattt aaaaaatgct gtagctgaag aacttataaa gattttagag    900

ccaattagaa agagattata a                                               921
```

<210> SEQ ID NO 24
<211> LENGTH: 306
<212> TYPE: PRT
<213> ORGANISM: Artificial
<220> FEATURE:
<223> OTHER INFORMATION: biphenylalanine aminoacyl-tRNA synthetase

<400> SEQUENCE: 24

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Gly Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Glu Pro Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Cys Ile His
145                 150                 155                 160

Tyr His Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 25
<211> LENGTH: 921
<212> TYPE: DNA
<213> ORGANISM: Artificial
<220> FEATURE:
<223> OTHER INFORMATION: biphenylalanine aminoacyl-tRNA synthetase

<400> SEQUENCE: 25

```
atggacgaat ttgaaatgat aaagagaaac acatctgaaa ttatcagcga ggaagagtta     60

agagaggttt taaaaaaaga tgaaaaatct gctgctatag gttttgaacc aagtggtaaa    120

atacatttag ggcattatct ccaaataaaa aagatgattg atttacaaaa tgctggattt    180

gatataatta tagggttggc tgatttacac gcctatttaa accagaaagg agagttggat    240

gagattagaa aaataggaga ttataacaaa aaagtttttg aagcaatggg gttaaaggca    300

aaatatgttt atggaagtga agagccgctt gataaggatt atacactgaa tgtctataga    360

ttggctttaa aaactacctt aaaaagagca agaaggagta tggaacttat agcaagagag    420

gatgaaaatc caaaggttgc tgaagttatc tatccaataa tgcaggttaa ttgtattcat    480

tatcatggcg ttgatgttgc agttggaggg atggagcaga gaaaaataca catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatggattt aaaaaatgct gtagctgaag aacttataaa gatttttagag    900

ccaattagaa agagattata a                                               921
```

<210> SEQ ID NO 26
<211> LENGTH: 306
<212> TYPE: PRT
<213> ORGANISM: Artificial
<220> FEATURE:
<223> OTHER INFORMATION: biphenylalanine aminoacyl-tRNA synthetase

<400> SEQUENCE: 26

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Thr Leu Ala Asp Leu Ser Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gly Val Asn Val Ile His
```

-continued

```
145                 150                 155                 160

Tyr His Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

```
<210> SEQ ID NO 27
<211> LENGTH: 921
<212> TYPE: DNA
<213> ORGANISM: Artificial
<220> FEATURE:
<223> OTHER INFORMATION: biphenylalanine aminoacyl-tRNA synthetase

<400> SEQUENCE: 27

atggacgaat ttgaaatgat aaagagaaac acatctgaaa ttatcagcga ggaagagtta     60

agagaggttt taaaaaaaga tgaaaaatct gctctgatag gttttgaacc aagtggtaaa    120

atacatttag ggcattatct ccaaataaaa aagatgattg atttacaaaa tgctggattt    180

gatataatta taactttggc tgatttatct gcctatttaa accagaaagg agagttggat    240

gagattagaa aaataggaga ttataacaaa aaagtttttg aagcaatggg gttaaaggca    300

aaatatgttt atggaagtga attccagctt gataaggatt atacactgaa tgtctataga    360

ttggctttaa aaactacctt aaaaagagca agaaggagta tggaacttat agcaagagag    420

gatgaaaatc caaaggttgc tgaagttatc tatccaataa tgggtgttaa tgttattcat    480

tatcatggcg ttgatgttgc agttggaggg atggagcaga gaaaaataca catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatggattt aaaaaatgct gtagctgaag aacttataaa gattttagag    900

ccaattagaa agagattata a                                              921

<210> SEQ ID NO 28
<211> LENGTH: 306
<212> TYPE: PRT
<213> ORGANISM: Artificial
<220> FEATURE:
```

<223> OTHER INFORMATION: biphenylalanine aminoacyl-tRNA synthetase

<400> SEQUENCE: 28

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Ser Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Arg Glu Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ser Ile His
145                 150                 155                 160

Tyr Ser Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 29
<211> LENGTH: 921
<212> TYPE: DNA
<213> ORGANISM: Artificial
<220> FEATURE:
<223> OTHER INFORMATION: biphenylalanine aminoacyl-tRNA synthetase

<400> SEQUENCE: 29

```
atggacgaat ttgaaatgat aaagagaaac acatctgaaa ttatcagcga ggaagagtta      60

agagaggttt taaaaaaaga tgaaaaatct gctgctatag gttttgaacc aagtggtaaa     120

atacatttag ggcattatct ccaaataaaa aagatgattg atttacaaaa tgctggattt     180
```

```
gatataatta tatcgttggc tgatttacac gcctatttaa accagaaagg agagttggat    240

gagattagaa aaataggaga ttataacaaa aaagtttttg aagcaatggg gttaaaggca    300

aaatatgttt atggaagtga aagggagctt gataaggatt atacactgaa tgtctataga    360

ttggctttaa aaactacctt aaaaagagca agaaggagta tggaacttat agcaagagag    420

gatgaaaatc caaaggttgc tgaagttatc tatccaataa tgcaggttaa tagtattcat    480

tatagtggcg ttgatgttgc agttggaggg atggagcaga gaaaaataca catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatggattt aaaaaatgct gtagctgaag aacttataaa gattttagag    900

ccaattagaa agagattata a                                              921
```

<210> SEQ ID NO 30
<211> LENGTH: 306
<212> TYPE: PRT
<213> ORGANISM: Artificial
<220> FEATURE:
<223> OTHER INFORMATION: biphenylalanine aminoacyl-tRNA synthetase

<400> SEQUENCE: 30

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala His
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Val Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Ser Lys Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Ile His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240
```

```
Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 31
<211> LENGTH: 921
<212> TYPE: DNA
<213> ORGANISM: Artificial
<220> FEATURE:
<223> OTHER INFORMATION: biphenylalanine aminoacyl-tRNA synthetase

<400> SEQUENCE: 31

```
atggacgaat ttgaaatgat aaagagaaac acatctgaaa ttatcagcga ggaagagtta     60

agagaggttt taaaaaaaga tgaaaaatct gctcatatag gttttgaacc aagtggtaaa    120

atacatttag ggcattatct ccaaataaaa aagatgattg atttacaaaa tgctggattt    180

gatataatta tagttttggc tgatttacac gcctatttaa accagaaagg agagttggat    240

gagattagaa aaataggaga ttataacaaa aaagtttttg aagcaatggg gttaaaggca    300

aaatatgttt atggaagtga atcgaagctt gataaggatt atacactgaa tgtctataga    360

ttggctttaa aaactacctt aaaaagagca agaaggagta tggaacttat agcaagagag    420

gatgaaaatc caaaggttgc tgaagttatc tatccaataa tgcaggttaa tggtattcat    480

tatcttggcg ttgatgttgc agttggaggg atggagcaga gaaaaataca catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatggattt aaaaaatgct gtagctgaag aacttataaa gattttagag    900

ccaattagaa agagattata a                                              921
```

<210> SEQ ID NO 32
<211> LENGTH: 306
<212> TYPE: PRT
<213> ORGANISM: Artificial
<220> FEATURE:
<223> OTHER INFORMATION: biphenylalanine aminoacyl-tRNA synthetase

<400> SEQUENCE: 32

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60
```

```
Val Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Ala Asp Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ser Ile His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 33
<211> LENGTH: 921
<212> TYPE: DNA
<213> ORGANISM: Artificial
<220> FEATURE:
<223> OTHER INFORMATION: biphenylalanine aminoacyl-tRNA synthetase

<400> SEQUENCE: 33

```
atggacgaat ttgaaatgat aaagagaaac acatctgaaa ttatcagcga ggaagagtta     60

agagaggttt taaaaaaaga tgaaaaatct gctgggatag gttttgaacc aagtggtaaa    120

atacatttag ggcattatct ccaaataaaa aagatgattg atttacaaaa tgctggattt    180

gatataatta tagttttggc tgatttacac gcctatttaa accagaaagg agagttggat    240

gagattagaa aaataggaga ttataacaaa aaagtttttg aagcaatggg gttaaaggca    300

aaatatgttt atggaagtga agcggatctt gataaggatt atacactgaa tgtctataga    360

ttggctttaa aaactacctt aaaaagagca agaaggagta tggaacttat agcaagagag    420

gatgaaaatc caaaggttgc tgaagttatc tatccaataa tgcaggttaa ttcgattcat    480

tatcgtggcg ttgatgttgc agttggaggg atggagcaga gaaaaataca catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660
```

gagattaggg ctaagataaa gaaagcatac tgcccagctg gagttgttga aggaaatcca 720
ataatggaga tagctaaata cttccttgaa tatcctttaa ccataaaaag gccagaaaaa 780
tttggtggag atttgacagt taatagctat gaggagttag agagtttatt taaaaataag 840
gaattgcatc caatggattt aaaaaatgct gtagctgaag aacttataaa gattttagag 900
ccaattagaa agagattata a 921

<210> SEQ ID NO 34
<211> LENGTH: 306
<212> TYPE: PRT
<213> ORGANISM: Artificial
<220> FEATURE:
<223> OTHER INFORMATION: biphenylalanine aminoacyl-tRNA synthetase

<400> SEQUENCE: 34

Met Asp Glu Phe Glu Met Ile Lys Arg Asn Thr Ser Glu Ile Ile Ser
1 5 10 15

Glu Glu Glu Leu Arg Glu Val Leu Lys Lys Asp Glu Lys Ser Ala His
20 25 30

Ile Gly Phe Glu Pro Ser Gly Lys Ile His Leu Gly His Tyr Leu Gln
35 40 45

Ile Lys Lys Met Ile Asp Leu Gln Asn Ala Gly Phe Asp Ile Ile Ile
50 55 60

Val Leu Ala Asp Leu His Ala Tyr Leu Asn Gln Lys Gly Glu Leu Asp
65 70 75 80

Glu Ile Arg Lys Ile Gly Asp Tyr Asn Lys Lys Val Phe Glu Ala Met
85 90 95

Gly Leu Lys Ala Lys Tyr Val Tyr Gly Ser Glu Arg Pro Leu Asp Lys
100 105 110

Asp Tyr Thr Leu Asn Val Tyr Arg Leu Ala Leu Lys Thr Thr Leu Lys
115 120 125

Arg Ala Arg Arg Ser Met Glu Leu Ile Ala Arg Glu Asp Glu Asn Pro
130 135 140

Lys Val Ala Glu Val Ile Tyr Pro Ile Met Gln Val Asn Gly Ile His
145 150 155 160

Tyr Leu Gly Val Asp Val Ala Val Gly Gly Met Glu Gln Arg Lys Ile
165 170 175

His Met Leu Ala Arg Glu Leu Leu Pro Lys Lys Val Val Cys Ile His
180 185 190

Asn Pro Val Leu Thr Gly Leu Asp Gly Glu Gly Lys Met Ser Ser Ser
195 200 205

Lys Gly Asn Phe Ile Ala Val Asp Asp Ser Pro Glu Glu Ile Arg Ala
210 215 220

Lys Ile Lys Lys Ala Tyr Cys Pro Ala Gly Val Val Glu Gly Asn Pro
225 230 235 240

Ile Met Glu Ile Ala Lys Tyr Phe Leu Glu Tyr Pro Leu Thr Ile Lys
245 250 255

Arg Pro Glu Lys Phe Gly Gly Asp Leu Thr Val Asn Ser Tyr Glu Glu
260 265 270

Leu Glu Ser Leu Phe Lys Asn Lys Glu Leu His Pro Met Asp Leu Lys
275 280 285

Asn Ala Val Ala Glu Glu Leu Ile Lys Ile Leu Glu Pro Ile Arg Lys
290 295 300

Arg Leu
305

<210> SEQ ID NO 35
<211> LENGTH: 921
<212> TYPE: DNA
<213> ORGANISM: Artificial
<220> FEATURE:
<223> OTHER INFORMATION: biphenylalanine aminoacyl-tRNA synthetase

<400> SEQUENCE: 35
atggacgaat ttgaaatgat aaagagaaac acatctgaaa ttatcagcga ggaagagtta 60
agagaggttt taaaaaaaga tgaaaaatct gctcatatag gttttgaacc aagtggtaaa 120
atacatttag ggcattatct ccaaataaaa aagatgattg atttacaaaa tgctggattt 180
gatataatta tagttttggc tgatttacac gcctatttaa accagaaagg agagttggat 240
gagattagaa aaataggaga ttataacaaa aaagtttttg aagcaatggg gttaaaggca 300
aaatatgttt atggaagtga aaggcctctt gataaggatt atacactgaa tgtctataga 360
ttggctttaa aaactacctt aaaaagagca agaaggagta tggaacttat agcaagagag 420
gatgaaaatc caaaggttgc tgaagttatc tatccaataa tgcaggttaa tggtattcat 480
tatctgggcg ttgatgttgc agttggaggg atggagcaga gaaaaataca catgttagca 540
agggagcttt taccaaaaaa ggttgtttgt attcacaacc ctgtcttaac gggtttggat 600
ggagaaggaa agatgagttc ttcaaaaggg aattttatag ctgttgatga ctctccagaa 660
gagattaggg ctaagataaa gaaagcatac tgcccagctg gagttgttga aggaaatcca 720
ataatggaga tagctaaata cttccttgaa tatcctttaa ccataaaaag gccagaaaaa 780
tttggtggag atttgacagt taatagctat gaggagttag agagtttatt taaaaataag 840
gaattgcatc caatggattt aaaaaatgct gtagctgaag aacttataaa gatttagag 900 ccaattagaa agagattata a 921

<210> SEQ ID NO 36
<211> LENGTH: 306
<212> TYPE: PRT
<213> ORGANISM: Artificial
<220> FEATURE:
<223> OTHER INFORMATION: biphenylalanine aminoacyl-tRNA synthetase

<400> SEQUENCE: 36

Met Asp Glu Phe Glu Met Ile Lys Arg Asn Thr Ser Glu Ile Ile Ser
1 5 10 15

Glu Glu Glu Leu Arg Glu Val Leu Lys Lys Asp Glu Lys Ser Ala His
20 25 30

Ile Gly Phe Glu Pro Ser Gly Lys Ile His Leu Gly His Tyr Leu Gln
35 40 45

Ile Lys Lys Met Ile Asp Leu Gln Asn Ala Gly Phe Asp Ile Ile Ile
50 55 60

His Leu Ala Asp Leu His Ala Tyr Leu Asn Gln Lys Gly Glu Leu Asp
65 70 75 80

Glu Ile Arg Lys Ile Gly Asp Tyr Asn Lys Lys Val Phe Glu Ala Met
85 90 95

Gly Leu Lys Ala Lys Tyr Val Tyr Gly Ser Glu Trp Met Leu Asp Lys
100 105 110

Asp Tyr Thr Leu Asn Val Tyr Arg Leu Ala Leu Lys Thr Thr Leu Lys
115 120 125

Arg Ala Arg Arg Ser Met Glu Leu Ile Ala Arg Glu Asp Glu Asn Pro
130 135 140

Lys Val Ala Glu Val Ile Tyr Pro Ile Met Gln Val Asn Gly Ile His

```
145                 150                 155                 160

Tyr Lys Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 37
<211> LENGTH: 921
<212> TYPE: DNA
<213> ORGANISM: Artificial
<220> FEATURE:
<223> OTHER INFORMATION: biphenylalanine aminoacyl-tRNA synthetase

<400> SEQUENCE: 37

```
atggacgaat ttgaaatgat aaagagaaac acatctgaaa ttatcagcga ggaagagtta      60

agagaggttt taaaaaaaga tgaaaaatct gctcatatag gttttgaacc aagtggtaaa     120

atacatttag ggcattatct ccaaataaaa aagatgattg atttacaaaa tgctggattt     180

gatataatta tacatttggc tgatttacac gcctatttaa accagaaagg agagttggat     240

gagattagaa aaataggaga ttataacaaa aaagtttttg aagcaatggg gttaaaggca     300

aaatatgttt atggaagtga atggatgctt gataaggatt atacactgaa tgtctataga     360

ttggctttaa aaactacctt aaaaagagca agaaggagta tggaacttat agcaagagag     420

gatgaaaatc caaaggttgc tgaagttatc tatccaataa tgcaggttaa tgggattcat     480

tataagggcg ttgatgttgc agttggaggg atggagcaga gaaaaataca catgttagca     540

agggagcttt taccaaaaaa ggttgtttgt attcacaacc ctgtcttaac gggtttggat     600

ggagaaggaa agatgagttc ttcaaaaggg aattttatag ctgttgatga ctctccagaa     660

gagattaggg ctaagataaa gaaagcatac tgcccagctg gagttgttga aggaaatcca     720

ataatggaga tagctaaata cttccttgaa tatcctttaa ccataaaaag gccagaaaaa     780

tttggtggag atttgacagt taatagctat gaggagttag agagtttatt taaaaataag     840

gaattgcatc caatggattt aaaaaatgct gtagctgaag aacttataaa gattttagag     900

ccaattagaa agagattata a                                               921
```

<210> SEQ ID NO 38
<211> LENGTH: 306
<212> TYPE: PRT
<213> ORGANISM: Artificial
<220> FEATURE:

<223> OTHER INFORMATION: bipyridylalanine aminoacyl-tRNA synthetase

<400> SEQUENCE: 38

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Glu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

His Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Trp Met Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly His His
145                 150                 155                 160

Tyr His Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 39
<211> LENGTH: 921
<212> TYPE: DNA
<213> ORGANISM: Artificial
<220> FEATURE:
<223> OTHER INFORMATION: bipyridylalanine aminoacyl-tRNA synthetase

<400> SEQUENCE: 39

```
atggacgaat ttgaaatgat aaagagaaac acatctgaaa ttatcagcga ggaagagtta      60

agagaggttt taaaaaaaga tgaaaaatct gctgagatag gttttgaacc aagtggtaaa     120

atacatttag ggcattatct ccaaataaaa aagatgattg atttacaaaa tgctggattt     180
```

```
gatataatta tacatttggc tgatttacac gcctatttaa accagaaagg agagttggat    240

gagattagaa aaataggaga ttataacaaa aaagtttttg aagcaatggg gttaaaggca    300

aaatatgttt atggaagtga atggatgctt gataaggatt atacactgaa tgtctataga    360

ttggctttaa aaactacctt aaaaagagca agaaggagta tggaacttat agcaagagag    420

gatgaaaatc caaaggttgc tgaagttatc tatccaataa tgcaggttaa tggtcatcat    480

tatcatggcg ttgatgttgc agttggaggg atggagcaga gaaaaataca catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatggattt aaaaaatgct gtagctgaag aacttataaa gattttagag    900

ccaattagaa agagattata a                                               921
```

<210> SEQ ID NO 40
<211> LENGTH: 306
<212> TYPE: PRT
<213> ORGANISM: Artificial
<220> FEATURE:
<223> OTHER INFORMATION: bipyridylalanine aminoacyl-tRNA synthetase

<400> SEQUENCE: 40

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Tyr Leu Ala Asp Leu Ala Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Glu Val Asn Gly Trp His
145                 150                 155                 160

Tyr Ser Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240
```

```
Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 41
<211> LENGTH: 921
<212> TYPE: DNA
<213> ORGANISM: Artificial
<220> FEATURE:
<223> OTHER INFORMATION: bipyridylalanine aminoacyl-tRNA synthetase

<400> SEQUENCE: 41

atggacgaat ttgaaatgat aaagagaaac acatctgaaa ttatcagcga ggaagagtta      60

agagaggttt taaaaaaaga tgaaaaatct gctggtatag gttttgaacc aagtggtaaa     120

atacatttag ggcattatct ccaaataaaa aagatgattg atttacaaaa tgctggattt     180

gatataatta tatatttggc tgatttagct gcctatttaa accagaaagg agagttggat     240

gagattagaa aaataggaga ttataacaaa aaagtttttg aagcaatggg gttaaaggca     300

aaatatgttt atggaagtga attccagctt gataaggatt atacactgaa tgtctataga     360

ttggctttaa aaactacctt aaaaagagca agaaggagta tggaacttat agcaagagag     420

gatgaaaatc caaaggttgc tgaagttatc tatccaataa tggaggttaa tggttggcat     480

tatagtggcg ttgatgttgc agttggaggg atggagcaga gaaaaataca catgttagca     540

agggagcttt taccaaaaaa ggttgtttgt attcacaacc ctgtcttaac gggtttggat     600

ggagaaggaa agatgagttc ttcaaaaggg aattttatag ctgttgatga ctctccagaa     660

gagattaggg ctaagataaa gaaagcatac tgcccagctg gagttgttga aggaaatcca     720

ataatggaga tagctaaata cttccttgaa tatcctttaa ccataaaaag gccagaaaaa     780

tttggtggag atttgacagt taatagctat gaggagttag agagtttatt taaaaataag     840

gaattgcatc caatggattt aaaaaatgct gtagctgaag aacttataaa gattttagag     900

ccaattagaa agagattata a                                               921


<210> SEQ ID NO 42
<211> LENGTH: 860
<212> TYPE: PRT
<213> ORGANISM: Artificial
<220> FEATURE:
<223> OTHER INFORMATION: 1,5-dansylalanine aminoacyl-tRNA synthetase

<400> SEQUENCE: 42

Met Glu Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Ser Lys
            20                  25                  30

Glu Lys Tyr Tyr Cys Leu Ser Ala Asn Pro Tyr Pro Ser Gly Arg Leu
        35                  40                  45

His Met Gly His Val Arg Asn Tyr Thr Ile Gly Asp Val Ile Ala Arg
    50                  55                  60
```

-continued

```
Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Thr Phe Met Gly Cys
                245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
        275                 280                 285

Lys Val Ala Glu Ala Glu Met Ala Thr Met Glu Lys Lys Gly Val Asp
    290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
        355                 360                 365

Asp Leu Ser Gln Gln Ala Leu Thr Glu Lys Gly Val Leu Phe Asn Ser
    370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
            420                 425                 430

Pro Met Val Thr Leu Glu Asp Gly Thr Val Met Pro Thr Pro Asp Asp
        435                 440                 445

Gln Leu Pro Val Ile Leu Pro Glu Asp Val Val Met Asp Gly Ile Thr
    450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495
```

```
Cys Trp Ile Tyr Ala Arg Tyr Thr Cys Pro Gln Tyr Lys Glu Gly Met
            500                 505                 510

Leu Asp Ser Glu Ala Ala Asn Tyr Trp Leu Pro Val Asp Ile Gly Ile
        515                 520                 525

Gly Gly Ile Glu His Ala Ile Met Thr Leu Leu Tyr Phe Arg Phe Phe
    530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
            580                 585                 590

Val Glu Arg Asp Glu Lys Gly Arg Ile Val Lys Ala Lys Asp Ala Ala
        595                 600                 605

Gly His Glu Leu Val Tyr Thr Gly Met Ser Lys Met Ser Lys Ser Lys
    610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
            660                 665                 670

Val Trp Lys Leu Val Tyr Glu His Thr Ala Lys Gly Asp Val Ala Ala
        675                 680                 685

Leu Asn Val Asp Ala Leu Thr Glu Asn Gln Lys Ala Leu Arg Arg Asp
    690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
            740                 745                 750

Ala Leu Leu Ala Val Val Arg Met Leu Asn Pro Phe Thr Pro His Ile
        755                 760                 765

Cys Phe Thr Leu Trp Gln Glu Leu Lys Gly Glu Gly Asp Ile Asp Asn
    770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
        835                 840                 845

Tyr Val Pro Gly Lys Leu Leu Asn Leu Val Val Gly
    850                 855                 860
```

<210> SEQ ID NO 43
<211> LENGTH: 2583
<212> TYPE: DNA
<213> ORGANISM: Artificial
<220> FEATURE:
<223> OTHER INFORMATION: 1,5-dansylalanine aminoacyl-tRNA synthetase

<400> SEQUENCE: 43

-continued

```
atggaagagc aataccgccc ggaagagata gaatccaaag tacagcttca ttgggatgag     60
aagcgcacat ttgaagtaac cgaagacgag agcaaagaga agtattactg cctgtctgct    120
aatccctatc cttctggtcg actacacatg ggccacgtac gtaactacac catcggtgac    180
gtgatcgccc gctaccagcg tatgctgggc aaaaacgtcc tgcagccgat cggctgggac    240
gcgtttggtc tgcctgcgga aggcgcggcg gtgaaaaaca acaccgctcc ggcaccgtgg    300
acgtacgaca acatcgcgta tatgaaaaac cagctcaaaa tgctgggctt tggttatgac    360
tggagccgcg agctggcaac ctgtacgccg gaatactacc gttgggaaca gaaattcttc    420
accgagctgt ataaaaaagg cctggtatat aagaagactt ctgcggtcaa ctggtgtccg    480
aacgaccaga ccgtactggc gaacgaacaa gttatcgacg gctgctgctg gcgctgcgat    540
accaaagttg aacgtaaaga gatcccgcag tggtttatca aaatcactgc ttacgctgac    600
gagctgctca acgatctgga taaactggat cactggccag acaccgttaa aaccatgcag    660
cgtaactgga tcggtcgttc cgaaggcgtg gagatcacct tcaacgttaa cgactatgac    720
aacacgctga ccgtttacac tacccgcccg gacaccttta tgggttgtac ctacctggcg    780
gtagctgcgg gtcatccgct ggcgcagaaa gcggcggaaa ataatcctga actggcggcc    840
tttattgacg aatgccgtaa caccaaagtt gccgaagctg aaatggcgac gatggagaaa    900
aaaggcgtcg atactggctt taaagcggtt cacccattaa cgggcgaaga aattcccgtt    960
tgggcagcaa acttcgtatt gatggagtac ggcacgggcg cagttatggc ggtaccgggg   1020
cacgaccagc gcgactacga gtttgcctct aaatacggcc tgaacatcaa accggttatc   1080
ctggcagctg acggctctga gccagatctt tctcagcaag ccctgactga aaaaggcgtg   1140
ctgttcaact ctggcgagtt caacggtctt gaccatgaag cggccttcaa cgccatcgcc   1200
gataaactga ctgcgatggg cgttggcgag cgtaaagtga actaccgcct gcgcgactgg   1260
ggtgtttccc gtcagcgtta ctggggcgcg ccgattccga tggtgactct agaagacggt   1320
accgtaatgc cgaccccgga cgaccagctg ccggtgatcc tgccggaaga tgtggtaatg   1380
gacggcatta ccagcccgat taaagcagat ccggagtggg cgaaaactac cgttaacggt   1440
atgccagcac tgcgtgaaac cgacactttc gacaccttta tggagtcctg ctggatttat   1500
gcgcgctaca cttgcccgca gtacaaagaa ggtatgctgg attccgaagc ggctaactac   1560
tggctgccgg tggatatcgg tattggtggt attgaacacg ccattatgac gctgctctac   1620
ttccgcttct tccacaaact gatgcgtgat gcaggcatgg tgaactctga cgaaccagcg   1680
aaacagttgc tgtgtcaggg tatggtgctg gcagatgcct tctactatgt tggcgaaaac   1740
ggcgaacgta actgggtttc cccggttgat gctatcgttg aacgtgacga gaaaggccgt   1800
atcgtgaaag cgaaagatgc ggcaggccat gaactggttt ataccggcat gagcaaaatg   1860
tccaagtcga agaacaacgg tatcgacccg caggtgatgg ttgaacgtta cggcgcggac   1920
accgttcgtc tgtttatgat gtttgcttct ccggctgata tgactctcga atggcaggaa   1980
tccggtgtgg aaggggctaa ccgcttcctg aaacgtgtct ggaaactggt ttacgagcac   2040
acagcaaaag gtgatgttgc ggcactgaac gttgatgcgc tgactgaaaa tcagaaagcg   2100
ctgcgtcgcg atgtgcataa aacgatcgct aaagtgaccg atgatatcgg ccgtcgtcag   2160
accttcaaca ccgcaattgc ggcgattatg gagctgatga acaaactggc gaaagcacca   2220
accgatggcg agcaggatcg cgctctgatg caggaagcac tgctggccgt tgtccgtatg   2280
cttaacccgt tcaccccgca catctgcttc acgctgtggc aggaactgaa aggcgaaggc   2340
gatatcgaca acgcgccgtg gccggttgct gacgaaaaag cgatggtgga agactccacg   2400
```

```
ctggtcgtgg tgcaggttaa cggtaaagtc cgtgccaaaa tcaccgttcc ggtggacgca   2460

acggaagaac aggttcgcga acgtgctggc caggaacatc tggtagcaaa atatcttgat   2520

ggcgttactg tacgtaaagt gatttacgta ccaggtaaac tcctcaatct ggtcgttggc   2580

taa                                                                 2583
```

<210> SEQ ID NO 44
<211> LENGTH: 860
<212> TYPE: PRT
<213> ORGANISM: Artificial
<220> FEATURE:
<223> OTHER INFORMATION: 1,5-dansylalanine aminoacyl-tRNA synthetase

<400> SEQUENCE: 44

```
Met Glu Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Ser Lys
            20                  25                  30

Glu Lys Tyr Tyr Cys Leu Ser Ala Asn Pro Tyr Pro Ser Gly Arg Leu
        35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Ala Phe Met Gly Cys
                245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
        275                 280                 285

Lys Val Ala Glu Ala Glu Met Ala Thr Met Glu Lys Lys Gly Val Asp
    290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335
```

```
Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
        355                 360                 365

Asp Leu Ser Gln Gln Ala Leu Thr Glu Lys Gly Val Leu Phe Asn Ser
    370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
            420                 425                 430

Pro Met Val Thr Leu Glu Asp Gly Thr Val Met Pro Thr Pro Asp Asp
        435                 440                 445

Gln Leu Pro Val Ile Leu Pro Glu Asp Val Val Met Asp Gly Ile Thr
    450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Cys Trp Ile Tyr Ala Arg Tyr Thr Cys Pro Gln Tyr Lys Glu Gly Met
            500                 505                 510

Leu Asp Ser Glu Ala Ala Asn Tyr Trp Leu Pro Val Asp Ile Gly Ile
        515                 520                 525

Gly Gly Ile Glu His Ala Ile Met Thr Leu Leu Tyr Phe Arg Phe Phe
    530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
            580                 585                 590

Val Glu Arg Asp Glu Lys Gly Arg Ile Val Lys Ala Lys Asp Ala Ala
        595                 600                 605

Gly His Glu Leu Val Tyr Thr Gly Met Ser Lys Met Ser Lys Ser Lys
    610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
            660                 665                 670

Val Trp Lys Leu Val Tyr Glu His Thr Ala Lys Gly Asp Val Ala Ala
        675                 680                 685

Leu Asn Val Asp Ala Leu Thr Glu Asn Gln Lys Ala Leu Arg Arg Asp
    690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
            740                 745                 750

Ala Leu Leu Ala Val Val Arg Met Leu Asn Pro Phe Thr Pro His Ile
```

```
        755                 760                 765

Cys Phe Thr Leu Trp Gln Glu Leu Lys Gly Glu Gly Asp Ile Asp Asn
    770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
        835                 840                 845

Tyr Val Pro Gly Lys Leu Leu Asn Leu Val Val Gly
    850                 855                 860


<210> SEQ ID NO 45
<211> LENGTH: 2589
<212> TYPE: DNA
<213> ORGANISM: Artificial
<220> FEATURE:
<223> OTHER INFORMATION: 1,5-dansylalanine aminoacyl-tRNA synthetase

<400> SEQUENCE: 45

atggaagagc aataccgccc ggaagagata gaatccaaag tacagcttca ttgggatgag      60

aagcgcacat ttgaagtaac cgaagacgag agcaaagaga agtattactg cctgtctgct     120

aatccctatc cttctggtcg actacacatg ggccacgtac gtaactacac catcggtgac     180

gtgatcgccc gctaccagcg tatgctgggc aaaaacgtcc tgcagccgat cggctgggac     240

gcgtttggtc tgcctgcgga aggcgcggcg gtgaaaaaca acaccgctcc ggcaccgtgg     300

acgtacgaca acatcgcgta tatgaaaaac cagctcaaaa tgctgggctt tggttatgac     360

tggagccgcg agctggcaac ctgtacgccg gaatactacc gttgggaaca gaaattcttc     420

accgagctgt ataaaaaagg cctggtatat aagaagactt ctgcggtcaa ctggtgtccg     480

aacgaccaga ccgtactggc gaacgaacaa gttatcgacg gctgctgctg gcgctgcgat     540

accaaagttg aacgtaaaga gatcccgcag tggtttatca aaatcactgc ttacgctgac     600

gagctgctca acgatctgga taaactggat cactggccag acaccgttaa aaccatgcag     660

cgtaactgga tcggtcgttc cgaaggcgtg gagatcacct tcaacgttaa cgactatgac     720

aacacgctga ccgtttacac tacccgcccg gacgcgttta tgggttgtac ctacctggcg     780

gtagctgcgg gtcatccgct ggcgcagaaa gcggcggaaa ataatcctga actggcggcc     840

tttattgacg aatgccgtaa caccaaagtt gccgaagctg aaatggcgac gatggagaaa     900

aaaggcgtcg atactggctt taaagcggtt cacccattaa cgggcgaaga aattcccgtt     960

tgggcagcaa acttcgtatt gatggagtac ggcacgggcg cagttatggc ggtaccgggg    1020

cacgaccagc gcgactacga gtttgcctct aaatacggcc tgaacatcaa accggttatc    1080

ctggcagctg acggctctga gccagatctt tctcagcaag ccctgactga aaaaggcgtg    1140

ctgttcaact ctggcgagtt caacggtctt gaccatgaag cggccttcaa cgccatcgcc    1200

gataaactga ctgcgatggg cgttggcgag cgtaaagtga actaccgcct gcgcgactgg    1260

ggtgtttccc gtcagcgtta ctggggcgcg ccgattccga tggtgactct agaagacggt    1320

accgtaatgc cgaccccgga cgaccagctg ccggtgatcc tgccggaaga tgtggtaatg    1380

gacggcatta ccagcccgat taaagcagat ccggagtggg cgaaaactac cgttaacggt    1440

atgccagcac tgcgtgaaac cgacactttc gacaccttta tggagtcctg ctggatttat    1500
```

-continued

```
gcgcgctaca cttgcccgca gtacaaagaa ggtatgctgg attccgaagc ggctaactac   1560

tggctgccgg tggatatcgg tattggtggt attgaacacg ccattatgac gctgctctac   1620

ttccgcttct tccacaaact gatgcgtgat gcaggcatgg tgaactctga cgaaccagcg   1680

aaacagttgc tgtgtcaggg tatggtgctg gcagatgcct tctactatgt tggcgaaaac   1740

ggcgaacgta actgggtttc cccggttgat gctatcgttg aacgtgacga gaaaggccgt   1800

atcgtgaaag cgaaagatgc ggcaggccat gaactggttt ataccggcat gagcaaaatg   1860

tccaagtcga agaacaacgg tatcgacccg caggtgatgg ttgaacgtta cggcgcggac   1920

accgttcgtc tgtttatgat gtttgcttct ccggctgata tgactctcga atggcaggaa   1980

tccggtgtgg aaggggctaa ccgcttcctg aaacgtgtct ggaaactggt ttacgagcac   2040

acagcaaaag gtgatgttgc ggcactgaac gttgatgcgc tgactgaaaa tcagaaagcg   2100

ctgcgtcgcg atgtgcataa aacgatcgct aaagtgaccg atgatatcgg ccgtcgtcag   2160

accttcaaca ccgcaattgc ggcgattatg gagctgatga acaaactggc gaaagcacca   2220

accgatggcg agcaggatcg cgctctgatg caggaagcac tgctggccgt tgtccgtatg   2280

cttaacccgt tcaccccgca catctgcttc acgctgtggc aggaactgaa aggcgaaggc   2340

gatatcgaca acgcgccgtg gccggttgct gacgaaaaag cgatggtgga agactccacg   2400

ctggtcgtgg tgcaggttaa cggtaaagtc cgtgccaaaa tcaccgttcc ggtggacgca   2460

acggaagaac aggttcgcga acgtgctggc caggaacatc tggtagcaaa atatcttgat   2520

ggcgttactg tacgtaaagt gatttacgta ccaggtaaac tcctcaatct ggtcgttggc   2580

taagcggcc                                                           2589
```

<210> SEQ ID NO 46
<211> LENGTH: 860
<212> TYPE: PRT
<213> ORGANISM: Artificial
<220> FEATURE:
<223> OTHER INFORMATION: 1,5-dansylalanine aminoacyl-tRNA synthetase

<400> SEQUENCE: 46

```
Met Glu Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Ser Lys
            20                  25                  30

Glu Lys Tyr Tyr Cys Leu Ser Ala Asn Pro Tyr Pro Ser Gly Arg Leu
        35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175
```

```
Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Thr Phe Met Gly Cys
                245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
        275                 280                 285

Lys Val Ala Glu Ala Glu Met Ala Thr Met Glu Lys Lys Gly Val Asp
    290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Ala Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
        355                 360                 365

Asp Leu Ser Gln Gln Ala Leu Thr Glu Lys Gly Val Leu Phe Asn Ser
    370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
            420                 425                 430

Pro Met Val Thr Leu Glu Asp Gly Thr Val Met Pro Thr Pro Asp Asp
        435                 440                 445

Gln Leu Pro Val Ile Leu Pro Glu Asp Val Val Met Asp Gly Ile Thr
    450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Cys Trp Ile Tyr Ala Arg Tyr Thr Cys Pro Gln Tyr Lys Glu Gly Met
            500                 505                 510

Leu Asp Ser Glu Ala Ala Asn Tyr Trp Leu Pro Val Asp Ile Gly Ile
        515                 520                 525

Gly Gly Ile Glu His Ala Ile Met Thr Leu Leu Tyr Phe Arg Phe Phe
    530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
            580                 585                 590

Val Glu Arg Asp Glu Lys Gly Arg Ile Val Lys Ala Lys Asp Ala Ala
```

```
        595                 600                 605

Gly His Glu Leu Val Tyr Thr Gly Met Ser Lys Met Ser Lys Ser Lys
    610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
            660                 665                 670

Val Trp Lys Leu Val Tyr Glu His Thr Ala Lys Gly Asp Val Ala Ala
        675                 680                 685

Leu Asn Val Asp Ala Leu Thr Glu Asn Gln Lys Ala Leu Arg Arg Asp
    690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
            740                 745                 750

Ala Leu Leu Ala Val Val Arg Met Leu Asn Pro Phe Thr Pro His Ile
        755                 760                 765

Cys Phe Thr Leu Trp Gln Glu Leu Lys Gly Glu Gly Asp Ile Asp Asn
    770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
        835                 840                 845

Tyr Val Pro Gly Lys Leu Leu Asn Leu Val Val Gly
    850                 855                 860


<210> SEQ ID NO 47
<211> LENGTH: 2589
<212> TYPE: DNA
<213> ORGANISM: Artificial
<220> FEATURE:
<223> OTHER INFORMATION: 1,5-dansylalanine aminoacyl-tRNA synthetase

<400> SEQUENCE: 47

atggaagagc aataccgccc ggaagagata gaatccaaag tacagcttca ttgggatgag     60

aagcgcacat ttgaagtaac cgaagacgag agcaaagaga agtattactg cctgtctgct    120

aatccctatc cttctggtcg actacacatg ggccacgtac gtaactacac catcggtgac    180

gtgatcgccc gctaccagcg tatgctgggc aaaaacgtcc tgcagccgat cggctgggac    240

gcgtttggtc tgcctgcgga aggcgcggcg gtgaaaaaca acaccgctcc ggcaccgtgg    300

acgtacgaca acatcgcgta tatgaaaaac cagctcaaaa tgctgggctt tggttatgac    360

tggagccgcg agctggcaac ctgtacgccg gaatactacc gttgggaaca gaaattcttc    420

accgagctgt ataaaaaagg cctggtatat aagaagactt ctgcggtcaa ctggtgtccg    480

aacgaccaga ccgtactggc gaacgaacaa gttatcgacg gctgctgctg gcgctgcgat    540

accaaagttg aacgtaaaga gatcccgcag tggtttatca aaatcactgc ttacgctgac    600
```

-continued

```
gagctgctca acgatctgga taaactggat cactggccag acaccgttaa aaccatgcag    660

cgtaactgga tcggtcgttc cgaaggcgtg gagatcacct tcaacgttaa cgactatgac    720

aacacgctga ccgtttacac tacccgcccg gacaccttta tgggttgtac ctacctggcg    780

gtagctgcgg gtcatccgct ggcgcagaaa gcggcggaaa ataatcctga actggcggcc    840

tttattgacg aatgccgtaa caccaaagtt gccgaagctg aaatggcgac gatggagaaa    900

aaaggcgtcg atactggctt taaagcggtt cacccattaa cgggcgaaga aattcccgtt    960

tgggcagcaa acttcgtatt gatggagtac ggcacgggcg cagttatggc ggcgccgggg   1020

cacgaccagc gcgactacga gtttgcctct aaatacggcc tgaacatcaa accggttatc   1080

ctggcagctg acggctctga gccagatctt tctcagcaag ccctgactga aaaaggcgtg   1140

ctgttcaact ctggcgagtt caacggtctt gaccatgaag cggccttcaa cgccatcgcc   1200

gataaactga ctgcgatggg cgttggcgag cgtaaagtga actaccgcct gcgcgactgg   1260

ggtgtttccc gtcagcgtta ctggggcgcg ccgattccga tggtgactct agaagacggt   1320

accgtaatgc cgaccccgga cgaccagctg ccggtgatcc tgccggaaga tgtggtaatg   1380

gacggcatta ccagcccgat taaagcagat ccggagtggg cgaaaactac cgttaacggt   1440

atgccagcac tgcgtgaaac cgacactttc gacaccttta tggagtcctg ctggatttat   1500

gcgcgctaca cttgcccgca gtacaaagaa ggtatgctgg attccgaagc ggctaactac   1560

tggctgccgg tggatatcgg tattggtggt attgaacacg ccattatgac gctgctctac   1620

ttccgcttct tccacaaact gatgcgtgat gcaggcatgg tgaactctga cgaaccagcg   1680

aaacagttgc tgtgtcaggg tatggtgctg gcagatgcct tctactatgt tggcgaaaac   1740

ggcgaacgta actgggtttc cccggttgat gctatcgttg aacgtgacga gaaaggccgt   1800

atcgtgaaag cgaaagatgc ggcaggccat gaactggttt ataccggcat gagcaaaatg   1860

tccaagtcga agaacaacgg tatcgacccg caggtgatgg ttgaacgtta cggcgcggac   1920

accgttcgtc tgtttatgat gtttgcttct ccggctgata tgactctcga atggcaggaa   1980

tccggtgtgg aaggggctaa ccgcttcctg aaacgtgtct ggaaactggt ttacgagcac   2040

acagcaaaag gtgatgttgc ggcactgaac gttgatgcgc tgactgaaaa tcagaaagcg   2100

ctgcgtcgcg atgtgcataa aacgatcgct aaagtgaccg atgatatcgg ccgtcgtcag   2160

accttcaaca ccgcaattgc ggcgattatg gagctgatga acaaactggc gaaagcacca   2220

accgatggcg agcaggatcg cgctctgatg caggaagcac tgctggccgt tgtccgtatg   2280

cttaacccgt tcaccccgca catctgcttc acgctgtggc aggaactgaa aggcgaaggc   2340

gatatcgaca acgcgccgtg gccggttgct gacgaaaaag cgatggtgga agactccacg   2400

ctggtcgtgg tgcaggttaa cggtaaagtc cgtgccaaaa tcaccgttcc ggtggacgca   2460

acggaagaac aggttcgcga acgtgctggc caggaacatc tggtagcaaa atatcttgat   2520

ggcgttactg tacgtaaagt gatttacgta ccaggtaaac tcctcaatct ggtcgttggc   2580

taagcggcc                                                           2589
```

<210> SEQ ID NO 48
<211> LENGTH: 860
<212> TYPE: PRT
<213> ORGANISM: Artificial
<220> FEATURE:
<223> OTHER INFORMATION: o-nitrobenzylcysteine aminoacyl-tRNA synthetase

<400> SEQUENCE: 48

```
Met Glu Glu Gln Tyr Arg Pro Glu Glu Ile Glu Ser Lys Val Gln Leu
1               5                   10                  15
```

```
His Trp Asp Glu Lys Arg Thr Phe Glu Val Thr Glu Asp Glu Ser Lys
            20                  25                  30

Glu Lys Tyr Tyr Cys Leu Ser Trp Ser Pro Tyr Pro Ser Gly Arg Leu
        35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Thr Phe Met Gly Cys
                245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
        275                 280                 285

Lys Val Ala Glu Ala Glu Met Ala Thr Met Glu Lys Lys Gly Val Asp
    290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
        355                 360                 365

Asp Leu Ser Gln Gln Ala Leu Thr Glu Lys Gly Val Leu Phe Asn Ser
    370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
            420                 425                 430

Pro Met Val Thr Leu Glu Asp Gly Thr Val Met Pro Thr Pro Asp Asp
```

-continued

```
        435                 440                 445

Gln Leu Pro Val Ile Leu Pro Glu Asp Val Val Met Asp Gly Ile Thr
    450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Cys Trp Ile Tyr Ala Arg Tyr Thr Cys Pro Gln Tyr Lys Glu Gly Met
            500                 505                 510

Leu Asp Ser Glu Ala Ala Asn Tyr Trp Leu Pro Val Asp Ile Ala Ile
        515                 520                 525

Gly Gly Ile Glu His Ala Ile Met Gly Leu Leu Tyr Phe Arg Phe Phe
    530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
            580                 585                 590

Val Glu Arg Asp Glu Lys Gly Arg Ile Val Lys Ala Lys Asp Ala Ala
        595                 600                 605

Gly His Glu Leu Val Tyr Thr Gly Met Ser Lys Met Ser Lys Ser Lys
    610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
            660                 665                 670

Val Trp Lys Leu Val Tyr Glu His Thr Ala Lys Gly Asp Val Ala Ala
        675                 680                 685

Leu Asn Val Asp Ala Leu Thr Glu Asn Gln Lys Ala Leu Arg Arg Asp
    690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
            740                 745                 750

Ala Leu Leu Ala Val Val Arg Met Leu Asn Pro Phe Thr Pro His Ile
        755                 760                 765

Cys Phe Thr Leu Trp Gln Glu Leu Lys Gly Glu Gly Asp Ile Asp Asn
    770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
        835                 840                 845

Tyr Val Pro Gly Lys Leu Leu Asn Leu Val Val Gly
    850                 855                 860
```

<210> SEQ ID NO 49
<211> LENGTH: 2583
<212> TYPE: DNA
<213> ORGANISM: Artificial
<220> FEATURE:
<223> OTHER INFORMATION: o-nitrobenzylcysteine aminoacyl-tRNA synthetase

<400> SEQUENCE: 49
atggaagagc aataccgccc ggaagagata gaatccaaag tacagcttca ttgggatgag 60
aagcgcacat ttgaagtaac cgaagacgag agcaaagaga agtattactg cctgtcttgg 120
tcgccctatc cttctggtcg actacacatg ggccacgtac gtaactacac catcggtgac 180
gtgatcgccc gctaccagcg tatgctgggc aaaaacgtcc tgcagccgat cggctgggac 240
gcgtttggtc tgcctgcgga aggcgcggcg gtgaaaaaca acaccgctcc ggcaccgtgg 300
acgtacgaca acatcgcgta tatgaaaaac cagctcaaaa tgctgggctt tggttatgac 360
tggagccgcg agctggcaac ctgtacgccg gaatactacc gttgggaaca gaaattcttc 420
accgagctgt ataaaaaagg cctggtatat aagaagactt ctgcggtcaa ctggtgcccg 480
aacgaccaga ccgtactggc gaacgaacaa gttatcgacg gctgctgctg gcgctgcgat 540
accaaagttg aacgtaaaga gatcccgcag tggtttatca aaatcactgc ttacgctgac 600
gagctgctca acgatctgga taaactggat cactggccag acaccgttaa aaccatgcag 660
cgtaactgga tcggtcgttc cgaaggcgtg gagatcacct tcaacgttaa cgactatgac 720
aacacgctga ccgtttacac tacccgcccg gacaccttta tgggttgtac ctacctggcg 780
gtagctgcgg gtcatccgct ggcgcagaaa gcggcggaaa ataatcctga actggcggcc 840
tttattgacg aatgccgtaa caccaaagtt gccgaagctg aaatggcgac gatggagaaa 900
aaaggcgtcg atactggctt taaagcggtt cacccattaa cgggcgaaga aattcccgtt 960
tgggcagcaa acttcgtatt gatggagtac ggcacgggcg cagttatggc ggtaccgggg 1020
cacgaccagc gcgactacga gtttgcctct aaatacggcc tgaacatcaa accggttatc 1080
ctggcagctg acggctctga gccagatctt tctcagcaag ccctgactga aaaaggcgtg 1140
ctgttcaact ctggcgagtt caacggtctt gaccatgaag cggccttcaa cgccatcgcc 1200
gataaactga ctgcgatggg cgttggcgag cgtaaagtga actaccgcct gcgcgactgg 1260
ggtgtttccc gtcagcgtta ctggggcgcg ccgattccga tggtgacgct ggaagacggt 1320
accgtaatgc cgaccccgga cgaccagctg ccggtgatcc tgccggaaga tgtggtaatg 1380
gacggcatta ccagcccgat taaagcagat ccggagtggg cgaaaactac cgttaacggt 1440
atgccagcac tgcgtgaaac cgacactttc gacaccttta tggagtcctg ctggatttat 1500
gcgcgctaca cttgcccgca gtacaaagaa ggtatgctgg attccgaagc ggctaactac 1560
tggctgccgg tggatatcgc gattggtggt attgaacacg ccattatggg gctgctctac 1620
ttccgcttct tccacaaact gatgcgtgat gcaggcatgg tgaactctga cgaaccagcg 1680
aaacagttgc tgtgtcaggg tatggtgctg gcagatgcct tctactatgt tggcgaaaac 1740
ggcgaacgta actgggtttc cccggttgat gctatcgttg aacgtgacga gaaaggccgt 1800
atcgtgaaag cgaaagatgc ggcaggccat gaactggttt ataccggcat gagcaaaatg 1860
tccaagtcga agaacaacgg tatcgacccg caggtgatgg ttgaacgtta cggcgcggac 1920
accgttcgtc tgtttatgat gtttgcttct ccggctgata tgactctcga atggcaggaa 1980
tccggtgtgg aaggggctaa ccgcttcctg aaacgtgtct ggaaactggt ttacgagcac 2040
acagcaaaag gtgatgttgc ggcactgaac gttgatgcgc tgactgaaaa tcagaaagcg 2100
ctgcgtcgcg atgtgcataa aacgatcgct aaagtgaccg atgatatcgg ccgtcgtcag 2160
accttcaaca ccgcaattgc ggcgattatg gagctgatga acaaactggc gaaagcacca 2220
accgatggcg agcaggaccg cgctctgatg caggaagcac tgctggccgt tgtccgtatg 2280
cttaacccgt tcaccccgca catctgcttc acgctgtggc aggaactgaa aggcgaaggc 2340
gatatcgaca acgcgccgtg gccggttgct gacgaaaaag cgatggtgga agactccacg 2400
ctggtcgtgg tgcaggttaa cggtaaagtc cgtgccaaaa tcaccgttcc ggtggacgca 2460
acggaagaac aggttcgcga acgtgctggc caggaacatc tggtagcaaa atatcttgat 2520
ggcgttactg tacgtaaagt gatttacgta ccaggtaaac tcctcaatct ggtcgttggc 2580
taa 2583

<210> SEQ ID NO 50
<211> LENGTH: 860
<212> TYPE: PRT
<213> ORGANISM: Artificial
<220> FEATURE:
<223> OTHER INFORMATION: o-nitrobenzylserine aminoacyl-tRNA synthetase

<400> SEQUENCE: 50

Met Glu Glu Gln Tyr Arg Pro Glu Glu Ile Glu Ser Lys Val Gln Leu
1 5 10 15

His Trp Asp Glu Lys Arg Thr Phe Glu Val Thr Glu Asp Glu Gly Lys
20 25 30

Glu Lys Tyr Tyr Cys Leu Ser Trp Ser Pro Tyr Pro Ser Gly Arg Leu
35 40 45

His Met Gly His Val Arg Asn Tyr Thr Ile Gly Asp Val Ile Ala Arg
50 55 60

Tyr Gln Arg Met Leu Gly Lys Asn Val Leu Gln Pro Ile Gly Trp Asp
65 70 75 80

Ala Phe Gly Leu Pro Ala Glu Gly Ala Ala Val Lys Asn Asn Thr Ala
85 90 95

Pro Ala Pro Trp Thr Tyr Asp Asn Ile Ala Tyr Met Lys Asn Gln Leu
100 105 110

Lys Met Leu Gly Phe Gly Tyr Asp Trp Ser Arg Glu Leu Ala Thr Cys
115 120 125

Thr Pro Glu Tyr Tyr Arg Trp Glu Gln Lys Phe Phe Thr Glu Leu Tyr
130 135 140

Lys Lys Gly Leu Val Tyr Lys Lys Thr Ser Ala Val Asn Trp Cys Pro
145 150 155 160

Asn Asp Gln Thr Val Leu Ala Asn Glu Gln Val Ile Asp Gly Cys Cys
165 170 175

Trp Arg Cys Asp Thr Lys Val Glu Arg Lys Glu Ile Pro Gln Trp Phe
180 185 190

Ile Lys Ile Thr Ala Tyr Ala Asp Glu Leu Leu Asn Asp Leu Asp Lys
195 200 205

Leu Asp His Trp Pro Asp Thr Val Lys Thr Met Gln Arg Asn Trp Ile
210 215 220

Gly Arg Ser Glu Gly Val Glu Ile Thr Phe Asn Val Asn Asp Tyr Asp
225 230 235 240

Asn Thr Leu Thr Val Tyr Ala Ser Arg Pro Asp Thr Phe Met Gly Cys
245 250 255

Thr Tyr Leu Ala Val Ala Ala Gly His Pro Leu Ala Gln Lys Ala Ala
260 265 270

Glu Asn Asn Pro Glu Leu Ala Ala Phe Ile Asp Glu Cys Arg Asn Thr

-continued

```
        275                 280                 285

Lys Val Ala Glu Ala Glu Met Ala Thr Met Glu Lys Lys Gly Val Asp
    290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
        355                 360                 365

Asp Leu Ser Gln Gln Ala Leu Thr Glu Lys Gly Val Leu Phe Asn Ser
    370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
            420                 425                 430

Pro Met Val Thr Leu Glu Asp Gly Thr Val Met Pro Thr Pro Asp Asp
        435                 440                 445

Gln Leu Pro Val Ile Leu Pro Glu Asp Val Val Met Asp Gly Ile Thr
    450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Cys Trp Ile Tyr Ala Arg Tyr Thr Cys Pro Gln Tyr Lys Glu Gly Met
            500                 505                 510

Leu Asp Ser Glu Ala Ala Asn Tyr Trp Leu Pro Val Asp Ile Ala Ile
        515                 520                 525

Gly Gly Ile Glu His Ala Ile Met Gly Leu Leu Tyr Phe Arg Phe Phe
    530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
            580                 585                 590

Val Glu Arg Asp Glu Lys Gly Arg Ile Val Lys Ala Lys Asp Ala Ala
        595                 600                 605

Gly His Glu Leu Val Tyr Thr Gly Ile Ser Lys Met Ser Lys Ser Lys
    610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
            660                 665                 670

Ala Trp Lys Leu Val Tyr Glu His Thr Ala Lys Gly Asp Val Ala Ala
        675                 680                 685

Leu Asn Val Asp Ala Leu Thr Glu Asn Gln Lys Ala Leu Arg Arg Asp
    690                 695                 700
```

```
Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
            740                 745                 750

Ala Leu Leu Ala Val Val Arg Met Leu Asn Pro Phe Thr Pro His Ile
        755                 760                 765

Cys Phe Thr Leu Trp Gln Glu Leu Lys Gly Glu Gly Asp Ile Asp Asn
    770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
        835                 840                 845

Tyr Val Pro Gly Lys Leu Leu Asn Leu Val Val Gly
    850                 855                 860


<210> SEQ ID NO 51
<211> LENGTH: 2844
<212> TYPE: DNA
<213> ORGANISM: Artificial
<220> FEATURE:
<223> OTHER INFORMATION: o-nitrobenzylserine aminoacyl-tRNA synthetase

<400> SEQUENCE: 51

atctcgaagc acacgaaact tttccttcc ttcattcacg cacactactc tctaatgagc      60

aacggtatac ggccttcctt ccagttactt gaatttgaaa taaaaaaaag tttgctgtct     120

tgctatcaag tataaataga cctgcaatta ttaatctttt gtttcctcgt cattgttctc     180

gttccctttc ttccttgttt ctttttctgc acaatatttc aagctatacc aagcatacaa     240

tcaactgaat tcagtatgga agagcaatac cgcccggaag agatagaatc caaagtacag     300

cttcattggg atgagaagcg cacatttgaa gtaaccgaag acgagggcaa agagaagtat     360

tactgcctgt cttggtcgcc ctatccttct ggtcgactac acatgggcca cgtacgtaac     420

tacaccatcg gtgacgtgat cgcccgctac cagcgtatgc tgggcaaaaa cgtcctgcag     480

ccgatcggct gggacgcgtt tggtctgcct gcggaaggcg cggcggtgaa aaacaacacc     540

gctccggcac cgtggacgta cgacaacatc gcgtatatga aaaaccagct caaaatgctg     600

ggctttggtt atgactggag ccgcgagctg gcaacctgta cgccggaata ctaccgttgg     660

gaacagaaat tcttcaccga gctgtataaa aaaggcctgg tatataagaa gacttctgcg     720

gtcaactggt gtccgaacga ccagaccgta ctggcgaacg aacaagttat cgacggctgc     780

tgctggcgct gcgataccaa agttgaacgt aaagagatcc cgcagtggtt tatcaaaatc     840

actgcttacg ctgacgagct gctcaacgat ctggataaac tggatcactg gccagacacc     900

gttaaaacca tgcagcgtaa ctggatcggt cgttccgaag gcgtggagat caccttcaac     960

gttaacgact atgacaacac gctgaccgtt tacgcttccc gcccggacac ctttatgggt    1020

tgtacctacc tggcggtagc tgcgggtcat ccgctggcgc agaaagcggc ggaaaataat    1080

cctgaactgg cggcctttat tgacgaatgc cgtaacacca aagttgccga agctgaaatg    1140

gcgacgatgg agaaaaaagg cgtcgatact ggctttaaag cggttcaccc attaacgggc    1200
```

```
gaagaaattc ccgtttgggc agcaaacttc gtattgatgg agtacggcac gggcgcagtt   1260

atggcggtac cggggcacga ccagcgcgac tacgagtttg cctctaaata cggcctgaac   1320

atcaaaccgg ttatcctggc agctgacggc tctgagccag atctttctca gcaagccctg   1380

actgaaaaag gcgtgctgtt caactctggc gagttcaacg gtcttgacca tgaagcggcc   1440

ttcaacgcca tcgccgataa actgactgcg atgggcgttg gcgagcgtaa agtgaactac   1500

cgcctgcgcg actggggtgt ttcccgtcag cgttactggg gcgcgccgat tccgatggtg   1560

actctagaag acggtaccgt aatgccgacc ccggacgacc agctgccggt gatcctgccg   1620

gaagatgtgg taatggacgg cattaccagc ccgattaaag cagatccgga gtgggcgaaa   1680

actaccgtta acggtatgcc agcactgcgt gaaaccgaca ctttcgacac ctttatggag   1740

tcctgctgga tttatgcgcg ctacacttgc ccgcagtaca aagaaggtat gctggattcc   1800

gaagcggcta actactggct gccggtggat atcgcgattg gtggtattga acacgccatt   1860

atggggctgc tctacttccg cttcttccac aaactgatgc gtgatgcagg catggtgaac   1920

tctgacgaac cagcgaaaca gttgctgtgt cagggtatgg tgctggcaga tgccttctac   1980

tatgttggcg aaaacggcga acgtaactgg gtttccccgg ttgatgctat cgttgaacgt   2040

gacgagaaag gccgtatcgt gaaagcgaaa gatgcggcag gccatgaact ggtttatacc   2100

ggcataagca aaatgtccaa gtcgaagaac aacggtatcg acccgcaggt gatggttgaa   2160

cgttacggcg cggacaccgt tcgtctgttt atgatgtttg cttctccggc tgatatgact   2220

ctcgaatggc aggaatccgg tgtggaaggg gctaaccgct tcctgaaacg tgcctggaaa   2280

ctggtttacg agcacacagc aaaaggtgat gttgcggcac tgaacgttga tgcgctgact   2340

gaaaatcaga aagcgctgcg tcgcgatgtg cataaaacga tcgctaaagt gaccgatgat   2400

atcggccgtc gtcagacctt caacaccgca attgcggcga ttatggagct gatgaacaaa   2460

ctggcgaaag caccaaccga tggcgagcag gatcgcgctc tgatgcagga agcactgctg   2520

gccgttgtcc gtatgcttaa cccgttcacc ccgcacatct gcttcacgct gtggcaggaa   2580

ctgaaaggcg aaggcgatat cgacaacgcg ccgtggccgg ttgctgacga aaaagcgatg   2640

gtggaagact ccacgctggt cgtggtgcag gttaacggta aagtccgtgc caaaatcacc   2700

gttccggtgg acgcaacgga agaacaggtt cgcgaacgtg ctggccagga acatctggta   2760

gcaaaatatc ttgatggcgt tactgtacgt aaagtgattt acgtaccagg taaactcctc   2820

aatctggtcg ttggctaagc ggcc                                          2844
```

<210> SEQ ID NO 52
<211> LENGTH: 306
<212> TYPE: PRT
<213> ORGANISM: Artificial
<220> FEATURE:
<223> OTHER INFORMATION: O-(2-nitrobenzyl)-L-tyrosine aminoacyl-tRNA synthetase

<400> SEQUENCE: 52

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Gly Leu Ala Asp Leu His Ala Tyr Leu Asn Gln Lys Gly Glu Leu Asp
```

```
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Ala Arg Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Glu Ile His
145                 150                 155                 160

Tyr Tyr Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 53
<211> LENGTH: 306
<212> TYPE: PRT
<213> ORGANISM: Artificial
<220> FEATURE:
<223> OTHER INFORMATION: O-(2-nitrobenzyl)-L-tyrosine aminoacyl-tRNA
      synthetase

<400> SEQUENCE: 53

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Gly Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Cys Asp Leu Asp Lys
            100                 105                 110

Asp Tyr Thr Leu Asn Val Tyr Arg Leu Ala Leu Lys Thr Thr Leu Lys
```

```
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile His
145                 150                 155                 160

Tyr Gly Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 54
<211> LENGTH: 306
<212> TYPE: PRT
<213> ORGANISM: Artificial
<220> FEATURE:
<223> OTHER INFORMATION: O-(2-nitrobenzyl)-L-tyrosine aminoacyl-tRNA
      synthetase

<400> SEQUENCE: 54

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Gly Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Glu Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ser Ile His
145                 150                 155                 160

Tyr Glu Gly Val Asp Val Ala Val Gly Gly Met Glu Gln Arg Lys Ile
```

165 170 175

His Met Leu Ala Arg Glu Leu Leu Pro Lys Lys Val Val Cys Ile His
180 185 190

Asn Pro Val Leu Thr Gly Leu Asp Gly Glu Gly Lys Met Ser Ser Ser
195 200 205

Lys Gly Asn Phe Ile Ala Val Asp Asp Ser Pro Glu Glu Ile Arg Ala
210 215 220

Lys Ile Lys Lys Ala Tyr Cys Pro Ala Gly Val Val Glu Gly Asn Pro
225 230 235 240

Ile Met Glu Ile Ala Lys Tyr Phe Leu Glu Tyr Pro Leu Thr Ile Lys
245 250 255

Arg Pro Glu Lys Phe Gly Gly Asp Leu Thr Val Asn Ser Tyr Glu Glu
260 265 270

Leu Glu Ser Leu Phe Lys Asn Lys Glu Leu His Pro Met Asp Leu Lys
275 280 285

Asn Ala Val Ala Glu Glu Leu Ile Lys Ile Leu Glu Pro Ile Arg Lys
290 295 300

Arg Leu
305

<210> SEQ ID NO 55
<211> LENGTH: 306
<212> TYPE: PRT
<213> ORGANISM: Artificial
<220> FEATURE:
<223> OTHER INFORMATION: p-cyanophenylalanine aminoacyl-tRNA synthetase

<400> SEQUENCE: 55

Met Asp Glu Phe Glu Met Ile Lys Arg Asn Thr Ser Glu Ile Ile Ser
1 5 10 15

Glu Glu Glu Leu Arg Glu Val Leu Lys Lys Asp Glu Lys Ser Ala Leu
20 25 30

Ile Gly Phe Glu Pro Ser Gly Lys Ile His Leu Gly His Tyr Leu Gln
35 40 45

Ile Lys Lys Met Ile Asp Leu Gln Asn Ala Gly Phe Asp Ile Ile Ile
50 55 60

Val Leu Ala Asp Leu His Ala Tyr Leu Asn Gln Lys Gly Glu Leu Asp
65 70 75 80

Glu Ile Arg Lys Ile Gly Asp Tyr Asn Lys Lys Val Phe Glu Ala Met
85 90 95

Gly Leu Lys Ala Lys Tyr Val Tyr Gly Ser Glu Trp Met Leu Asp Lys
100 105 110

Asp Tyr Thr Leu Asn Val Tyr Arg Leu Ala Leu Lys Thr Thr Leu Lys
115 120 125

Arg Ala Arg Arg Ser Met Glu Leu Ile Ala Arg Glu Asp Glu Asn Pro
130 135 140

Lys Val Ala Glu Val Ile Tyr Pro Ile Met Gln Val Asn Gly Ala His
145 150 155 160

Tyr Leu Gly Val Asp Val Ala Val Gly Gly Met Glu Gln Arg Lys Ile
165 170 175

His Met Leu Ala Arg Glu Leu Leu Pro Lys Lys Val Val Cys Ile His
180 185 190

Asn Pro Val Leu Thr Gly Leu Asp Gly Glu Gly Lys Met Ser Ser Ser
195 200 205

Lys Gly Asn Phe Ile Ala Val Asp Asp Ser Pro Glu Glu Ile Arg Ala
210 215 220

```
Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 56
<211> LENGTH: 921
<212> TYPE: DNA
<213> ORGANISM: Artificial
<220> FEATURE:
<223> OTHER INFORMATION: p-cyanophenylalanine aminoacyl-tRNA synthetase

<400> SEQUENCE: 56

```
atggacgaat ttgaaatgat aaagagaaac acatctgaaa ttatcagcga ggaagagtta     60

agagaggttt taaaaaaaga tgaaaaatct gctctgatag gttttgaacc aagtggtaaa    120

atacatttag ggcattatct ccaaataaaa aagatgattg atttacaaaa tgctggattt    180

gatataatta tagttttggc tgatttacat gcctatttaa accagaaagg agagttggat    240

gagattagaa aaataggaga ttataacaaa aaagtttttg aagcaatggg gttaaaggca    300

aaatatgttt atggaagtga atggatgctt gataaggatt atacactgaa tgtctataga    360

ttggctttaa aaactacctt aaaaagagca agaaggagta tggaacttat agcaagagag    420

gatgaaaatc caaaggttgc tgaagttatc tatccaataa tgcaggttaa tggtgctcat    480

tatcttggcg ttgatgttgc agttgggggg atggagcaga gaaaaataca catgttagca    540

agggagcttt taccaaaaaa ggttgtttgt attcacaacc ctgtcttaac gggtttggat    600

ggagaaggaa agatgagttc ttcaaaaggg aattttatag ctgttgatga ctctccagaa    660

gagattaggg ctaagataaa gaaagcatac tgcccagctg gagttgttga aggaaatcca    720

ataatggaga tagctaaata cttccttgaa tatcctttaa ccataaaaag gccagaaaaa    780

tttggtggag atttgacagt taatagctat gaggagttag agagtttatt taaaaataag    840

gaattgcatc caatggattt aaaaaatgct gtagctgaag aacttataaa gattttagag    900

ccaattagaa agagattata a                                              921
```

<210> SEQ ID NO 57
<211> LENGTH: 306
<212> TYPE: PRT
<213> ORGANISM: Artificial
<220> FEATURE:
<223> OTHER INFORMATION: m-cyanophenylalanine aminoacyl-tRNA synthetase

<400> SEQUENCE: 57

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala His
            20                  25                  30

Ile Gly Phe Glu Pro Ser Gly Lys Ile His Leu Gly His Tyr Leu Gln
        35                  40                  45
```

-continued

```
Ile Lys Lys Met Ile Asp Leu Gln Asn Ala Gly Phe Asp Ile Ile Ile
    50                  55                  60

Leu Leu Ala Asp Leu Ser Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ser Ser His
145                 150                 155                 160

Tyr Pro Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 58
<211> LENGTH: 921
<212> TYPE: DNA
<213> ORGANISM: Artificial
<220> FEATURE:
<223> OTHER INFORMATION: m-cyanophenylalanine aminoacyl-tRNA synthetase

<400> SEQUENCE: 58

```
atggacgaat ttgaaatgat aaagagaaac acatctgaaa ttatcagcga ggaagagtta      60

agagaggttt taaaaaaaga tgaaaaatct gctcatatag gttttgaacc aagtggtaaa     120

atacatttag ggcattatct ccaaataaaa aagatgattg atttacaaaa tgctggattt     180

gatataatta tattgttggc tgatttatct gcctatttaa accagaaagg agagttggat     240

gagattagaa aaataggaga ttataacaaa aaagtttttg aagcaatggg gttaaaggca     300

aaatatgttt atggaagtga attccagctt gataaggatt atacactgaa tgtctataga     360

ttggctttaa aaactacctt aaaaagagca agaaggagta tggaacttat agcaagagag     420

gatgaaaatc caaaggttgc tgaagttatc tatccaataa tgcaggttaa tagttcgcat     480

tatcctggcg ttgatgttgc agttggaggg atggagcaga gaaaaataca catgttagca     540

agggagcttt taccaaaaaa ggttgtttgt attcacaacc ctgtcttaac gggtttggat     600
```

ggagaaggaa agatgagttc ttcaaaaggg aattttatag ctgttgatga ctctccagaa 660
gagattaggg ctaagataaa gaaagcatac tgcccagctg gagttgttga aggaaatcca 720
ataatggaga tagctaaata cttccttgaa tatcctttaa ccataaaaag gccagaaaaa 780
tttggtggag atttgacagt taatagctat gaggagttag agagtttatt taaaaataag 840
gaattgcatc caatggattt aaaaaatgct gtagctgaag aacttataaa gattttagag 900
ccaattagaa agagattata a 921

<210> SEQ ID NO 59
<211> LENGTH: 306
<212> TYPE: PRT
<213> ORGANISM: Artificial
<220> FEATURE:
<223> OTHER INFORMATION: p-(2-amino-1-hydroxyethyl)-L-phenylalanine
aminoacyl-tRNA synthetase

<400> SEQUENCE: 59

Met Asp Glu Phe Glu Met Ile Lys Arg Asn Thr Ser Glu Ile Ile Ser
1 5 10 15

Glu Glu Glu Leu Arg Glu Val Leu Lys Lys Asp Glu Lys Ser Ala Asp
20 25 30

Ile Gly Phe Glu Pro Ser Gly Lys Ile His Leu Gly His Tyr Leu Gln
35 40 45

Ile Lys Lys Met Ile Asp Leu Gln Asn Ala Gly Phe Asp Ile Ile Ile
50 55 60

Glu Leu Ala Asp Leu His Ala Tyr Leu Asn Gln Lys Gly Glu Leu Asp
65 70 75 80

Glu Ile Arg Lys Ile Gly Asp Tyr Asn Lys Lys Val Phe Glu Ala Met
85 90 95

Gly Leu Lys Ala Lys Tyr Val Tyr Gly Ser Glu Arg Gln Leu Asp Lys
100 105 110

Asp Tyr Thr Leu Asn Val Tyr Arg Leu Ala Leu Lys Thr Thr Leu Lys
115 120 125

Arg Ala Arg Arg Ser Met Glu Leu Ile Ala Arg Glu Asp Glu Asn Pro
130 135 140

Lys Val Ala Glu Val Ile Tyr Pro Ile Met Gln Val Asn Gly Ile His
145 150 155 160

Tyr Asn Gly Val Asp Val Ala Val Gly Gly Met Glu Gln Arg Lys Ile
165 170 175

His Met Leu Ala Arg Glu Leu Leu Pro Lys Lys Val Val Cys Ile His
180 185 190

Asn Pro Val Leu Thr Gly Leu Asp Gly Glu Gly Lys Met Ser Ser Ser
195 200 205

Lys Gly Asn Phe Ile Ala Val Asp Asp Ser Pro Glu Glu Ile Arg Ala
210 215 220

Lys Ile Lys Lys Ala Tyr Cys Pro Ala Gly Val Val Glu Gly Asn Pro
225 230 235 240

Ile Met Glu Ile Ala Lys Tyr Phe Leu Glu Tyr Pro Leu Thr Ile Lys
245 250 255

Arg Pro Glu Lys Phe Gly Gly Asp Leu Thr Val Asn Ser Tyr Glu Glu
260 265 270

Leu Glu Ser Leu Phe Lys Asn Lys Glu Leu His Pro Met Asp Leu Lys
275 280 285

Asn Ala Val Ala Glu Glu Leu Ile Lys Ile Leu Glu Pro Ile Arg Lys
290 295 300

Arg Leu
305

<210> SEQ ID NO 60
<211> LENGTH: 306
<212> TYPE: PRT
<213> ORGANISM: Artificial
<220> FEATURE:
<223> OTHER INFORMATION: p-ethylthiocarbonyl-L-phenylalanine
      aminoacyl-tRNA synthetase

<400> SEQUENCE: 60

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Phe Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Trp Ser Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ser Ile His
145                 150                 155                 160

Tyr His Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 61
<211> LENGTH: 306
<212> TYPE: PRT
<213> ORGANISM: Artificial

<220> FEATURE:
<223> OTHER INFORMATION: p-(3-oxobutanoyl)-L-phenylalanine
aminoacyl-tRNA synthetase

<400> SEQUENCE: 61

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Val Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Thr Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Ile His
145                 150                 155                 160

Tyr Ser Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 62
<211> LENGTH: 306
<212> TYPE: PRT
<213> ORGANISM: Artificial
<220> FEATURE:
<223> OTHER INFORMATION: p-isopropylthiocarbonyl-L-phenylalanine
aminoacyl-tRNA synthetase

<400> SEQUENCE: 62

```
Met Asp Glu Phe Glu Met Ile Lys Arg Asn Thr Ser Glu Ile Ile Ser
1               5                   10                  15
```

Glu Glu Glu Leu Arg Glu Val Leu Lys Lys Asp Glu Lys Ser Ala Gly
20 25 30

Ile Gly Phe Glu Pro Ser Gly Lys Ile His Leu Gly His Tyr Leu Gln
35 40 45

Ile Lys Lys Met Ile Asp Leu Gln Asn Ala Gly Phe Asp Ile Ile Ile
50 55 60

Cys Leu Ala Asp Leu His Ala Tyr Leu Asn Gln Lys Gly Glu Leu Asp
65 70 75 80

Glu Ile Arg Lys Ile Gly Asp Tyr Asn Lys Lys Val Phe Glu Ala Met
85 90 95

Gly Leu Lys Ala Lys Tyr Val Tyr Gly Ser Glu Cys Met Leu Asp Lys
100 105 110

Asp Tyr Thr Leu Asn Val Tyr Arg Leu Ala Leu Lys Thr Thr Leu Lys
115 120 125

Arg Ala Arg Arg Ser Met Glu Leu Ile Ala Arg Glu Asp Glu Asn Pro
130 135 140

Lys Val Ala Glu Val Ile Tyr Pro Ile Met Gln Val Asn Gly Ile His
145 150 155 160

Tyr Tyr Gly Val Asp Val Ala Val Gly Gly Met Glu Gln Arg Lys Ile
165 170 175

His Met Leu Ala Arg Glu Leu Leu Pro Lys Lys Val Val Cys Ile His
180 185 190

Asn Pro Val Leu Thr Gly Leu Asp Gly Glu Gly Lys Met Ser Ser Ser
195 200 205

Lys Gly Asn Phe Ile Ala Val Asp Asp Ser Pro Glu Glu Ile Arg Ala
210 215 220

Lys Ile Lys Lys Ala Tyr Cys Pro Ala Gly Val Val Glu Gly Asn Pro
225 230 235 240

Ile Met Glu Ile Ala Lys Tyr Phe Leu Glu Tyr Pro Leu Thr Ile Lys
245 250 255

Arg Pro Glu Lys Phe Gly Gly Asp Leu Thr Val Asn Ser Tyr Glu Glu
260 265 270

Leu Glu Ser Leu Phe Lys Asn Lys Glu Leu His Pro Met Asp Leu Lys
275 280 285

Asn Ala Val Ala Glu Glu Leu Ile Lys Ile Leu Glu Pro Ile Arg Lys
290 295 300

Arg Leu
305

<210> SEQ ID NO 63
<211> LENGTH: 306
<212> TYPE: PRT
<213> ORGANISM: Artificial
<220> FEATURE:
<223> OTHER INFORMATION: 7-amino-coumarin alanine and 7-hydroxy-coumarin alanine aminoacyl-tRNA synthetase

<400> SEQUENCE: 63

Met Asp Glu Phe Glu Met Ile Lys Arg Asn Thr Ser Glu Ile Ile Ser
1 5 10 15

Glu Glu Glu Leu Arg Glu Val Leu Lys Lys Asp Glu Lys Ser Ala Arg
20 25 30

Ile Gly Phe Glu Pro Ser Gly Lys Ile His Leu Gly His Tyr Leu Gln
35 40 45

Ile Lys Lys Met Ile Asp Leu Gln Asn Ala Gly Phe Asp Ile Ile Ile
50 55 60

-continued

```
Ala Leu Ala Asp Leu Met Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asn Ile His
145                 150                 155                 160

Tyr Thr Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 64
<211> LENGTH: 14
<212> TYPE: PRT
<213> ORGANISM: Artificial
<220> FEATURE:
<223> OTHER INFORMATION: tryptic peptide from mutant myoglobin

<400> SEQUENCE: 64

His Gly Val Thr Val Leu Thr Ala Leu Gly Tyr Ile Leu Lys
1               5                   10


<210> SEQ ID NO 65
<211> LENGTH: 14
<212> TYPE: PRT
<213> ORGANISM: Artificial
<220> FEATURE:
<223> OTHER INFORMATION: tryptic peptide from mutant myoglobin
<220> FEATURE:
<221> NAME/KEY: MISC_FEATURE
<222> LOCATION: (11)..(11)
<223> OTHER INFORMATION: X is deuterated O-(2-nitrobenzyl)-L-tyrosine

<400> SEQUENCE: 65

His Gly Val Thr Val Leu Thr Ala Leu Gly Xaa Ile Leu Lys
1               5                   10
```